US011135301B2

(12) United States Patent
Chilkoti et al.

(10) Patent No.: US 11,135,301 B2
(45) Date of Patent: Oct. 5, 2021

(54) TRIBLOCK POLYPEPTIDE-BASED NANOPARTICLES FOR THE DELIVERY OF HYDROPHILIC DRUGS

(71) Applicant: Duke University, Durham, NC (US)

(72) Inventors: Ashutosh Chilkoti, Durham, NC (US); Jayanta Bhattacharyya, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/332,865

(22) PCT Filed: Sep. 14, 2017

(86) PCT No.: PCT/US2017/051661
§ 371 (c)(1),
(2) Date: Mar. 13, 2019

(87) PCT Pub. No.: WO2018/053201
PCT Pub. Date: Mar. 22, 2018

(65) Prior Publication Data
US 2020/0164082 A1    May 28, 2020

Related U.S. Application Data

(60) Provisional application No. 62/394,662, filed on Sep. 14, 2016.

(51) Int. Cl.
| A61K 47/00 | (2006.01) |
| A61K 47/64 | (2017.01) |
| A61P 35/00 | (2006.01) |
| A61K 9/51 | (2006.01) |
| A61K 31/506 | (2006.01) |
| B82Y 5/00 | (2011.01) |

(52) U.S. Cl.
CPC ........ *A61K 47/6455* (2017.08); *A61K 9/5169* (2013.01); *A61K 31/506* (2013.01); *A61P 35/00* (2018.01); *B82Y 5/00* (2013.01)

(58) Field of Classification Search
IPC .................................................. A61K 47/6455
See application file for complete search history.

(56) References Cited

U.S. PATENT DOCUMENTS

| 4,554,101 A | 11/1985 | Hopp |
| 4,976,734 A | 12/1990 | Urry et al. |
| 5,250,516 A | 10/1993 | Urry |
| 5,336,256 A | 8/1994 | Urry |
| 5,578,577 A | 11/1996 | Ching et al. |
| 5,580,859 A | 12/1996 | Felgner et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,623,950 B1 | 9/2003 | Von Der Osten et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,429,458 B2 | 9/2008 | Chilkoti |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,497,356 B2 | 7/2013 | Chilkoti et al. |
| 8,506,963 B2 | 8/2013 | Li et al. |
| 9,127,047 B2 | 9/2015 | Chilkoti |
| 9,132,179 B2 | 9/2015 | Philip |
| 9,592,303 B2 | 3/2017 | Chilkoti et al. |
| 10,385,115 B2 | 8/2019 | Chilkoti et al. |
| 2001/0034050 A1 | 10/2001 | Chilkoti |

(Continued)

FOREIGN PATENT DOCUMENTS

| CA | 2327325 A1 | 11/1999 |
| CA | 2423488 A1 | 4/2002 |

(Continued)

OTHER PUBLICATIONS

U.S. Appl. No. 62/985,179, filed Mar. 4, 2020.
U.S. Appl. No. 62/898,353, filed Sep. 12, 2019.
U.S. Appl. No. 17/015,315, filed Sep. 9, 2020.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019.
U.S. Appl. No. 62/200,726, filed Aug. 4, 2015.

(Continued)

*Primary Examiner* — Jeanette M Lieb
(74) *Attorney, Agent, or Firm* — Michael Best & Friedrich LLP

(57) ABSTRACT

Described herein are compositions that may include a triblock self-assembling polypeptide and a molecule attached to the polypeptide. Also described herein are methods of making the compositions and methods of using the compositions.

26 Claims, 74 Drawing Sheets

Specification includes a Sequence Listing.

(56) References Cited

U.S. PATENT DOCUMENTS

| | | | |
|---|---|---|---|
| 2002/0052443 | A1 | 5/2002 | Greenwald et al. |
| 2002/0146794 | A1 | 10/2002 | Tomycz |
| 2003/0175290 | A1 | 9/2003 | Renner et al. |
| 2003/0225251 | A1 | 12/2003 | Sallberg et al. |
| 2003/0233675 | A1 | 12/2003 | Cao et al. |
| 2004/0053976 | A1 | 3/2004 | Martinez et al. |
| 2004/0101852 | A1 | 5/2004 | Bennett et al. |
| 2004/0192072 | A1 | 9/2004 | Snow et al. |
| 2005/0186214 | A1 | 8/2005 | Liu et al. |
| 2005/0255554 | A1 | 11/2005 | Chilkoti |
| 2005/0288229 | A1 | 12/2005 | Sindrey et al. |
| 2006/0025524 | A1 | 2/2006 | Schneider et al. |
| 2006/0034796 | A1 | 2/2006 | Ashwell et al. |
| 2007/0087114 | A1 | 4/2007 | Chilkoti et al. |
| 2007/0117173 | A1 | 5/2007 | Levison et al. |
| 2008/0181861 | A1 | 7/2008 | Jiang et al. |
| 2009/0098652 | A1 | 4/2009 | Stupp et al. |
| 2010/0015070 | A1 | 1/2010 | Bollschweiler et al. |
| 2010/0048473 | A1 | 2/2010 | Chaikof et al. |
| 2010/0241054 | A1 | 9/2010 | Dacey et al. |
| 2010/0311059 | A1 | 12/2010 | Didion et al. |
| 2010/0325765 | P1 | 12/2010 | Pait et al. |
| 2011/0082283 | A1 | 4/2011 | Dagher et al. |
| 2011/0119778 | A1 | 5/2011 | Liss |
| 2011/0165557 | A1 | 7/2011 | Ah et al. |
| 2011/0207673 | A1 | 8/2011 | Chilkoti et al. |
| 2011/0248698 | A1 | 10/2011 | Kikuchi et al. |
| 2011/0294189 | A1 | 12/2011 | Chilkoti et al. |
| 2011/0305718 | A1 | 12/2011 | Mugica et al. |
| 2012/0172298 | A1 | 7/2012 | Andersen et al. |
| 2012/0208742 | A1 | 8/2012 | Primiano et al. |
| 2013/0079277 | A1 | 3/2013 | Chilkoti |
| 2013/0079280 | A1 | 3/2013 | Baca et al. |
| 2013/0096058 | A1 | 4/2013 | Baca et al. |
| 2013/0102993 | A1 | 4/2013 | Kim et al. |
| 2013/0130384 | A1* | 5/2013 | Okamoto .............. C12M 33/00 435/397 |
| 2013/0157889 | A1 | 6/2013 | Chilkoti et al. |
| 2013/0165389 | A1 | 6/2013 | Schellenberger et al. |
| 2013/0172274 | A1 | 7/2013 | Chilkoti |
| 2013/0315823 | A1 | 11/2013 | Trieu |
| 2013/0330335 | A1 | 12/2013 | Bremel et al. |
| 2014/0024600 | A1 | 1/2014 | Chilkoti et al. |
| 2014/0163201 | A1 | 6/2014 | Winter et al. |
| 2014/0294932 | A1 | 10/2014 | Kim et al. |
| 2015/0094270 | A1 | 4/2015 | Harris et al. |
| 2015/0099707 | A1 | 4/2015 | Pastan et al. |
| 2015/0112022 | A1 | 4/2015 | Chilkoti et al. |
| 2016/0114053 | A1 | 4/2016 | Chilkoti |
| 2016/0120952 | A1 | 5/2016 | Chilkoti |
| 2016/0209356 | A1 | 7/2016 | Herget et al. |
| 2016/0220727 | A1 | 8/2016 | Lu et al. |
| 2016/0271262 | A1 | 9/2016 | Lopez et al. |
| 2016/0303091 | A1 | 10/2016 | Wang |
| 2016/0355802 | A1 | 12/2016 | Isaacs et al. |
| 2017/0088670 | A1 | 3/2017 | Rowan et al. |
| 2017/0102357 | A1 | 4/2017 | Liang et al. |
| 2017/0166621 | A1 | 6/2017 | Boettcher et al. |
| 2017/0170142 | A1 | 6/2017 | Edelstein et al. |
| 2017/0233714 | A1 | 8/2017 | Chilkoti et al. |
| 2017/0369651 | A1 | 12/2017 | Cheng et al. |
| 2018/0171337 | A1 | 6/2018 | O'Neill et al. |
| 2019/0345228 | A1 | 11/2019 | Chilkoti et al. |

FOREIGN PATENT DOCUMENTS

| | | |
|---|---|---|
| EP | 2664340 B1 | 2/2020 |
| WO | WO 2003/040165 A2 | 10/2002 |
| WO | WO 2004/096124 A2 | 11/2004 |
| WO | WO 2006/004778 A2 | 1/2006 |
| WO | WO 2007/073486 A2 | 6/2007 |
| WO | WO 2007/108013 A2 | 9/2007 |
| WO | WO 2007/134245 A2 | 11/2007 |
| WO | 2008/012543 A1 | 1/2008 |
| WO | 2008/030968 A2 | 3/2008 |
| WO | WO 2009/067584 A1 | 5/2009 |
| WO | WO 2010/054699 A1 | 5/2010 |
| WO | WO 2010/057154 A1 | 5/2010 |
| WO | WO 2010/096422 A1 | 8/2010 |
| WO | 2011/025572 A1 | 3/2011 |
| WO | WO 2011/123813 A2 | 10/2011 |
| WO | WO 2013/065009 A1 | 5/2013 |
| WO | WO 2014/194244 A1 | 12/2014 |
| WO | WO 2015/130846 A2 | 9/2015 |
| WO | WO 2016/065273 A1 | 4/2016 |
| WO | WO 2016/090103 A1 | 6/2016 |
| WO | WO 2016/154530 A1 | 9/2016 |
| WO | WO 2017/015132 A1 | 1/2017 |
| WO | WO 2017/024182 A1 | 2/2017 |
| WO | WO 2017/112825 A2 | 6/2017 |
| WO | WO 2017/112826 A2 | 6/2017 |
| WO | 2017/192449 A1 | 11/2017 |
| WO | WO 2018/144854 A1 | 8/2018 |
| WO | 2019/147954 A1 | 8/2019 |

OTHER PUBLICATIONS

PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018.
U.S. Appl. No. 62/728,582, filed Sep. 7, 2018.
PCT/US2019/050077, Sep. 6, 2019, WO2020/051541, Mar. 12, 2020.
U.S. Appl. No. 62/767,736, filed Nov. 15, 2018.
PCT/US2019/061144, Nov. 13, 2019, WO2020/102324, May 22, 2020.
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020.
U.S. Appl. No. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020.
U.S. Appl. No. 62/713,752, filed Aug. 2, 2018.
PCT/US2019/044911, Aug. 2, 2019, WO2020/028806, Feb. 6, 2020.
U.S. Appl. No. 62/985,174, filed Mar. 4, 2020.
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
U.S. Appl. No. 62/138,847, filed Mar. 26, 2015.
PCT/US2016/024202, Mar. 25, 2016, WO2016/154530, Sep. 26, 2016.

(56) References Cited

OTHER PUBLICATIONS

U.S. Appl. No. 15/561,799, filed Sep. 26, 2017, U.S. Pat. No. 10/385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/355,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
PCT/US2016/032785, May 15, 2018, WO2018/213320, Nov. 22, 2018.
U.S. Appl. No. 62/534,019, filed Jul. 18, 2018.
U.S. Appl. No. 16/625,989, filed Dec. 23, 2019.
PCT/US2019/050077, Sep. 6, 2019.
PCT/US2019/061144, Nov. 13, 2019.
PCT/US2019/044911, Aug. 2, 2019.
Aaron et al., "Elastin as a Random-Network Elastomer—a Mechanical and Optical Analysis of Single Elastin Fibers," Biopolymers, 1981, 20(6):1247-1260.
Allen et al., "Liposomal drug delivery systems: from concept to clinical applications," Adv Drug Deliv Rev, 2013, 65(1):36-48.
Anselmo et al., "Nanoparticles in the clinic, " Bioeng Transl Med, Jun. 2016, 1(1):10-29.
Arami et al., "In vivo delivery, pharmacokinetics, biodistribution and toxicity of iron oxide nanoparticles," Chem Soc Rev, Dec. 2015, 44(23):8576-8607.
Astete et al., "Synthesis and characterization of PLGA nanoparticles," Journal of Biomaterials Science, Polymer Edition 2006, 17(3):247-289.
Babu, "The contribution of intrinsically disordered regions to protein function, cellular complexity, and human disease," Biochem Soc Trans, Oct. 2016, 44(5):1185-1200.
Bae et al., "Targeted drug delivery to tumors: myths, reality and possibility," J Control Release, 2011, 153(3):198-205.
Balu et al., "An16-resilin: an advanced multi-stimuli-responsive resilin-mimetic protein polymer," Acta Biomater, Nov. 2014, 10:4768-4777.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, 2011, 104:489-507.
Banjade et al., "Phase transitions of multivalent proteins can promote clustering of membrane receptors," Elife, Oct. 2014, 3:e04123.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Bates et al., "Block copolymer thermodynamics: theory and experiment," Annu Rev. Phys. Chem., 1990, 41:525-57.

Best, "Computational and theoretical advances in studies of intrinsically disordered proteins," Curr Opin Struct Biol, Feb. 2017, 42:147-154.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Boeynaems et al., "Protein Phase Separation: A New Phase in Cell Biology," Trends Cell Biol, Jun. 2018, 28(6):420-435.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by in integrins," Journal of Biological Chemistry, 1994, 269(14):10856-10863.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, 2012, 64(11):206-212.
Broome et al., "Expanding the utility of beta-galactosidase complementation: piece by piece," Mol Pharm, 2010, 7(1):60-74.
Burke et al., "Multimodal nanoparticle imaging agents: design and applications," Philos Trans A Math Phys Eng Sci, Nov. 2017, 375:20170261.
Carreiras et al., "Expression and localization of alpha v integrins and their ligand vitronectin in normal ovarian epithelium and in ovarian carcinoma," Gynecol Oncol, 1996, 62(2):260-7.
Champion et al., "Particle shape: a new design parameter for micro- and nanoscale drug delivery carriers," J Control Release, 2007, 121(1-2):3-9.
Champion et al., "Role of particle size in phagocytosis of polymeric microspheres," Pharm Res, 2008, 25(8):1815-21.
Champion et al., "Role of target geometry in phagocytosis," Proc Natl Acad Sci U S A, 2006, 103(13):4930-4.
Champion et al., "Shape induced inhibition of phagocytosis of polymer particles," Pharm Res, 2009, 26(1):244-9.
Chen, "Small-molecule delivery by nanoparticles for anticancer therapy," Trends Mol Med, 2010, 16(12):594-602.
Chithrani et al., "Elucidating the mechanism of cellular uptake and removal of protein-coated gold nanoparticles of different sizes and shapes," Nano letters, 2007, 7(6):1542-1550.
Conner et al., "Regulated portals of entry into the cell," Nature, 2003, 422(6927):37-44.
Costa et al., "Active Targeting of Cancer Cells by Nanobody Decorated Polypeptide Micelle with Bio-orthogonally Conjugated Drug," Nano letters, Dec. 2018, 19(1):247-254.
Dai et al., "Versatile biomanufacturing through stimulus-responsive cell—material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Das et al., "Conformations of intrinsically disordered proteins are influenced by linear sequence distributions of oppositely charged residues," Proc Natl Acad Sci U S A, 2013, 110(33):13392-13397.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Duan et al., "Improving the thermostability and catalytic efficiency of Bacillus deramificans pullulanase by site-directed mutagenesis," Appl Environ Microbiol, 2013, 79(13):4072-4077.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.

(56) References Cited

OTHER PUBLICATIONS

Ehlerding et al., "Biodegradable and Renal Clearable Inorganic Nanoparticles," Adv Sci (Weinh), Feb. 2016, 3(2):1500223.

Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.

Elsabahy et al., "Design of polymeric nanoparticles for biomedical delivery applications," Chem Soc Rev, 2012, 41(7):2545-61.

Elvin et al., "Synthesis and properties of crosslinked recombinant pro-resilin," Nature, 2005, 437(7061):999-1002.

Elzoghby et al., "Implications of Protein- and Peptide-Based Nanoparticles as Potential Vehicles for Anticancer Drugs," Advances in Protein Chemistry and Structural Biology, 2015, Chapter Six, vol. 98, pp. 169-221.

Farokhzad et al., "Targeted nanoparticle-aptamer bioconjugates for cancer chemotherapy in vivo," Proc Natl Acad Sci U S A, 2006, 103(16):6315-20.

Franzmann et al., "Phase separation of a yeast prion protein promotes cellular fitness," Science, Jan. 2018, 359(6371):eaao5654.

Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D 11972.pdf?sequence=I&isAllowed=y.

Geng et al., Shape effects of filaments versus spherical particles in flow and drug delivery, Nat Nanotechnol, 2007, 2(4):249-55.

Gilbreth et al., "Structural insights for engineering binding proteins based on non-antibody scaffolds," Curr Opin Struct Biol, 2012, 22(4):413-20.

Gillies et al., "Dendrimers and dendritic polymers in drug delivery," Drug Discovery Today, 2005, 10(1):35-43.

Goldsmith et al., "Enzyme engineering: reaching the maximal catalytic efficiency peak," Curr Opin Struct Biol, Dec. 2017, 47:140-150.

Graff et al., "Theoretical analysis of antibody targeting of tumor spheroids: importance of dosage for penetration, and affinity for retention," Cancer Research, 2003, 63(6):1288-1296.

Gratton et al., "The effect of particle design on cellular internalization pathways," Proc Natl Acad Sci U S A, 2008, 105(33):11613-8.

Gu et al., "Precise engineering of targeted nanoparticles by using self-assembled biointegrated block copolymers," Proc Natl Acad Sci U S A, 2008, 105(7):2586-91.

Hofmann et al., "A kinetic study on the enzymatic hydrolysis of fluoresceindiacetate and fluorescein-di-β-D-galactopyranoside," Analytical biochemistry, 1983, 131(1):180-186.

Holehouse et al.,"Functional Implications of Intracellular Phase Transitions," Biochemistry, May 2018, 57(17):2415-2423.

Huber et al., "Designer amphiphilic proteins as building blocks for the intracellular formation of organelle-like compartments," Nat Mater, Jan. 2015, 14(1):125-132.

Jiang et al., "Nanoparticle-mediated cellular response is size-dependent," Nat Nanotechnol, 2008, 3(3):145-50.

Jokerst et al., "Nanoparticle PEGylation for imaging and therapy," Nanomedicine (Lond), 2011, 6(4):715-28.

Jurney et al., "Unique size and shape-dependent uptake behaviors of non-spherical nanoparticles by endothelial cells due to a shearing flow," J Control Release, Jan. 2017, 245:170-176.

Kamaly et al., "Targeted polymeric therapeutic nanoparticles: design, development and clinical translation," Chem Soc Rev, 2012, 41(7):2971-3010.

Karagoz et al., "Polymerization-Induced Self-Assembly (PISA)—control over the morphology of nanoparticles for drug delivery applications," Polym. Chem., Jan. 2014, 5(2):350-355.

Kataoka et al., "Block copolymer micelles for drug delivery: Design, characterization and biological significance," Advanced Drug Delivery Reviews, 2001, 47:113-131.

Kelly et al., "Shape-specific, monodisperse nano-molding of protein particles," J Am Chem Soc, 2008, 130(16):5438-9.

Kesharwani et al., "Dendrimer as nanocarrier for drug delivery," Progress in Polymer Science, Feb. 2014, 39(2):268-307.

Kulkarni et al., "Design of lipid nanoparticles for in vitro and in vivo delivery of plasmid DNA," Nanomedicine, May 2017, 13(4):1377-1387.

Lee et al., "Polymersomes for drug delivery: design, formation and characterization," J Control Release, 2012, 161(2):473-83.

Lewis et al., "Use of digitized video microscopy with a fluorogenic enzyme substrate to demonstrate cell-and compartment-specific gene expression in Salmonella enteritidis and Bacillus subtilis," Molecular microbiology, 1994, 13:655-662.

Li et al., "Phase transitions in the assembly of multivalent signalling proteins," Nature, 2012, 483(7389):336-340.

Li et al., "Tunable Assembly of Protein-Microdomains in Living Vertebrate Embryos," Advanced Biosystems, Oct. 2018, 2(10):1800112.

Lin et al., "Formation and Maturation of Phase-Separated Liquid Droplets by RNA-Binding Proteins," Mol Cell, Oct. 2015, 60(2):208-219.

Lin et al., "Intrinsically disordered sequences enable modulation of protein phase separation through distributed tyrosine motifs," J Biol Chem, Nov. 2017, 292(46):19110-19120.

Lin et al., "Phase Separation and Single-Chain Compactness of Charged Disordered Proteins Are Strongly Correlated," Biophys J, May 2017, 112(10):2043-2046.

Lin et al., "Sequence-Specific Polyampholyte Phase Separation in Membraneless Organelles," Phys Rev Lett, Oct. 2016, 117(17):178101.

Liong et al., "Multifunctional inorganic nanoparticles for imaging, targeting, and drug delivery," ACS Nano, 2008, 2(5):889-96.

Liu et al., "Integrin $\alpha_v\beta_3$-Targeted Cancer Therapy," Drug Dev Res, 2008, 69(6):329-339.

Loh et al., "Utilising inorganic nanocarriers for gene delivery," Biomater Sci, Jan. 2016, 4(1):70-86.

LoPresti et al., "Polymersomes: nature inspired nanometer sized compartments," Journal of Materials Chemistry 2009, 19(22):3576-3590.

Lukyanov et al., "Tumor-targeted liposomes: doxorubicin-loaded long-circulating liposomes modified with anti-cancer antibody," J Control Release, 2004, 100(1):135-44.

Lyons et al., "Comparisons of Recombinant Resilin-like Proteins: Repetitive Domains Are Sufficient to Confer Resilin-like Properties," Biomacromolecules, 2009, 10(11):3009-3014.

Lyons et al., "Design and facile production of recombinant resilin-like polypeptides: Gene construction and a rapid protein purification method," Protein Engineering Design & Selection, 2007, 20(1):25-32.

Maeda et al., "Tumoritropic and lymphotropic principles of macromolecular drugs," Critical reviews in therapeutic drug carrier systems, 1989, 6(3):193-210.

Maeda, "The enhanced permeability and retention (EPR) effect in tumor vasculature: the key role of tumor-selective macromolecular drug targeting," Advances in Enzyme Regulation, 2001, 41(1):189-207.

Malam et al., "Liposomes and nanoparticles: nanosized vehicles for drug delivery in cancer," Trends Pharmacol Sci 2009, 30(11):592-9.

Manders et al., "Dynamics of three-dimensional replication patterns during the S-phase, analysed by double labelling of DNA and confocal microscopy," Journal of cell science, 1992, 103(Pt 3):857-862.

Mao et al., "Net charge per residue modulates conformational ensembles of intrinsically disordered proteins," Proc Natl Acad Sci U S A, 2010, 107(18):8183-8188.

Masood, "Polymeric nanoparticles for targeted drug delivery system for cancer therapy," Mater Sci Eng C Mater Biol Appl, Mar. 2016, 60:569-578.

Mastria et al., "Nanoparticle formulation improves doxorubicin efficacy by enhancing host antitumor immunity," J Control Release, Jan. 2018, 269:364-373.

McKenzie et al., "Multivalent Binding of a Ligand-Coated Particle: Role of Shape, Size, and Ligand Heterogeneity," Biophys J, Apr. 2018, 114(8):1830-1846.

Meng et al., "Stimuli-responsive polymersomes for programmed drug delivery," Biomacromolecules, 2009, 10(2):197-209.

(56) References Cited

OTHER PUBLICATIONS

Merkel et al., "Using mechanobiological mimicry of red blood cells to extend circulation times of hydrogel microparticles," Proc Natl Acad Sci U S A, 2011, 108(2):586-91.
Mitragotri et al., "Physical approaches to biomaterial design," J. Nat Mater, 2009, 8(1):15-23.
Modery et al., "Heteromultivalent liposomal nanoconstructs for enhanced targeting and shear-stable binding to active platelets for site-selective vascular drug delivery," Biomaterials, 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Muiznieks et al., "Proline periodicity modulates the self-assembly properties of elastin-like polypeptides," J Biol Chem, 2010, 285(51):39779-39789.
Muro, "Challenges in design and characterization of ligand-targeted drug delivery systems," J Control Release, 2012, 164(2):125-37.
Napier et al., "Nanoparticle drug delivery platform," Journal of Macromolecular Science, Part C: Polymer Reviews, 2007, 47(3):321-327.
Nayeem et al., "Engineering enzymes for improved catalytic efficiency: a computational study of site mutagenesis in epothilone-B hydroxylase," Protein Eng Des Sel, 2009, 22(4):257-266.
Ni et al., "Engineering of inorganic nanoparticles as magnetic resonance imaging contrast agents," Chem Soc Rev, Nov. 2017, 46(23):7438-7468.
Niu et al., "The role of adhesion molecules, $\alpha v\beta 3$, $\alpha v\beta 5$ and their ligands in the tumor cell and endothelial cell adhesion," Eur J Cancer Prev, 2007, 16(6):517-27.
Nott et al., "Phase transition of a disordered nuage protein generates environmentally responsive membraneless organelles," Mol Cell, Mar. 2015, 57(5):936-947.
Ortega et al., "Hydrodynamic properties of rodlike and dislike particles in dilute solution," The Journal of Chemical Physics, 2003, 119(18):9914-9919.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Pardridge, "The blood-brain barrier: bottleneck in brain drug development," NeuroRx, 2005, 2(1):3-14.
Parker et al., "Antibody mimics based on human fibronectin type three domain engineered for thermostability and high-affinity binding to vascular endothelial growth factor receptor two," Protein Eng Des Sel, 2005, 18(9):435-44.
Pastuszka et al., "A tunable and reversible platform for the intracellular formation of genetically engineered protein microdomains," Biomacromolecules, 2012, 13(11):3439-3444.
Peng et al., "Length-dependent prediction of protein intrinsic disorder," BMC Bioinformatics, 2006, 7:208.
Petros et al., "Strategies in the design of nanoparticles for therapeutic applications," Nat Rev Drug Discov, 2010, 9(8):615-27.
Qamar et al., "FUS Phase Separation Is Modulated by a Molecular Chaperone and Methylation of Arginine Cation-pi Interactions," Cell, Apr. 2018, 173(3):720-734.e15.
Quiroz et al., "Intrinsically disordered proteins access a range of hysteretic phase separation behaviors," Scientific advances, Oct. 2019, 5(10):eaax5177.
Ravikumar et al., "Mimicking adhesive functionalities of blood platelets using ligand-decorated liposomes," Bioconjugate chemistry, 2012, 23(6):1266-1275.
Rolland et al., "Direct fabrication and harvesting of monodisperse, shape-specific nanobiomaterials," J Am Chem Soc, 2005, 127(28):10096-100.
Rosenholm et al., "Towards multifunctional, targeted drug delivery systems using mesoporous silica nanoparticles—opportunities & challenges," Nanoscale, 2010, 2(10):1870-83.
Rosier et al., "Advanced drug delivery devices via self-assembly of amphiphilic block copolymers," Advanced Drug Delivery Reviews, 2001, 53:95-108.
Ryu et al., "Elastin-like polypeptide for improved drug delivery for anticancer therapy: preclinical studies and future applications," Expert Opinion on Drug Delivery, 2014, 12(4):653-667.
Sanna et al., "Targeted therapy using nanotechnology: focus on cancer," Int J Nanomedicine, Jan. 2014, 9:467-83.
Schnell et al., "Expression of integrin $\alpha v\beta 3$ in gliomas correlates with tumor grade and is not restricted to tumor vasculature," Brain Pathol, 2008, 18(3):378-86.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, 2010, 147(3):408-412.
Shi et al., "Triggered sorting and co-assembly of genetically engineered protein microdomains in the cytoplasm," Adv Mater, 2014, 26(3):449-454.
Shin et al., "Liquid phase condensation in cell physiology and disease," Science, Sep. 2017, 357(6357):eaaf4382.
Sickmeier et al., "DisProt: the Database of Disordered Proteins," Nucleic Acids Res, 2007, 35:D786-793.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Skerra, "Alternative non-antibody scaffolds for molecular recognition," Curr Opin Biotechnol, 2007, 18(4):295-304.
Smits et al., "Elastin-Like Polypeptide Based Nanoparticled: Design Rationale Toward Nanomedicine," Macromolecular Bioscience, 2014, 15(1):36-51.
Steichen et al., "A Review of Current Nanoparticle and Targeting Moieties for the Delivery of Cancer Therapeutics," Eur J Pharm Sci, 2013, 48(3):416-27.
Strulson et al., "RNA catalysis through compartmentalization," Nat Chem, 2012, 4(11):941-946.
Suk et al., "PEGylation as a Strategy for Improving Nanoparticle-Based Drug and Gene Delivery," Adv Drug Deliv Rev, Apr. 2016, 99(Pt A):28-51.
Swider et al., "Customizing Poly(lactic-Co-Glycolic Acid) Particles for Biomedical Applications," Acta Biomater, Jun. 2018, 73:38-51.
Talelli et al., "Core-Crosslinked Polymeric Micelles: Principles, Preparation, Biomedical Applications and Clinical Translation," Nano Today, Feb. 2015, 10(1):93-117.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, 2013, 1(1):e24360.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, 2011, 32(33):8462-73.

(56) References Cited

OTHER PUBLICATIONS

Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, 2010, 1804(6):1231-1264.
Vazquez-Lombardi et al., "Challenges and Opportunities for Non-Antibody Scaffold Drugs," Drug Discov Today, Oct. 2015, 20(10):1271-83.
Venkataraman et al., "The Effects of Polymeric Nanostructure Shape on Drug Delivery," Adv Drug Deliv Rev, 2011, 63(14-15):1228-46.
Verma et al., "Effect of surface properties on nanoparticle-cell interactions," Small, 2010, 6(1):12-21.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, 2006, 78(3):620-8.
Vrhovski et al., "Coacervation Characteristics of Recombinant Human Tropoelastin," European Journal of Biochemistry, 1997, 250(1):92-98.
Wang et al., "A Molecular Grammar Governing the Driving Forces for Phase Separation of Prion-like RNA Binding Proteins," Cell, Jul. 2018, 174(3):688-699.e616.
Wang et al., "More effective nanomedicines through particle design," Small, 2011, 7(14):191-931.
Wang et al., "Nanoparticle delivery of cancer drugs," Annu Rev Med, 2012, 63:185-98.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface to Enhance Cancer Cell Targeting by Polymer Micelles," Nano Lett Oct. 2017, 17(10):5995-6005.
Wechsel et al., "Renal Cell Carcinoma: Immunohistological Investigation of Expression of the Integrin $\alpha v \beta 3$," Anticancer research, 1999, 19(2C):1529-1532.
Weis et al., "$\alpha V$ Integrins in Angiogenesis and Cancer," Cold Spring Harb Perspect Med, 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wilkins et al., "Hydrodynamic Radii of Native and Denatured Proteins Measured by Pulse Field Gradient NMR Techniques," Biochemistry, 1999, 38(50):16424-16431.
Wimley et al., "Experimentally determined hydrophobicity scale for proteins at membrane interfaces," Nature Structural & Molecular Biology, 1996, 3(10):842-848.
Wright et al., "Intrinsically disordered proteins in cellular signalling and regulation," Nat Rev Mol Cell Biol, Jan. 2015, 16(1):18-29.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, 2011, 155(2):248-61.
Xu et al., "Inorganic nanoparticles as carriers for efficient cellular delivery," Chemical Engineering Science, 2006, 61(3):1027-1040.
Zhao et al., "Cellular uptake, intracellular trafficking, and cytotoxicity of nanomaterials," Small, 2011, 7(10):1322-37.
Zhao et al., "Tumor $\alpha v \beta 3$ Integrin Is a Therapeutic Target for Breast Cancer Bone Metastases," Cancer Res, 2007, 67(12):5821-30.
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
European Patent Office Extended Search Report for Application No. 17851568.0 dated Mar. 16, 2020 (9 pages).
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
United States Patent Office Action for U.S. Appl. No. 15/749,797 dated Oct. 20, 2020 (16 pages).
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 15/561,799, filed Sep. 26, 2017, 2018/0258157, Sep. 13, 2018.
U.S. Appl. No. 16/525,374, filed Jul. 29, 2019.
U.S. Appl. No. 16/335,734, filed Mar. 22, 2019.
U.S. Appl. No. 16/477,229, filed Jul. 11, 2019.
PCT/US2019/023583, Mar. 22, 2019.
PCT/US2019/030022, Apr. 30, 2019.
Merriam Webster Dictionary, "Plurality," <https://www.merriam-webster.com/dictionary/plurality> webpage accessed Jun. 25, 2020.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
International Search Report and Written Opinion for Application No. PCT/US20191061144 dated May 21, 2020 (15 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
Chockalingam et al., "Design and application of stimulus-responsive peptide systems," Protein Engineering, Design & Selection, 2007, 20(4):155-161.
Park et al., "Protein stitchery: Design of a protein for selective binding to a specific DNA sequence," PNAS, 1992, vol. 89:9094-9096.
Olafsen et al., "Covalent disulfide-linked anti-CEA diabody allows site-specific conjugation and radiolabeling for tumor targeting applications," Protein Engineering, Design & Selection, 2004, 17(1):21-27.
Hu et al., "Nanografting De Novo Proteins onto Gold Surfaces," Langmuir, 2005, vol. 21:9103-9109.
McDaniel, "Assembly of Highly Asymmetric Genetically-Encoded Amphiphiles for Thermally Targeted Delivery of Therapeutics," Dissertation, 2013, 295 pages.
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
United States Patent Office Action for U.S. Appl. No. 16/058,924 dated Nov. 26, 2019 (23 pages).
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
American Diabetes Association (2018) Standards of medical care in diabetes—2018. Diabetes Care 41(Suppl 1):S1-S159.
Amer et al., "FGF21 attenuates lipolysis in human adipocytes—a possible link to improved insulin sensitivity," FEBS Lett, 2008, 582(12):1725-1730.
Badi, "Non-linear PEG-based thermoresponsive polymer systems," Progress in Polymer Science, 2017, 66, 54-79.
Baggio et al., "Biology of Incretins: GLP-1 and GIP," Gastroenterology, 2007, 132(6):2131-2157.
Beenken et al., "The FGF family: biology, pathophysiology and therapy," Nat Rev Drug Discov, 2009, 8(3):235-253.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, 2017, 27(12):1-9.

(56) References Cited

OTHER PUBLICATIONS

Bobo et al., "Nanoparticle-based medicines: a review of FDA-approved materials and clinical trials to date." Pharmaceutical research 33.10 (2016): 2373-2387.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabrera et al., "Automated, High-Throughput Assays for Evaluation of Human Pancreatic Islet Function," Cell Transplant, 2008, 16(10):1039-1048.
Cabrera et al., "Glutamate Is a Positive Autocrine Signal for Glucagon Release," Cell Metab, 2008, 7(6):545-554.
Centers for Disease Control and Prevention (2017) National Diabetes Statistics Report, 2017. ed U.S. Dept of Health and Human Services (Atlanta).
Chatterjee et al., "Type 2 diabetes," The Lancet, 2017, 389(10085): 2239-2251.
Chilkoti et al., "Stimulus responsive elastin biopolymers: applications in medicine and biotechnology," Curr Opin Chem Biol, 2006, 10(6):652-657.
Coskun et al., "Fibroblast Growth Factor 21 Corrects Obesity in Mice," Endocrinology, 2008, 149(12):6018-6027.
Day et al., "A new glucagon and GLP-1 co-agonist eliminates obesity in rodents," Nat Chem Biol, 2009, 5:749.
DeYoung et al.,"Encapsulation of exenatide in poly-(D,L-lactide-co-glycolide) microspheres produced an investigational long-acting once-weekly formulation for type 2 diabetes," Diabetes Technol Ther, 2011, 13, 1145-1154.
Ding et al., "βKlotho Is Required for Fibroblast Growth Factor 21 Effects on Growth and Metabolism," Cell Metab, 2012, 16(3):387-393.
Drucker "Mechanisms of Action and Therapeutic Application of Glucagon-like Peptide-1," Cell Metab, 2018, 27(4):740-756.
Drucker, "Incretin action in the pancreas: potential promise, possible perils, and pathological pitfalls," Diabetes, 2013, 62, 3316-3323.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
El-Assaad et al., "Saturated Fatty Acids Synergize with Elevated Glucose to Cause Pancreatic β-Cell Death," Endocrinology, 2003, 144(9):4154-4163.
Finan et al., "A rationally designed monomeric peptide triagonist corrects obesity and diabetes in rodents," Nat Med, 2015, 21:27-36.
Finan et al., "Unimolecular Dual Incretins Maximize Metabolic Benefits in Rodents, Monkeys, and Humans," Sci Transl Med, 2013, 5(209):209ra151.
Fosgerau et al., "Peptide therapeutics: current status and future directions," Drug Discovery Today, 2015, 20, 122-128.
Gaich et al., "The Effects of LY2405319, an FGF21 Analog, in Obese Human Subjects with Type 2 Diabetes," Cell Metab, 2013, 18(3):333-340.
Ganson et al., "Pre-existing anti-polyethylene glycol antibody linked to first-exposure allergic reactions to pegnivacogin, a PEGylated RNA aptamer," J Allergy Clin Immunol, 2016, 137(5): 1610-1613, e1617.
Gao, "Site-specific andin situgrowth of stealth polymer conjugates of proteins with significally improved pharmacology," Journal of Controlled Release, 2013, 172(1):e116-e117.
Gilroy et al., "Fusion of fibroblast growth factor 21 to a thermally responsive biopolymer forms an injectable depot with sustained anti-diabetic action," J Control Release, 2018, 277:154-164.
Gu et al., "Enzymatic Synthesis of Nucleobase-Modified Single-Stranded DNA Offers Turnable Resistance to Nuclease Degradation," Biomacromolecules, 2018, 19, 3525-3535.
Gu et al., "Photocontrolled micellar aggregation of amphiphilic DNA-azobenzene conjugates," Colloids Surfaces B: Biointerfaces, 2015, 135, 126-132.

Ha et al., "Immunoglobulin Fc Heterodimer Platform Technology: From Design to Applications in Therapeutic Antibodies and Proteins," Front Immunol, 2016, 7(394) (in English).
Hampp et al., "Use of Antidiabetic Drugs in the U.S., 2003-2012," Diabetes Care, 2014, 37: 1367-1374.
Hart et al., "Attenuation of FGF signalling in mouse β-cells leads to diabetes," Nature, 2000, 408:864.
Ito et al., "Impaired negative feedback suppression of bile acid synthesis in mice lacking βKlotho," J Clin Invest, 2005, 115(8):2202-2208.
Johnson et al., "Fibroblast Growth Factor 21 Reduces the Severity of Cerulein-Induced Pancreatitis in Mice," Gastroenterology, 2009, 137(5):1795-1804.
Kaspar et al., "Future directions for peptide therapeutics development," Drug Discovery Today, 2013, 18, 807-817.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, 2015, 26(11):608-617.
Kharitonenkov et al., "Fibroblast growth factor 21 night watch: advances and uncertainties in the field," J Intern Med, 2016, 281(3):233-246.
Kharitonenkov et al., "Inventing new medicines: The FGF21 story," Mol Metab, 2014, 3(3):221-229.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, 2007, 30, 1487-93.
Kurosu et al., "Tissue-specific Expression of βKlotho and Fibroblast Growth Factor (FGF) Receptor Isoforms Determines Metabolic Activity of FGF19 and FGF21," J Biol Chem, 2007, 282(37):26687-26695.
Laybutt et al., "Endoplasmic reticulum stress contributes to beta cell apoptosis in type 2 diabetes," Diabetologia, 2007, 50(4):752-763.
Lee et al., "Nanoparticle-Delivered Chemotherapy: Old Drugs in New Packages." Oncology (Williston Park, NY) 31.3 (2017): 198-208.
Lee et al., "Structures of β-klotho reveal a 'zip code'-like mechanism for endocrine FGF signaling," Nature, 2018, 553:501-505.
Leibowitz et al., "Glucose-Regulated Proinsulin Gene Expression Is Required for Adequate Insulin Production during Chronic Glucose Exposure," Endocrinology, 2002, 143(9):3214-3220.
Li et al., "Prediction of solvent-induced morphological changes of polyelectrolyte diblock copolymer micelles," Soft Matter, 2015, 11(42): 8236-45.
Lin et al., "Adiponectin Mediates the Metabolic Effects of FGF21 on Glucose Homeostasis and Insulin Sensitivity in Mice," Cell Metab, 2013, 17(5):779-789.
Lin et al., "Functional expression of a biologically active fragment of soluble gp130 as an ELP-fusion protein in transgenic plants: purification via inverse transition cycling," Biochem J, 2006, 398(3):577-583.
Lin et al., "Statistical properties of the traditional algorithm-based designs for phase I cancer clinical trials," Biostatistics, 2001, 2(2):203-215.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, 2006, 39, 893-896.
Magnusson et al., "Ion-Sensitive "Isothermal" Responsive Polymers Prepared in Water," Journal of the American Chemical Society, 2008, 130, 10852-10853.

(56) References Cited

OTHER PUBLICATIONS

Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, 2008, 93(12):4810-4817.
Meier et al., "Determination of Optimal Sample Size for Quantification of β-Cell Area, Amyloid Area and β-Cell Apoptosis in Isolated Islets," J Histochem Cytochem, 2015, 63(8):663-673.
Mu et al., "FGF21 Analogs of Sustained Action Enabled by Orthogonal Biosynthesis Demonstrate Enhanced Antidiabetic Pharmacology in Rodents," Diabetes, 2012, 61(2):505-512.
Nanoprecision Medical, "Pipeline, Type II Diabetes," <http://www.nanoprecisionmedical.com/pipeline/diabetes> webpage available as early as Aug. 2018.
Nauck "Glucagon-like Peptide 1 (GLP-1) in the Treatment of Diabetes," Horm Metab Res, 2004, 36(11/12):852-858 (in English).
Nies et al., "Fibroblast Growth Factor Signaling in Metabolic Regulation," Front Endocrinol, 2016, 6(193) (in English).
Ozer et al., "Site-Specific and Stoichiometric Stealth Polymer Conjugates of Therapeutic Peptides and Proteins," Bioconjug Chem, 2017, 28(3):713-723.
Pang et al., "A Modular Method for the High-Yield Synthesis of Site-Specific Protein-Polymer Therapeutics," Angew Chem Int Ed Engl, 2016, 55, 10296-10300.
Park et al., "Exendin-4 and exercise improve hepatic glucose homeostasis by promoting insulin signaling in diabetic rats," Metabolism, 2010, 59, 123-133.
Poitout et al., "Glucolipotoxicity: Fuel Excess and β-Cell Dysfunction," Endocr Rev, 2008, 29(3):351-366.
Potthoff et al., "Endocrine fibroblast growth factors 15/19 and 21: from feast to famine," Genes Dev, 2012, 26(4):312-324.
Qi et al., "A brush-polymer conjugate of exendin-4 reduces blood glucose for up to five days and eliminates poly(ethylene glycol) antigenicity," Nat Biomed Eng, 2016, 1:0002.
Ray et al., "Aptamer-mediated delivery of chemotherapy to pancreatic cancer cells." Nucleic acid therapeutics, 2012, 22(5): 295-305.
Riedel et al., "Engineered glucagon-like peptide-1-producing hepatocytes lower plasma glucose levels in mice," Am J Physiol Endocrinol Metab, 2009, 296(4):E936-E944.
Rodriguez-Diaz et al., "Alpha cells secrete acetylcholine as a non-neuronal paracrine signal priming beta cell function in humans," Nat Med, 2011, 17:888-892.
Schwendeman et al., "Injectable controlled release depots for large molecules," J Control Release, 2014, 190, 240-253.
Shusharina et al., "Micelles of Diblock Copolymers with Charged and Neutral Blocks: Scaling and Mean-Field Lattice Approaches," Macromolecules, 2000, 33(10): 3892-3901.
Singhal et al., "Fibroblast Growth Factor 21 (FGF21) Protects against High Fat Diet Induced Inflammation and Islet Hyperplasia in Pancreas," PLoS One, 2016, 11(2):e0148252.
Smith et al., "The Role of Beta Cell Glucagon-like Peptide-1 Signaling in Glucose Regulation and Response to Diabetes Drugs," Cell Metab, 2014, 19(6):1050-1057.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, 2017, 158(5):1314-1327.
Sun et al., "Autofluorescence Imaging of Living Pancreatic Islets Reveals Fibroblast Growth Factor-21 (FGF21)-Induced Metabolism," Biophys J, 2012, 103(11):2379-2388.
Sun et al., "On the Thermally Reversible Dynamic Hydration Behavior of Oligo(ethylene glycol) Methacrylate-Based Polymers in Water," Macromolecules, 2013, 46, 236-246.
Talukdar et al., "A Long-Acting FGF21 Molecule, PF-05231023, Decreases Body Weight and Improves Lipid Profile in Non-human Primates and Type 2 Diabetic Subjects," Cell Metab, 2016, 23(3):427-440.

Tang et al., "Enzymatic Polymerization of High Molecular Weight DNA Amphiphiles That Self-Assemble into Star-Like Micelles," Advanced Materials, 2014, 26(19): 3050-3054.
Tang et al., "High-Molecular-Weight Polynucleotides by Transferase-Catalyzed Living Chain-Growth Polycondensation," Angew. Chem., 2017, 56(24): 6778-6782.
Tomiyama et al., "Relevant use of Klotho in FGF19 subfamily signaling system in vivo," Proc Natl Acad Sci USA, 2010, 107(4):1666-71.
Tschop et al., "Unimolecular Polypharmacy for Treatment of Diabetes and Obesity," Cell Metab, 2016, 24(1):51-62.
Urry, "Free energy transduction in polypeptides and proteins based on inverse temperature transitions," Prog Biophys Mol Biol, 1992, 57(1):23-57.
Vlieghe et al., "Synthetic therapeutic peptides: science and market," Drug Discovery Today, 2010, 15, 40-56.
Wali et al., "Measuring Death of Pancreatic Beta Cells in Response to Stress and Cytotoxic T Cells," Methods in Molecular Biology, 2015, 1292:165-176.
Wei et al., "Fibroblast growth factor 21 promotes bone loss by potentiating the effects of peroxisome proliferator-activated receptor γ," Proc Natl Acad Sci USA, 2012, 109(8):3143-3148.
Wente et al., "Fibroblast Growth Factor-21 Improves Pancreatic β-Cell Function and Survival by Activation of Extracellular Signal-Regulated Kinase 1/2 and Akt Signaling Pathways," Diabetes, 2006, 55(9):2470-2478.
Xiaodong et al., "FGF21 Is Not a Major Mediator for Bone Homeostasis or Metabolic Actions of PPARα and PPARγ Agonists," J Bone Miner Res, 2017, 32(4):834-845.
Xu et al., "Downregulation of GLP-1 and GIP Receptor Expression by Hyperglycemia," Diabetes, 2007, 56(6):1551-58.
Xu et al., "Fibroblast Growth Factor 21 Reverses Hepatic Steatosis, Increases Energy Expenditure, and Improves Insulin Sensitivity in Diet-Induced Obese Mice," Diabetes, 2009, 58(1):250-259.
Yamamoto et al., "ATRP Synthesis of Thermally Responsive Molecular Brushes from Oligo(ethylene oxide) Methacrylates," Macromolecules, 2007, 40, 9348-9353.
Yang et al., "Long Term Exendin-4 Treatment Reduces Food Intake and Body Weight and Alters Expression of Brain Homeostatic and Reward Markers," Endocrinology, 2014, 155, 3473-3483.
Yusta et al., "GLP-1 receptor activation improves β cell function and survival following induction of endoplasmic reticulum stress," Cell Metab, 2006, 4(5):391-406.
Zhang et al., "In Depth Analysis on the Unusual Multistep Aggregation Process of Oligo(ethylene glycol) Methacrylate-Based Polymers in Water," Macromolecules, 2014, 47, 4728-4737.
Zununi Vahed et al., "Targeted cancer drug delivery with aptamer-functionalized polymeric nanoparticles," Journal of drug targeting, 2019, 27(3):292-299.
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
U.S. Appl. No. 16/058,924, filed Aug. 8, 2018.
U.S. Appl. No. 15/387,536, filed Dec. 21, 2016, 2017/0239363, Aug. 24, 2017.
U.S. Appl. No. 15/387,540, filed Dec. 21, 2016, 2017/0233714, Aug. 17, 2017.
U.S. Appl. No. 16/064,424, ffiled Jun. 20, 2018, 2019/0015520, Jan. 17, 2019.
PCT/US20217/035530, Jun. 1, 2017, WO2017/210476, Dec. 7, 2018.
PCT/US2019/015176, Jan. 25, 2019.
U.S. Pat. No. 8,470,967 2012/0121709, Chilkoti et al., Jun. 25, 2013.
U.S. Pat. No. 8,912,310 2013/0281624, Chilkoti et al., Dec. 16, 2014.
U.S. Pat. No. 9,771,396 2015/0112022, Chilkoti et al., Sep. 26, 2017.
AACR, "AACR Cancer Progress Report 2016," Clin Cancer Res, 2016, 22, 143 pages.

(56) References Cited

OTHER PUBLICATIONS

Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, 2009, 90, 67-74.
Adamska et al., "Pancreatic ductal adenocarcinoma: Current and evolving therapies," J Mol Sci, 2017, 18, 1338-1380.
Adiseshaiah et al., "Nanomedicine strategies to overcome the pathophysiological barriers of pancreatic cancer," Nat Rev Clin Oncol, 2016, 13, 750-765.
Aladini et al., "Chemical Synthesis and Characterization of Elastin-Like Polypeptides (ELPs) With Variable Guest Residues," J Pept Sci, 2016, 22(5):334-342.
Albanese et al., "The effect of nanoparticle size, shape, and surface chemistry on biological systems," Annu. Rev. Biomed. Eng., 2012, 14, 1-16.
Alconcel et al., "FDA-approved poly(ethylene glycol)-protein conjugate drugs," Polym. Chem. 2, 2011, 1442-1448.
Alley et al., "Feasibility of drug screening with panels of human tumor cell lines using a microculture tetrazolium assay," Cancer Res., 1998, 48, 589-601.
Aluri et al., "Elastin-like peptide amphiphiles Form nanofibers with tunable length," Biomacromolecules, 2012, 13, 2645-2654.
Amiram et al., "A depot-forming glucagon-like peptide-1 fusion protein reduces blood glucose for five days with a single injection," J. Control. Release, 2013, 172, 144-151.
Amiram et al., "Injectable protease-operated depots of glucagon-like peptide-1 provide extended and tunable glucose control," Proc. Natl. Acad. Sci. 110, 2013, 2792-2797.
Andersen et al., "Extending Half-life by Indirect Targeting of the Neonatal Fc Receptor (FcRn) Using a Minimal Albumin Binding Domain," Journal of Biological Chemistry, 2011, 286(7): p. 5234-5241.
Antos et al., "Lipid Modification of Proteins through Sortase-Catalyzed Transpeptidation," J. Am. Chem. Soc. 2008, 130, 16338-16343.
Antos et al., "Site-Specific N- and C-Terminal Labeling of a Single Polypeptide Using Sortases of Different Specificity," J. Am. Chem. Soc. 2009, 131, 10800-10801.
Arias et al., "Superior preclinical efficacy of gemcitabine developed as chitosan nanoparticulate system," Biomacromolecules 2011, 12, 97-104.
Armstrong et al., "Antibody against poly(ethylene glycol) adversely affects PEG-asparaginase therapy in acute lymphoblastic leukemia patients," Cancer 110, 2007, 103-111.
Armstrong et al., "The Hydrodynamic Radii of Macromolecules and Their Effect on Red Blood Cell Aggregation," Biophys. J., 2004, 87, 4259-4270.
Arnida et al., "Geometry and surface characteristics of gold nanoparticles influence their biodistribution and uptake by macrophages," Eur J Pharm Biopharm, 2011, 77, 417-423.
Asai et al., "Protein polymer hydrogels by in situ, rapid and reversible self-gelation," Biomaterials, 2012, 33, 5451-5458.
Atun et al., "Expanding global access to radiotherapy," Lancet Oncol, 2015, 16, 1153-1186.
Averick et al., "ATRP under biologically relevant conditions: grafting from a protein," ACS Macro. Lett. 1, 2012, 6-10.
Averick et al., "Protein-polymer hybrids: conducting ARGET ATRP from a genetically encoded cleavable ATRP initiator," Eur. Polym. J. 49, 2013, 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, 2013, 34, 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, 2012, 109(40):16101-16106.
Azhdarinia et al., "Regional radiochemotherapy using in situ hydrogel," PharmRes., 2005, 22, 776-783.
Bache et al., "Investigating the accuracy of microstereotactic-body-radiotherapy utilizing anatomically accurate 3D printed rodent-morphic dosimeters," Medical Physics, 2015, 42, 846-855.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Bailey et al., "Genomic analyses identify molecular subtypes of pancreatic cancer," Nature, 2016, 531, 47-52.
Bamford et al., "The COSMIC (Catalogue of Somatic Mutations in Cancer) database and website," British Journal of Cancer, 2004, 91, 355-358.
Banga et al., "Parenteral controlled delivery and parmacokinetics of therapeutic peptides and proteins," (CRC Press, Boca Raton, FL, 2005).
Bansal et al., "PEGylation improves pharmacokinetic profile, liver uptake and efficacy of Interferon gamma in liver fibrosis," J. Control. Release 2011, 154, 233-240.
Barbuti et al., "Paclitaxel through the ages of anticancer therapy: Exploring its role in chemoresistance and radiation therapy," Cancers, 2015, 7, 2360-2371.
Barnett et al., "Normal tissue reactions to radiotherapy: towards tailoring treatment dose by genotype," Nat Rev Cancer, 2009, 9, 134-142.
Barton et al., "Estimating the demand for radiotherapy form the evidence: A review of changes from 2003 to 2012," Radiother Oncol, 2014, 112, 140-144.
Baskar et al., "Cancer and Radiation Therapy: Current Advances and Future Directions," Int. J. Med. Sci., 2012, 9, 193-199.
Bedford et al., "WW domain-mediated interactions reveal a spliceosome-associated protein that binds a third class of proline-rich motif: The proline glycine and methionine-rich motif," PNAS, 1998, 95: 10602-10607.
Begg et al., "Strategies to improve radiotherapy with targeted drugs," Nat Rev Cancer, 2011, 11, 239-253.
Bellucci et al., "A noncanonical function of sortase enables site-specific conjugation of small molecules to lysine residues inproteins," Angew. Chem. Int. Ed. 54, 2015, 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, 2013, 52(13):3703-3708.
Bender et al., "Synthesis, Crystallization, and Biological Evaluation of an Orally Active Prodrug of Gemcitabine," J. Med. Chem. 2009, 52, 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, 2011, 50, 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, 2010, 142, 312-318.
Bhattacharyya et al., "A paclitaxel-loaded recombinant polypeptide nanoparticle outperforms Abraxane in multiple murine cancer models," Nat. Commun. 2015, 6, 7939.
Bidwell et al., "Development of elastin-like polypeptide for thermally targeted delivery of doxorubicin," Biochemical Pharmacology, 2007, 73(5):620-631.
Blasko et al., "Brachytherapy for carcinoma of the prostate: Techniques, patient selection, and clinical outcomes," Seminars in Radiation Oncology, 2002, 12, 81-94.

(56) References Cited

OTHER PUBLICATIONS

Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, 2013, 49, 245-253.
Bocci et al., "The pharmacological bases of the antiangiogenic activity of paclitaxel," Angiogenesis, 2013, 16, 481-492.
Bochicchio et al., "Investigating by Cd the molecular mechanism of elasticity of elastomeric proteins," Chirality, 2008, 20, 985-994.
Boekhorst et al., "Genome-wide detection and analysis of cell wall-bound proteins with LPxTG-like sorting motifs," J. Bacteriol. 187, 2005, 4928-4934.
Boldt, "Use of albumin: an update," Br J. Anaesth, 2010, 104 (3), 276-284.
Bond, "Exenatide (Byetta) as a novel treatment option for type 2 diabetes mellitus," Proc. (Bayl. Univ. Med. Cent.) 19, 2006, 281-284.
Bontempo et al., "Streptavidin as a macroinitiator for polymerization: in situ protein-polymer conjugate formation," J. Am. Chem. Soc., 2005, 6508-6509.
Boyer et al., "Well-Defined Protein-Polymer Conjugates via in Situ RAFT Polymerization," J. Am. Chem. Soc. 2007, 129, 7145-7154.
Branco et al., "Self-assembling materials for therapeutic delivery," Acta Biomaterialia, 2009, 5(3): p. 817-831.
Broyer et al., "Emerging synthetic approaches for protein-polymer conjugations," Chem. Commun. 2011, 47, 2212.
Brusa et al., "Antitumor activity and pharmacokinetics of liposomes containing lipophilic gemcitabine prodrugs," Anticancer Res. 2007, 27, 195-199.
Burchard, "Light Scattering Techniques," Physical techniques for the study of food biopolymers, 1994, 151-213.
Burnouf, "Modern plasma fractionation," Transfus. Med. Rev., 2007, 21 (2), 101-117.
Cabral et al., "Accumulation of sub-100 nm polymeric micelles in poorly permeable tumours depends on size," Nature Nanotechnology, 2011, 6, 815-823.
Cai et al., "Long-acting preparations of exenatide," Drug Des. Dev. Ther. 7, 2013, 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, 2012, 12, 2165-2170.
Camilloni et al., "Determination of secondary structure populations in disordered states of proteins using nuclear magnetic resonance chemical shifts," Biochemistry, 2012, 51, 2224-2231.
Campbell et al., "Pegylated peptides V. Carboxy-terminal PEGlyted analogs of growth hormone-releasing factor (GRF) display enhanced duration of biological activity invivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, 2014, 88, 412-418.
Cardenes et al., "Locally advanced pancreatic cancer: Current therapeutic approach," The Oncologist, 2006, 11, 612-623.
Carrico et al., "Introducing genetically encoded aldehydes into proteins," Nat Chem Biol, 2007, 3(6):321-322.
Cataldo et al., "Radiation-induced crosslinking of collagen gelatin into a stable hydrogel," Journal of Radioanalytical and Nuclear Chemistry, 2008, 275, 125-131.

Ceska et al., "A new and rapid method for the clinical determination of $\alpha$-amylase activities in human serum and urine. Optimal conditions," Clinica Chimica Acta, 1969, 26, 437-444.
Chakrabartty et al., "Stability of $\alpha$-Helices," Adv Protein Chem, 1995, 46, 141-176.
Chang et al., "Tumor-stroma interaction in orthotopic primary pancreatic cancer xenografts during hedgehog pathway inhibition," Int. J. Cancer, 2013, 133, 225-235.
Chaudhury et al., "The major histocompatibility complex-related Fc receptor for IgG (FcRn) binds albumin and prolongs its lifespan," J Exp Med, 2003, 197(3): p. 315-322.
Chen et al., "Anisotropic hydrogels fabricated with directional freezing and radiation-induced polymerization and crosslinking method," Materials Letters, 2012, 89, 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers to Probe the Mechanism of Elastin Elasticity," J. Am. Chem. Soc., 2009, 132(13):4577-4579.
Chen et al., "Rheology of Soft Materials," Annual Review of Condensed Matter Physics, 2010, 1, 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials 34, 2013, 8776-8785.
Chilkoti et al., "Design of thermally responsive, recombinant polypeptide carriers for targeted drug delivery," Advance Drug Delivery Reviews, 2002, 54:1093-1111.
Chilkoti et al., "Targeted drug delivery by thermally responsive polymers," Advanced Drug Delivery Reviews, 2002, 54:613-630.
Chithrani et al., "Determining the size and shape dependence of gold nanoparticle uptake into mammalian cells," Nano Lett, 2006, 6, 662-668.
Chitkara et al., "Self-Assembling, Amphiphilic Polymer-Gemcitabine Conjugate Shows Enhanced Antitumor Efficacy Against Human Pancreatic Adenocarcinoma," Bioconjug. Chem. 2013, 24, 1161-1173.
Cho et al., "Effects of hofmeister anions on the phase transition temperature of elastin-like polypeptides," J. Phys. Chem. B., 2008, 112, 13765-13771.
Cho et al., "Hydrogen bonding of $\beta$-turn structure is stabilized in D(2)O," J Am Chem Soc, 2009, 131, 15188-15193.
Cho et al., "Therapeutic nanoparticles for drug delivery in cancer," Clin. Cancer Res., 2008, 14, 1310-1316.
Choi et al., "Renal Clearance of Nanoparticles," Nature biotechnology, 2007, 25(10): p. 1165-1170.
Chow et al., "Peptide-based biopolymers in biomedicine and biotechnology," Mater. Sci. Eng. R Reports, 2008, 62, 125-155.
Chow et al., "Ultra-High Expression of a Thermally Responsive Recombinant Fusion Protein in E. coli," Biotechnology Progress, 2006, 22(3):638-646.
Choy et al., "Investigation of taxol as a potential radiation sensitizer," Cancer, 1993, 71, 3774-3778.
Christensen et al., "Fusion order controls expression level and activity of elastin-like polypeptide fusion proteins," Protein Science, 2009, 18:1377-1387.
Christensen et al., "Predicting Transition Temperatures of Elastin-Like Polypeptide Fusion Proteins," Biomacromolecules, 2013, 14(5): p. 1514-1519.
Cid-Arregui et al., "Perspectives in the treatment of pancreatic adenocarcinoma," World Journal of Gastroenterology, 2015, 21, 9297-9316.
Ciezki et al., "Brachytherapy or surgery? A composite view," Oncology, 2009, 23, 960-964.
Cima, "AVMA Guidelines for the Euthanasia of Animal: 2013 Edition," Journal of the American Veterinary Medical Association, 2013, 242, 102 pages.
Cirulis et al., "Viscoelastic properties and gelation of an elastin-like polypeptide," Journal of Rheology, 2009, 53, 1215-1228.

(56) References Cited

OTHER PUBLICATIONS

Clarke et al., "Tropoelastin massively associates during coacervation to form quantized protein spheres," Biochemistry, 2006, 45, 9989-9996.
Clave et al., "Amylase, lipase, pancreatic isoamylase, and phospholipase A in diagnosis of acute pancreatitis," Clinical Chemistry, 1995, 41, 1129-1134.
Coin et al., "Solid-phase peptide synthesis: from standard procedures to the synthesis of difficult sequences," Nat. Protoc., 2007, 2, 3247.
Colomb et al., "Radiation-Convertible Polymers from Norbornenyl Derivatives. Crosslinking with Ionizing Radiation," Journal of Applied Polymer Science, 1970, 14, 1659-1670.
Conrad et al., "ELPylated anti-human TNF therapeutic single-domain antibodies for prevention of lethal septic shock," Plant Biotechnology Journal, 2011, 9, 22-31.
Craik et al., "The future of peptide-based drugs," Chemical biology & drug design 81, 2013, 136-147.
Cui et al., "Amino acid sequence in constitutionally isomeric tetrapeptide amphiphiles dictates architecture of one-dimensional nanostructures," J. Am. Chem. Soc., 2014, 136, 12461-12468.
Cui et al., "Self-assembly of peptide amphiphiles: from molecules to nanostructures to biomaterials," Biopolymers, 2010, 94, 1-18.
Dalla Poza et al., "Targeting gemcitabine containing liposomes to CD44 expressing pancreatic adenocarcinoma cells causes an increase in the antitumoral activity," Biochim. Biophys. Acta, 2013, 1828, 1396-1404.
Darzynkiewicz et al., "DNA content measurement for DNA ploidy and cell cycle analysis," Current Protocols in Cytometry, 2001, 7.5.1-7.5.24.
Dasgupta et al., "Isopeptide Ligation Catalyzed by Quintessential Sortase A: Mechanistic Cues From Cyclic and Branched Oligomers of Indolicidin," The Journal of Biological Chemistry, 2011, vol. 286, No. 27, pp. 23996-24006, Supplemental Information.
De et al., "Temperature-Regulated Activity of Responsive Polymer-Protein Conjugates Prepared by Grafting—from via RAFT Polymerization," J. Am. Chem. Soc. 2008, 130, 11288-11289.
De Simone et al., "Accurate random coil chemical shifts from an analysis of loop regions in native states of proteins," J Am Chem Soc, 2009, 131, 16332-16333.
Deer et al., "Phenotype and genotype of pancreatic cancer cell lines," Pancreas, 2010, 39, 425-435.
Dejana et al., "The role of adherens junctions and VE-cadherin in the control of vascular permeability," J Cell Sci, 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression," PNAS, 2010, 107, 18616-18621.
Dennis et al., "Albumin binding as a general strategy for improving the pharmacokinetics of proteins," J Biol Chem, 2002, 277(38): p. 35035-35043.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologics," Acta Biomater. 2009, 5, 560-569.
Deshayes et al., "Radium 223 dichloride for prostate cancer treatment," Drug Des Devel Ther, 2017, 11, 2643-2651.
Diana et al., "Prognostic role and correlation of CA9, CD31, CD68 and CD20 with the desmoplastic stroma in pancreatic ductal adenocarcinoma," Oncotarget, 2016, 7, 72819-72832.
Diehl et al., "A Good Practice Guide to the Administration of Substances and Removal of Blood Including Routes and Volumes," J Appl Toxicol, 2001, 21, 15-23.
Ding et al., "Mechanism for the alpha-helix to beta-hairpin transition," Proteins, 2003, 53, 220-228.

Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. 2008, 130, 687-694.
Dreher et al., "Thermal cycling enhances the accumulation of a temperature-sensitive biopolymer in solid tumors," Cancer Res, 2007, 67, 4418-4424.
Dreher, M. R. PhD. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., 2007, 341, 207-214.
Drucker et al., "The incretin system: glucagon-like peptide-1 receptor agonists and dipeptidyl peptidase-4 inhibitors in type 2 diabetes," Lancet 368, 2006, 1696-1705.
Drucker, "Glucagon-like peptides," Diabetes 47, 1998, 159-169.
Du et al., "Endoscope-assisted brachytherapy for pancreatic cancer: From tumor killing to pain relief and drainage," Journal of interventional gastroenterology, 2011, 1, 23-27.
Du et al., "Tailor-made dual pH-sensitive polymer-doxorubicin nanoparticles for efficient anticancer drug delivery," J. Am. Chem. Soc., 2011, 133, 17560-17563.
Duan et al., "Fibronectin type III domain based monobody with high activity," Biochemistry, 2007 46(44):12656-12664.
Dubey et al., "Development and evaluation of folate functionalized albumin nanoparticles for targeted delivery of gemcitabine," Int J Pharm., 2015, 492(1-2):80-91.
Ducreux et al., "Radiation plus docetaxel and cisplatin in locally advanced pancreatic carcinoma: A non-comparative randomized phase II trial," Digestive and Liver Disease, 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Eisenhaber et al., "Prediction of lipid posttranslational modifications and localization signals from protein sequences: Big-II, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, 2017, 45, 228-247.
Ellis, "Macromolecular crowding: obvious but underappreciated," Trends Biochem. Sci., 2001, 26 (10), 597-604.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) invitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.

(56) References Cited

OTHER PUBLICATIONS

Feng et al., "Protein resistant surfaces: comparison of acrylate graft polymers bearing oligo-ethylene oxide and phosphorylcholine side chains," Biointerphases, 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, 2015, 16, 3389-3398.
Fluegel et al., "Chain stiffness of elastin-like polypeptides," Biomacromolecules 2010, 11, 3216-3218.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, 2018, 130:A19112.
Friedman et al., "Directed Evolution to Low Nano molar Affinity of a Tumor-Targeting Epidermal Growth Factor Receptor-Binding Affibody Molecule," J. Mol. Biol., 2008, 376, 1388-1402.
Frilling et al., "Recommendations for management of patients with neuroendocrine liver metastases," The lancet oncology, 2014, 15, e8-21.
Fu et al., Recent Patents on Anti-Cancer Drug Discovery, 2009. 4(3): p. 262-272.
Fujiwara et al., "Modulating effect of the PI3-kinase inhibitor LY294002 on cisplatin in human pancreatic cancer cells," Journal of Experimental & Clinical Cancer Research, 2008, 27, 76.
Furgeson et al., "Structural optimization of a "smart" doxorubicin-polypeptide conjugate for thermally targeted delivery to solid tumors," Journal of Controlled Release, 2006, 110:362-369.
Furumoto et al., "Effect of coupling of albumin onto surface of PEG liposome on its in vivo disposition," International Journal of Pharmaceutics, 2007, 329(1-2): p. 110-116.
Gaberc-Porekar et al., "Obstacles and pitfalls in the PEGylation of therapeutic proteins," Curr. Opin. Drug Discov. Devel. 11, 2008, 242-250.
Gabizon et al., "Prolonged circulation time and enhanced accumulation in malignant exudates of doxorubicin encapsulated in poly-ethylene-glycol coated liposomes," Cancer Res. 1994, 987-992.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, 2006, R12-R22.
Ganson et al., "Pre-existing anti-PEG antibody linked to first-exposure allergic reactions to Pegnivacogin, a PEGylated RNA aptamer," J. Allergy Clin. Immunology, (2015).
Gao et al., "In situ growth of a PEG-like polymer from the C terminus of an intein fusion protein improves pharmacokinetics and tumor accumulation" PNAS Early Edition, 2010, vol. 107, 1-6.
Gao et al., "In situ growth of a PEG-like polymer from the C terminus of an intein fusion protein improves pharmacokinetics and tumor accumulation," Proc. Natl. Acad. Sci. 107, 2010, 16432-16437.
Gao et al., "In situ growth of a stoichiometric PEG-like conjugate at a protein's N-terminus with significantly improved pharmacokinetics," Proc. Natl. Acad. Sci., 2009, 15231-15236.
Garanger et al., "Structural Evolution of a Stimulus-Responsive Diblock Polypeptide Micelle by Temperature Tunable Compaction of its Core," Macromolecules, 2015, 48, 6617-6627.
Garay et al., "Antibodies against polyethylene glycol in healthy subjects and inpatients treated with PEG-conjugated agents," Expert Opinion. Drug Deliv. 9, 2012, 1319-1323.
Gauthier et al., "Peptide/protein-polymer conjugates: synthetic strategies and design concepts," Chem. Commun., 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (2017).
Ghoorchian et al., "Molecular architecture influences the thermally induced aggregation behavior of elastin-like polypeptides," Biomacromolecules, 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, 2009, 27, 607-612.
Gibson et al., "Enzymatic assembly of DNA molecules up to several hundred kilobases," Nat Methods, 2009, 6, 343-345.
Glassman et al., "Toughening of Thermoresponsive Arrested Networks of Elastin-Like Polypeptides to Engineer Cytocompatible Tissue Scaffolds," Biomacromolecules, 2016, 17, 415-426.
Gluck et al., "Single Vector System for Efficient N-myristoylation of Recombinant Proteins in *E. coli*," Plos One. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, 2008, 633-648.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, 2006, 17, 1263-1268.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin, 2003, 31(3): 529-540.
Greenfield, "Using circular dichroism spectra to estimate protein secondary structure," Nat. Protoc., 2006, 1(6):2876-90.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Güngör et al., "Pancreatic cancer," British Journal of Pharmacology, 2014, 171, 849-858.
Guo et al., "Nanoparticles escaping RES and endosome: challenges for siRNA delivery for cancer therapy," J. Nanomaterials, 2011, 2011: 1-12.
Gustafsson, "Nonlinear structured-illumination microscopy: wide-field fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, 2016, 139, 2116-2126.
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, 2013, vol. 4, Article 331, 7 pages.
Hamidi et al., "Pharmacokinetic Consequences of Pegylation," Drug Deliv. 2006, 13, 399-409.

(56) References Cited

OTHER PUBLICATIONS

Hamley, "Self-assembly of amphiphilic peptides," Soft Matter, 2011, 7, 4122.
Han et al., "Survival of patients with advanced pancreatic cancer after iodine[125] seeds implantation brachytherapy: A meta-analysis," Medicine, 2017, 96, e5719.
Harmon et al., "A Model for Hysteresis Observed in Phase Transitions of Thermally Responsive Instrinsically Disordered Protein Polymers," Biophysical Journal, 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, 2015, 48, 4183-4195.
Hassouneh et al., "Elastin-Like Polypeptides as a Purification Tag for Recombinant Proteins," Curr Protoc Protein Sci., 2010, Chapter 6. Unit 6.11. 10.1002/0471140864.ps0611s61.
Hassouneh et al., "Fusions of elastin-like polypeptides to pharmaceutical proteins," Methods Enzymol., 2012, 502, 215-37.
Hassouneh et al., "Unexpected Multivalent Display of Proteins by Temperature Triggered Self-assembly of Elastin-like Polypeptide Block Copolymers," Biomacromolecules, 2012, vol. 13, Issue 4, pp. 1598-1605.
Hathout et al., "Analysis of seed loss and pulmonary seed migration inpatients treated with virtual needle guidance and robotic seed delivery," American journal of clinical oncology, 2011, 34, 449-453.
He et al., "Comparative genomics of elastin: Sequence analysis of a highly repetitive protein," Matrix Biology, 2007, 26:524-540.
He et al., "Improving protein resistance of α-A12O3 membranes by modification with POEGMA brushes," Applied Surface Science, 2011, 258 (3), 1038-1044.
Heagerty et al., Biometrics, "Time-dependent ROC curves for censored survival data and a diagnostic marker," 2000, 56(2):337-44.
Heal et al., "N-Myristoyl transferase-mediated protein labelling in vivo," Org. Biomol. Chain, 2008, 6(13):2308-2315.
Heal et al., "Site-specific N-terminal labelling of proteins in vitro and in vivo using N-myristoyl transferase and bioorthogonal ligation chemistry," Chem. Commun., 2008, 3, 480-482.
Heredia et al., "In Situ Preparation of Protein-"Smart" Polymer Conjugates with Retention of Bioactivity," J. Am. Chem. Soc. 2005, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, 2014, R63.
Hidalgo, "Pancreatic Cancer," N Engl J Med, 2010, 362, 1605-1617.
Hingorani et al., "Phase Ib Study of PEGylated Recombinant Human Hyaluronidase and Gemcitabine in Patients with Advanced Pancreatic Cancer," Clinical Cancer Research, 2016, 22, 2848-2854.
Ho et al., "Chemoenzymatic Labeling of Proteins for Imaging in Bacterial Cells," J. Am. Chem. Soc., 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, 2007, pp. 40-47.
Hochkoeppler, "Expanding the landscape of recombinant protein production in *Escherichia coli*," Biotechnol. Lett., 2013, 35, 1971-1981.
Holehouse et al., "CIDER: Classification of Intrinsically Disordered Ensemble Regions," Biophysical Journal, 2015, vol. 108, Issue 2, Supplement 1, p. 228a.
Holm et al., "Transperineal [125]iodine seed implantation in prostatic cancer guided by transrectal ultrasonography," The Journal of urology, 2002, 167, 985-988.
Hopp et al., "The effects of affinity and valency of an albumin-binding domain (AbD) on the half-life of a single-chain diabody-ABD fusion protein," Protein Engineering Design and Selection, 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, 2007, 119, 25-33.
Hruby et al., "Thermoresponsive polymeric radionuclide delivery system—an injectable brachytherapy," Eur J Pharm Sci., 2011, 42, 484-488.
Hrycushko et al., "Direct intratumoral infusion of liposome encapsulated rhenium radionuclides for cancer therapy: effects of non-uniform intratumoral dose distribution," Med Phys, 2011, 38, 1339-1347.
Hu et al., "Design of tumor-homing and pH-responsive polypeptide-doxorubicin nanoparticles with enhanced anticancer efficacy and reduced side effects," Chemical Communications, 2015, 51, 11405-11408.
Huang et al., "Photodynamic Therapy Synergizes with Irinotecan to Overcome Compensatory Mechanisms and Improve Treatment Outcomes in Pancreatic Cancer," Cancer Research, 2016, 76, 1066-1077.
Huotari et al., "Endosome maturation," EMBO J, 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., 2015, 7, 1-8.
Ishida et al., "Accelerated blood clearance (ABC) phenomenon upon repeated injection of PEGylated liposomes," International Journal of Pharmaceutics, 2008, 354(1-2):56-62.
Ito et al., "Invivo antitumor effect of the mTOR inhibitor CCI-779 and gemcitabine in xenograft models of human pancreatic cancer," International Journal of Cancer, 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., 2006, 4482-4486.
Janes et al., "Chitosan nanoparticles as delivery systems for doxorubicin," J. Control Release, 2001, 73, 255-267.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, 2012, 13, 206-215.

(56) References Cited

OTHER PUBLICATIONS

Jia et al., "Preparation, physicochemical characterization and cytotoxicity in vitro of gemcitabine-loaded PEG-PDLLA nanovesicles," World J. Gastroenterol. 2010, 16(8):1008-1013.
Jiang et al., "The internal structure of self-assembled peptide amphiphiles nanofibers," Soft Matter, 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Jonsson et al., "Engineering of a fe mto molar affinity binding protein to human serum albumin," Protein Engineering Design and Selection, 2008, 21(8): 515-527.
Junutula et al., "Site-specific conjugation of a cytotoxic drug to an antibody improves the therapeutic index," Nat Biotechnol, 2008, 26(8):925-932.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, 2011, 89, 183-188.
Kamisawa et al., "Pancreatic cancer," Lancet, 2016, 388, 73-85.
Kanoski et al., "The role of nausea in food intake and body weight suppression by peripheral GLP-1 receptor agonists, exendin-4 and liraglutide," Neuropharmacology 62, 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karamanolis et al., "Increased expression of VEGF and CD31 in postradiation rectal tissue: implications for radiation proctitis," Mediators Inflamm, 2013, 515048.
Karperien, A. FracLac for Image J, version 2.5 <http://rsb.info.nih.gov/ij/plugins/fraclac/FLHelp/Introduction.htm> 1999-2012.
Katakura, "Nuclear Data Sheets for A = 125," Nuclear Data Sheets, 2011, 112, 495-705.
Kato et al., "Acidic extracellular microenvironment and cancer," Cancer Cell Int, 2013, 13, 89, 8 pages.
Katti et al., "Amino acid repeat patterns in protein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem, 2012, 4(1):59-63.
Keller et al., "Empirical Statistical Model to Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Keten et al., "Nanoconfinement controls stiffness, strength and mechanical toughness of β-sheet crystals in silk," Nat Mater, 2010, 9, 359-367.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., 2006, 24, 1065-1066.
Khazov et al., "Nuclear Data Sheets for A = 131," Nuclear Data Sheets, 2006, 107, 2715-2930.
Kim et al., "Recombinant elastin-mimetic biomaterials: Emerging applications in medicine," Adv Drug Deliv Rev, 2010, 62, 1468-1478.

Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem. 2012, 23, 2214-2220.
Kim et al., "Ultrasensitive Carbon nanotube-based biosensors using antibody-binding fragments," Analytical Biochemistry, 2008, 381, 193-198.
Knop et al., "Poly(ethylene glycol) in Drug Delivery: Pros and Cons as Well as Potential Alternatives," Angewandte Chemie International Edition, 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment of an NMR-lnvisible Solubility Enhancement Tag Using a Sortase-Mediated Protein Ligation Method," J Biomol NMR. Mar. 2009, vol. 43, No. 3; pp. 145-150.
Kobayashi et al., "Summary of recombinant human serum albumin development," Biologicals, 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, 2012, 41(7):2686-2695.
Koong et al., "Phase II study to assess the efficacy of conventionally fractionated radiotherapy followed by a stereotactic radiosurgery boost inpatients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, 2008, 1389-1399.
Kramer et al., "Quantitative Side-Chain Modifications of Methionine-Containing Elastin-Like Polypeptides as a Versatile Tool to Tune Their Properties," ACS Macro Lett., 2015, 4(11):1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, 2008, 1778, 631-645.
Krempien et al., "Neoadjuvant chemoradiation in patients with pancreatic adenocarcinoma," HPB (Oxford), 2006, 8, 22-28.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., 2015, 26(10):2153-2160.
Kulkarni et al., "Selective functionalization of the protein N terminus with N-myristoyl transferase for bioconjugation in cell lysate," ChemBioChem, 2013, 14, 1958-1962.
Kumar et al., "N-Terminal Region of the Catalytic Domain of Human N-Myristoyltransferase 1 Acts as an Inhibitory Module," PLoS One, 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Le Droumaguet et al., "Recent advances in the design of biocoiljugates from controlled/living radical polymerization," Polym. Chem. 2010, 1, 563-598.
Le Meins et al., "Hybrid polymer/lipid vesicles: State of the art and future perspectives," Mater. Today, 2013, 16, 397-402.

(56) References Cited

OTHER PUBLICATIONS

Leader et al., "Protein therapeutics: a summary and pharmacological classification," Nat. Rev. Drug Discov. 7, 2008, 21-39.
Lee et al., "Atomistic molecular dynamics simulations of peptide amphiphile self-assembly into cylindrical nanofibers," J. Am. Chem. Soc., 2011, 133, 3677-3683.
Lee et al., "Immunohistochemical analysis of claudin expression in pancreatic cystic tumors," Oncology Reports, 2011, 25(4): 971-978.
Lee et al., "In vivo bioluminescent imaging of irradiated orthotopic pancreatic cancer xenografts in nonobese diabeti-sever combined immunodeficient mice: a novel method for targeting and assaying efficacy of ionizing radiation," Transl. Oncol., 2010, 3, 153-159.
Lee et al., "Mechanical properties of cross-linked syntheti elastomeric polypentapeptides," Macromolecules, 2001, 34, 5968-5974.
Lee et al., "Phase transition and elasticity of protein-based hydrogels," J. Biomater. Sci. Polymer Edn, 2001, 12, 229-242.
Lee et al., "Theranostic nanoparticles with controlled release of gemcitabine for targeted therapy and MRI of pancreatic cancer," ACS Nano 2013, 7(3):2078-2089.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., 2011, 77(22):8114-28.
Leung et al., "Bio-Click Chemistry: Enzymatic Functionalization of PEGylated Capsules for Targeting Applications**," Angew. Chem. Int. Ed. 2012, 51, 7132-7136.
Le Vine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS ONE, 2014, 9(2): e87704, 9 pages.
Li et al., "Elastin is an essential determinant of arterial morphogenesis," Nature, 1998, 393, 276-280.
Li et al., "Molecular description of the Lcst behavior of an elastin-like polypeptide," Biomacromolecules, 2014, 15, 3522-3530.
Li et al., "Nanoparticles Evading the Reticuloendothelial System: Role of the Supported Bilayer," Biochim. Biophys. Acta, 2009, 1788 (10), 2259-2266.
Li et al., "Pancreatic cancer," Lancet, 2004, 363, 1049-1057.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun, 2015, 36(1):90-95.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, 2007, 8(5): 1417-1424.
Lim et al., "In situ cross-linking of elastin-like polypeptide block copolymers for tissue repair," Biomacromolecules, 2008, 9, 222-230.
Lim et al., "In vivo post-translational modifications of recombinant mussel adhesive protein in insect cells," Biotechnol. Prog., 2011, 27, 1390-1396.
Lin et al., "Utility of immunohistochemistry in the pancreatobiliary tract," Arch Pathol Lab Med, 2015, 139, 24-38.
Linder et al., "Lipid Modifications of G Protein Subunits," J. Biol. Chem., 1991, 266(7):4654-4659.
Ling et al., "Protein thioester synthesis enabled by sortase," J. Am Chem Soc, 2012, 134(26):10749-10752.

Litiere et al., "RECIST—learning from the past to build the future," Nat Rev Clin Oncol, 2017, 14, 187-192.
Liu et al., "Brachytherapy using injectable seeds that are self-assembled from genetically encoded polypeptides in situ," Cancer Res, 2012, 72, 5956-5965.
Liu et al., "Hydrophobic modifications of cationic polymers for gene delivery," Prog. In Polym. Sci., 2010, 35, 1144-1162.
Liu et al., "In Situ Formation of Protein-Polymer Conjugates through Reversible Addition Fragmentation Chain Transfer Polymerization**," Angew. Chem. Int. Ed. 2007, 46, 3099-3103.
Liu et al., "Injectable intratumoral depot of thermally responsive polypeptide-radionuclide conjugates delays tumor progression in a mouse model," J. Control Release, 2010, 144(1):2-9.
Liu et al., "Tracking the in vivo fate of recombinant polypeptides by isotopic labeling" Journal of Controlled Release, 2006, 114, 184-192.
Liu et al., "Tumor accumulation, degradation and pharmacokinetics of elastin-like polypeptides in nude mice," Journal of Controlled Release, 2006, 116, 170-178.
Livingstone, "Theoretical property predictions. Curr Top Med Chem FIELD Full Journal Title: Current topics in medicinal chemistry," Curr. Top. Med. Chem. 2003, 3, 1171-1192.
Lovshin et al., "Incretin-based therapies for type 2 diabetes mellitus," Nat. Rev. Endocrinol. 5, 2009, 262-269.
Ludden, "Nonlinear pharmacokinetics: clinical Implications," Clin. Pharmacokinet., 1991, 20 (6), 429-446.
Luginbuhl et al., "One-week glucose control via zero-order release kinetics from an injectable depot of glucagon-like peptide-1 fused to a thermosensitive biopolymer," Nat. Biomed. Eng., 2017, 1, 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., 2017, 56: 13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lund et al., "Phase II study of gemcitabine (2',2'-difluorodeoxycytidine) in previously treated ovarian cancer patients," J. Natl. Cancer. Inst 1994, 86(20):1530-1533.
Luo et al., "Noncovalent Modulation of the Inverse Temperature Transition and Self-Assembly of Elastin-b-Collagen-like Peptide Biocoiljugates," J Am Chem Soc, 2015, 137, 15362-15365.
Ma et al., "Non-fouling" oligo(ethylene glycol)-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir: the ACS journal of surfaces and colloids, 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, 2006, 16 (5), 640-648.
MacEwan et al., "Applications of elastin-like polypeptides in drug delivery," Journal of Controlled Release, 2014, 190: p. 314-330.
MacEwan et al., "Controlled apoptosis by a thermally toggled nanoscale amplifier of cellular uptake," Nano Letters, 2014, 14, 2058-2064.
MacEwan et al., "Digital switching of local arginine density in a genetically encoded self-assembled polypeptide nanoparticle controls cellular uptake," Nano Lett., 2012, 12, 3322-3328.
MacEwan et al., "Elastin-like polypeptides: Biomedical applications of tunable biopolymers," Biopolymers, 2010, 94, 60-77.
MacEwan et al., "Non-chromatographic Purification of Recombinant Elastin-like Polypeptides and their Fusions with Peptides and Proteins from *Escherichia coli*," 2014, 88, p. e51583.
MacEwan et al., "Phase Behavior and Self-Assembly of Perfectly Sequence-Defined and Monodisperse Multib Copolypeptides," Biomacromolecules, 2017, 18(2):599-609.
Mack et al., "Antiobesity action of peripheral exenatide (exendin-4) in rodents: effects on food intake, body weight, metabolic status and side-effect measures," Int. J. Obes. 30, 2006, 1332-1340.

(56) References Cited

OTHER PUBLICATIONS

MacKay et al., "Self-assembling chimeric polypeptide-doxorubicin conjugate nanoparticles the abolish tumors after single injection," Nat Mater, 2009, 8(12):993-999.

Maeda et al., "Tumor vascular permeability and the EPR effect in macro molecular therapeutics: a review," J. Control. Release, 2000, 65(1-2)271-284.

Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, 2010, 671-678.

Maitra et al., "Pancreatic Cancer," Annu Rev Pathol Mech Dis, 2008, 3, 157-188.

Malik et al., "Recent advances in protein and peptide drug delivery systems," Curr. Drug Deliv. 2, 2007, 141-151.

Mann et al., "Proteomic analysis of post-translational modifications," Nat. Biotechnol., 2003, 21, 255-61.

Manzoor et al., "Overcoming limitations in nanoparticle drug delivery: triggered, intravascular release to improve drug penetration into tumors," Cancer Res, 2012, 72, 5566-5575.

Mao et al., "DNA repair by nonhomologous end joining and homologous recombination during cell cycle in human cells," Cell cycle, 2008, 7, 2902-2906.

Mao et al., "Sortase-mediated protein ligation: a new method for protein engineering," J. Am. Chem. Soc., 2004, 126(9):2670-2671.

Maraffini et al., "Sortases and the art of anchoring proteins to the envelopes of Gram-positive bacteria," Microbiol Mol Biol Rev, 2006, 70(1):192-221.

Mariam et al., "Albumin corona on nanoparticles—a strategic approach in drug delivery," Drug Deliv., 2016, 23 (8), 2668-2676.

Marr et al., "Effect of Temperature on the Composition of Fatty Acids in *Escherichia coli*," J Bacteriol., 1962, 84(6):1260-7.

Marten et al., "A randomized multicentre phase II trial comparing adjuvant therapy inpatients with interferon alpha-2b and 5-FU alone or in combination with either external radiation treatment and cisplatin (CapRI) or radiation alone regarding event-free survival—CapRI-2," BMC Cancer, 2009, 9, 1-8.

Maskarinec et al., "Protein engineering approaches to biomaterials design," Curr. Opin. Biotechnol., 2005, 16, 422-426.

Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.

Mastria et al., "Doxorubicin-conjugated polypeptide nanoparticles inhibit metastasis in two murine models of carcinoma," J Control Release, 2015, 208:52-8.

Matsumura et al., "A new concept for macromolecular therapeutics in cancer chemotherapy: mechanism of tumoritropic accumulation of proteins and the antitumor agent smancs," Cancer Res. 1986, 46, 6387-6392.

Matsumura, "Cancer stromal targeting (CAST) therapy," Advanced Drug Delivery Reviews, 2012, 64, 710-719.

Matyjaszewski et al., "Atom transfer radical polymerization," Chem. Rev. 101, 2001, 2921-2990.

Matyjaszewski et al., "Macromolecular engineering by atom transfer radical polymerization," J. Am. Chem. Soc. 136, 2014, 6513-6533.

Maurer-Stroh et al., "N-terminal N-myristoylation of proteins: prediction of substrate proteins from amino acid sequence" J Mol Biol., 2002, 317(4):541-557.

Maurer-Stroh et al., "N-terminal N-myristoylation of proteins: Refinement of the sequence motif and its taxon-specific differences," J Mol Biol., 2002, 317(4):523-540.

Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.

McConkey et al., "Molecular Characterization of Pancreatic Cancer Cell Lines," Pancreatic Cancer, 2010, 457-469.

McDaniel et al., "A unified model for de novo design of elastin-like polypeptides with tunable inverse transition temperatures," Biomacromolecules, 2013, 14(8):2866-2872.

McDaniel et al., "Actively targeting solid tumours with thermoresponsive drug delivery systems that respond to mild hyperthermia," Int J Hyperthermia, 2013, 29, 501-510.

McDaniel et al., "Doxorubicin-conjugated chimeric polypeptide nanoparticles that respond to mild hyperthermia," Control. Release, 2012, 159 (3), 362-367.

McDaniel et al., "Drug delivery to solid tumors by elastin-like polypeptides," Adc. Drug Deliver. Rev., 2010, 62(15):1456-1467.

McDaniel et al., "Noncanonical Self-Assembly of Highly Asymmetric Genetically Encoded Polypeptide Amphiphiles into Cylindrical Micelles," Nano Lett, 2014, 14(11):6590-6598.

McDaniel et al., "Rational design of "heat seeking" drug loaded polypeptide nanoparticles that thermally target solid tumors," Nano Letters, 2014, 14, 2890-2895.

McDaniel et al., "Self-assembly of thermally responsive nanoparticles of a genetically encoded peptide polymer by drug conjugation," Chem. Int. Ed. 2013, 52, 1683-1687.

McDaniel et al., "Recursive Directional Ligation by Plasmid Reconstruction Allows Rapid and Seamless Cloning of Oligomeric Genes," Biomacromolecules, 2010, 11(4):944-952.

McHale et al., "Synthesis and in vitro evaluation of enzymatically cross-linked elastin-like polypeptide gels for cartilaginous tissue repair," Tissue Eng, 2005, 11, 1768-1779.

McIlhinney et al., "Characterization of a polyhistidine-tagged form of human myristoyl-CoA: protein N-myristoyltransferase produced in *Escherichia coli*," European Journal of Biochemistry, 1994, 222(1):137-146.

Mejuch et al., "Synthesis of lipidated proteins," Bioconjug. Chem. 27, 2016, 1771-1783.

Mero et al., "Transglutaminase-mediated PEGylation of proteins: direct identification of the sites protein medificationby mass spectrometry using a novel monodisperse PEG," Bioconjug Chem, 2009, 20(2):384-389.

Merrick et al., "Seed fixity in the prostate/periprostatic region following brachytherapy," International journal of radiation oncology, biology, physics, 2000, 46, 215-220.

Methods and Welfare Considerations in Behavioral Research with Animal. (2002).

Meyer et al., "Drug targeting using thermally responsive polymers and local hyperthermia," Journal of Controlled Release, 2001, 74, 213-224.

Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.

Meyer et al., "Purification of recombinant proteins by fusion with thermally-responsive polypeptide," Nat. Biotechnol., 1999, 17(11):1112-1115.

Meyer et al., "Quantification of the effects of chain length and concentration on the thermal behavior of elastin-like polypeptides," Biomacromolecules, 2004, 5(3):846-51.

Meyer et al., "Targeting a Genetically Engineered Elastin-Like Polypeptide to Solid Tumors by Local Hyperthermia," Cancer Res., 2001, 61(4):1548-1554.

Miao et al., "Sequence and domain arrangements influence mechanical properties of elastin-like polymeric elastomers," Biopolymers, 2013, 99, 392-407.

Miao et al., "Structural determinants of cross-linking and hydrophobic domains for self-assembly of elastin-like polypeptides," Biochemistry, 2005, 44, 14367-14375.

Michl et al., "Current concepts and novel targets in advanced pancreatic cancer," Gut, 2013, 62, 317-326.

Micsonai et al. "Accurate secondary structure prediction and fold recognition for circular dichroism spectroscopy," Proc Natl Acad Sci U S A, 2015, 112, E3095-3103.

Milenic et al., "Antibody-targeted radiation cancer therapy," Nature Reviews Drug Discovery, 2004, 3, 488-498.

(56) References Cited

OTHER PUBLICATIONS

Miller et al., "Solubilized, Spaced Polyalanines: A Context-Free System for Determining Amino Acid α-Helix Propensities," Journal of the American Chemical Society, 2002, 124, 945-962.
Miyata et al., "Polymeric micelles for nano-scale drug delivery," Reaction & Functional Polymers, 2011, 71, 227-234.
Mjelle et al., "Cell cycle regulation of human DNA repair and chromatin remodeling genes," DNA Repair, 2015, 30, 53-67.
Morgan et al., "The combination of epidermal growth factor receptor inhibitors with gemcitabine and radiation in pancreatic cancer," Clin Cancer Res, 2008, 14, 5142-5149.
Mosbach et al., "Formation of proinsulinby immobilized Bacillus subtilis," Nature, 1983, 302, 543-545.
Muiznieks et al., "Structural changes and facilitated association of tropoelastin," Archives of Biochemistry and Biophysics, 2003, 410, 317-323.
Muiznies et al., "Modulated growth, stability and interactions of liquid-like coacervate assemblies of elastin," Matrix Biology 36, 2014, pp. 39-50.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, 2006, vol. 3, No. 6, pp. 429-438.
Murphy et al., "A dosimetric model of duodenal toxicity after stereotactic body radiotherapy for pancreatic cancer," Int J Radiation Oncology Biol Phys, 2010, 78, 1420-1426.
Na et al., "Thermoresponsive pore structure of biopolymer microspheres for a smart drug carrier," Langmuir, 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials 2014, 35(24):6482-6497.
Nairn et al., "A Synthetic Resilin Is Largely Unstructured," Biophysical Journal, 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, 2010, 62, 1479-1485.
Nettles et al., "In situ crosslinking elastin-like polypeptide gels for application to articular cartilage repair in a goat osteochondral defect model," Tissue Eng Part A, 2008, 14, 1133-1140.
Newcomb et al., "Advances in cryogenic transmission electron microscopy for the characterization of dynamic self-assembling nanostructures," Current Opinion in Colloid and Interface Science, 2012, 17, 350-359.
Newton et al., "Commissioning a small-field biological irradiator using point, 2D, and 3D dosimetry techniques," Medical Physics, 2011, 38, 6754-6762.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. 2006, 45, 4697-4699.
Nie, "Understanding and overcoming major barriers in cancer nanomedicine," Nanomedicine (Lond) 2010, 5 (4), 523-528.
Nielsen, "Incretin mimetics and DPP-IV inhibitors for the treatment of type 2 diabetes," Drug Discov. Today 10, 2005, 703-710.
Nilvebrant et al., "The albumin-binding domain as a scaffold for protein engineering," Computational and Structural Biotechnology Journal, 2013, 6: e201303009, 8 pages.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, 2008, 9, 2755-2763.
O'Day et al., "Therapeutic Protein-polymer Conjugates: Advancing beyond PEGylation," J. Am. Chem. Soc., 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Ortony et al., "Internal dynamics of a supramolecular nanofibre," Nat. Mater., 2014, 13, 1-5.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, 2010, 102, 456-463.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, 2016, 96, S204-S205.
Palva et al., "Secretion of interferon by Bacillus subtilis," Gene, 1983, 22, 229-235.
Paolino et al., "Folate-targeted supramolecular vesicular aggregates as a new frontier for effective anticancer treatment in invivo model," Eur. J. Pharm. Biopharm. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release 2010, 144(2):144-150.
Paoloni et al., "Translation of new cancer treatments from pet dogs to humans," Nat. Rev. Cancer 2008, 8 (2), 147-156.
Papa et al., "PEGylated Liposomal Gemcitabine: Insights Into a Potential Breast Cancer Therapeutic," Cell Oncol. (Dordr) 2013, 36(6):449-457.
Paramonov et al., "Self-assembly of peptide-amphiphile nanofibers: The roles of hydrogen bonding and amphiphilic packing," J. Am. Chem. Soc., 2006, 128, 7291-7298.
Park et al., "Formulation optimization and in vivo proof-of-concept study of thermosensitive liposomes balanced by phospholipid, elastin-like polypeptide, and cholesterol," PLoS One, 2014, 9: e103116, 13 pages.
Parkes et al. "Discovery and development of exenatide: the first antidiabetic agent to leverage the multiple benefits of the incretin hormone, GLP-1," Expert Opinion. Drug Deliv. 8, 2012, 219-244.
Parveen et al., "Nanomedicine," Clinical Pharmacokinetics, 2006, 45(10):965-988.
Patil et al., "Cellular delivery of doxorubicin via pH-controlled hydrazone linkage using multifunctional nano vehicle based on poly(beta-l-malic acid)," Int J Mol Sci, 2012, 13, 11681-11693.
Peeler et al., "Genetically encoded initiator for polymer growth from proteins," J. Am. Chem. Soc. 132, 2010, 13575-13577.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., 2017, 28(5):1403-1412.
Phan et al., "Temperature-responsive self-assembly of charged and uncharged hydroxyethylcellulose-graft-poly(N-isopropylacrylamide) copolymer in aqueous solution," Colloid Polym. Sci., 2011, 289 (9), 993-1003.
Pinkas et al., "Tunable, post-translational hydroxylation of collagen domains in *Escherichia coli*," ACS Chem. Biol., 2011, 6, 320-324.
Pliarchopoulou et al., "Pancreatic cancer: Current and future treatment strategies," Cancer Treatment Reviews, 2009, 35, 431-436.

(56) References Cited

OTHER PUBLICATIONS

Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, 2009, 15.13.1-15.13.9.
Popp et al., "Sortase-Catalyzed Transformations That Improve the Properties of Cytokines," PNAS, 2011, vol. 108, No. 8, pp. 3169-3174.
Potters et al., "12-year outcomes following permanent prostate brachytherapy inpatients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, 2014, 355, 607-619.
Prostate Seed Center, "Brachytherapy seed pre-plan rendering" <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, 2012, 21, 418-429.
Provenzano et al., "Hyaluronan, fluid pressure, and stromal resistance in pancreas cancer," Br J Cancer, 2013, 108, 1-8.
Pulaski et al., "Mouse 4T1 breast tumor model," Curr. Protoc. Immunol., 2001, Chapter 20, Unit 20.2.
Qi et al., Dataset for a brush-polymer conjugate of exendin-4 reduces blood glucose for up to five days and eliminates poly(ethylene glycol) antigenicity. Figshare, 2016, <http://dx.doi.org/10.6084/m9.figshare.3976761> 28 pages.
Qi et al., "Growing polymers from peptides and proteins: a biomedical perspective," Polym. Chem. 5, 2014, 266-276.
Qi et al., "Protein-polymer conjugation—moving beyond PEGylation," Curr. Opin. Chem. Biol. 28, 2015, 181-193.
Qi et al., "Sortase-catalyzed initiator attachment enables high yield growth of a stealth polymer from the C terminus of a protein," Macromol. Rapid Commun. 34, 2013, 1256-1260.
Qiu et al., "Development of Orthotopic Pancreatic Tumor Mouse Models," Methods Mol Biol, 2013, 980: 215-223.
Qiu et al., "Polymer Architecture and Drug Delivery," Pharmaceutical Research, 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Sequence heuristics to encode phase behaviour in intrinsically disordered protein polymers," Nat. Mater., 2015, 14, 1164-1171.
Rabotyagova et al., "Protein-based block copolymers," Biomacromolecules, 2011, 12, 269-289.
Radivojac et al., "Intrinsic Disorder and Functional Proteomics," Biophysical Journal, 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, 2016, 76.
Rankine et al., "Investigating end-to-end accuracy of image guided radiation treatment delivery using a micro-irradiator," Physics in Medicine and Biology, 2013, 58, 7791-7801.
Rao et al., "Synthetic nanoparticles camouflaged with biometric erythrocyte membranes for reduced reticuloendothelial system uptake," Nanotechnology, 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, 2016, 3, 107-110.
Rauscher et al. "Proline and Glycine Control Protein Self-Organization into Elastomeric or Amyloid Fibrils," Structure, 2006, 14:1667-1676.
Regier et al., American Heart Association 2014 Scientific Sessions, 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, 2008, 2(2): p. 141-150.
Ribeiro et al., "Influence of the amino-acid sequence on the inverse temperature transition of elastin-like polypeptides," Biophysical Journal, 2009, 97, 312-320.
Richards et al., "Engineered fibronectin type III domain with a RGDWE sequence binds with enhanced affinity and specificity to human $\alpha v\beta 3$ integrin," J Mol Biol, 2003, 326(5):1475-1488.
Richards et al., "Man's best friend: what can pet dogs teach us about non-Hodgkin lymphoma?" Inmunol Rev., 2016, 263 (1), 173-191.
Riddles et al., "Ellman's reagent: 5,5'-dithiobis(2-nitrobenzoic acid)—a reexamination," Anal Biochem. 1979, 94(1):75-81.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, 2015, 17, 661-670.
Pitcher et al., "Antibodies against polyethylene glycol produced in animals by immunization with monomethoxy polyethylene glycol modified proteins," Int. Arch. Allergy Appl. Immunol 70, 1983, 124-131.
Pitcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., 2015, 589, 2477-2486.
Robinet et al. "Elastin-derived peptides enhance angiogenesis by promoting endothelial cell migration and tubulogenesis through upregulation of MTI-MMP," J. Cell Science, 2005, 118:343-356.
Römer et al., "The elaborate structure of spider silk: structure and function of a natural high performance fiber," Prion 2, 2008, 154-161.
Roopenian et al., "FcRn: the neonatal Fc receptor comes of age," Nat. Rev. Immunol., 2007, vol. 7, No. 9, 715-725.
Rosenberg et al., "Present and future innovations in radiation oncology," Surg Oncol Clin N Am, 2013, 22, 599-618.
Rozak et al., "G148-GA3: a streptococcal virulence module with atypical thermodynamics of folding optimally binds human serum albumin at physiological temperatures," Biochim Biophys Acta, 2005, 1753(2): p. 226-233.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, 2016, 12, 669-685.

(56) References Cited

OTHER PUBLICATIONS

Ryerson et al., "Annual report to the nation on the status of cancer, 1975-2012, featuring the Increasing incidence of liver cancer," Cancer, 2016, 122, 1312-1337.
Saba et al., "A Comparative Oncology Study of Iniparib Defines Its Pharmacokinetic Profile and Biological Activity in a Naturally-Occurring Canine Cancer Model," PLoS One, 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, 2009, 131, 9304-9310.
Saifer et al., "Selectivity of binding of PEGs and PEG-like oligomers to anti-PEG antibodies induced by metho xyPEG-proteins," Molecular Immunology 57, 2014, 236-246.
Sandler et al., "Gemcitabine: Single-Agent and Combination Therapy in Non-Small Cell Lung Cancer," Oncologist 1999, 4(3)241-251.
Schaal et al., "Biopolymer β-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, 2016, 228, 58-66.
Schellenberg et al., "Gemcitabine chemotherapy and single-fraction stereotactic body radiotherapy for locally advanced pancreatic cancer," Int J Radiation Oncol Biol Phys, 2008, 72, 678-686.
Schellenberg et al., "Single-fraction stereotactic body radiation therapy and sequential gemcitabine for the treatment of locally advanced pancreatic cancer," Int J Radiation Oncology Biol Phys, 2011, 81, 181-188.
Schellenberger et al., "A recombinant polypeptide extends the in vivo half-life of peptides and proteins in a tunable manner," Nat. Biotechnol. 27, 2009, 1186-1188.
Schlaff et al., "Bringing the heavy: carbon ion therapy in the radiobiological clinical context," Radiation Oncology, 2014, 9, 1-18.
Schneider et al., "NIH Image to ImageJ: 25 years of image analysis," Nature Methods, 2012, 9, 671-675.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., 2007, 93, 2429-2435.
Shadwick, "Mechanical design in arteries," J Exp Biol, 1999, 202, 3305-3313.
Shang et al., "pH-Dependent Protein Conformational Changes in Albumin:Gold Nanoparticle Bioconjugates: A Spectroscopic Study," Langmuir, 2007, 23 (5), 2714-2721.
Shao et al., "Super-resolution 3D microscopy of live whole cells using structured illumination," Nat Methods, 2011, 8, 1044-1046.
Shen et al., "Conjugation site modulates the in vivo stability and thearpeutic activity of antibody-drug conjugates," Nat Biotechnol, 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, 2009, 10:1955-1961.
Sherman et al., "Next-Generation PEGylation Enables Reduced Immunoreactivity of PEG-Protein Conjugates," Drug and Development & Delivery, 2012, vol. 12, No. 5, 36-42.
Sherman et al., "Role of the Methoxy Group in Immune Responses to mPEG-Protein Conjugates," Bioconjugate Chemistry, 2012, 23, 485-499.
Shi et al., "Cell adhesion on a POEGMA-modified topographical surface," Langmuir: the ACS journal of surfaces and colloids, 2012, 28 (49), 17011-8.
Shimoboji et al., "Temperature-Induced Switching of Enzyme Activity with Smart Polymer-Enzyme Conjugates," Bioconjugate Chem. 2003, 14, 517-525.
Siegel et al., "Absorbed fractions for electrons and beta particles in spheres of various sizes," J Nucl Med, 1994, 35, 152-156.
Siegwart et al., "ATRP in the Design of Functional Materials for Biomedical Applications," Prog Polymer Science, 2012, vol. 37, No. 1, pp. 18-37.
Silberstein et al., "The SNM Practice Guideline for Therapy of Thyroid Disease with $^{131}$I, 3.0," J Nucl Med, 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules 45, 2012, 6371-6379.
Simnick et al., "In vivo tumor targeting by a NGR-decorated micelle of a recombinant diblock copolypeptide," J Control Release, 2011, 155, 144-151.
Simnick et al., "Morphing low-affinity ligands into high-avidity nanoparticles by thermally triggered self-assembly of a genetically encoded polymer," ACS Nano, 2010, 4, 2217-2227.
Sisson et al., "Radiation safety in the treatment of patients with thyroid diseases by radioiodine 131I: practice recommendations of the American Thyroid Association," Thyroid, 2011, 21, 335-346.
Sonawane et al., "Hydrazo linkages in pH responsive drug delivery systems," European Journal Pharmaceutical Sciences, 2017, 99, 45-65.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, 2016, 234:83-89.
Sriraman et al., "Barriers to drug delivery in solid tumors," Tissue Barriers, 2014, 2, 2-10.
Stefl et al., "RNA sequence-and shape-dependent recognition by proteins in the ribonucleoprotein particle" EMBO reports (2005) 6(1):33-38.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, 2007, 20(11): p. 569-576.
Strohmaier et al., "Comparison of $^{60}$Co and $^{192}$Ir sources in HDR brachytherapy," J Contemp Brachyther, 2011, 3, 199-208.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, 2015, 10, 1-17.
Sumerlin, "Proteins as Initiators of Controlled Radical Polymerization: Grafting-from via ATRP and RAFT," ACS Macro Lett. 2012, 1, 141-145.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, 2015, 16, 438-449.
Sun et al., "Eus-guided interstitial brachytherapy of the pancreas: a feasibility study," Gastrointestinal Endoscopy, 2005, 62, 775-779.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.

(56) References Cited

OTHER PUBLICATIONS

Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng 2014, 42, 1508-1516.
Swee et al., "Sortase-mediated modification of αDEC205 affords optimization of antigen presentation and immunization against a set of viral epitopes," Proc Natl Acad Sci USA, 2013, 110(4):1428-1433.
Swers et al., Multivalent Scaffold Proteins as Superagonists of TRAIL Receptor 2-Induced Apoptosis, Mol Cancer Ther, 2013, 12, 1235-1244.
Takalkar et al., "Radium-223 dichloride bone-targeted alpha particle therapy for hormone-refractory breast cancer metastatic to bone," Exp Hematol Oncol, 2014, 8, 23.
Tallarida, "Quantitative methods for assessing drug synergism," Genes & Cancer, 2011, 2, 1003-1008.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, 2006, 45, 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., 2016, 15, 419-424.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., 2016, 15, 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, 2012, 3 (10), 2743-2751.
Teicher, "Invivo/ex vivo and in situ assays used in cancer research: a brief review," Toxicol. Pathol., 2009, 37 (1), 114-122.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tompa et al., "Fuzzy complexes: polymorphism and structural disorder in protein-protein interactions," Trends Biochem Sci, 2008, 33, 2-8.
Tong et al., "Protein Modification with Amphiphilic Block Copoly(2-oxazoline)s as a New Platform for Enhanced Cellular Delivery," Mol. Pharm., 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, 2014, 24, 140-147.
Trieu et al., "P0157 Preclinical evaluation of NBN-paclitaxel in pancreatic cancer xenograft models," Eur J Cancer, 2014, 50, e53.
Triola et al., "Chemical biology of lipidated proteins," ACS Chemical Biology, 2012, 7, 87-99.
Troyanskaya et al., "Nonparametric methods for identifying differentially expressed genes in microarray data," Bioinformatics, 2002, 18(11):1454-61.
Tsarevsky et al., "Deactivation efficiency and degree of control over polymerization in ATRP in protic solvents," Macromolecules 37, 2004, 9768-9778.
Tsume et al., "The development of orally administrable gemcitabine prodrugs with D-enantiomer amino acids: Enhanced membrane permeability and enzymatic stability," Eur. J. Pharm. Biopharm. 2014, 86(3):514-523.
Tu et al., "Stages in tropoelastin coalescence during synthetic elastin hydrogel formation," Micron, 2010, 41, 268-272.
Turunen et al., "Paclitaxel Succinate Analogs: Anionic Introduction as a Strategy to Impart Blood Brain Barrier Permeability," Bioorg Med Chem Lett, 2008, 18(22):5971-5974.
Tward et al., "Survival of men with clinically localized prostate cancer treated with prostatectomy, brachytherapy, or no definitive treatment: impact of age at diagnosis," Cancer, 2006, 107, 2392-2400, doi:10.1002/cncr.22261.
Uchida et al., "Potential of adenovirus-mediated REIC/Dkk-3 gene therapy for use in the treatment of pancreatic cancer," Journal of Gastroenterology and Hepatology, 2014, 29, 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Nail Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Protein elasticity based on conformations of sequential polypeptides: The biological elastic fiber," J Protein Chemistry, 1984, 3, 403-436.
Valkenburg et al., "Targeting the tumour stroma to improve cancer therapy," Nature Reviews Clinical Oncology, 2018, 15, 366-381.
Van der Lee et al., "Classification of intrinsically disordered regions and proteins," Chem Rev, 2014, 114, 6589-6631.
Van Roey et al., "Short linear motifs: ubiquitous and functionally diverse protein interaction modules directing cell regulation," Chem Rev, 2014, 114, 6733-6778.
Van Roy, "Beyond E-cadherin: roles of other cadherin superfamily members in cancer," Nat Rev Cancer, 2014, 14, 121-134.
Vasey et al., "Phase I clinical and Pharmacokinetic study of PK1 (N-(2-Hydroxypropyl)methacrylamide Copolymer Doxorubicin): First

(56) References Cited

OTHER PUBLICATIONS member of a New Class of Chemotherapeutic Agents-Drugs-Polymer Conjugates" Clinical Cancer Research, 1999, 5:83-94.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., 2011, vol. 22, pp. 976-986.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., 2011, vol. 7, No. 4, pp. 214-220.
Vrhovski et al., "Biochemistry of tropoelastin," Eur J Biochem, 1998, 258, 1-18.
Vrignaud et al., "Strategies for the nanoencapsulation of hydrophilic molecules in polymer-based nanoparticles," Biomaterials 2011, 32(33):8593-8604.
Walczak, "Death Receptor-Ligand Systems in Cancer, Cell Death, and Inflammation," Cold Spring Harb. Perspect. Biol., 2013, 5, a008698.
Walsh et al., "Post-translational modifications in the context of therapeutic proteins," Nat. Biotechnol., 2006, 24, 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "Enhanced Tumor Delivery of Gemcitabine via PEG-DSPE/TPGS Mixed Micelles," Mol. Pharm. 2014, 11, 1140-1150.
Wang et al., "Extending Half Life of H-Ferritin Nanoparticle by Fusing Albumin Binding Domain for Doxorubicin Encapsulation," Biomacromolecules, 2018, 12, 19(3):773-781.
Wang et al., "Quantitative Mapping of the Spatial Distribution of Nanoparticles in Endo-Lysosomes by Local pH," Nano Lett, 2017, 17(2): 1226-1232.
Wang et al., "Size and dynamics of caveolae studied using nanoparticles in living endothelial cells," ACS nano, 2009, 3(12): p. 4110-4116.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wei et al., "Anticancer drug nanomicelles formed by self-assembling amphiphilic dendrimer to combat cancer drug resistance," Proceedings of the National Academy of Sciences of the United States of America, 2015, 112(10): 2978-2983.
Wendt et al., "DNA-mediated Folding and Assembly of MyoD-E47 Heterodimers," Journal of Biol. Chem., 1998, 273(10):5735-5743.
Werle et al., "Strategies to improve plasma half life time of peptide and protein drugs," Amino Acids 30, 2006, 351-367.
Wienkers et al., "Predicting in vivo drug interactions from in vitro drug discovery data," Nat. Rev. Drug. Discov. 2005, 4(10):825-833.
Williams et al., "Targeted radionuclide therapy," Medical Physics, 2008, 35, 3062-3068.
Williamson et al., "Efficient N-terminal labeling of proteins by use of sortase," Angew Chem Int ed Engl, 2012, 51(37):9377-9380.
Winzell et al., "The high-fat diet-fed mouse: a model for studying mechanisms and treatment of impaired glucose tolerance and type 2 diabetes," Diabetes 53, 2004, S215-S219.

Wold, "Invivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc. 2010, 132, 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, 2016, 79, 405-412.
Xia et al., "Tunable self-assembly of genetically engineered silk-elastin-like protein polymers," Biomacromolecules, 2011, 12, 3844-3850.
Xu et al., "A quality by design (QbD) case study on liposomes containing hydrophilic API: II. Screening of critical variables, and establishment of design space at laboratory scale," Int. J. Pharm. 2012, 423(2):543-553.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Genetically engineered block copolymers: influence of the length and structure of the coiled-coil blocks on hydrogel self-assembly," Pharm Res, 2008, 25, 674-682.
Xu et al., "Role of pancreatic stellate cells in pancreatic cancer metastasis," Am J of Pathology, 2010, 177, 2585-2596.
Xu et al., "Self-assembly behavior of peptide amphiphiles (PAs) with different length of hydrophobic alkyl tails," Colloids Surfaces B Biointerfaces, 2010, 81, 329-335.
Yang et al., "Poly(carboxybetaine) nanomaterials enable long circulation and prevent polymer-specific antibody production," Nano Today, 2014, 9(1):10-16.
Yates et al., "Contemporary management of patients with high-risk non-muscle-invasive bladder cancer who fail intravesical BCG therapy," World journal of urology, 2011, 29, 415-422.
Yeo et al., "Coacervation of tropoelastin," Adv Colloid Interface Sci, 2011, 167, 94-103.
Yokoe et al., "Albumin-conjugated PEG liposome enhances tumor distribution of liposomal doxorubicin in rats," International Journal of Pharmaceutics, 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release 117, 2007, 371-379.
Yousefpour et al., "Co-opting biology to deliver drugs," Biotechnol Bioeng, 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett 2018, 18(12): 7784-7793.

(56) References Cited

OTHER PUBLICATIONS

Yu et al., "Effectiveness and security of CT-guided percutaneous implantation of (125)I seeds in pancreatic carcinoma," The Britishjournal of radiology, 2014, 87, 20130642, 7 pages.
Zhang et al., "A self-assembly pathway to aligned monodomain gels," Nat. Mater., 2010, 9, 594-601.
Zhang et al., "Nanoparticles in medicine: therapeutic applications and developments," Clin. Pharmacol. Ther. 2008, 83(5):761-769.
Zhang et al., "Novel agents for pancreatic ductal adenocarcinoma: emerging therapeutics and future directions," Jounral of Hematology & Oncology, 2018, 11:14, 17 pages.
Zhang et al., "Shape Effects of Nanoparticles Conjugated with Cell-Penetrating Peptides (HIV Tat PTD) on CHO Cell Uptake," Bioconjugate Chem, 2008, 19(9):1880-1887.
Zhao et al., "A new Bliss Independence model to analyze drug combination data," J Biomol Screen, 2014, 19, 817-821.
Zhao et al., "Fluorescence probe techniques used to study micelle formation in water-soluble block copolymers," Langmuir 1990, 6(2):514-516.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, 2011, 60, 1055-1065.
Zong et al., "Crystal structures of *Staphylococcus aureus* sortase A and its substrate complex," J. Biol. Chem. 279, 2004, 31383-31389.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Agarwal et al., "One-step microfluidic generation of pre-hatching embryo-like core-shell microcapsules for miniaturized 3D culture of pluripotent stem cells," Lab Chip, 2013, 13: 4525-4533.
Amiram et al., "Evolution of translation machinery in recoded bacteria enables multi-site incorporation of nonstandard amino acids," Nat Biotechnol, 2015, 33: 1272-1279.
Appleyard et al., "Multiplexed protein quantification with barcoded hydrogel microparticles," Anal Chem, 2011, 83: 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci U S A, 2019, 116: 7889-7898.
Cha et al., "Microfluidics-assisted fabrication of gelatin-silica core-shell microgels for injectable tissue constructs," Biomacromolecules, 2014, 15: 283-290.
Chapin et al., "Rapid microRNA profiling on encoded gel microparticles," Angew Chem Int Ed Engl, 2011, 50: 2289-2293.
Chin et al., "Addition of p-azido-l-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84 9370-9378.
Choi et al., "Recent advances in engineering microparticles and their nascent utilization in biomedical delivery and diagnostic applications," Lab Chip, 2017,17: 591-613.
Chu et al., "Controllable monodisperse multiple emulsions," Angew Chem Int Ed Engl, 2007,46: 8970-8974.
Costa et al., "Photo-crosslinkable unnatural amino acids enable facile synthesis of thermoresponsive nano-to microgels of intrinsically disordered polypeptides," Adv Mater, 2018, 30(5): 1704878.
Darling et al., "Viscoelastic properties of zonal articular chondrocytes measured by atomic force microscopy," Osteoarthritis Cartilage, 2006, 14: 571-579.
Griffin et al., "Accelerated wound healing by injectable microporous gel scaffolds assembled from annealed building blocks," Nat Mater, 2015, 14: 737-744.
Hutter et al., "Calibration of atomic-force microscope tips," Review of Scientific Instruments, 1993, 64:1868-1873.
Hwang et al., "Differentially degradable janus particles for controlled release applications," Macromol Rapid Commun, 2012, 33:1178-1183.
Jang et al., "Engineering Globular Protein Vesicles through Tunable Self-Assembly of Recombinant Fusion Proteins," Small, 2017, 13(36): 1700399.
Khademhosseini et al., "Micromolding of photocrosslinkable hyaluronic acid for cell encapsulation and entrapment," J Biomed Mater Res A, 2006, 79: 522-532.
Kim et al., "Generation of core-shell microcapsules with three-dimensional focusing device for efficient formation of cell spheroid," Lab Chip, 2011, 11: 246-252.
Liu, L. et al., "Monodisperse core-shell chitosan microcapsules for pH-responsive burst release of hydrophobic drugs," Soft Matter, 2011, 7: 4821-4827.
Ma et al., "Core-shell hydrogel microcapsules for improved islets encapsulation," Adv Healthc Mater, 2013,2: 667-672.
Matsunaga et al., "Molding cell beads for rapid construction of macroscopic 3D tissue architecture," Adv Mater, 2011, 23: H90-94.

(56) References Cited

OTHER PUBLICATIONS

Oh et al., "The development of microgels/nanogels for drug delivery applications," Progress in Polymer Science, 2008, 33(4): 448-477.
Panda et al., "Stop-flow lithography to generate cell-laden microgel particles," Lab Chip, 2008, 8:1056-1061.
Paulsen et al., "Optofluidic fabrication for 3D-shaped particles," Nat Commun, 2015, 6: 6976.
Roberts et al., "Injectable tissue integrating networks from recombinant polypeptides with tunable order," Nature Materials, 2018, 17(12): 1154-1163.
Rodriguez-Cabello et al., "Elastin-like polypeptides in drug delivery," Adv Drug Deliv Rev, 2016, 97: 85-100.
Song et al., "Budding-like division of all-aqueous emulsion droplets modulated by networks of protein nanofibrils," Nat Commun, 2018, 9: 2110.
Srinivas et al., "Aptamer-functionalized microgel particles for protein detection," Anal Chem, 2011, 83: 9138-9145.
Tsuda et al., "Monodisperse cell-encapsulating peptide microgel beads for 3D cell culture," Langmuir, 2010, 26 2645-2649.
Utada et al., "Monodisperse double emulsions generated from a microcapillary device," Science, 2005, 308: 537-541.
Uversky, "Protein intrinsic disorder-based liquid-liquid phase transitions in biological systems: Complex coacervates and membraneless organelles," Adv Colloid Interface Sci, 2017, 239: 97-114.
Volodkin et al., "One-Step Formulation of Protein Microparticles with Tailored Properties: Hard Templating at Soft Conditions," Advanced Functional Materials, 2012, 22:1914-1922.
Wang et al., "Functional polymeric microparticles engineered from controllable microfluidic emulsions," Acc Chem Res, 2014, 47: 373-384.
Yeh et al., "Micromolding of shape-controlled, harvestable cell-laden hydrogels," Biomaterials, 2006, 27: 5391-5398.
United States Patent Office Action for U.S. Appl. No. 16/305,696 dated Jan. 28, 2021 (15 pages).
Resh, "Covalent Lipid Modifications of Proteins," Curr Biol., May 2013, 23(10): R431-R435.
United States Patent Office Action for U.S. Appl. No. 16/477,229 dated Apr. 12, 2021 (14 pages).
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
UniProtKB—P15214 (GST_PROM1) acessed online at <https://www.uniprot.org/uniprot/P152146/> on Jun. 8, 2021, 7 pages.
Frandsen et al., "Recombinant protein-based polymers for advanced drug delivery," Chem Soc Rev, 2012, 41:2696-2706.
Hess et al., "Graphene Transistors for Multifunctional Polymer Brushes for Biosensing Applications," Applied Materials & Interfaces, 2014, 6: 9705-9710.
Hwang et al., "Synthesis and Characterization of Polystyrene Brushes for Organic Thin Film Transistors," Journal of Nanoscience and Nanotechnology, 2012, 12: 4137-4141.
Park et al., "Polymer Brush As a Facile Dielectric Surface Treatment for High-Performance, Stable, Soluble Acene-Based Transistors," Chemistry of Materials, 2010, 22: 5377-5382.
United States Patent Office Action for U.S. Appl. No. 15/749,797 dated May 12, 2021 (19 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).

* cited by examiner

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: REPEAT
<222> LOCATION: (1)..(5)
<223> OTHER INFORMATION: Repeat unit: repeating between 20 to 240 times

<400> SEQUENCE: 1

Xaa Gly Val Pro Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is Y, F or W
<220> FEATURE:
<221> NAME/KEY: REPEAT
<222> LOCATION: (1)..(4)
<223> OTHER INFORMATION: Repeat unit: repeating between 1 to 50 times
<220> FEATURE:
<221> NAME/KEY: REPEAT
<222> LOCATION: (2)..(4)
<223> OTHER INFORMATION: Repeat unit: G repeating between 0 to 3 times

<400> SEQUENCE: 2

Xaa Gly Gly Gly
1

<210> SEQ ID NO 3
<211> LENGTH: 6
```

```
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(3)
<223> OTHER INFORMATION: Repeat unit: more than 1 CGG repeat unit may be
      present
<220> FEATURE:
<221> NAME/KEY: REPEAT
<222> LOCATION: (4)..(6)
<223> OTHER INFORMATION: Repeat unit: more than 1 CGG repeat unit may be
      present

<400> SEQUENCE: 3

Cys Gly Gly Cys Gly Gly
1               5

<210> SEQ ID NO 4
<211> LENGTH: 2
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(2)
<223> OTHER INFORMATION: Repeat unit:  Xaa Gly may repeat 4 to 8 times
<220> FEATURE:
<221> NAME/KEY: misc_feature
<222> LOCATION: (1)..(1)
<223> OTHER INFORMATION: Xaa is Y, F or W

<400> SEQUENCE: 4

Xaa Gly
1

<210> SEQ ID NO 5
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(36)
<223> OTHER INFORMATION: Repeat unit: up to 8 CGG repeat units may be
      absent

<400> SEQUENCE: 5

Cys Gly Gly Cys Gly Gly Cys Gly Gly Cys Gly Gly Cys Gly Gly Cys
1               5                   10                  15

Gly Gly Cys Gly Gly Cys Gly Gly Cys Gly Gly Cys Gly Gly Cys Gly
                20                  25                  30

Gly Cys Gly Gly
        35

<210> SEQ ID NO 6
<211> LENGTH: 800
<212> TYPE: PRT
<213> ORGANISM: Artificial Sequence
<220> FEATURE:
<223> OTHER INFORMATION: Synthetic

<400> SEQUENCE: 6

Ala Gly Val Pro Gly Ala Gly Val Pro Gly Ala Gly Val Pro Gly Ala
1               5                   10                  15

Gly Val Pro Gly Ala Gly Val Pro Gly Ala Gly Val Pro Gly Ala Gly
```

```
            20                  25                  30
Val Pro Gly Ala Gly Val Pro Gly Ala Gly Val Pro Gly Ala Gly Val
            35                  40                  45
Pro Gly Ala Gly Val Pro Gly Ala Gly Val Pro Gly Ala Gly Val Pro
            50                  55                  60
Gly Ala Gly Val Pro Gly Ala Gly Val Pro Gly Ala Gly Val Pro Gly
65                  70                  75                  80
Ala Gly Val Pro Gly Ala Gly Val Pro Gly Ala Gly Val Pro Gly Ala
            85                  90                  95
Gly Val Pro Gly Ala Gly Val Pro Gly Ala Gly Val Pro Gly Ala Gly
            100                 105                 110
Val Pro Gly Ala Gly Val Pro Gly Ala Gly Val Pro Gly Ala Gly Val
            115                 120                 125
Pro Gly Ala Gly Val Pro Gly Ala Gly Val Pro Gly Ala Gly Val Pro
            130                 135                 140
Gly Ala Gly Val Pro Gly Ala Gly Val Pro Gly Ala Gly Val Pro Gly
145                 150                 155                 160
Ala Gly Val Pro Gly Ala Gly Val Pro Gly Ala Gly Val Pro Gly Ala
            165                 170                 175
Gly Val Pro Gly Ala Gly Val Pro Gly Ala Gly Val Pro Gly Ala Gly
            180                 185                 190
Val Pro Gly Ala Gly Val Pro Gly Ala Gly Val Pro Gly Ala Gly Val
            195                 200                 205
Pro Gly Ala Gly Val Pro Gly Ala Gly Val Pro Gly Ala Gly Val Pro
            210                 215                 220
Gly Ala Gly Val Pro Gly Ala Gly Val Pro Gly Ala Gly Val Pro Gly
225                 230                 235                 240
Ala Gly Val Pro Gly Ala Gly Val Pro Gly Ala Gly Val Pro Gly Ala
            245                 250                 255
Gly Val Pro Gly Ala Gly Val Pro Gly Ala Gly Val Pro Gly Ala Gly
            260                 265                 270
Val Pro Gly Ala Gly Val Pro Gly Ala Gly Val Pro Gly Ala Gly Val
            275                 280                 285
Pro Gly Ala Gly Val Pro Gly Ala Gly Val Pro Gly Ala Gly Val Pro
            290                 295                 300
Gly Ala Gly Val Pro Gly Ala Gly Val Pro Gly Ala Gly Val Pro Gly
305                 310                 315                 320
Ala Gly Val Pro Gly Ala Gly Val Pro Gly Ala Gly Val Pro Gly Ala
            325                 330                 335
Gly Val Pro Gly Ala Gly Val Pro Gly Ala Gly Val Pro Gly Ala Gly
            340                 345                 350
Val Pro Gly Ala Gly Val Pro Gly Ala Gly Val Pro Gly Ala Gly Val
            355                 360                 365
Pro Gly Ala Gly Val Pro Gly Ala Gly Val Pro Gly Ala Gly Val Pro
            370                 375                 380
Gly Ala Gly Val Pro Gly Ala Gly Val Pro Gly Ala Gly Val Pro Gly
385                 390                 395                 400
Ala Gly Val Pro Gly Ala Gly Val Pro Gly Ala Gly Val Pro Gly Ala
            405                 410                 415
Gly Val Pro Gly Ala Gly Val Pro Gly Ala Gly Val Pro Gly Ala Gly
            420                 425                 430
Val Pro Gly Ala Gly Val Pro Gly Ala Gly Val Pro Gly Ala Gly Val
            435                 440                 445
```

Pro Gly Ala Gly Val Pro Gly Ala Gly Val Pro Gly Ala Gly Val Pro
        450                 455                 460
Gly Ala Gly Val Pro Gly Ala Gly Val Pro Gly Ala Gly Val Pro Gly
465                 470                 475                 480
Ala Gly Val Pro Gly Ala Gly Val Pro Gly Ala Gly Val Pro Gly Ala
            485                 490                 495
Gly Val Pro Gly Ala Gly Val Pro Gly Ala Gly Val Pro Gly Ala Gly
        500                 505                 510
Val Pro Gly Ala Gly Val Pro Gly Ala Gly Val Pro Gly Ala Gly Val
    515                 520                 525
Pro Gly Ala Gly Val Pro Gly Ala Gly Val Pro Gly Ala Gly Val Pro
        530                 535                 540
Gly Ala Gly Val Pro Gly Ala Gly Val Pro Gly Ala Gly Val Pro Gly
545                 550                 555                 560
Ala Gly Val Pro Gly Ala Gly Val Pro Gly Ala Gly Val Pro Gly Ala
            565                 570                 575
Gly Val Pro Gly Ala Gly Val Pro Gly Ala Gly Val Pro Gly Ala Gly
        580                 585                 590
Val Pro Gly Ala Gly Val Pro Gly Ala Gly Val Pro Gly Ala Gly Val
    595                 600                 605
Pro Gly Ala Gly Val Pro Gly Ala Gly Val Pro Gly Ala Gly Val Pro
        610                 615                 620
Gly Ala Gly Val Pro Gly Ala Gly Val Pro Gly Ala Gly Val Pro Gly
625                 630                 635                 640
Ala Gly Val Pro Gly Ala Gly Val Pro Gly Ala Gly Val Pro Gly Ala
            645                 650                 655
Gly Val Pro Gly Ala Gly Val Pro Gly Ala Gly Val Pro Gly Ala Gly
        660                 665                 670
Val Pro Gly Ala Gly Val Pro Gly Ala Gly Val Pro Gly Ala Gly Val
    675                 680                 685
Pro Gly Ala Gly Val Pro Gly Ala Gly Val Pro Gly Ala Gly Val Pro
        690                 695                 700
Gly Ala Gly Val Pro Gly Ala Gly Val Pro Gly Ala Gly Val Pro Gly
705                 710                 715                 720
Ala Gly Val Pro Gly Ala Gly Val Pro Gly Ala Gly Val Pro Gly Ala
            725                 730                 735
Gly Val Pro Gly Ala Gly Val Pro Gly Ala Gly Val Pro Gly Ala Gly
        740                 745                 750
Val Pro Gly Ala Gly Val Pro Gly Ala Gly Val Pro Gly Ala Gly Val
    755                 760                 765
Pro Gly Ala Gly Val Pro Gly Ala Gly Val Pro Gly Ala Gly Val Pro
        770                 775                 780
Gly Ala Gly Val Pro Gly Ala Gly Val Pro Gly Ala Gly Val Pro Gly
785                 790                 795                 800

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Tyr Gly Tyr Gly Tyr Gly Tyr Gly Tyr Gly Tyr Gly
1               5                   10

<210> SEQ ID NO 8
<211> LENGTH: 24
<212> TYPE: PRT
<213> ORGANISM: Artificial Sequence
<220> FEATURE:
<223> OTHER INFORMATION: Synthetic

<400> SEQUENCE: 8

Cys Gly Gly Cys Gly Gly Cys Gly Gly Cys Gly Gly Cys Gly Gly Cys
1               5                   10                  15

Gly Gly Cys Gly Gly Cys Gly Gly
            20

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Ser Lys Gly Pro Gly
1               5

<210> SEQ ID NO 10
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: REPEAT
<222> LOCATION: (6)..(10)
<223> OTHER INFORMATION: Repeat unit: repeating between 20 to 240 times
<220> FEATURE:
<221> NAME/KEY: MISC_FEATURE
<222> LOCATION: (11)..(11)
<223> OTHER INFORMATION: Xaa is Y, F or W
<220> FEATURE:
<221> NAME/KEY: REPEAT
<222> LOCATION: (11)..(14)
<223> OTHER INFORMATION: Repeat unit: repeating between 1 to 50 times
<220> FEATURE:
<221> NAME/KEY: REPEAT
<222> LOCATION: (12)..(14)
<223> OTHER INFORMATION: Repeat unit: G repeating between 0 to 3 times
<220> FEATURE:
<221> NAME/KEY: REPEAT
<222> LOCATION: (15)..(17)
<223> OTHER INFORMATION: Repeat unit: more than 1 CGG repeat unit may be
      present
<220> FEATURE:
<221> NAME/KEY: REPEAT
<222> LOCATION: (18)..(20)
<223> OTHER INFORMATION: Repeat unit: more than 1 CGG repeat unit may be
      present

<400> SEQUENCE: 10

Ser Lys Gly Pro Gly Xaa Gly Val Pro Gly Xaa Gly Gly Cys Gly
1               5                   10                  15

Gly Cys Gly Gly Trp Pro
            20

<210> SEQ ID NO 11
<211> LENGTH: 5

<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: REPEAT
<222> LOCATION: (1)..(5)
<223> OTHER INFORMATION: Repeat unit: repeating between 120 to 200
      times

<400> SEQUENCE: 11

Xaa Gly Val Pro Gly
1               5

<210> SEQ ID NO 12
<211> LENGTH: 77
<212> TYPE: DNA
<213> ORGANISM: Artificial Sequence
<220> FEATURE:
<223> OTHER INFORMATION: Synthetic

<400> SEQUENCE: 12
gggccggagt gcctggtgca ggtgtgccag gcgcgggtgt tccaggagca ggcgttccag    60
gtgcgggtgt tcctggc                                                  77

<210> SEQ ID NO 13
<211> LENGTH: 77
<212> TYPE: DNA
<213> ORGANISM: Artificial Sequence
<220> FEATURE:
<223> OTHER INFORMATION: Synthetic

<400> SEQUENCE: 13
ccgccaggaa cacccgcacc tggaacgcct gctcctggaa cacccgcgcc tggcacacct    60
gcaccaggca ctccggc                                                  77

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Met Ser Lys Gly Pro Gly
1               5

<210> SEQ ID NO 15
<211> LENGTH: 843
<212> TYPE: PRT
<213> ORGANISM: Artificial Sequence
<220> FEATURE:
<223> OTHER INFORMATION: Synthetic

<400> SEQUENCE: 15

Ser Lys Gly Pro Gly Ala Gly Val Pro Gly Ala Gly Val Pro Gly Ala
1               5                   10                  15

Gly Val Pro Gly Ala Gly Val Pro Gly Ala Gly Val Pro Gly Ala Gly
                20                  25                  30

Val Pro Gly Ala Gly Val Pro Gly Ala Gly Val Pro Gly Ala Gly Val
            35                  40                  45

```
Pro Gly Ala Gly Val Pro Gly Ala Gly Val Pro Gly Ala Gly Val Pro
    50                  55                  60
Gly Ala Gly Val Pro Gly Ala Gly Val Pro Gly Ala Gly Val Pro Gly
65                  70                  75                  80
Ala Gly Val Pro Gly Ala Gly Val Pro Gly Ala Gly Val Pro Gly Ala
                85                  90                  95
Gly Val Pro Gly Ala Gly Val Pro Gly Ala Gly Val Pro Gly Ala Gly
            100                 105                 110
Val Pro Gly Ala Gly Val Pro Gly Ala Gly Val Pro Gly Ala Gly Val
        115                 120                 125
Pro Gly Ala Gly Val Pro Gly Ala Gly Val Pro Gly Ala Gly Val Pro
    130                 135                 140
Gly Ala Gly Val Pro Gly Ala Gly Val Pro Gly Ala Gly Val Pro Gly
145                 150                 155                 160
Ala Gly Val Pro Gly Ala Gly Val Pro Gly Ala Gly Val Pro Gly Ala
                165                 170                 175
Gly Val Pro Gly Ala Gly Val Pro Gly Ala Gly Val Pro Gly Ala Gly
            180                 185                 190
Val Pro Gly Ala Gly Val Pro Gly Ala Gly Val Pro Gly Ala Gly Val
        195                 200                 205
Pro Gly Ala Gly Val Pro Gly Ala Gly Val Pro Gly Ala Gly Val Pro
    210                 215                 220
Gly Ala Gly Val Pro Gly Ala Gly Val Pro Gly Ala Gly Val Pro Gly
225                 230                 235                 240
Ala Gly Val Pro Gly Ala Gly Val Pro Gly Ala Gly Val Pro Gly Ala
                245                 250                 255
Gly Val Pro Gly Ala Gly Val Pro Gly Ala Gly Val Pro Gly Ala Gly
            260                 265                 270
Val Pro Gly Ala Gly Val Pro Gly Ala Gly Val Pro Gly Ala Gly Val
        275                 280                 285
Pro Gly Ala Gly Val Pro Gly Ala Gly Val Pro Gly Ala Gly Val Pro
    290                 295                 300
Gly Ala Gly Val Pro Gly Ala Gly Val Pro Gly Ala Gly Val Pro Gly
305                 310                 315                 320
Ala Gly Val Pro Gly Ala Gly Val Pro Gly Ala Gly Val Pro Gly Ala
                325                 330                 335
Gly Val Pro Gly Ala Gly Val Pro Gly Ala Gly Val Pro Gly Ala Gly
            340                 345                 350
Val Pro Gly Ala Gly Val Pro Gly Ala Gly Val Pro Gly Ala Gly Val
        355                 360                 365
Pro Gly Ala Gly Val Pro Gly Ala Gly Val Pro Gly Ala Gly Val Pro
    370                 375                 380
Gly Ala Gly Val Pro Gly Ala Gly Val Pro Gly Ala Gly Val Pro Gly
385                 390                 395                 400
Ala Gly Val Pro Gly Ala Gly Val Pro Gly Ala Gly Val Pro Gly Ala
                405                 410                 415
Gly Val Pro Gly Ala Gly Val Pro Gly Ala Gly Val Pro Gly Ala Gly
            420                 425                 430
Val Pro Gly Ala Gly Val Pro Gly Ala Gly Val Pro Gly Ala Gly Val
        435                 440                 445
Pro Gly Ala Gly Val Pro Gly Ala Gly Val Pro Gly Ala Gly Val Pro
    450                 455                 460
Gly Ala Gly Val Pro Gly Ala Gly Val Pro Gly Ala Gly Val Pro Gly
```

-continued

```
465                 470                 475                 480
Ala Gly Val Pro Gly Ala Gly Val Pro Gly Ala Gly Val Pro Gly Ala
                485                 490                 495
Gly Val Pro Gly Ala Gly Val Pro Gly Ala Gly Val Pro Gly Ala Gly
                500                 505                 510
Val Pro Gly Ala Gly Val Pro Gly Ala Gly Val Pro Gly Ala Gly Val
                515                 520                 525
Pro Gly Ala Gly Val Pro Gly Ala Gly Val Pro Gly Ala Gly Val Pro
        530                 535                 540
Gly Ala Gly Val Pro Gly Ala Gly Val Pro Gly Ala Gly Val Pro Gly
545                 550                 555                 560
Ala Gly Val Pro Gly Ala Gly Val Pro Gly Ala Gly Val Pro Gly Ala
                565                 570                 575
Gly Val Pro Gly Ala Gly Val Pro Gly Ala Gly Val Pro Gly Ala Gly
                580                 585                 590
Val Pro Gly Ala Gly Val Pro Gly Ala Gly Val Pro Gly Ala Gly Val
                595                 600                 605
Pro Gly Ala Gly Val Pro Gly Ala Gly Val Pro Gly Ala Gly Val Pro
        610                 615                 620
Gly Ala Gly Val Pro Gly Ala Gly Val Pro Gly Ala Gly Val Pro Gly
625                 630                 635                 640
Ala Gly Val Pro Gly Ala Gly Val Pro Gly Ala Gly Val Pro Gly Ala
                645                 650                 655
Gly Val Pro Gly Ala Gly Val Pro Gly Ala Gly Val Pro Gly Ala Gly
                660                 665                 670
Val Pro Gly Ala Gly Val Pro Gly Ala Gly Val Pro Gly Ala Gly Val
                675                 680                 685
Pro Gly Ala Gly Val Pro Gly Ala Gly Val Pro Gly Ala Gly Val Pro
        690                 695                 700
Gly Ala Gly Val Pro Gly Ala Gly Val Pro Gly Ala Gly Val Pro Gly
705                 710                 715                 720
Ala Gly Val Pro Gly Ala Gly Val Pro Gly Ala Gly Val Pro Gly Ala
                725                 730                 735
Gly Val Pro Gly Ala Gly Val Pro Gly Ala Gly Val Pro Gly Ala Gly
                740                 745                 750
Val Pro Gly Ala Gly Val Pro Gly Ala Gly Val Pro Gly Ala Gly Val
                755                 760                 765
Pro Gly Ala Gly Val Pro Gly Ala Gly Val Pro Gly Ala Gly Val Pro
        770                 775                 780
Gly Ala Gly Val Pro Gly Ala Gly Val Pro Gly Ala Gly Val Pro Gly
785                 790                 795                 800
Ala Gly Val Pro Gly Tyr Gly Tyr Gly Tyr Gly Tyr Gly Tyr Gly Tyr
                805                 810                 815
Gly Cys Gly Gly Cys Gly Gly Cys Gly Cys Gly Cys Gly Gly
                820                 825                 830
Cys Gly Gly Cys Gly Gly Cys Gly Gly Trp Pro
        835                 840
```

TRIBLOCK POLYPEPTIDE-BASED NANOPARTICLES FOR THE DELIVERY OF HYDROPHILIC DRUGS

CROSS-REFERENCE TO RELATED APPLICATIONS

This present patent application is a national stage filing under 35 U.S.C. § 371 of International Application No. PCT/US2017/051661, filed on Sep. 14, 2017, which application claims priority to U.S. Provisional Application No. 62/394,662 filed on Sep. 14, 2016, the content of which are incorporated fully herein by reference in their entirety.

SEQUENCE LISTING

The instant application includes a Sequence Listing which has been submitted electronically in ASCII format and is hereby incorporated by reference in its entirety. Said ASCII copy, created on Oct. 28, 2019, is named 028193-9249 Substitute Sequence Listing.txt and is 19,154 bytes in size.

BACKGROUND

Hydrophilic small molecule drugs suffer from sub-optimal pharmacokinetics due to their rapid renal clearance and can also suffer from premature in vivo degradation. Furthermore, hydrophilic drugs also can exhibit poor intracellular uptake, which compromises their in vivo efficacy. Because of these limitations, multiple high-dose injections of hydrophilic drugs are necessary to attain a therapeutically relevant concentration, but the maximum dose is limited by systemic side effects to healthy organs. Accordingly, better methods to delivery hydrophilic chemotherapeutics are needed.

SUMMARY

In one aspect, disclosed are compositions comprising an aggregate of self-assembling polypeptides, wherein a self-assembling polypeptide comprises (a) a first amino acid sequence $(X^1GVPG)_x$ (SEQ ID NO:1), wherein $X^1$ is an amino acid and x is 20 to 240; (b) a second amino acid sequence $(X^2G_m)y$ (SEQ ID NO:2), wherein $X^2$ is Y, F or W, m is 0 to 3, and y is 1 to 50; (c) a third amino acid sequence $(CGG)_z$ (SEQ ID NO:3), wherein z is greater than 1 and (d) at least one molecule attached to the third amino acid sequence through a cysteine group, wherein the molecule has an octanol-water distribution coefficient (log D) of less than or equal to 1.5 at a pH of 7.4.

In another aspect, disclosed are methods of killing multiple cancer cells comprising contacting multiple cancer cells with a composition as disclosed herein.

In another aspect, disclosed are methods of treating a disease or disorder in a subject comprising administering to the subject a composition as disclosed herein.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1(A) shows the sequence of an ATBP having three segments: an ELP segment that includes 160 repeats of AGVPG (SEQ ID NO: 6), a self-assembly promoting $(YG)_6$ (SEQ ID NO: 7) segment, and a cysteine-rich $(CGG)_8$ (SEQ ID NO: 8) drug attachment segment that provides reactive cysteine (Cys) residues for the covalent conjugation of maleimide derivatives of varying molecules. FIG. 1(B) shows the structure and log(D) of SMMs. The circle serves as a visual map of the structure of model compounds and their hydrophobicity, as measured by their log D; The hydrophobicity increases in clockwise fashion in the diagram. FIG. 1(C) is a schematic showing that the attachment of GEM does not disrupt self-assembly of an ATBP into cylindrical nanoparticles with a drug-rich core surrounded by a hydrophobic core and hydrophilic polypeptide corona.

FIG. 2(A) is a plot of angular dependence of hydrodynamic radius $(R_h)$ for ATBP-SMM1 conjugates measured by dynamic light scattering (DLS). FIG. 2(B) is a partial Zimm Plot (Kc/R vs $q^2$) obtained by SLS for ATBP-SMM1 conjugates. FIG. 2(C) is a cryo-TEM micrograph of ATBP-SMM1 conjugates. FIG. 2(D) is the determination of transition temperature $(T_t)$ of ATBP-SMM1 conjugates by thermal turbidimetry at 350 nm. FIG. 2(E) is the determination of critical aggregation concentration (CAC) of ATBP-SMM1 conjugates by pyrene fluorescence assay.

FIG. 3(A): SDS-PAGE and FIG. 3(B): MALDI-MASS of an ATBP and ATBP-GEM conjugate. FIG. 3(C) is the determination of hydrodynamic radius by single-angle DLS. FIG. 3(D) is a plot of angular dependence of hydrodynamic radii for ATBP-GEM nanoparticles measured by DLS. FIG. 3(E) is a partial Zimm Plot (Kc/R vs $q^2$) obtained by SLS for ATBP-GEM conjugates, FIG. 3(F) is a cryo-TEM micrograph of ATBP-GEM conjugates. FIG. 3(G) is the determination of transition temperature (T) of ATBP-GEM conjugates by thermal turbidimetry at 350 nm. FIG. 3(H) is the determination of CAC of ATBP-GEM conjugates by pyrene fluorescence assay.

FIG. 4(A)-(B) show cell viability for ATBP-GEM and free GEM in HCT-116 and Colo 205 cells, respectively, (mean±95% CI). FIG. 4(C) is a plot of plasma cyanine 5 (cy5) concentration as a function of time post-administration. FIG. 4(D) is a plot of in vivo tumor uptake. The cy5 concentration in tumor at 1, 6 and 24 h post-administration of cy5 labelled GEM, and cy5-ATBP-GEM nanoparticles.  and ** indicates p<0.01 and p<0.0001 respectively (Two way ANOVA, Sidak's test) (mean±95% CI, n=4). FIGS. 4(E)-(F) are plots of tumor volume and percentage survival, respectively, for mice inoculated with tumor cells (HCT-116) in the right flank.

FIG. 5(A) shows the determination of molecular weight of ATBP by MALDI-MS. FIG. 5(B) is a plot showing angular dependence of $R_1$ of ATBP nanoparticles measured by multi-angle DLS. FIG. 5(C) is a partial Zimm plot (Kc/R vs $q^2$) for ATBP nanoparticles. FIG. 5(D) is a cryo-TEM micrograph of ATBP nanoparticles (Scale bar: 200 nm). FIG. 5(E) is the determination of transition temperature $(T_t)$ of ATBP nanoparticles by thermal turbidimetry at 350 nm. FIG. 5(F) is the determination of CAC of ATBP nanoparticles by pyrene fluorescence assay.

SDS-PAGE of ATBP and ATBP-SMM conjugates with FIG. 6(A): SMM 1-4 and FIG. 6(B): SMM 5-8.

FIG. 7(A) is a plot of angular dependence of $R_h$ of SMM2 nanoparticles measured by multi-angle DLS. FIG. 7(B) is a partial Zimm plot (Kc/R vs $q^2$) for SMM2 conjugates. FIG. 7(C) is the determination of T of SMM2 conjugates by thermal turbidimetry at 350 nm. FIG. 7(D) is the determination of CAC of SMM2 conjugates by pyrene fluorescence assay.

FIG. 8(A) is a plot of angular dependence of $R_h$ of SMM3 nanoparticles measured by multi-angle DLS. FIG. 8(B) is a partial Zimm plot (Kc/R vs $q^2$) for SMM3 conjugates. FIG. 8(C) is a cryo-TEM micrograph of SMM3 conjugates (Scale bar: 200 nm). FIG. 8(D) is the determination of $T_t$ of SMM3 conjugates by thermal turbidimetry at 350 nm. FIG. 8(E) is the determination of CAC of SMM3 conjugates by pyrene fluorescence assay.

FIG. 9(A) is a plot of angular dependence of $R_h$ of SMM4 nanoparticles measured by multi-angle DLS. FIG. 9(B) is a partial Zimm plot (Kc/R vs $q^2$) for SMM4 conjugates. FIG. 9(C) is a cryo-TEM micrograph of SMM4 conjugates (Scale bar: 200 nm). FIG. 9(D) is the determination of $T_t$ of SMM4 conjugates by thermal turbidimetry at 350 nm. FIG. 9(E) is the determination of CAC of SMM4 conjugates by pyrene fluorescence assay.

FIG. 10(A) shows a plot of angular dependence of $R_h$ of SMM5 nanoparticles measured by multi-angle DLS. FIG. 10(B) is a partial Zimm plot (Kc/R vs $q^2$) for SMM5 conjugates. FIG. 10(C) is a cryo-TEM micrograph of SMM5 conjugates (Scale bar: 200 nm). FIG. 10(D) is the determination of $T_T$ of SMM5 conjugates by thermal turbidimetry at 350 nm. FIG. 10(E) is the determination of CAC of SMM5 conjugates by pyrene fluorescence assay.

FIG. 11(A)-(E) show characterization of exemplary ATBP-N-ethyl maleimide (SMM6) conjugates. FIG. 11(A) shows a plot of angular dependence of $R_h$ of SMM6 nanoparticles measured by multi-angle DLS. FIG. 11(B) is a partial Zimm plot (Kc/R vs $q^2$) for SMM6 conjugates (Scale bar: 200 nm). FIG. 11(C) is a cryo-TEM micrograph of SMM6 conjugates. FIG. 11(D) is the determination of $T_t$ of SMM6 conjugates by thermal turbidimetry at 350 nm. FIG. 11(E) is the determination of CAC of SMM6 conjugates by pyrene fluorescence assay.

FIG. 12(A) shows a plot of angular dependence of R of SMM7 nanoparticles measured by multi-angle DLS. FIG. 12(B) is a partial Zimm plot (Kc/R vs $q^2$) for SMM7 conjugates. FIG. 12(C) is a cryo-TEM micrograph of SMM7 conjugates (Scale bar: 200 nm). FIG. 12(D) is the determination of T of SMM7 conjugates by thermal turbidimetry at 350 nm. FIG. 12(E) is the determination of CAC of SMM7 conjugates by pyrene fluorescence assay.

FIG. 13(A) is a plot showing angular dependence of $R_6$ of SMM8 nanoparticles measured by multi-angle DLS. FIG. 13(B) is a partial Zimm plot (Kc/R vs $q^2$) of SMM8 conjugates. FIG. 13(C) is a cryo-TEM micrograph of SMM8 conjugates (Scale bar: 200 nm). FIG. 13(D) is the determination of $T_t$ of SMM8 conjugates by thermal turbidimetry at 350 nm. FIG. 13(E) is the determination of CAC of SMM8 conjugates by pyrene fluorescence assay.

FIG. 15(A): an exemplary ATBP and FIG. 15(B): exemplary ATBP-GEM conjugates.

FIG. 18(A): HCT 116 and FIG. 18(B): Colo 205 cells were treated with either cy5-labelled ATBP-GEM conjugates or PBS. After 4 h of treatment, cells were fixed with 4% paraformaldehyde in PBS and stained with Hoechst 33342 and CellMask™ Green Plasma Membrane Stain in Hank's balanced salt solution (HBSS) and imaged immediately in an inverted fluorescent microscope with a 60×1.25NA oil immersion objective.

DETAILED DESCRIPTION

Figure 1A:
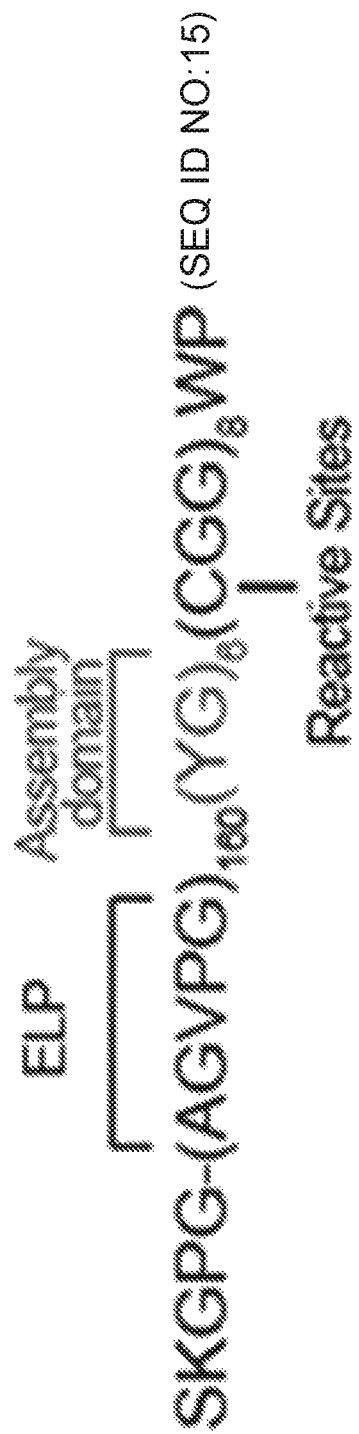
FIG. 1(A)-(C) show the structure of an exemplary asymmetric triblock polypeptide (ATBP), small molecule malemide derivatives (SMM) and schematic of the synthesis of exemplary ATBP-SMM/gemcitabine (GEM) nanoparticles.

Hydrophilic small-molecule cancer drugs utilized in the clinic often have poor bioavailability and suboptimal pharmacokinetics because of their rapid clearance, poor tissue absorption, and rapid metabolism. Encapsulating hydrophilic drugs by attaching them to self-assembling peptide-based nanoparticles may overcome these limitations by increasing their half-life, tissue penetration and decreasing premature degradation as compared to the free drug. However, it is generally known that conjugation/encapsulation of hydrophilic drugs destabilizes the self-assembly of polypeptides.

Disclosed herein is an approach to package hydrophilic molecules into nanoparticles via the use of a triblock self-assembling polypeptide. It was unexpectedly found that hydrophilic molecules could be conjugated to the self-assembling peptides without disrupting the polypeptide's ability to self-assemble. Furthermore, by conjugating the hydrophilic molecule to the self-assembling polypeptides, the pharmacokinetics and pharmacodynamics can be significantly improved relative to the hydrophilic molecule alone, as demonstrated by the improved delivery of gemcitabine in a tumor model.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

2. COMPOSITIONS

Disclosed herein are compositions that may include an aggregate of self-assembling polypeptides. The self-assembling polypeptide may include at least three distinct amino acid sequences and a hydrophilic molecule attached to one of the amino acid sequences. The aggregate of polypeptides may self-assemble upon the appropriate conditions, and may form a variety of differently shaped particles. Attempting to attach molecules, such as hydrophilic drug molecules, may perturb the ability of a polypeptide to self-assemble. Moreover, it is difficult to predict as to whether such alterations will ablate the polypeptide's ability to self-assemble.

As mentioned above, the aggregate of self-assembling polypeptides may self-assemble into a variety of shapes and sizes. The aggregate of self-assembling polypeptides may have a critical aggregation concentration (CAC) of about 1 $\mu M$ to about 10 $\mu M$, such as about 1.2 $\mu M$ to about 9 $\mu M$ or about 1.5 $\mu M$ to about 8.5 $\mu M$. In some embodiments, the aggregate of self-assembling polypeptides may be a nanoparticle. The nanoparticle may be rod-shaped or spherical, or the composition may include combinations of differently shaped nanoparticles. In some embodiments, the nanoparticle may be a micelle. In some embodiments, the nanoparticle may be a rod-shaped micelle.

The nanoparticle may have a varying average hydrodynamic radius. For example, the nanoparticle may have an average hydrodynamic radius of about 20 nm to about 200 nm, such as about 25 nm to about 150 nm or about 40 nm to about 100 nm. In some embodiments, the nanoparticle may have an average hydrodynamic radius of greater than 20 nm, greater than 25 nm, greater than 30 nm, greater than 35 nm, greater than 40 nm, greater than 45 nm, or greater than 50 nm. In some embodiments, the nanoparticle may have an average hydrodynamic radius of less than 200 nm, less than 175 nm, less than 150 nm, less than 125 nm, less than 100 nm, or less than 75 nm.

The nanoparticle may also be described by its average radius of gyration. For example, the nanoparticle may have an average radius of gyration of about 20 nm to about 200 nm, such as about 25 nm to about 150 nm or about 40 nm to about 100 nm. In some embodiments, the nanoparticle may have an average radius of gyration of greater than 20 nm, greater than 25 nm, greater than 30 nm, greater than 35 nm, greater than 40 nm, greater than 45 nm, or greater than 50 nm. In some embodiments, the nanoparticle may have an average radius of gyration of less than 200 nm, less than 175 nm, less than 150 nm, less than 125 nm, less than 100 nm, or less than 75 nm.

The aggregate of self-assembling polypeptides may include varying amounts of self-assembling polypeptides. For example, the aggregate of polypeptides may include about 50 to about 1,000 self-assembling polypeptides per aggregate, such as about 75 to about 800, about 80 to about 600 or about 90 to about 400 self-assembling polypeptides per aggregate. In some embodiments, the aggregate of polypeptides may include greater than 50 self-assembling polypeptides per aggregate, greater than 60 self-assembling polypeptides per aggregate, greater than 70 self-assembling polypeptides per aggregate, greater than 80 self-assembling polypeptides per aggregate, or greater than 90 self-assembling polypeptides per aggregate. In some embodiments, the aggregate of self-assembling polypeptides may include less than 1,000 self-assembling polypeptides per aggregate, less than 900 self-assembling polypeptides per aggregate, less than 800 self-assembling polypeptides per aggregate, less than 700 self-assembling polypeptides per aggregate, less than 600 self-assembling polypeptides per aggregate, or less than 500 self-assembling polypeptides per aggregate. As mentioned above, in some embodiments, the aggregate may be a nanoparticle and the description for the number of self-assembling polypeptides per aggregate can also be applied to the nanoparticle.

In addition, the self-assembling polypeptide may have a range of molecular weight. For example, each self-assembling polypeptide individually may have a molecular weight of about 20 kDa to about 300 kDa, such as about 30 kDa to about 200 kDa or about 30 kDa to about 100 kDa. In some embodiments, each self-assembling polypeptide individually may have a molecular weight of greater than 20 kDa, greater than 30 kDa, greater than 40 kDa, or greater than 50 kDa. In some embodiments, each self-assembling polypeptide individually may have a molecular weight of less than 300 kDa, less than 250 kDa, less than 200 kDa, less than 150 kDa, or less than 100 kDa.

The self-assembling polypeptide may include other amino acid sequences that can provide further advantages, such as improved yield, ease of purification, and/or enhanced self-assembly. For example, the self-assembling polypeptide may include a fourth amino acid sequence SKGPG (SEQ ID NO: 9) and/or a fifth amino acid sequence WP. The fourth amino acid sequence may be attached to the 5' end of the self-assembling polypeptide (e.g., attached to the first amino acid sequence). The fifth amino acid sequence may be attached to the 3' end of the self-assembling polypeptide (e.g., attached to the third amino acid sequence) and it may enable facile quantification of protein concentration via UV-VIS spectroscopy.

In some embodiments, the self-assembling polypeptide may be SKGPG-first amino acid sequence-second amino acid sequence-third amino acid sequence-WP (SEQ ID NO: 10), where the first, second and third amino acid sequences are described in further detail below.

A. First Amino Acid Sequence

The first amino acid sequence may be hydrophilic and thermally responsive. The first amino acid sequence may be an elastin-like polypeptide (ELP). ELPs are inspired by human elastin and they can have a lower critical solution temperature phase transition behavior that can be useful for stimulus-responsive applications in biological environments. For example, ELPs may be soluble at temperatures below a characteristic cloud point temperature ($T_t$) (also known as the inverse transition temperature) and aggregate into nanometer to micron scale particles above the $T_t$. Further description for elastin-like polypeptides can be found in U.S. Pat. Nos. 8,470,967, 8,912,310, 9,127,047 and U.S. Patent Application Publication No. 2014/0024600, all of which are incorporated by reference herein in their entirety.

The first amino acid sequence may be $(X^1GVPG)_x$ (SEQ ID NO: 1), wherein $X^1$ is an amino acid and x is 20 to 240. In some embodiments, the first amino acid sequence may be $(X^1GVPG)_m$ (SEQ ID NO:11), wherein $X^1$ is an amino acid and m is 120 to 200. In some embodiments, $X^1$ may be A. In some embodiments, the first amino acid sequence may be $(AGVPG)_{160}$ (SEQ ID NO:6).

B. Second Amino Acid Sequence

The second amino acid sequence may be hydrophobic and may aid in driving self-assembly of the polypeptides. The second amino acid sequence may be attached to the first amino acid sequence and may be attached to the third amino acid sequence (e.g., see FIG. 1).

The second amino acid sequence may be $(X^2G_m)_y$ (SEQ ID NO:2), wherein $X^2$ is Y, F or W, m is 0 to 3, and y is 1 to 50. In some embodiments, the second amino acid sequence may be $(X^2G)_n$ (SEQ ID NO:4), wherein n is 4 to 8. In some embodiments, $X^2$ may be Y. In some embodiments, the second amino acid sequence may be $(YG)_6$ (SEQ ID NO:7).

C. Third Amino Acid Sequence

The third amino acid sequence may be attached to the second amino acid sequence and may also include reactive sites, such as cysteine groups, that the molecule can attach to (e.g., see FIG. 1). The third amino acid sequence may be $(CGG)_z$ (SEQ ID NO:3), wherein z is greater than 1. In some embodiments, the third amino acid sequence may be $(CGG)_p$ (SEQ ID NO:5), wherein p is 4 to 12. In some embodiments, the third amino acid sequence may be $(CGG)_8$ (SEQ ID NO:8).

D. Molecule

The composition may include any hydrophilic molecule (e.g., drugs, chemotherapeutics, imaging agents, etc.) that can be attached to the third amino acid sequence through a cysteine group. The molecule may be located in the core of the aggregate of self-assembling polypeptides (e.g., located in the core of a nanoparticle). The molecule's hydrophilicity may be characterized by its octanol-water distribution coefficient (log D), where a larger value indicates greater hydrophobicity. For example, the molecule may have a log(D) of less than or equal to 1.5 at a pH of 7.4, less than or equal to 1.4 at a pH of 7.4, less than or equal to 1.3 at a pH of 7.4, less than or equal to 1.2 at a pH of 7.4, less than or equal to 1.1 at a pH of 7.4, or less than or equal to 1 at a pH of 7.4. In some embodiments, the molecule has a log D of about −1 to about 1.5 at a pH of 7.4.

The molecule may be a chemotherapeutic or an imaging agent. In some embodiments, the molecule may be gemcitabine. The term "imaging agent," as used herein, refers to a molecule or compound that can be detected directly or after applying a stimulus. Examples of imaging agents include luminescent labels which emit radiation on exposure to an external source of radiation or other stimulus, e.g. fluorescent materials or fluorophores (which emit light when exposed to light), chemiluminescent materials (which emit light during chemical reaction), electroluminescent materials (which emit light on application of an electric current), phosphorescent materials (in which emission of light continues after exposure to light stimulus has ended) and thermoluminescent materials (which emit light once a certain temperature is exceeded). Examples of fluorophores include fluoresceins, xanthenes, cyanines, naphthalenes, coumarins, oxadiazoles, pyrenes, oxazines, acridines, arylmethines, Alexa Fluors and tetrapyrroles. Further fluorophores include quantum dots, which emit highly specific wavelengths of electromagnetic radiation after stimulation, for example by electricity or light.

Other imaging agents include radioactive labels, including positron emitting nuclei such as $^{18}F$, $^{64}Cu$ or $^{124}I$ which can be detected by imaging techniques such as positron emission topography (PET). Other radioactive labels such as $^{14}C$, $^{3}H$, or iodine isotopes such as $^{123}I$ and $^{131}I$, which can be detected using autoradiographic analysis or scintillation detection for example, can also be used. In the case of gamma-emitting nuclei, imaging techniques such as single photon emission computed tomography (SPECT) can be used. Other imaging agents include those that are NMR-active, which can be detected by magnetic resonance techniques, for example magnetic resonance imaging (MRI) or nuclear magnetic resonance (NMR) detectors, the agents typically comprising one or more NMR-active nuclei that are not generally found in concentrated form elsewhere in the organism or biological sample, examples being $^{13}C$, $^{2}H$ (deuterium) or $^{19}F$. Further imaging agents include those comprising atoms with large nuclei, for example atoms with atomic number of 35 or more, preferably 40 or more and even more preferably 50 or more, for example iodine or barium, which are effective contrast agents for X-ray photographic techniques or computed tomography (CT) imaging techniques.

The molecule may be attached to the third amino acid sequence through a thiol group present on the third amino acid sequence. Or in other words, the molecule may be attached to the third amino acid sequence through any suitable type of thiol bioconjugation linkage. Examples include, but are not limited to, thiol-maleimide linkage, disulfide linkage, thiol-vinyl linkage (e.g., thiol-vinyl sulfone), and other types of Michael addition-type reactions that are mediated through a thiol group on the third amino acid sequence.

In some embodiments, the molecule may be considered a small molecule. For example, the molecule may have a molecular weight of less than or equal to 1.5 kDa, less than or equal to 1.4 kDa, less than or equal to 1.3 kDa, less than or equal to 1.2 kDa, less than or equal to 1.1 kDa, less than or equal to 1 kDa, less than or equal to 0.9 kDa, less than or equal to 0.8 kDa, less than or equal to 0.7 kDa, less than or equal to 0.6 kDa, or less than or equal to 0.5 kDa.

The composition may include varying amounts of the molecule. For example, the composition may include about 2 to about 15 molecules attached to the third amino acid sequence, such as about 3 to about 12 molecules or about 4 to about 10 molecules attached to the third amino acid sequence. In some embodiments, the composition may include greater than 1 molecule, greater than 2 molecules, greater than 3 molecules, greater than 4 molecules, greater than 5 molecules, greater than 6 molecules, or greater than 7 molecules attached to the third amino acid sequence. In some embodiments, the composition may include less than 15 molecules, less than 14 molecules, less than 13 molecules, less than 12 molecules, less than 11 molecules, or less than 10 molecules attached to the third amino acid sequence.

E. Additional Components

The composition may further include a pharmaceutically acceptable carrier. As used herein, "pharmaceutical acceptable carrier" refers to a physiologically acceptable diluent including, but not limited to water, phosphate buffered saline, or saline. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. The compositions including a pharmaceutically acceptable carrier optionally may be sterile. The compositions may be frozen or lyophilized for storage and reconstituted in a suitable sterile carrier prior to use. The compositions having a pharmaceutically acceptable carrier can be generated in accordance with conventional techniques described in, e.g., *Remington: The Science and Practice of Pharmacy*, 21st Edition, Lippincott Williams & Wilkins, Philadelphia, Pa. (2001), which is incorporated by reference herein in its entirety.

F. Methods of Making the Compositions

Disclosed herein are methods of making the compositions. Methods of making the self-assembling polypeptides are described in the Examples section and further description of similar and alternative methods may be found in U.S. Pat. Nos. 8,470,967, 8,912,310, 9,127,047 and U.S. Patent Application Publication No. 2014/0024600, all of which are incorporated by reference herein in their entirety.

To provide the disclosed compositions, the self-assembling polypeptide may be contacted with the molecule. For example, the self-assembling polypeptide may be added to a first solvent to provide a polypeptide solution and the molecule may be added to a second solvent to provide a molecule solution. The first solvent may include phosphate buffer and/or dimethylformamide, and the second solvent may include dimethylformamide. The first and second solvents may include at least one solvent that is the same and/or the first and second solvents may each include at least one solvent that is miscible with a solvent in the other. The polypeptide solution may be stirred for varying periods of time (e.g., at least 1 minute, at least 5 minutes, at least 10 minutes, at least 15 minutes, etc.), and it may have further added to it a reducing agent, such as tris(2-carboxyethyl) phosphine.

After a period of time spent stirring, the molecule solution may be added to the polypeptide solution to provide a first mixture. In some embodiments, the molecule solution is added drop-wise. Once the first mixture is provided, it can be allowed to stir at least 15 minutes, at least 30 minutes, at least 1 hour, at least 2 hours, at least 3 hours, or at least 4 hours. The stirring of the first mixture may be performed at room temperature. During the stirring of the first mixture the molecule may be conjugated to the self-assembling polypeptide through, e.g., a thiol group present on the third amino acid sequence.

Following conjugation, the composition may be purified via chromatography and ultra-filtration techniques, such as using gel filtration columns and centrifugal filter units. Once purified, the composition may be lyophilized and stored at a temperature of below −10° C. The self-assembling aggregate of polypeptides may be provided by self-assembly of individual polypeptides into an aggregate by self-assembly principles known within the art (e.g., via threshold concentration).

3. METHODS OF USING THE COMPOSITIONS

Also disclosed herein are methods of using the compositions. In one aspect, disclosed are methods of killing multiple cancer cells comprising contacting multiple cancer cells with the disclosed composition. The cancer cells may be in an in vitro environment or an in vivo environment. In some embodiments, the cells are in a subject. The subject of the disclosed methods may be a human subject, although it is to be understood that the methods described herein are effective with respect to all vertebrate species, which are intended to be included in the term "subject." Accordingly, a "subject" can include a human subject for medical purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. In some embodiments, the subject is a human or a dog.

In another aspect, disclosed are methods of treating a disease or disorder in a subject comprising administering to the subject the disclosed composition. The disease or disorder may be cancer, and in particular may be a cancer comprising solid tumors. Examples of cancers that comprise solid tumors include, but are not limited to, pancreatic, bladder, non-small cell lung cancer (NSCLC), breast and ovarian cancers.

The term "administering" as used herein refers to contacting a subject with the disclosed compositions. The composition can be administered using a variety of methods known in the art depending on the subject and the particular disease, disorder, or condition being investigated. The administering can be carried out by, for example, intravenous infusion; injection by intravenous, intraperitoneal, intramuscular, intraocular, or intraarterial. In certain embodiments, administering the composition includes injecting the composition intravenously into the vasculature of the subject.

The administration of the composition may be a systemic administration. The phrase "systemic administration," and "administered systemically" as used herein refers to the administration of a compound, or drug, such that it enters the patient's system and, thus, is subject to metabolism and other like processes, for example, subcutaneous administration.

The composition may be administered and/or contacted a varying amount of time depending on subject, disease, cell type, etc. For example, the composition may be administered 1 to 4 times daily for a period of 6 months, at any suitable interval. The composition may also be administered 1 to 10 times (total) over a period of 6 months, at any suitable interval. Starting from the administration of the composition, the method may be performed over a period of about 10 seconds to about 6 months.

The composition may be administered and/or contacted at varying dosages depending on the subject, disease, cell type, etc. The composition may be administered at a dosage of about 0.1 mg/kg to about 35 mg/kg, such as about 1 mg/kg to about 30 mg/kg, or about 5 mg/kg to about 25 mg/kg. In certain embodiments, the composition is administered at a dosage of less than or equal to 35 mg/kg, less than or equal to 34 mg/kg, less than or equal to 33 mg/kg, less than or equal to 32 mg/kg, less than or equal to 31 mg/kg, less than or equal to 30 mg/kg, less than or equal to 25 mg/kg, less than or equal to 20 mg/kg, or less than or equal to 15 mg/kg. In certain embodiments, the composition may be administered at a dosage of greater than or equal to 0.1 mg/kg, greater than or equal to 1 mg/kg, greater than or equal to 2 mg/kg, greater than or equal to 4 mg/kg, greater than or equal to 6 mg/kg, greater than or equal to 8 mg/kg, or greater than or equal to 10 mg/kg.

The methods may include the composition having a chemotherapeutic. The methods may have increased efficacy relative to the chemotherapeutic being administered alone. For example, the method may be able to reduce tumor volume at least 1.1× greater, at least 1.2× greater, at least 5× greater, at least 10× greater, at least 15× greater, at least 20× greater, at least 25× greater, at least 50× greater, at least 100× greater, at least 250× greater, or at least 500× greater relative to the chemotherapeutic being administered alone as measured about 10 to about 30 days post-administration.

Reduction in tumor volume may improve survival rates of the subject. For example, the method may improve survival time (as measured by time living with disease, e.g., days, months, years, etc.) of the subject by at least 1.1× greater, at least 1.2× greater, at least 5× greater, at least 10× greater, at least 15× greater, or at least 20× greater relative to the chemotherapeutic being administered alone.

The methods and compositions may also allow the chemotherapeutic to localize to the diseased tissue (e.g., solid tumor) at a greater amount relative to the chemotherapeutic being administered alone. For example, the composition including a chemotherapeutic may localize to a diseased tissue (after administration of the composition) 1.1× greater, 1.2× greater, 1.3× greater, 1.4× greater, 1.5× greater, 2× greater, 2.5× greater, 3× greater, 4× greater, 5× greater, or 10× greater relative to the chemotherapeutic being administered alone as measured by percentage of injected dose/gram of tissue (% ID/g) at approximately 24 hours post-administration.

The ability of a composition including a chemotherapeutic to localize to specific tissues may be due to its advantageous pharmacokinetics compared to the pharmacokinetics of the chemotherapeutic alone. For example, the composition including a chemotherapeutic may have a $C_{max}$ of about 0.5 µg/mL to about 6 µg/mL, such as about 0.75 µg/mL to about 5 µg/mL or about 1 µg/mL to about 4 µg/mL. In some embodiments, the composition including a chemotherapeutic may have a $C_{max}$ of greater than 0.5 µg/mL, greater than 0.75 µg/mL, greater than 1 µg/mL, greater than 1.5 µg/mL, greater than 2 µg/mL, or greater than 2.5 µg/mL.

The composition including a chemotherapeutic may have a $t_{1/2}$ of about 5 hours to about 20 hours, such as about 6 hours to about 18 hours or about 10 hours to about 15 hours. In some embodiments, the composition including a chemotherapeutic may have a $t_{1/2}$ of greater than 5 hours, greater than 6 hours, greater than 7 hours, greater than 8 hours, greater than 9 hours, or greater than 10 hours. In addition, the composition including a chemotherapeutic may have a tin of at least 1.1× greater, 1.2× greater, 1.5× greater, 2× greater, 2.5× greater, 3× greater, 4× greater, 5× greater, 10× greater, 20× greater, 100× greater, or 500× greater than the $tv_2$ of the chemotherapeutic alone.

The composition including a chemotherapeutic may have an AUC(total) of about 15 µg*h/mL to about 50 µg*h/mL, such as about 20 µg*h/mL to about 45 µg*h/mL or about 25 to about 40 µg*h/mL.

In addition, the methods and compositions may have reduced dose-limiting toxicity relative to the chemotherapeutic alone. For example, the disclosed methods may allow the composition to be administered at a lower dose relative to the chemotherapeutic being administered alone.

4. EXAMPLES

The compositions and methods of the invention will be better understood by reference to the following examples, which are intended as an illustration of and not a limitation upon the scope of the invention.

Example 1

Synthesis and Characterization of ATBP-Conjugates

Methods
Synthesis of Asymmetric Triblock Polypeptides:
An exemplary ATBP (referred to as ATBP throughout the Examples) used for conjugation to SMM was synthesized from commercially purchased oligomers (IDT Inc.). Briefly, a 77-bp oligomer (5-GGGCCG-GAGTGCCTGGTGCAGGTGTGCCAGGCGCGGG TGTTCCAG-GAGCAGGCGTTCCAGGTGCGGGTGTCCTGGC-3') (SEQ ID NO: 12)and its complement (5'-CCGCCAG-GAACACCCGCACCTGGAACGCCTGCTCCTG-GAACACCCGCGCCTGGCACACCTGCACCAGG-CACTCCGGC-3') (SEQ ID NO: 13) were hybridized and inserted into a pET-24a+ vector purchased from Novagen Inc. (Madison, Wis.). The sequence was then lengthened by recursively dimerizing the sequence with itself using a process known as plasmid reconstruction recursive directional ligation. A short MSKGPG (SEQ ID NO: 14) leading oligomer was appended to the 5' end of the finalized biopolymer sequence to enhance the yield, and three trailing oligomers were sequentially appended to the 3' end of the biopolymer sequence: $(YG)_6$ (SEQ ID NO: 7) to promote the assembly of the biopolymer into core-shell worm-like micellar structures, $(CGG)_8$ (SEQ ID NO: 8) to provide orthogonal thiols for the chemical conjugation of maleimide containing small molecules, and WP to enable facile quantification of protein concentration by UV-VIS spectroscopy. The final structure of the ATBP biopolymer includes the sequence SKGPG-$(AGVPG)_{160}$-$(YG)_6$-$(CGG)_8$-WP (SEQ ID NO: 15).

Expression and Purification of ATBP:

The ATBP was expressed using a pET-24a+ expression plasmid transfected into *Escherichia coli* strain BL21(DE3). 50 mL cultures were inoculated and grown for 16 h at 37° C. and 210 rpm, and were then transferred to six 1 L flasks of TB Dry supplemented with 45 μg/mL kanamycin. The 1 L flask was then incubated at 37° C. and 210 rpm for 8 h, induced with 2 mM IPTG, and grown for an additional 16 h, after which the cell suspension was centrifuged at 3,000 rpm for 10 min at 4° C. The ATBP was purified using standard protocols known in the art. In short, the resuspended cell pellet was lysed via sonication on ice for 3 min (10 s on, 40 s off) (Masonix S-4000; Farmingdale, N.Y.), followed by addition of Polyethyleneimine (PEI) 0.7% w/v to precipitate the nucleic acids. The supernatant was then purified by two to three rounds of inverse transition cycling (ITC) as follows: 3 M NaCl was added to the supernatant and was heated to 37° C. to trigger the phase transition of the ATBP from the aqueous phase into a water-insoluble coacervate phase. The solution was centrifuged for 10-15 min at 14,000 g and 37 OC, and the aqueous compartment (containing soluble contaminants) was discarded. The ATBP coacervate pellet was then resuspended in chilled 20 mM TCEP in water, pH 6-8. This mixture was cooled to 4° C., and then centrifuged for 10 min at 14,000 and 4° C. to remove any insoluble contaminants. Generally, 2-3 rounds of ITC yielded a significantly pure protein (>95% by SDS-PAGE).

Purity Analysis:

The purity of ATBP was analyzed by SDS-PAGE on Biorad Ready Gels with a 4-20% Tris gradient. The gels were visualized by copper staining (0.5 M). The endotoxin of the purified ATBP was removed by a chromatography technique using Detoxi-Gel Endotoxin Removing Gel (Thermo Scientific) as a matrix and PBS as an eluent.

Synthesis of ATBP-Small Molecule Maleimide (ATBP-SMM) Conjugates:

25 mg of lyophilized ATBP was resuspended in 700 μL of 100 mM phosphate buffer, pH 7.4, and 100 μL of dimethyl formamide (DMF) was added to it. The solution was stirred for 15 min and spiked with an additional 100 uL of 100 mM TCEP in water (pH 7.4). Finally 100 μL of a 50 mM solution of each maleimide derivative in DMF was added to the ATBP solution dropwise, and allowed to mix for 3 h. Following conjugation, the ATBP-SMM conjugate was purified by passing through a PD-10 gel filtration column (GE Healthcare Life Sciences). The eluted fraction was diluted with 20% acetonitrile in ddH$_2$O and further purified by centrifuging the mixture in an Amicon Ultra-15 Centrifugal Filter Units (MWCO: 10 KDa, Millipore) at 2,500 rpm at 10° C. The ATBP-SMM conjugate was washed twice with ddH$_2$O. The solution was centrifuged at 13,000 g for 10 minutes at 4° C., lyophilized, and stored at −20° C.

Determination of SMM Conjugation Ratio:

Following purification, 2-3 mg of lyophilized ATBP was dissolved in 1 mL ddH$_2$0. In order to break any pre-existing disulfide bonds between unconjugated cysteine residues, 100 μL of the conjugate was incubated with 100 μL of Immobilized TCEP Reducing Gel (Thermo Fisher Scientific; Rockford, Ill.) for 1 hr at 25° C. Included spin columns were utilized to separate the TCEP beads from the ATBP conjugates. The solution was then split for use in two parallel assays. To determine the ATBP concentration, a 96-well bicinchoninic acid assay (Thermo Fisher Scientific) was used on a Victor3™ microplate reader (Perkin Elmer; Waltham, Mass.). 10 μL of ATBP solution was mixed with 200 μL of BCA working reagent, incubated for 30 min at 37° C., and was compared to an ATBP standard curve (100, 50, 25, 10, 5, 0 μM) fit to a $2^{nd}$ order polynomial in order to estimate the ATBP concentration for the absorbance at 560 nm. Each conjugate was measured in triplicate. To determine the concentration of free thiols, a 96-well Ellman's assay was developed for use on the Victor3™ microplate reader at an absorbance of 405 nm. 40 μL of an ATBP solution was mixed with 200 μL of a working reagent (25 μM Ellman's reagent in 100 mM phosphate buffer, 1 mM EDTA, pH 8.0), incubated for 2 h at 25° C., and was compared to a standard curve of the ATBP prior to conjugation (100, 50, 25, 10, 5, 0 μM). The unreacted cysteine residues in each sample could then be calculated by determining the ratio between the Ellman's assay standard curve (assumed to have 8 free cysteine residues per ATBP) and the Ellman's assay sample measurement at the concentration determined by the BCA assay. The conjugation ratio was the difference between the number of cysteines (8/ATBP) and the calculated number of free cysteines.

Static and Dynamic Light Scattering:

Static and dynamic light scattering measurements were performed on an ALV/CGS-3 goniometer system (Langen, Germany) to determine the $R_h$ and $R_g$ of the ATBP and ATBP-SMM nanoparticle. For the ALV/CGS-3 goniometer system, ATBP and ATBP-SMM conjugates were resuspended in PBS and filtered through 0.22 μm Millex-GV filters into a 10 mm diameter disposable borosilicate glass tube (Fisher). SLS and DLS were measured simultaneously at 22° C. for angles between 30°-150° at 5° increments, where the measurements at each angle was of 3 runs for 15 seconds. The differential refractive index (dn/dc) was quantified by determining the refractive index at five different dilutions using an Abbemat 500 refractometer (Anton Paar, Graz, Austria). DLS data were analyzed by fitting the autocorrelation function to a biexponential decay using the HDRC software package (Germany). The $R_h$ was plotted against angle and extrapolated to zero scattering angle in order to eliminate the effect of the form factor and observe the true hydrodynamic radius. Partial Zimm plots were used to analyze the SLS measurements and ALV/Dynamic and Static FIT and PLOT software was used to determine the $R_g$ and MW of the nanoparticles. The $N_{agg}$ was calculated by dividing the MW of the nanoparticles by the MW of the ATBP or ATBP-SMM conjugate.

Temperature-Programmed Turbidimetry:

To determine the $T_t$, ATBP-SMM conjugate or parent ATBP were resuspended in PBS at ATBP concentrations of 25, 50 and 100 giM and the optical density of each sample was measured at 350 nm by ramping the temperature at a rate of 1° C./min on a temperature-controlled UV-vis spectrophotometer (Cary 300 Bio; Varian Instruments, Palo Alto, Calif.). The $T_t$ was determined from the inflection point of the turbidity profile.

CryoTEM:

Cryo-TEM was performed at Duke University's Shared Materials Instrumentation Facility (Durham, N.C.). Lacey holey carbon grids (Ted Pella, Redding, Calif.) were glow discharged in a PELCO EasiGlow Cleaning System (Ted Pella, Redding, Calif.). A 3 µl drop of a sample was deposited onto the grid, blotted for 3 s with an offset of –3 mm, and vitrified in liquid ethane using the Vitrobot Mark III (FEI, Eindhoven, Netherlands). Prior to vitrification, the sample chamber was maintained at 22° C. and 100% relative humidity to prevent sample evaporation. Grids were transferred to a Gatan 626 cryoholder (Gatan, Pleasanton, Calif.) and imaged on a FEI Tecnai G2 Twin TEM (FEI, Eindhoven, Netherlands)), operating under low-voltage conditions at 80 keV.

Determination of CAC:

The CAC of ATBP and ATBP-SMM conjugates were determined by fluorescence spectroscopy using pyrene which was utilized as a probe of the local hydrophobicity. The ratio of the first fluorescence emission peak ($I_{370-373}$) and the third peak ($I_{381-394}$) were measured at different ATBP concentrations. The inflection point of the curves was used to determine the CAC.

Synthesis of ATBP-GEM Conjugate:

GEM was first activated by reacting it with N-ε-Maleimidocaproic acid (EMCA). EMCA (0.04 g, 0.189 mmol) and 1-Ethyl-3-(3-dimethylaminopropyl)carbodiimide (EDCI) (0.036 g, 0.189 mmol) were separately dissolved in dry dimethylformamide (DMF) and mixed, with stirring at –20° C. for 30 min. GEM (0.025 g, 0.168 mmol) was dissolved in anhydrous DMF and added to this mixture. The reaction mixture was stirred at 4° C. for 24 h, and was then filtered, and the DMF was evaporated to dryness. The dried product was purified with column chromatography using silica gel and 4:1 to 3:1 Acetone in chloroform as eluent. Retention Factor ($R_f$): 0.25 in $CHCl_3$/Acetone/EtOH=5:4:1. ESI-MS: 457 [M+H]. $^1$H NMR (400 MHz, DMSO-d6): δ 1.17 (m, 2H, 11), 1.48 (m, 4H, 10, 12), 2.35 (t, 2H, 9), 3.34 (t, 2H, 13), 3.63 (m, 1H, 5'A), 3.85 (m, 1H, 5'B), 4.14 (m, 1H, 3'), 5.27 (m, 1H, 4'), 6.294 (s, 1H, 1'), 6.97 (s, 2H, 16), 7.22 (d, 1H, 5), 8.19 (d, 1H, 6).

Prior to the reaction with activated GEM, ATBP was resuspended in reaction buffer (0.1 M sodium phosphate, 1 mM Ethylenediaminetetraacetic acid (EDTA), pH 7.0). To reduce any spontaneously formed disulfides in the ATBP, 1 mL of 100 mM Tris(2-carboxyethyl)phosphine hydrochloride (TCEP) (pH 7.4) was added at ~5 molar excess to thiols. Unreacted TCEP was removed from the mixture by triggering the phase transition of the ATBP to aggregate it, by adding sodium chloride (2.5 M), followed by centrifugation at 4,000 rpm at 25° C. for 10 min to isolate the ATBP. The ATBP pellet obtained in the previous step was re-suspended in ~2 mL of reaction buffer, conditions under with the ATBP pellet dissolves. The purified GEM-EMCA was re-suspended in ~2 mL of DMF and slowly added to the stirring ATBP solution. 1 mL of TCEP (100 mM, pH 7.4) was added and the mixture were stirred at 20° C. in the dark for 16 h. After reaction, the unreacted GEM-EMCA was separated by centrifugation at 13,000 rpm for 10 min at 10° C. The ATBP-GEM conjugate was further purified by diluting it in 20% acetonitrile in PBS and centrifuging the solution in an Amicon Ultra-15 centrifugal filter unit (MWCO: 10 KDa, Millipore) at 2,500 rpm at 10° C. The ATBP-GEM product was washed twice with $NH_4HCO_3$ buffer (pH 7.4) and then freeze dried.

Determination of GEM Conjugation Ratio:

The conjugation ratio of GEM to ATBP was measured by MALDI-TOF-MS of the ATBP-GEM conjugates and free ATBP using a Voyager DE-Pro MALDI-MS (Applied Biosystems) instrument equipped with a nitrogen laser (337 nm). The samples were prepared in an aqueous solution containing 50% acetonitrile and 0.1% trifluoroacetic acid (TFA), using sinapinic acid as a matrix. The conjugation ratio was calculated from the increase in the MW of the ATBP-GEM conjugate relative the unmodified ATBP.

Characterization of ATBP-GEM Conjugate:

ATBP-GEM was characterized by DLS, SLS, cryo-TEM, AFM, temperature programmed turbidimetry and pyrene fluorescence assay. The detailed procedure was identical to that used to characterize ATBP-SMM conjugates. The $T_E$ of ATBP-GEM conjugate was measured in PBS at ATBP concentrations of 1, 2.5, 5, 10, 25, 50 and 100 µM.

Atomic-Force Microscopy (AFM)

Samples for AFM imaging were prepared by placing a drop of sample solution (~0.2 mg/ml) onto a freshly cleaved mica surfaces and incubating for 15 minutes. Then, the sample was gently rinsed with Milli-Q $H_2O$ and dried under a $N_2$ stream. All AFM images were acquired with Tapping Mode under ambient conditions using a MultiMode AFM (Bruker). TappingMode silicon cantilever was used for all the AFM images (kF=40 N/m, fres=300 kHz).

Results

Figure 5A:
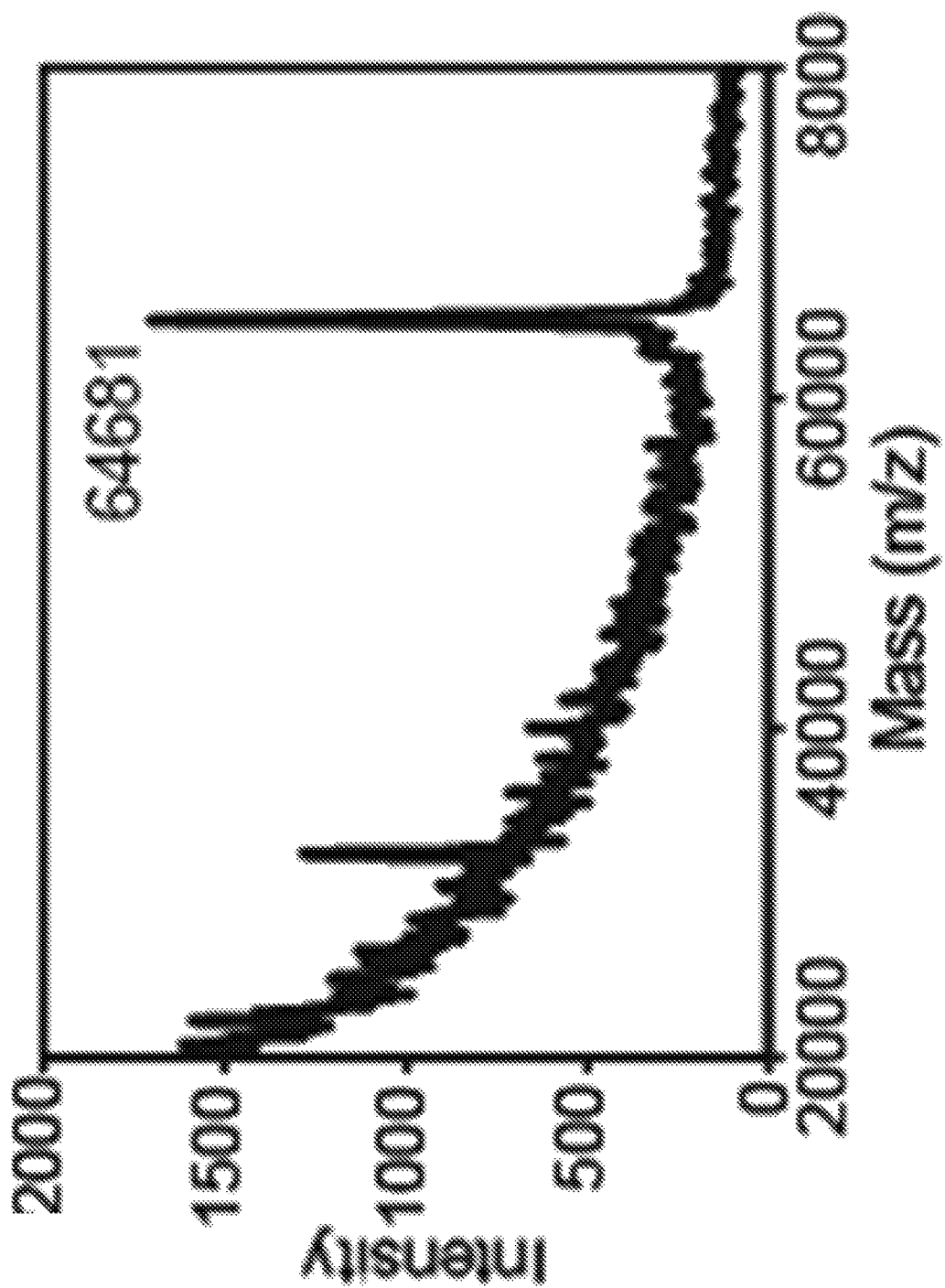
FIG. 5(A)-(F) show characterization of an exemplary ATBP.
Figure 5B:
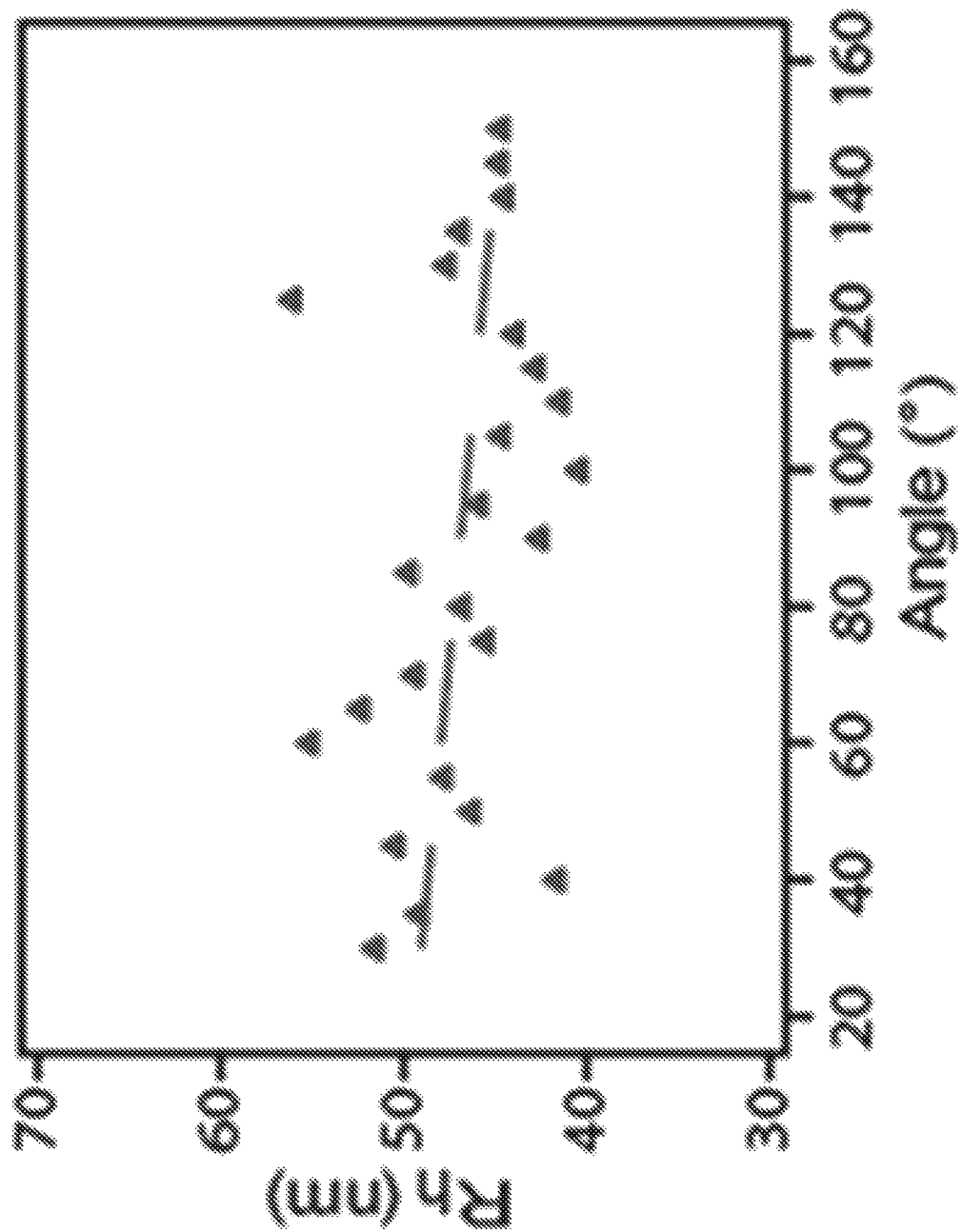
Figure 5C:
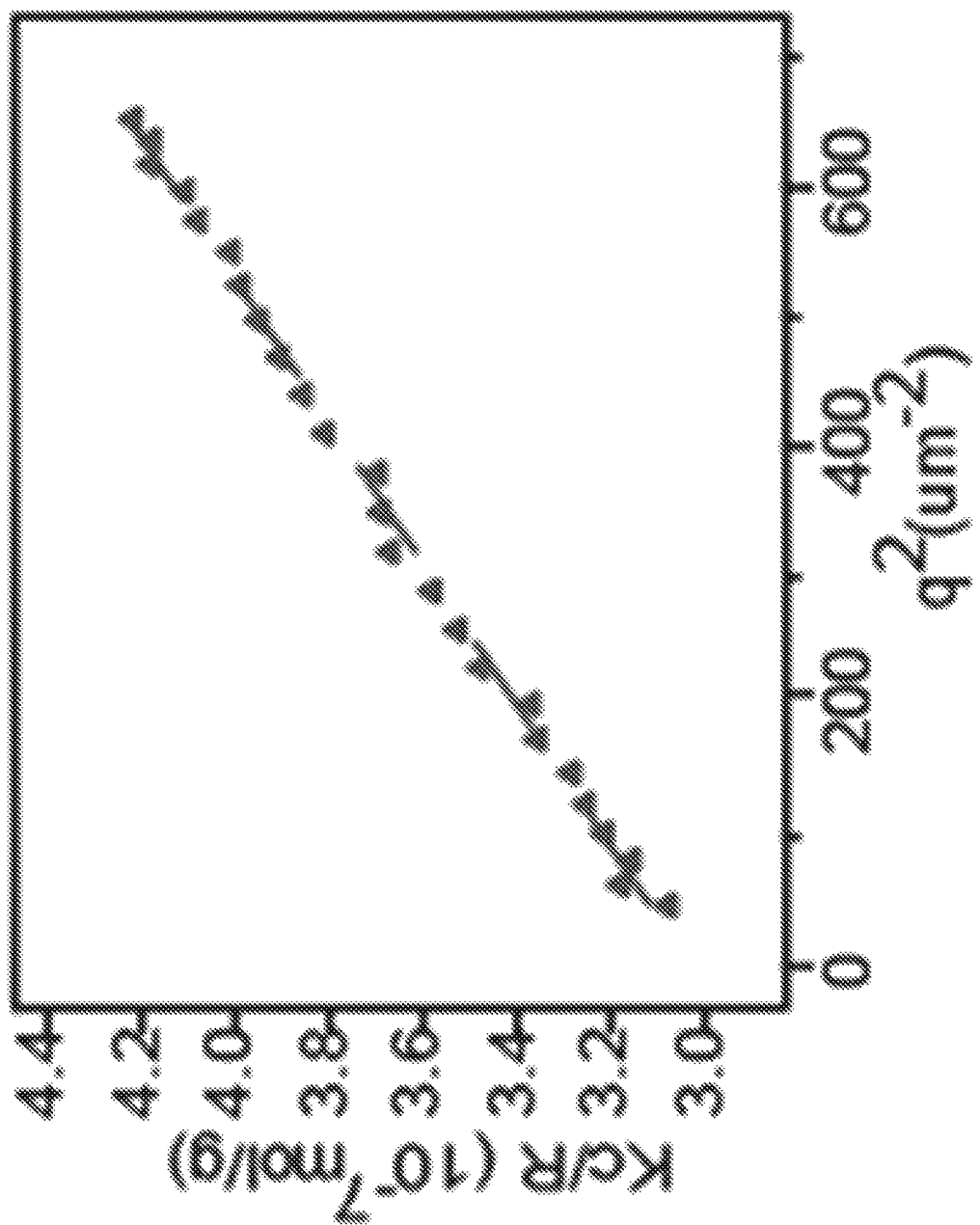
Figure 5:
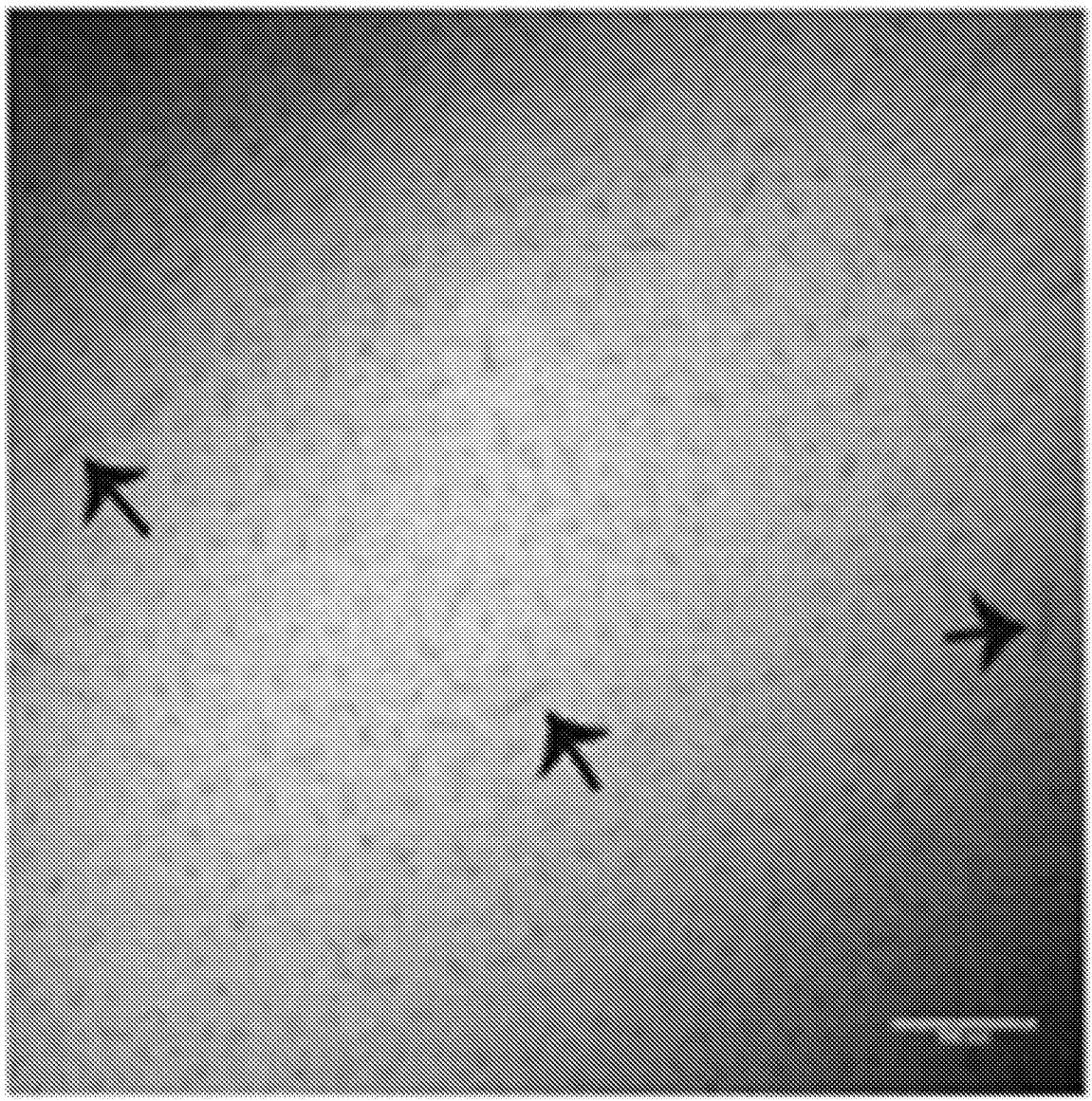
Figure 5E:
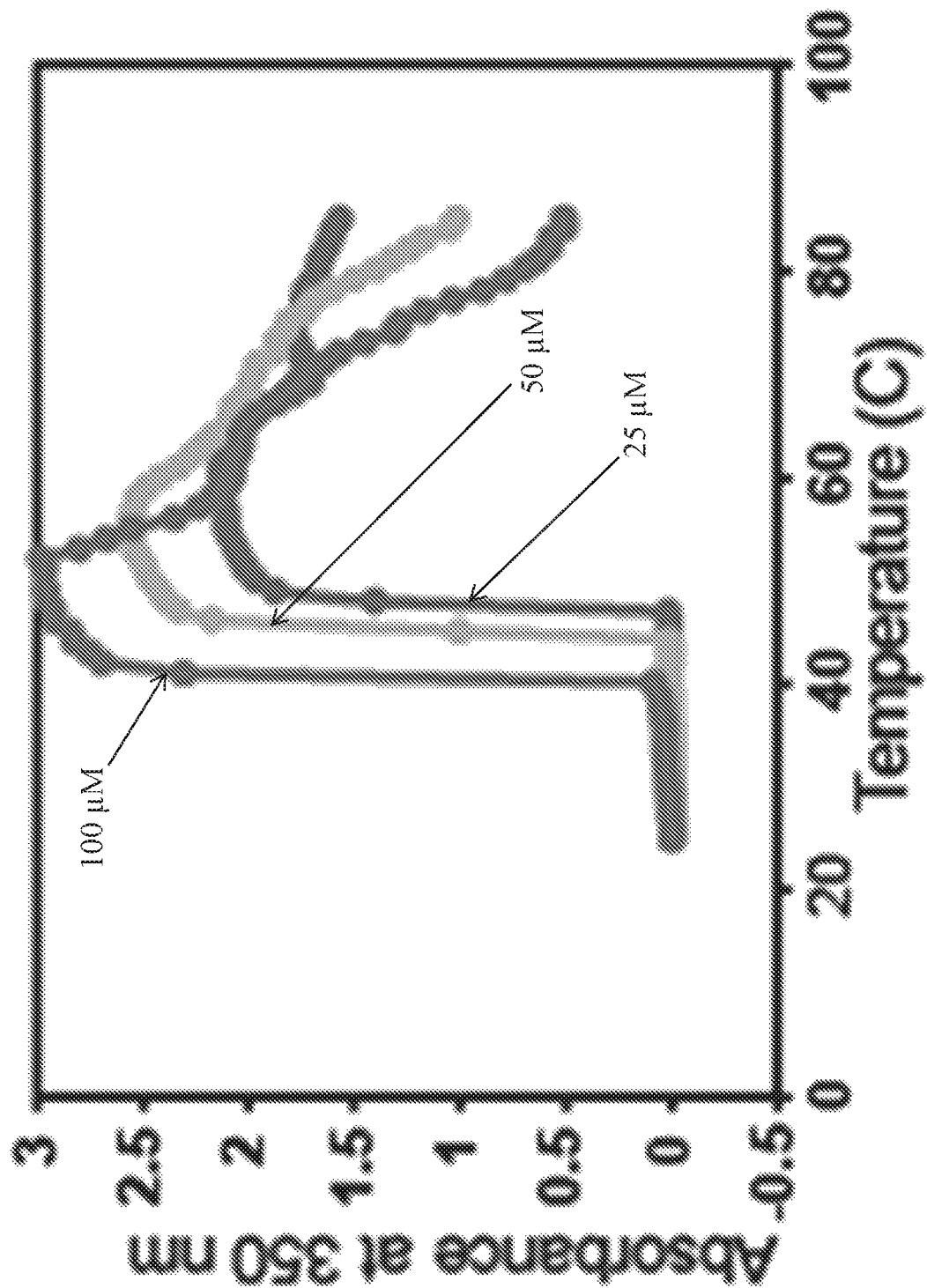
Figure 5F:
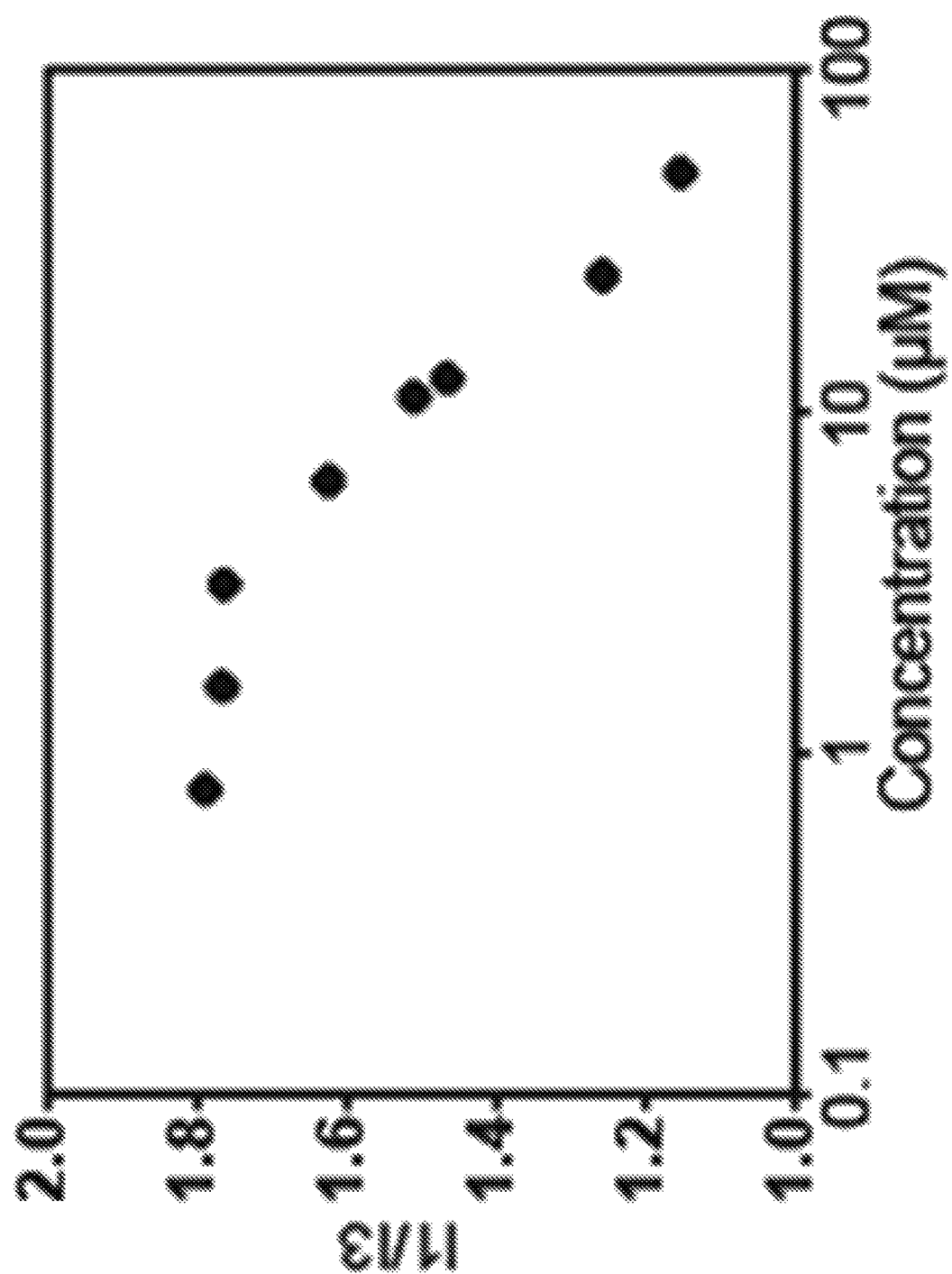
Figure 6A:
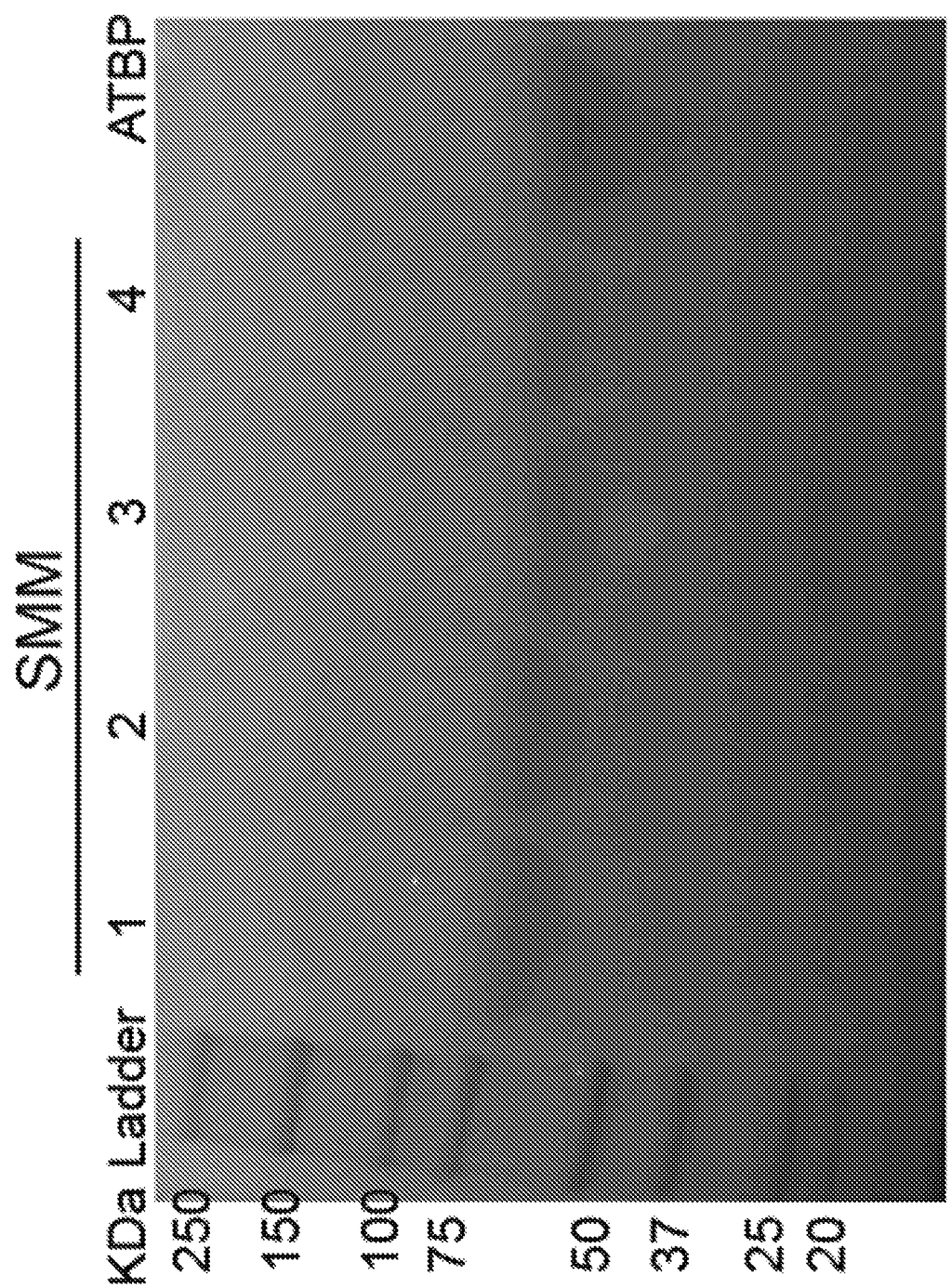
FIG. 6(A)-(B) are images showing the purity of an exemplary ATBP and exemplary ATBP-SMM conjugates.
Figure 6B:
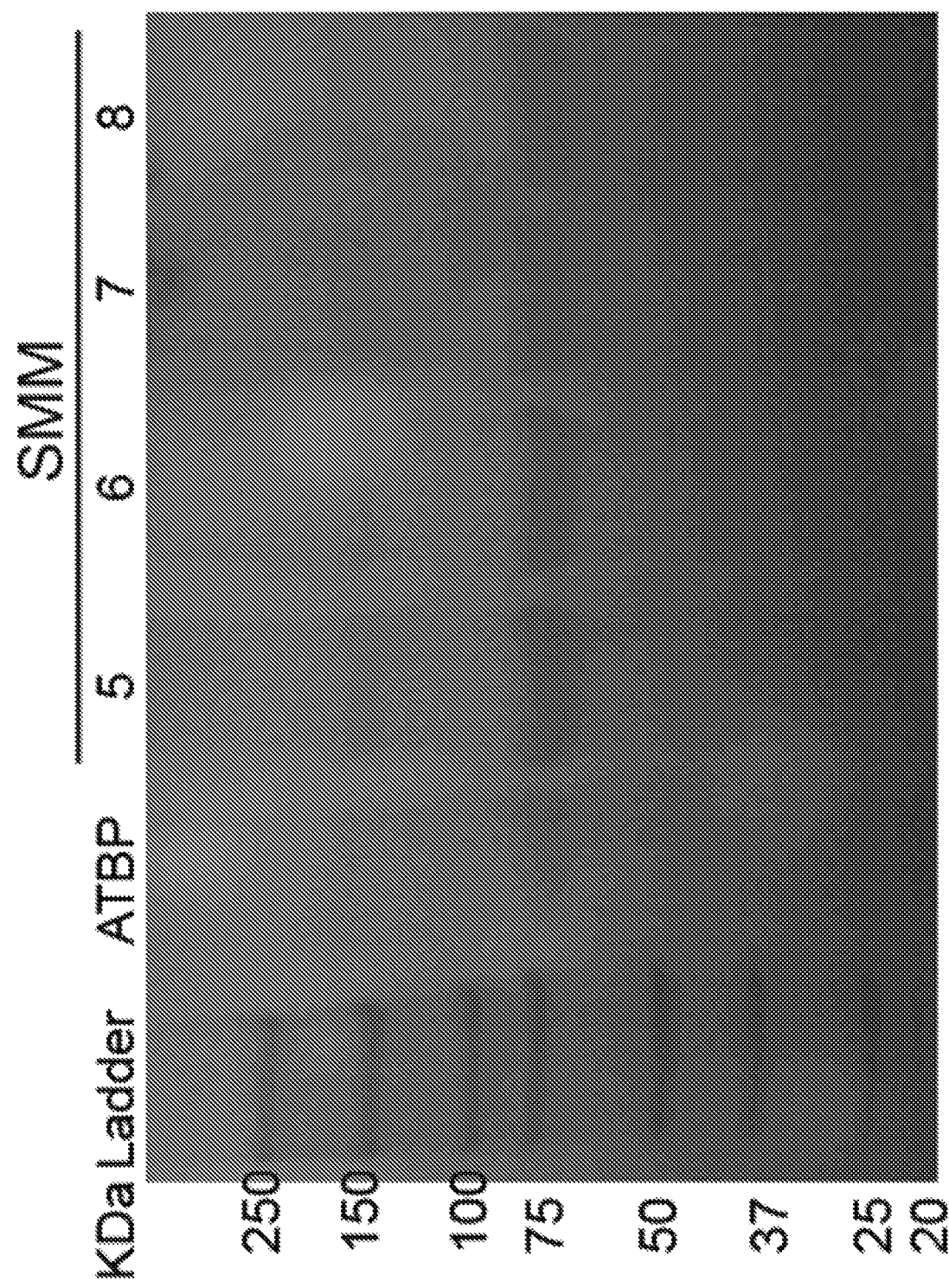
Figure 7:
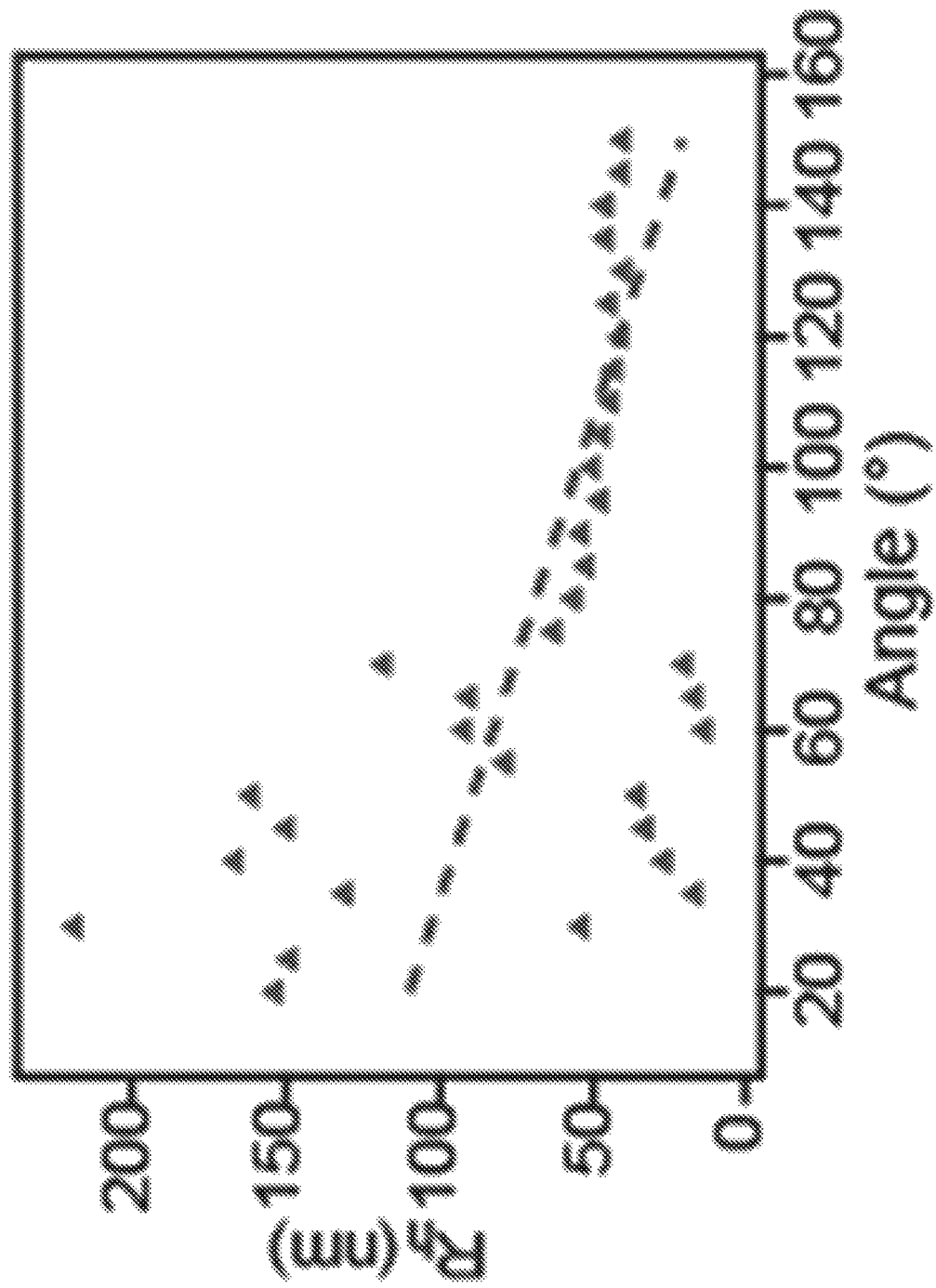
FIG. 7(A)-(D) show characterization of exemplary ATBP-N-1-(2-Amino-ethyl)-pyrrole-2,5-dione hydrochloride (SMM2) conjugates.
Figure 7B:
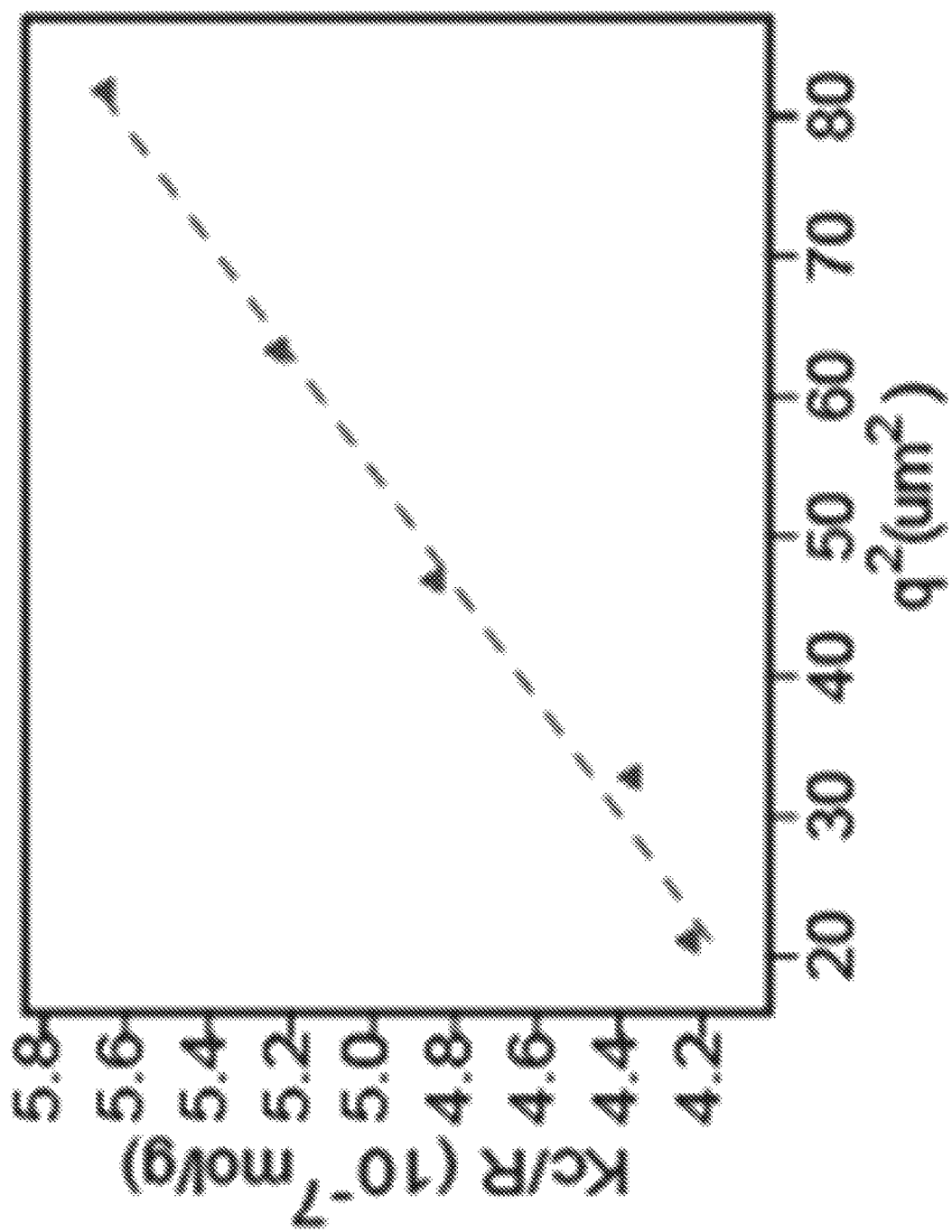
Figure 7C:
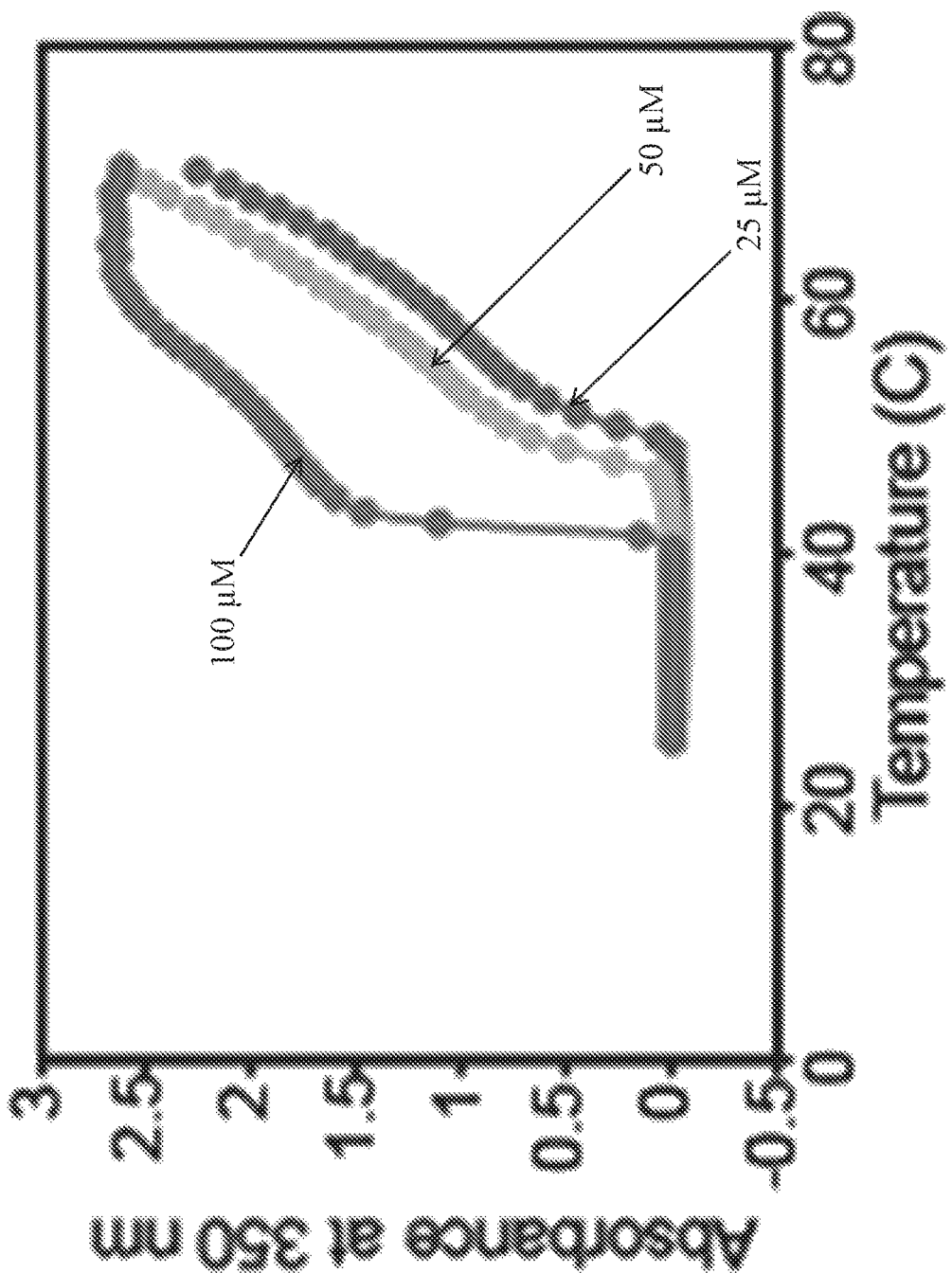
Figure 7D:
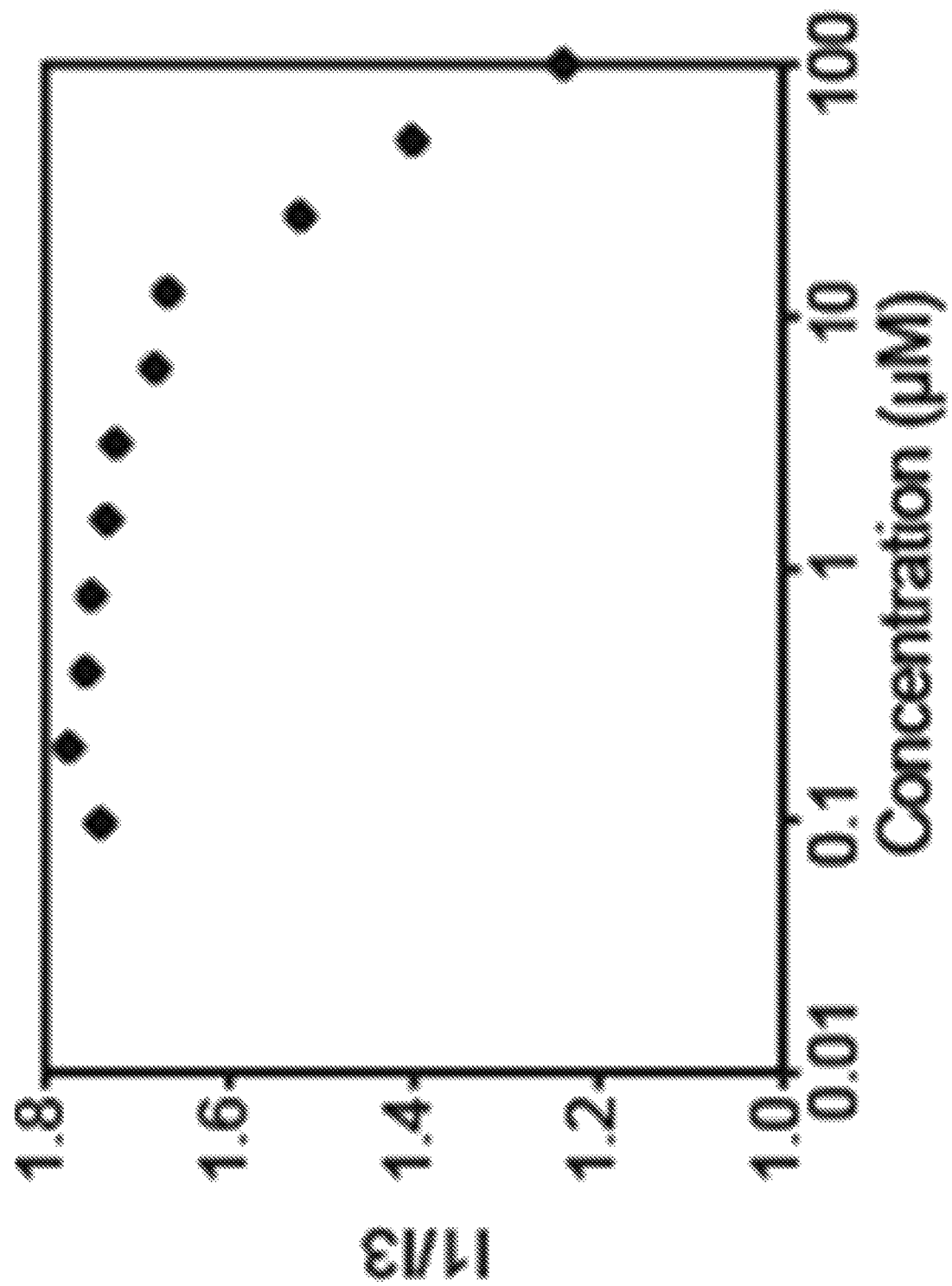
Figure 8A:
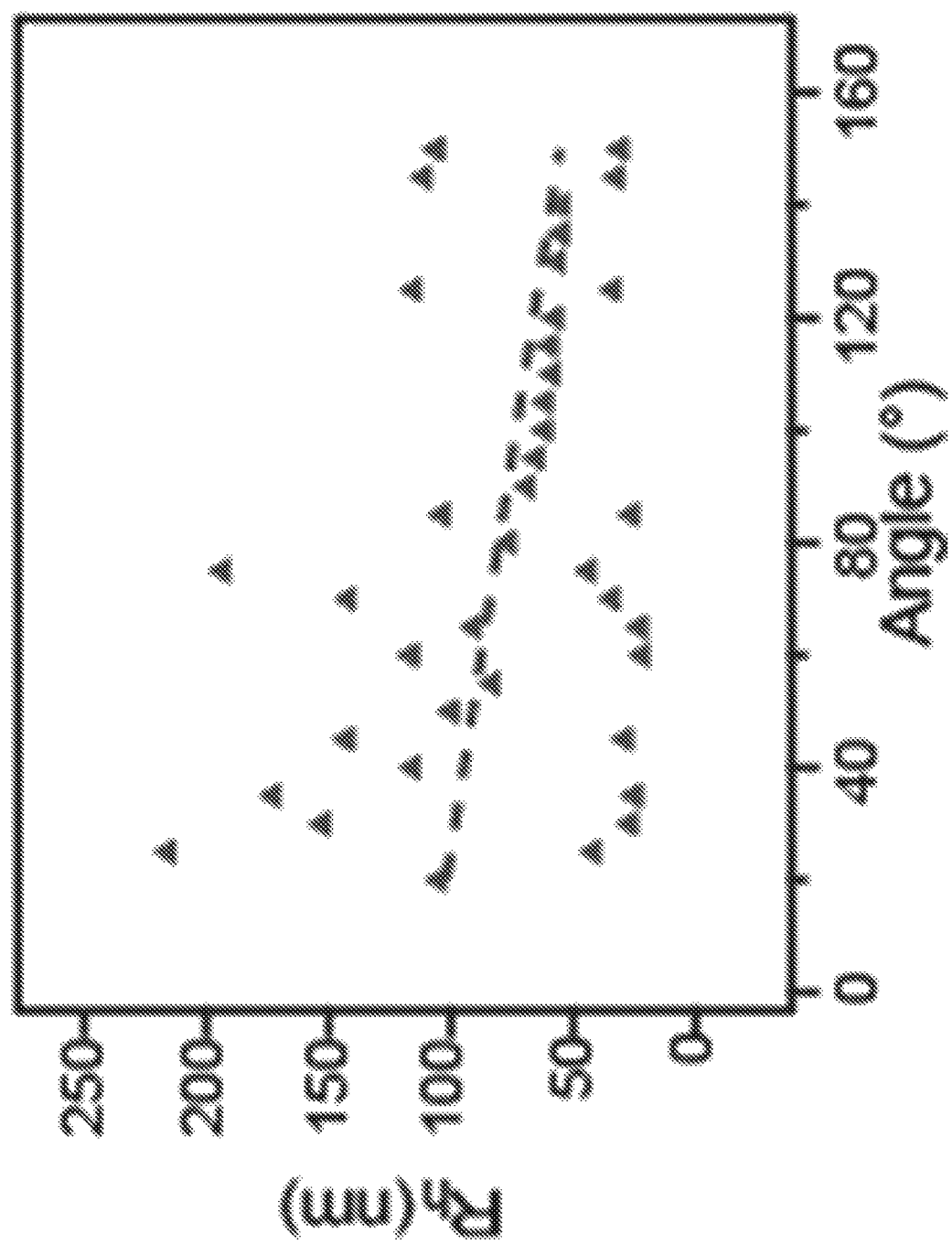
FIG. 8(A)-(E) show characterization of exemplary ATBP-N-2-Maleimidoethyl mesylate (SMM3) conjugates.
Figure 8B:
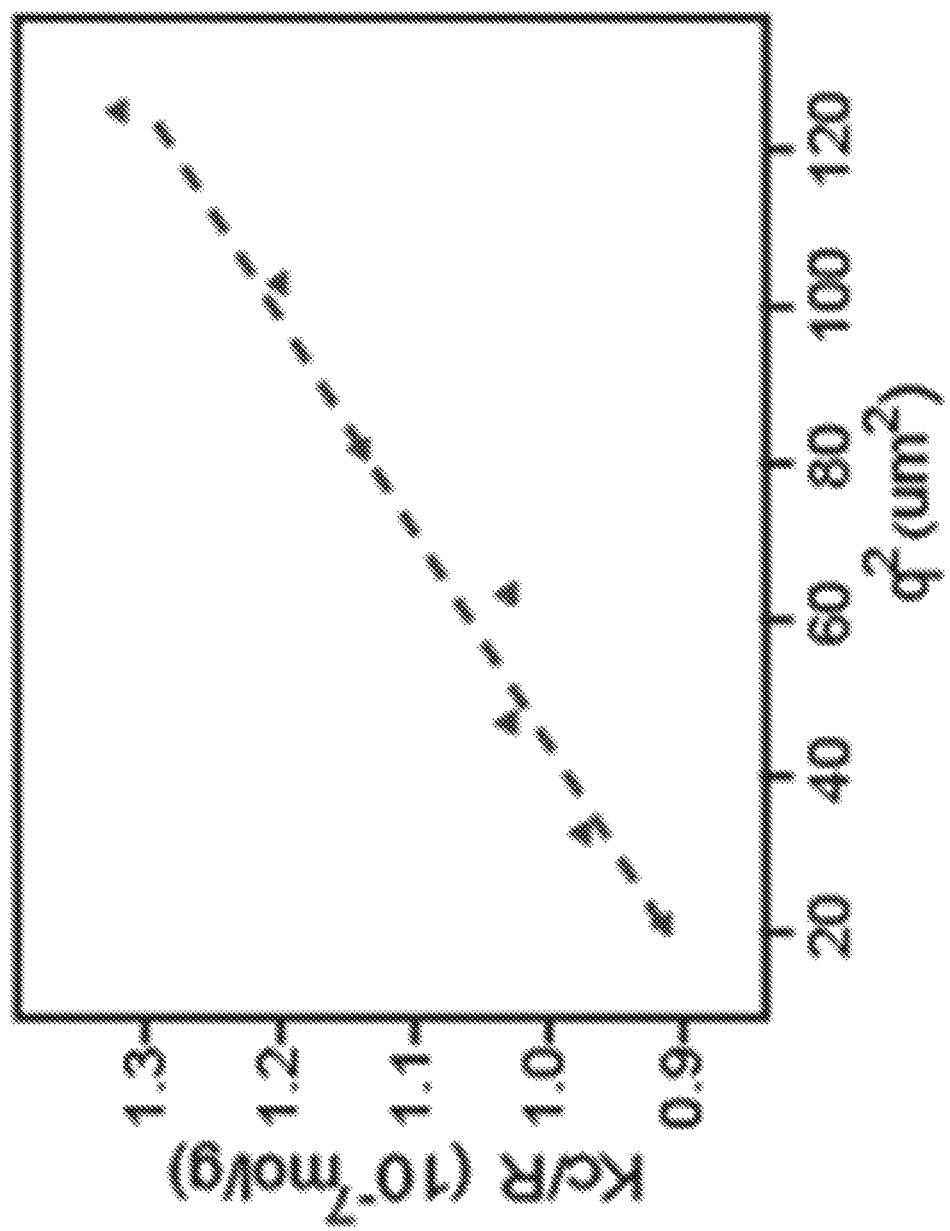
Figure 8C:
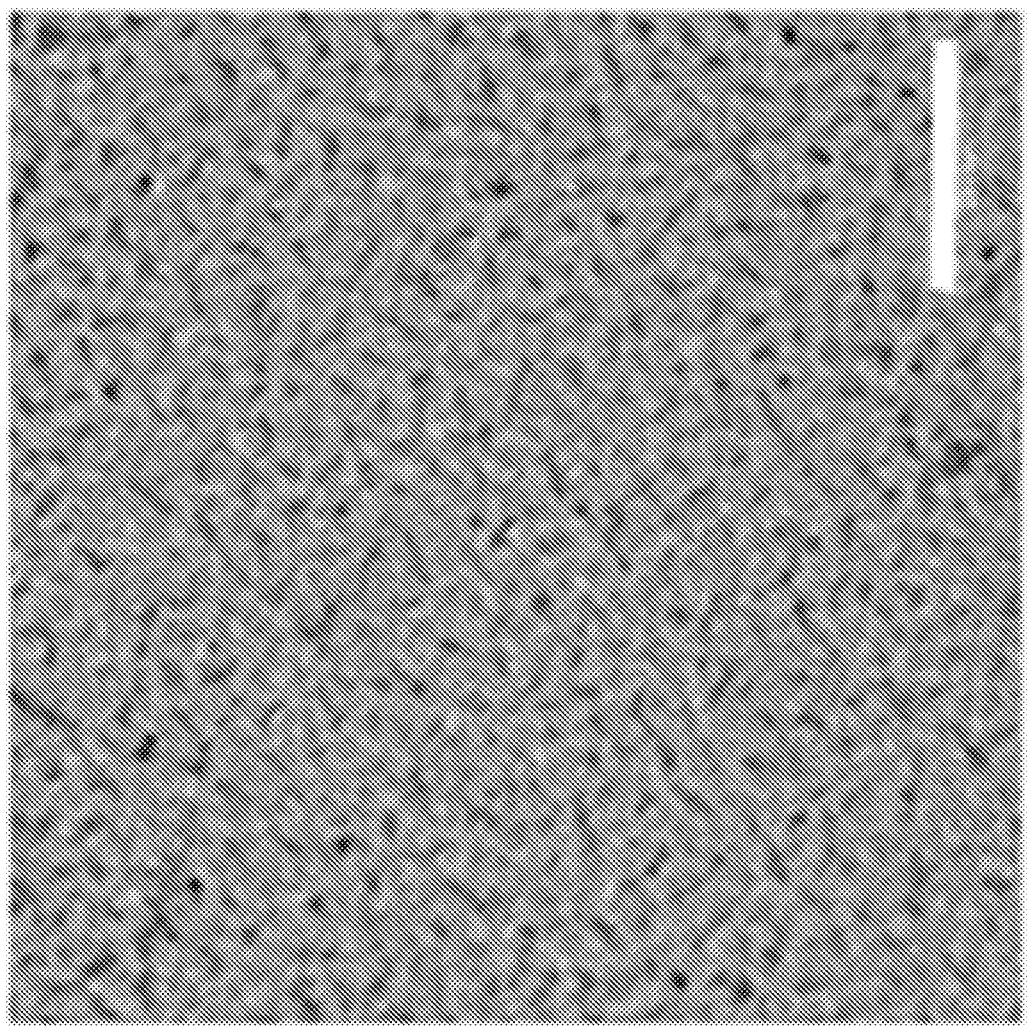
Figure 8:
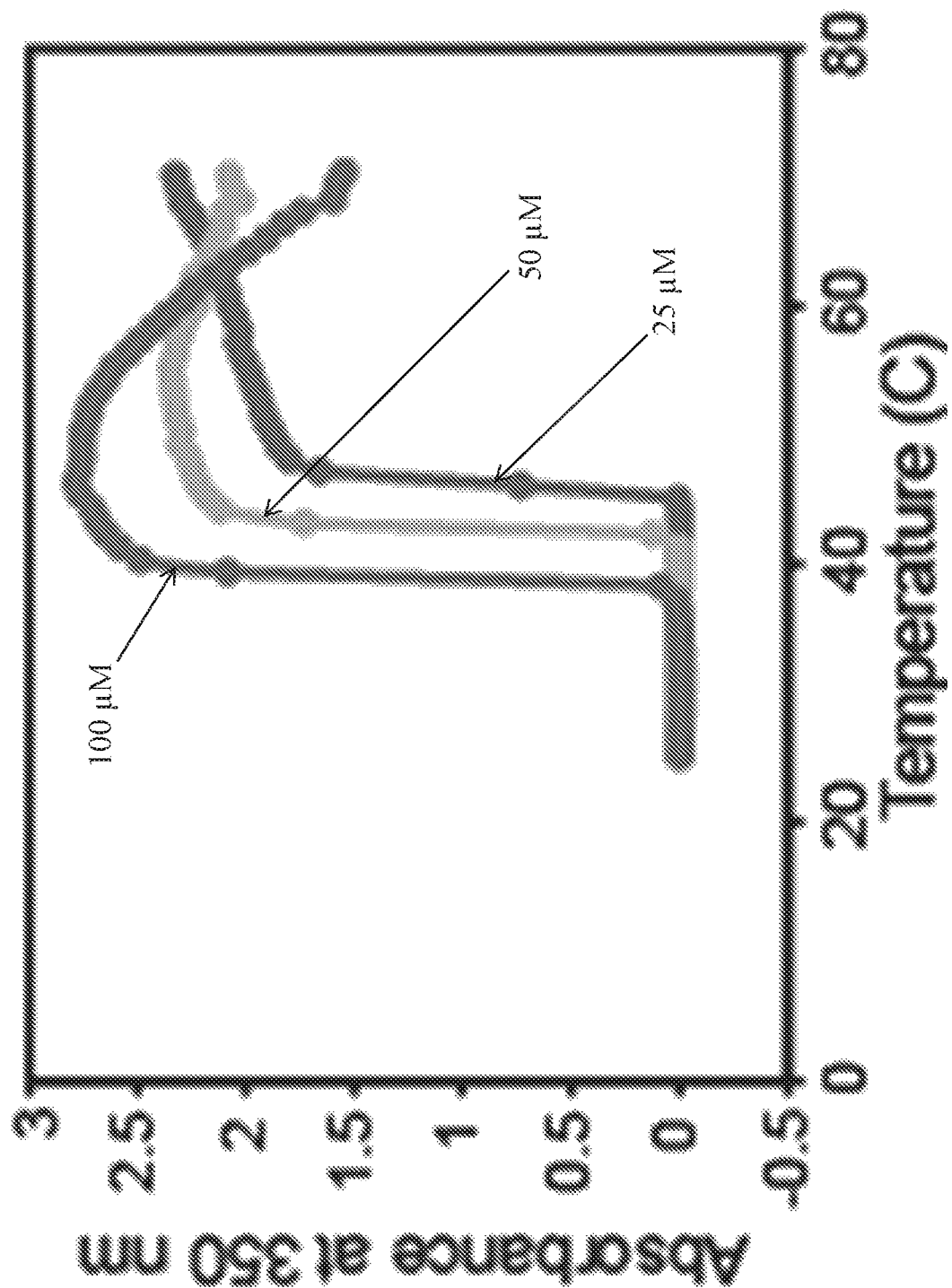
Figure 8E:
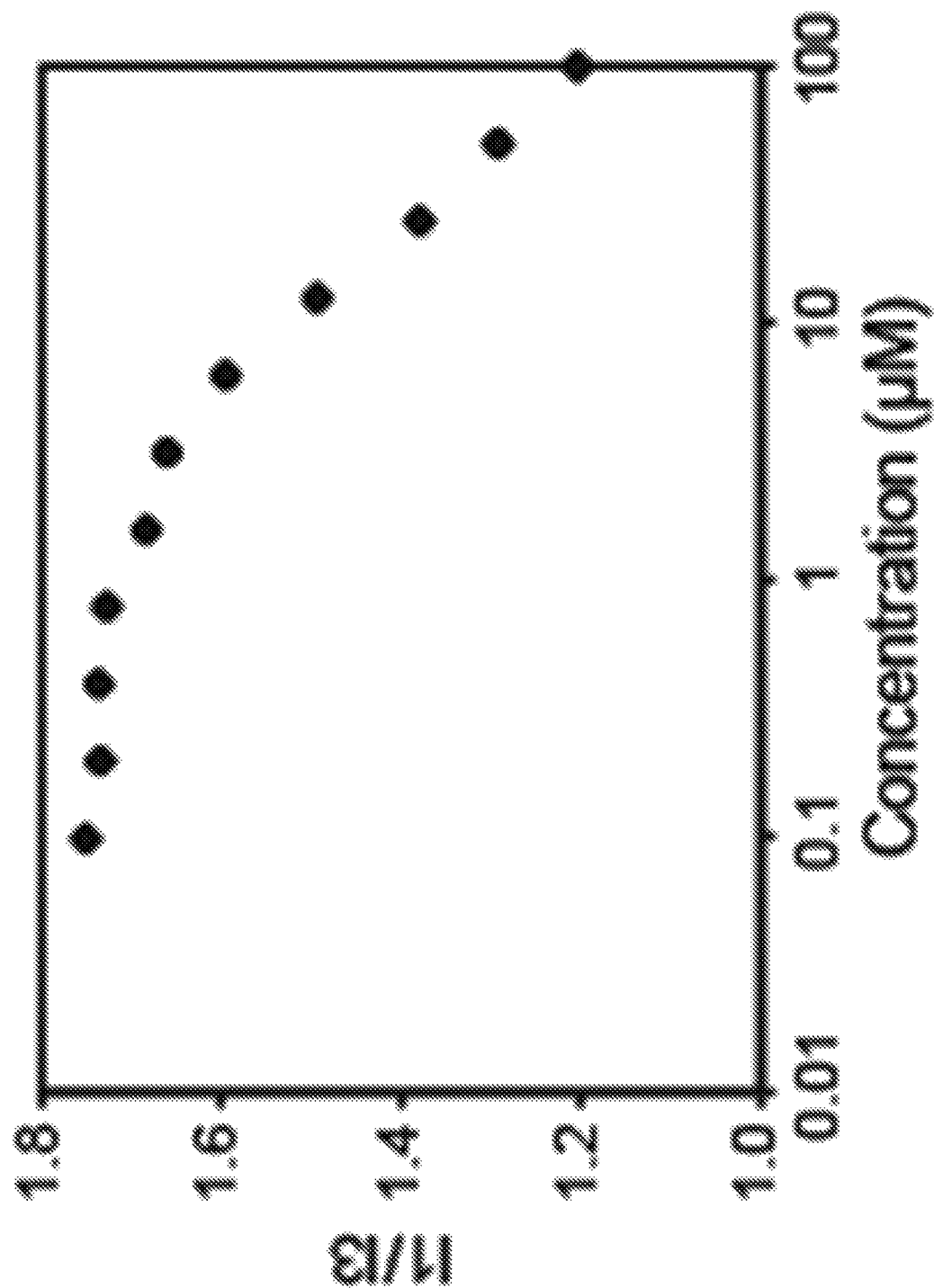
Figure 9A:
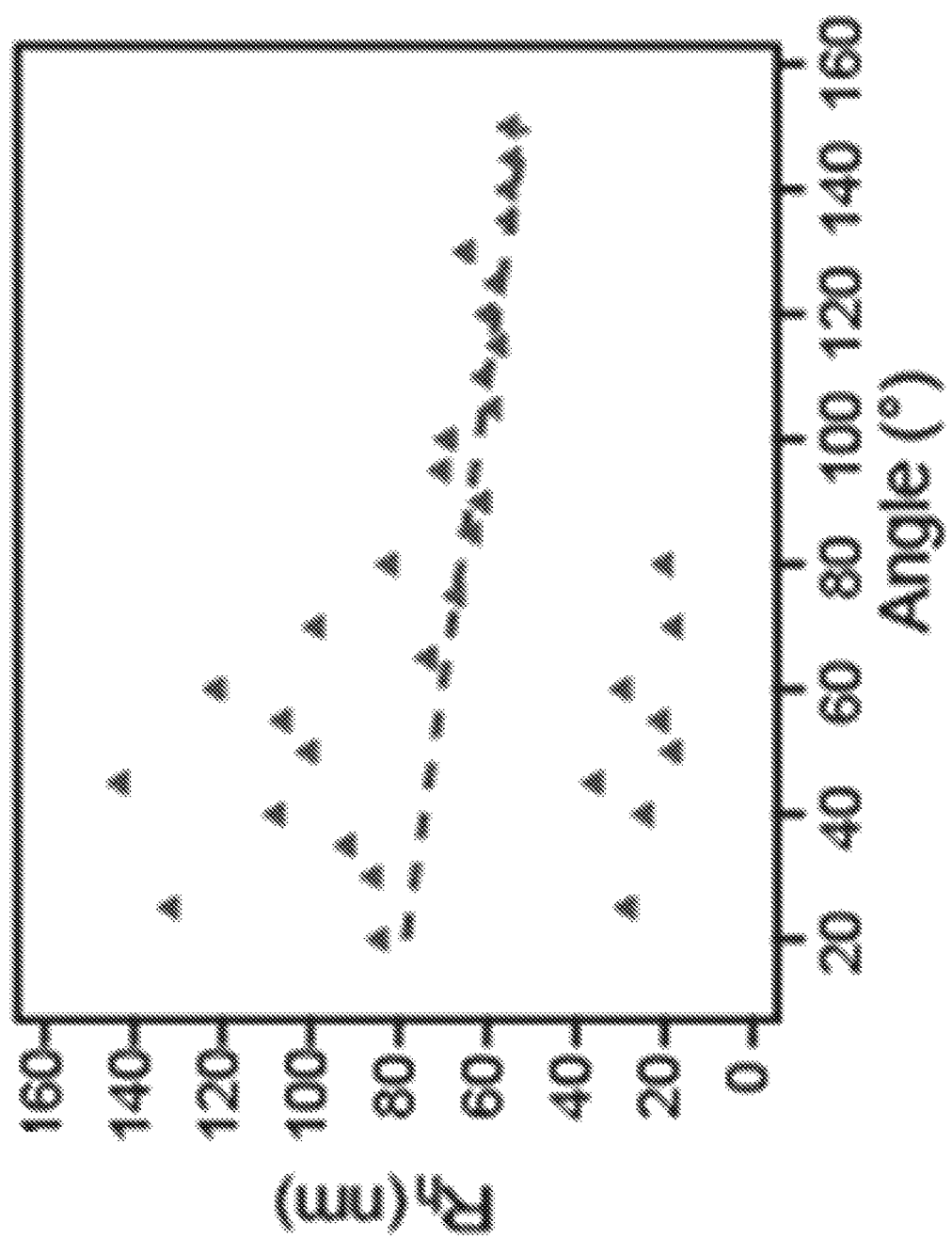
FIG. 9(A)-(E) show characterization of exemplary ATBP-N-Maleoyl-β-alanine (SMM4) conjugates.
Figure 9B:
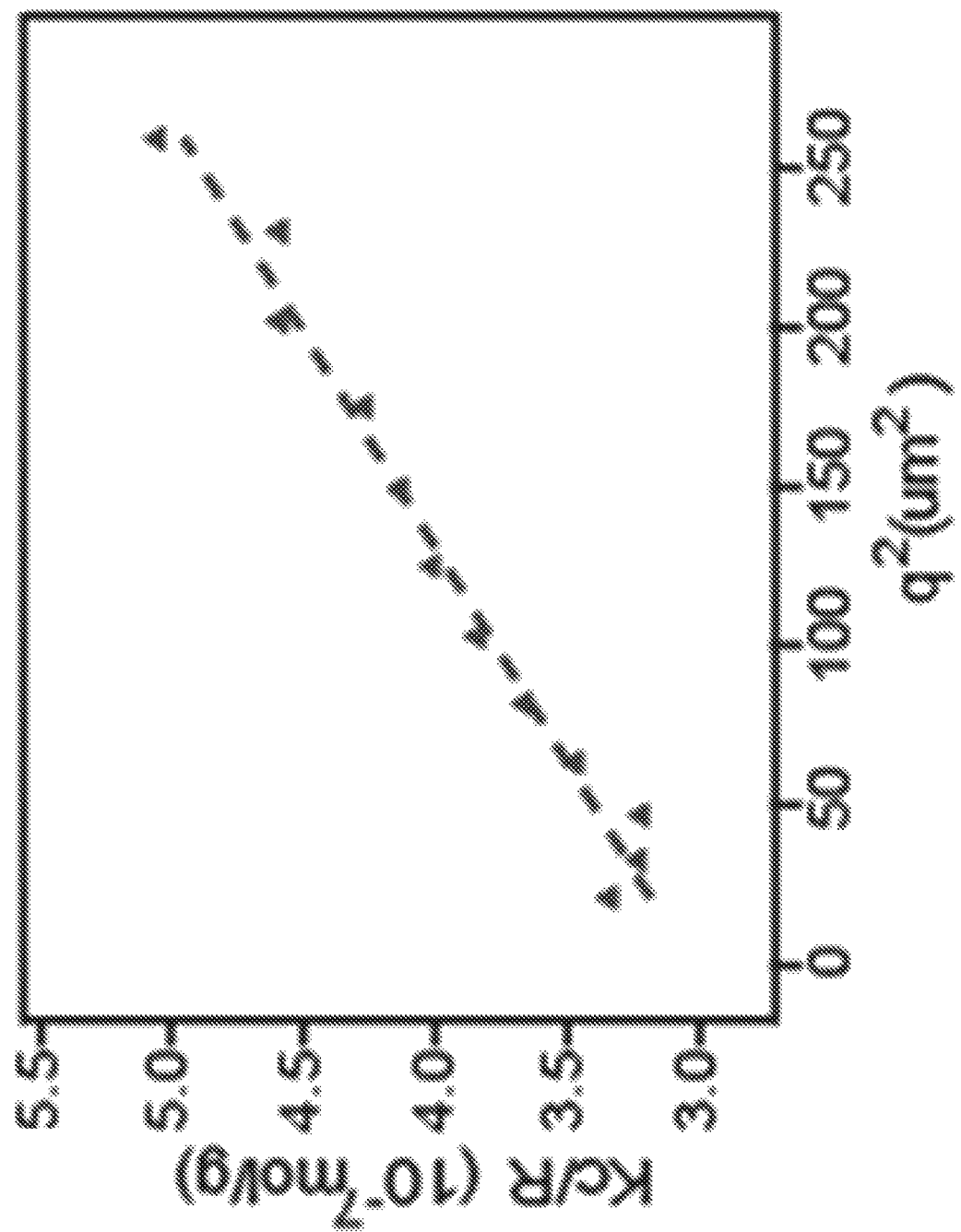
Figure 9C:
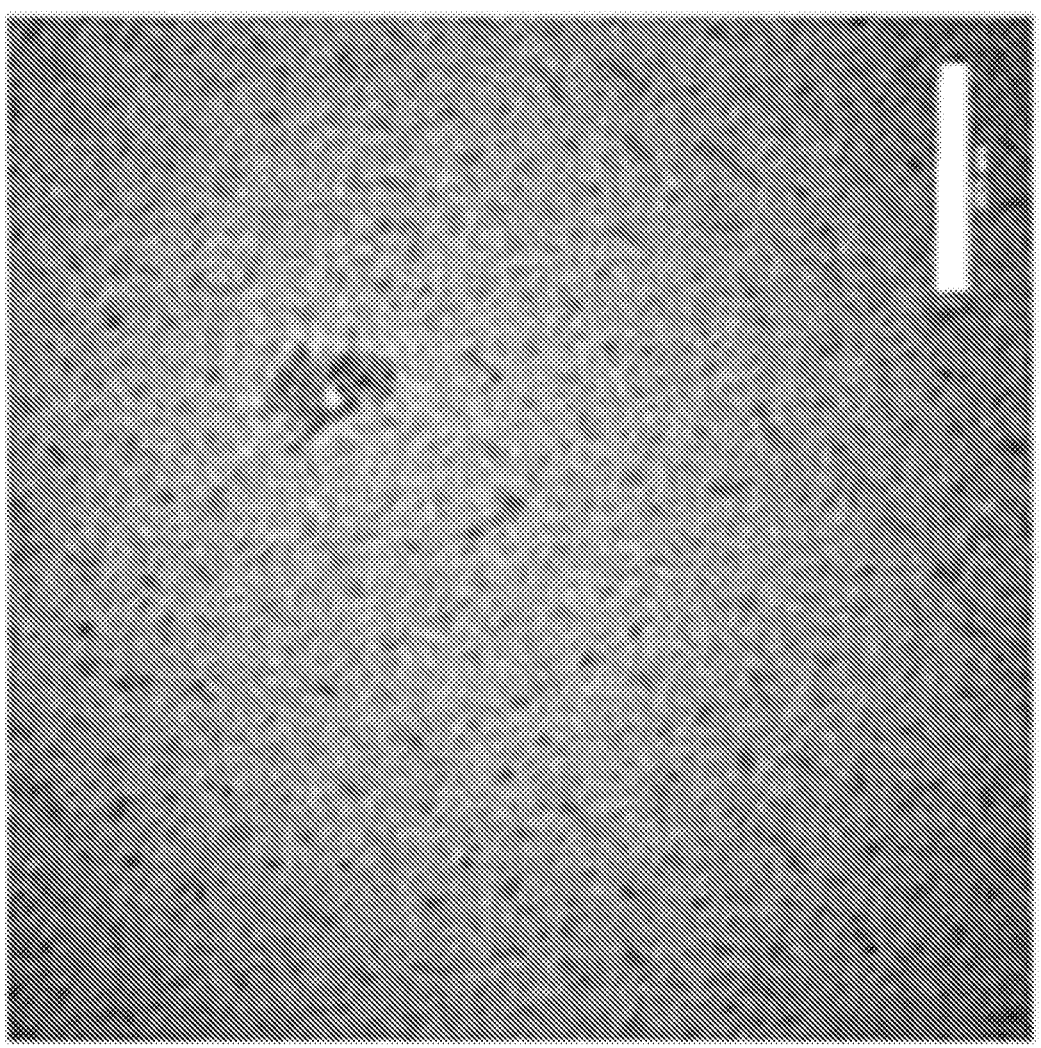
Figure 9:
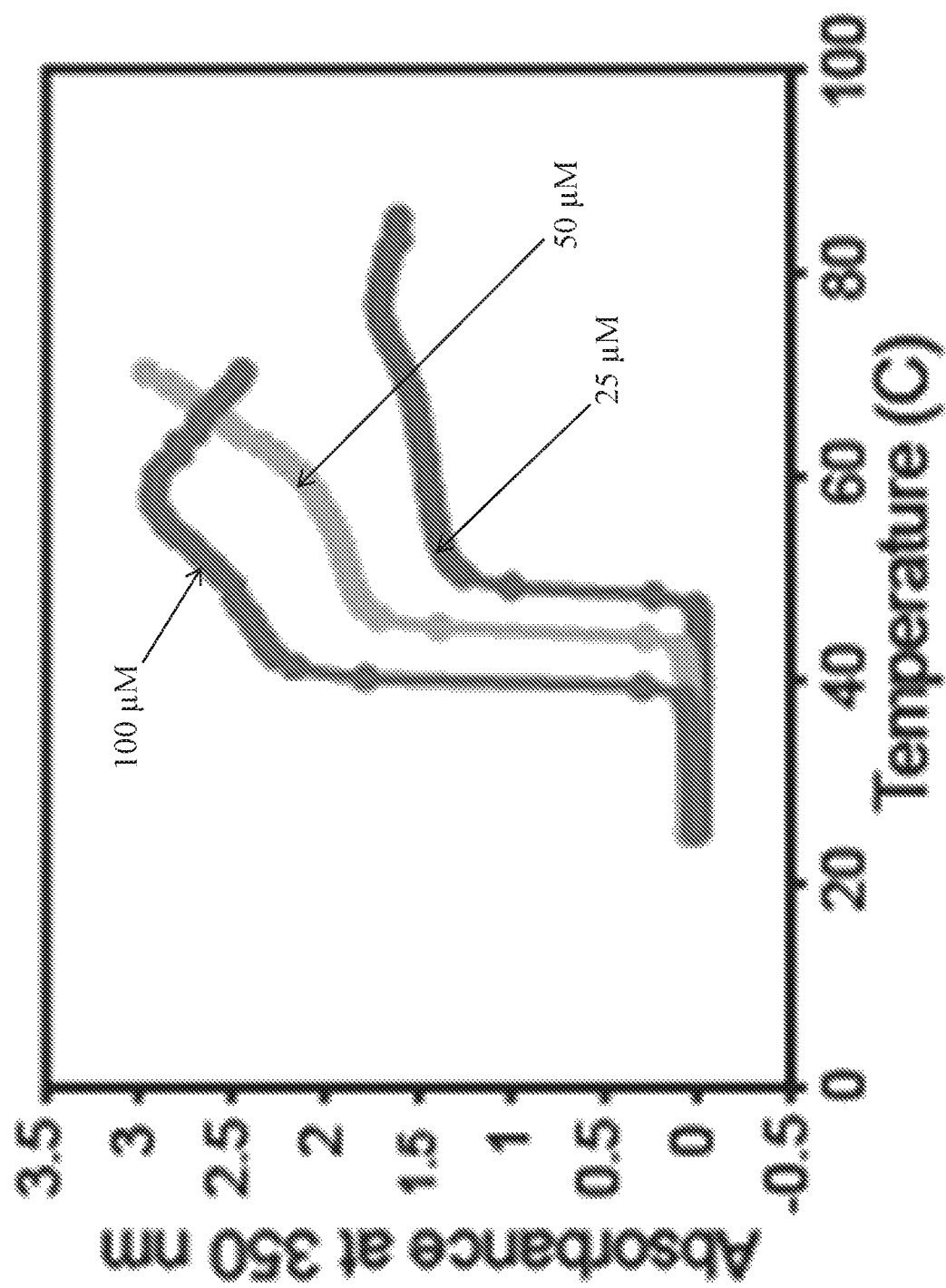
Figure 9E:
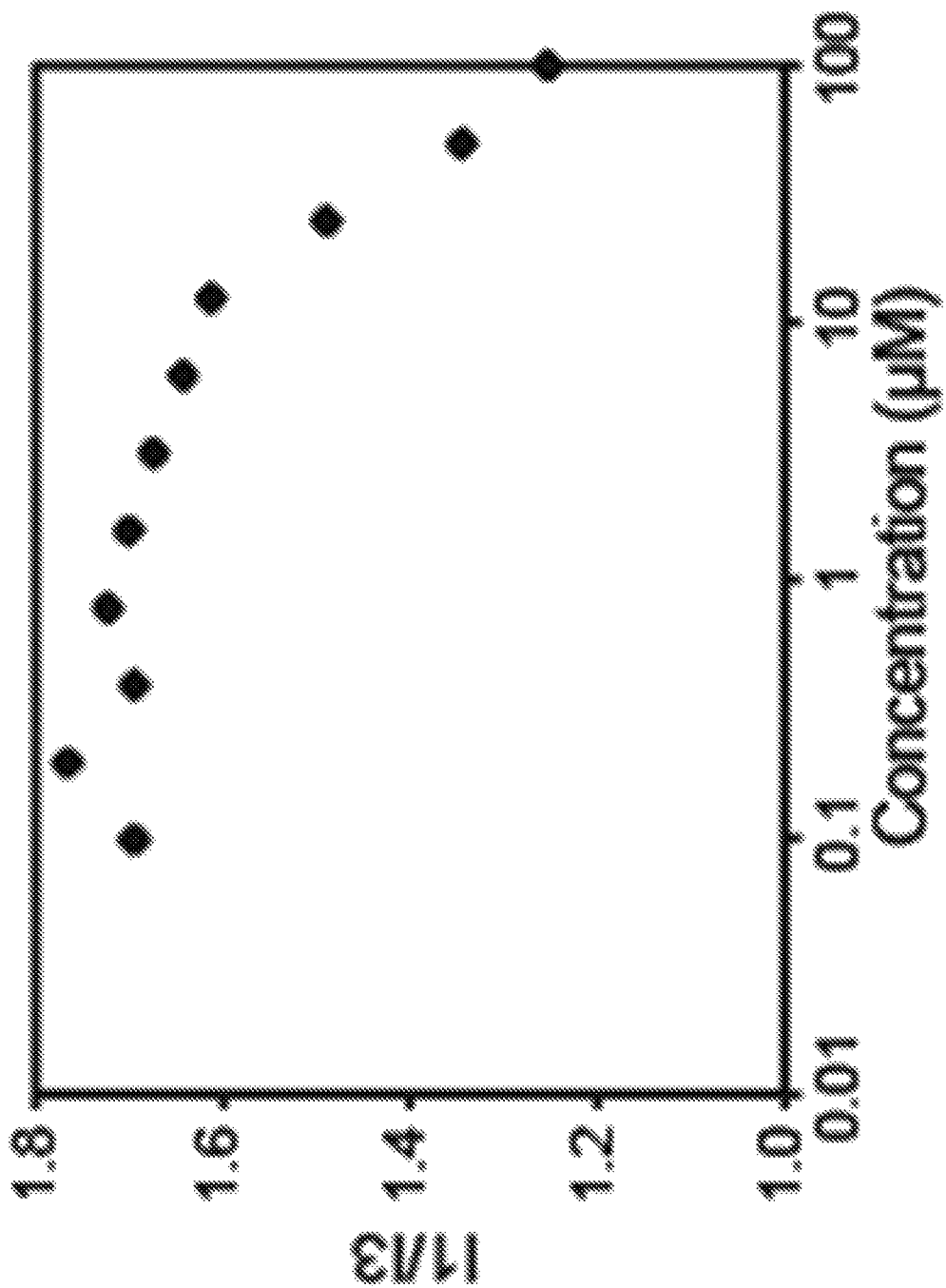
Figure 10A:
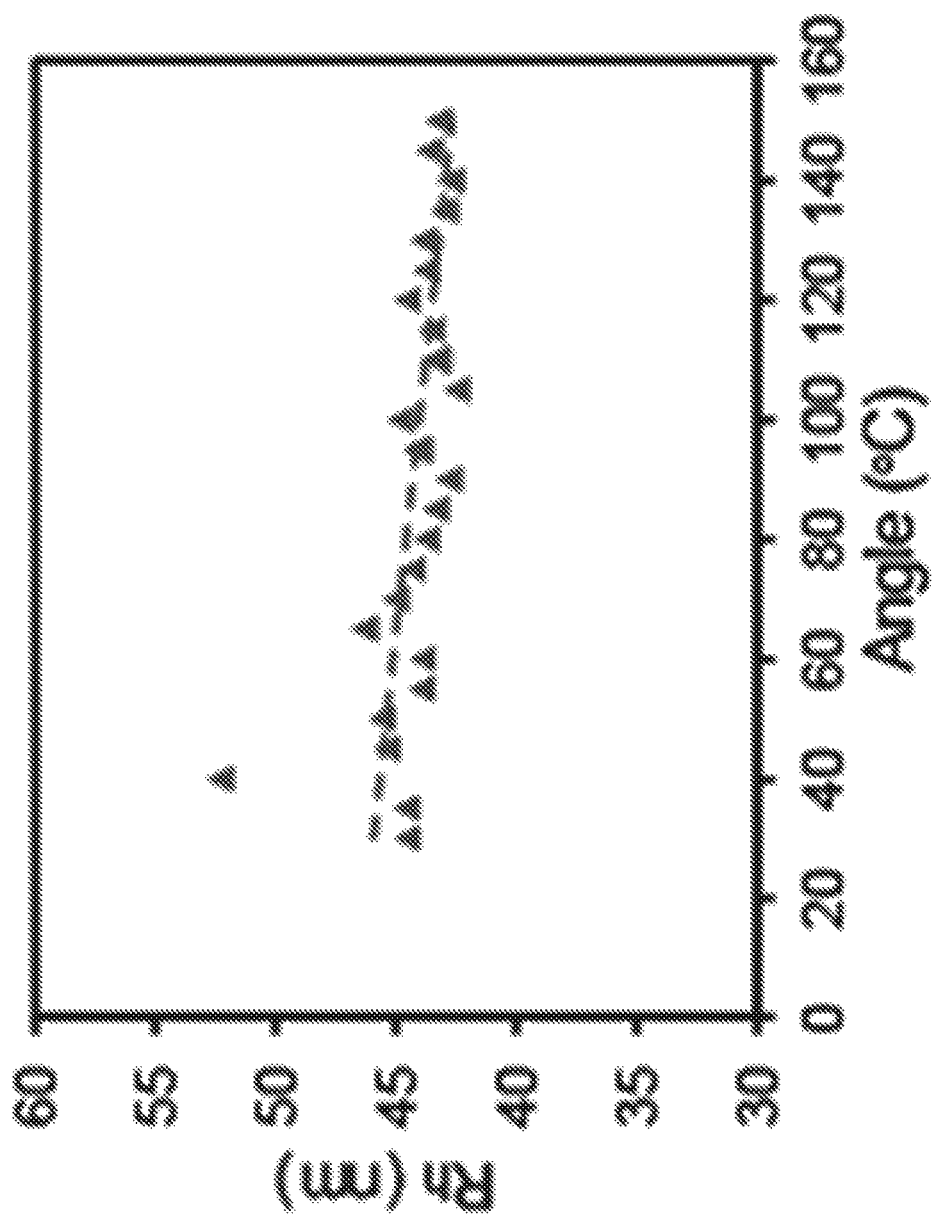
FIG. 10(A)-(E) show characterization of exemplary ATBP-N-methyl maleimide (SMM5) conjugates.
Figure 10B:
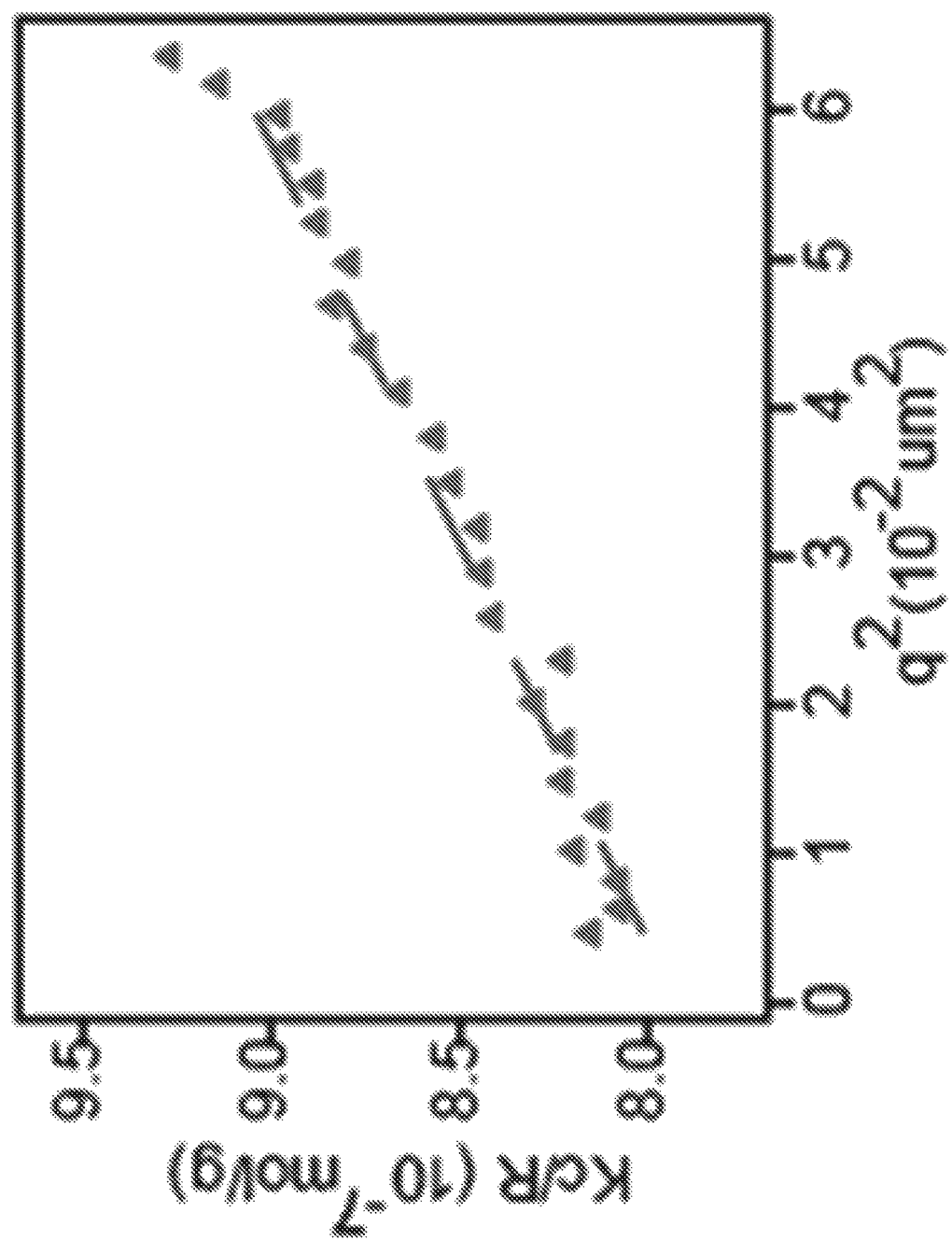
Figure 10C:
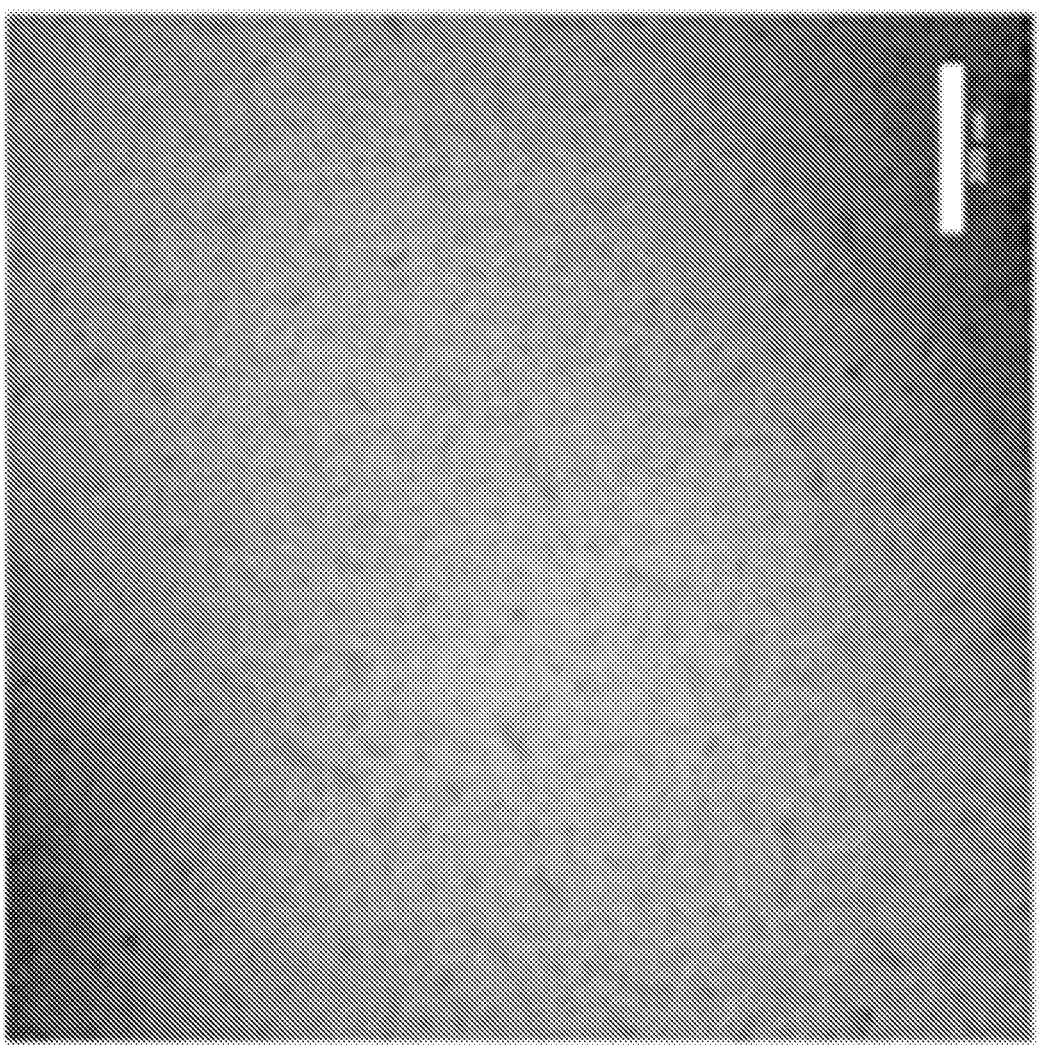
Figure 10D:
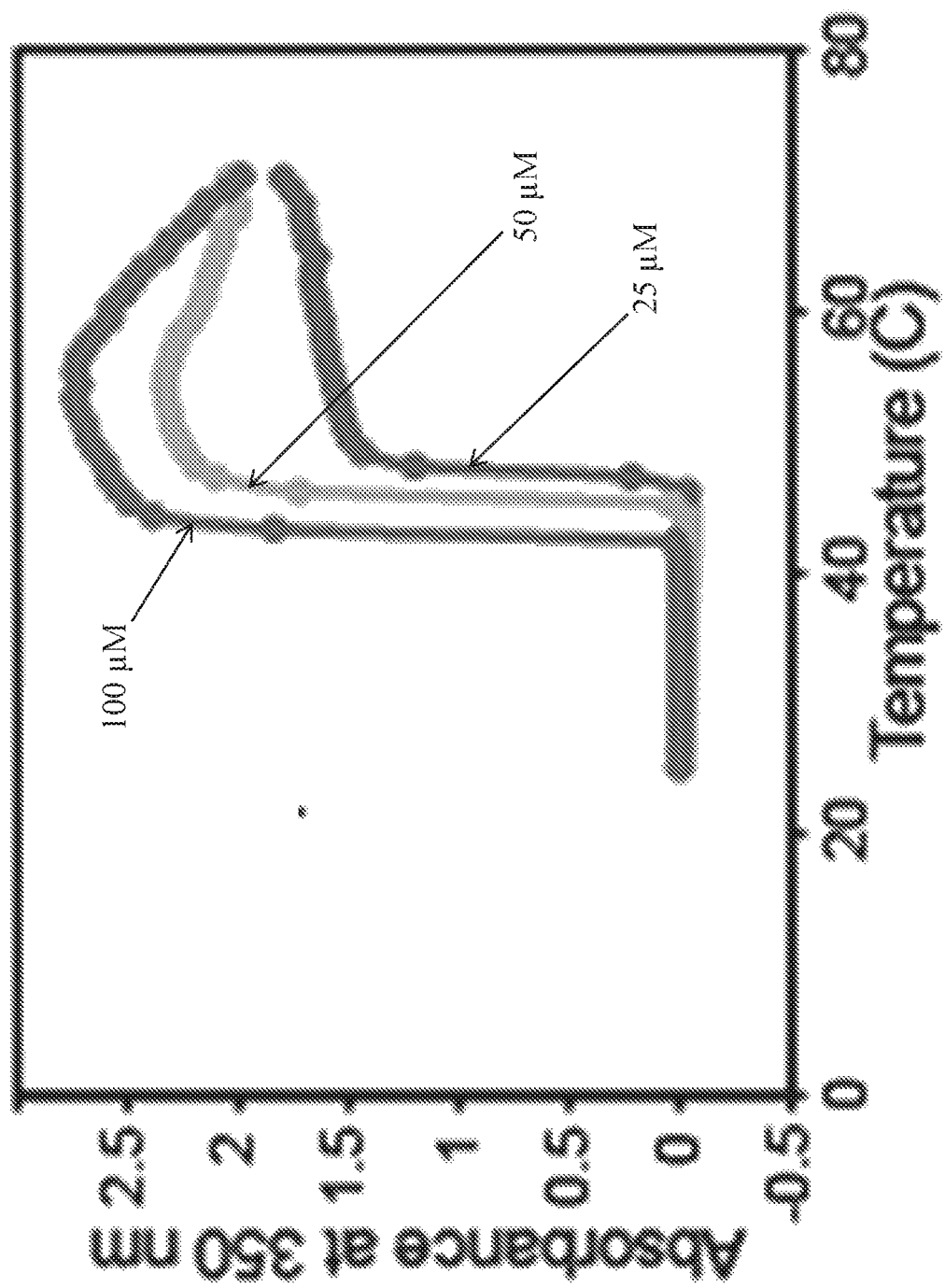
Figure 10E:
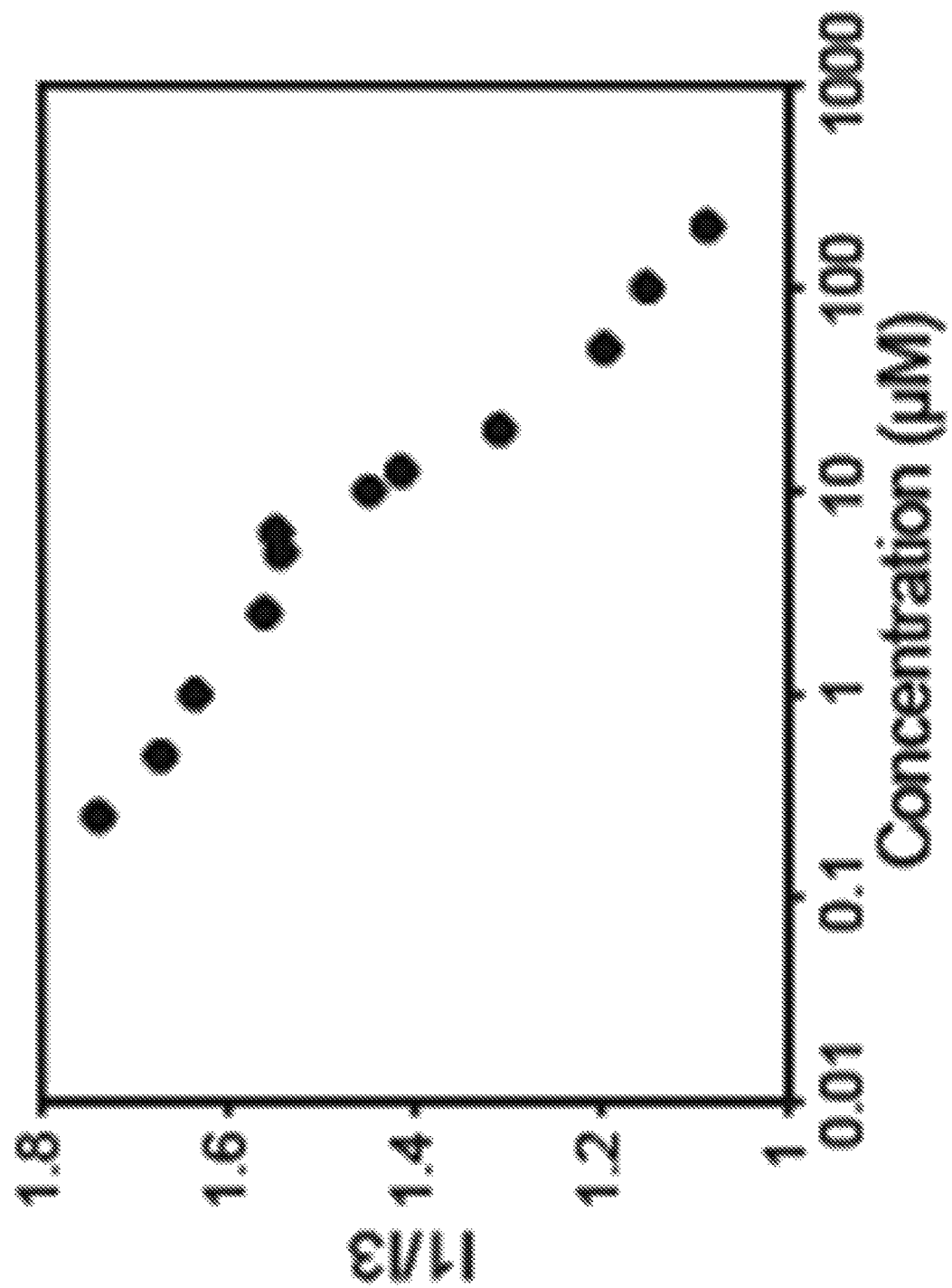
Figure 11A:
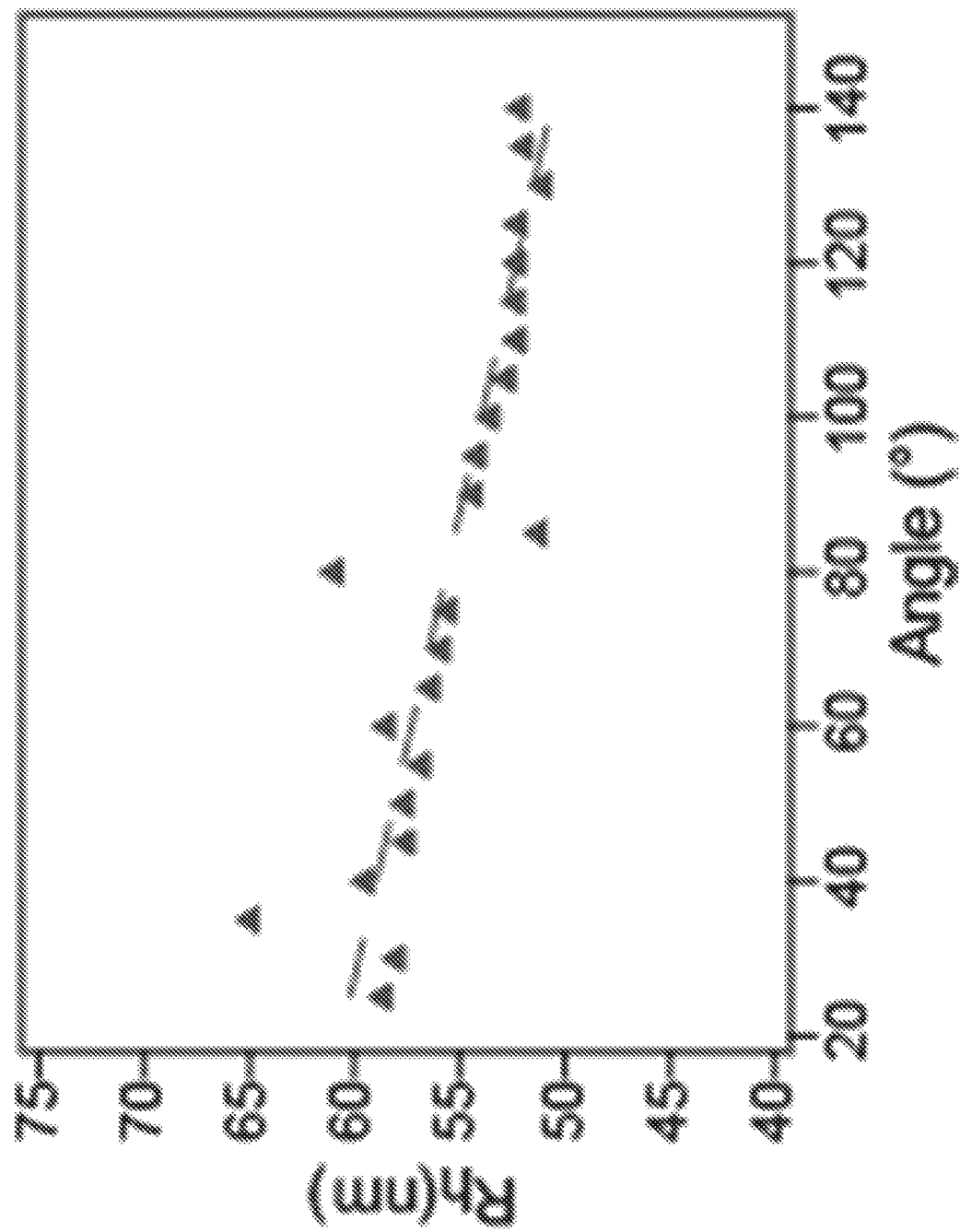
Figure 11B:
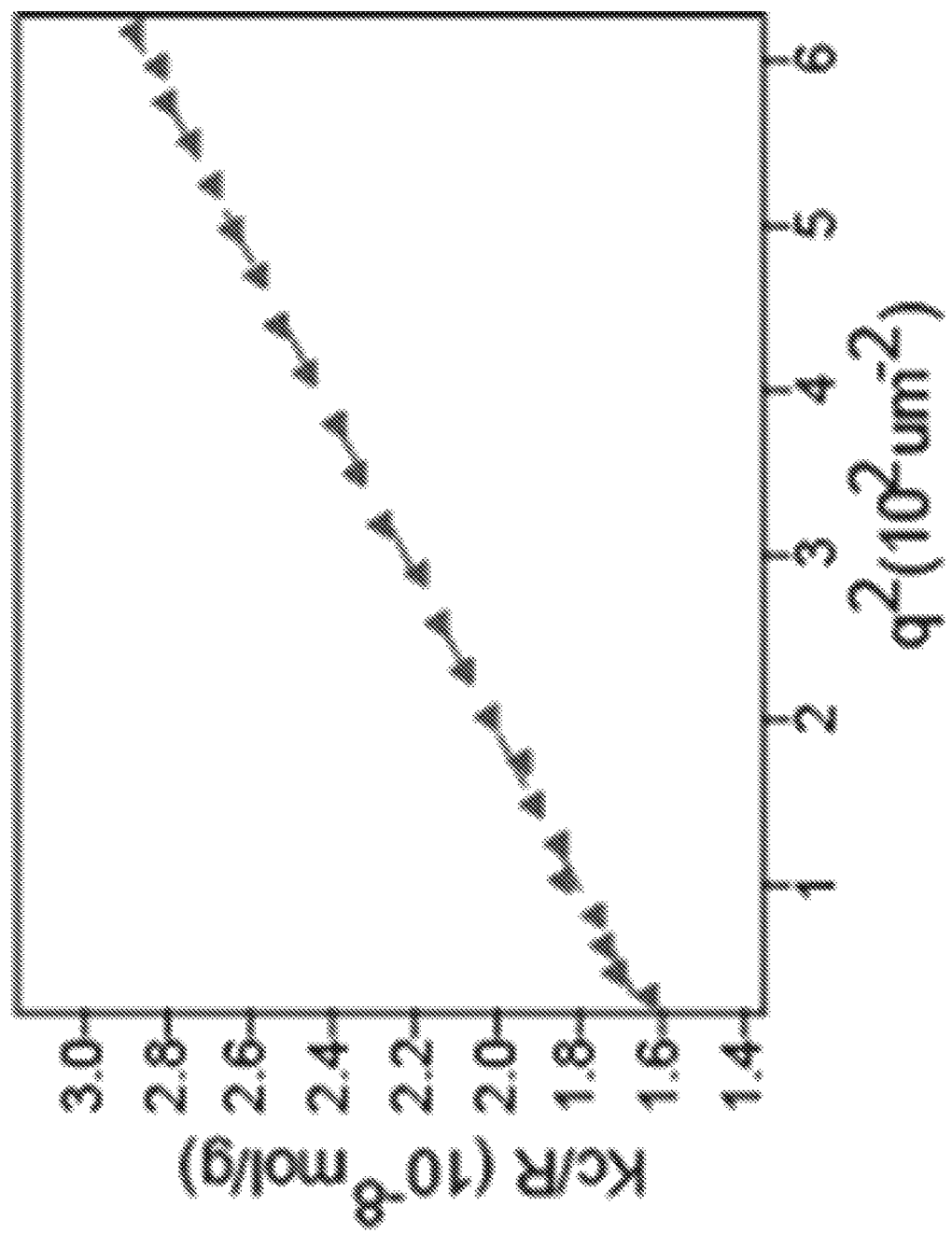
Figure 1C:
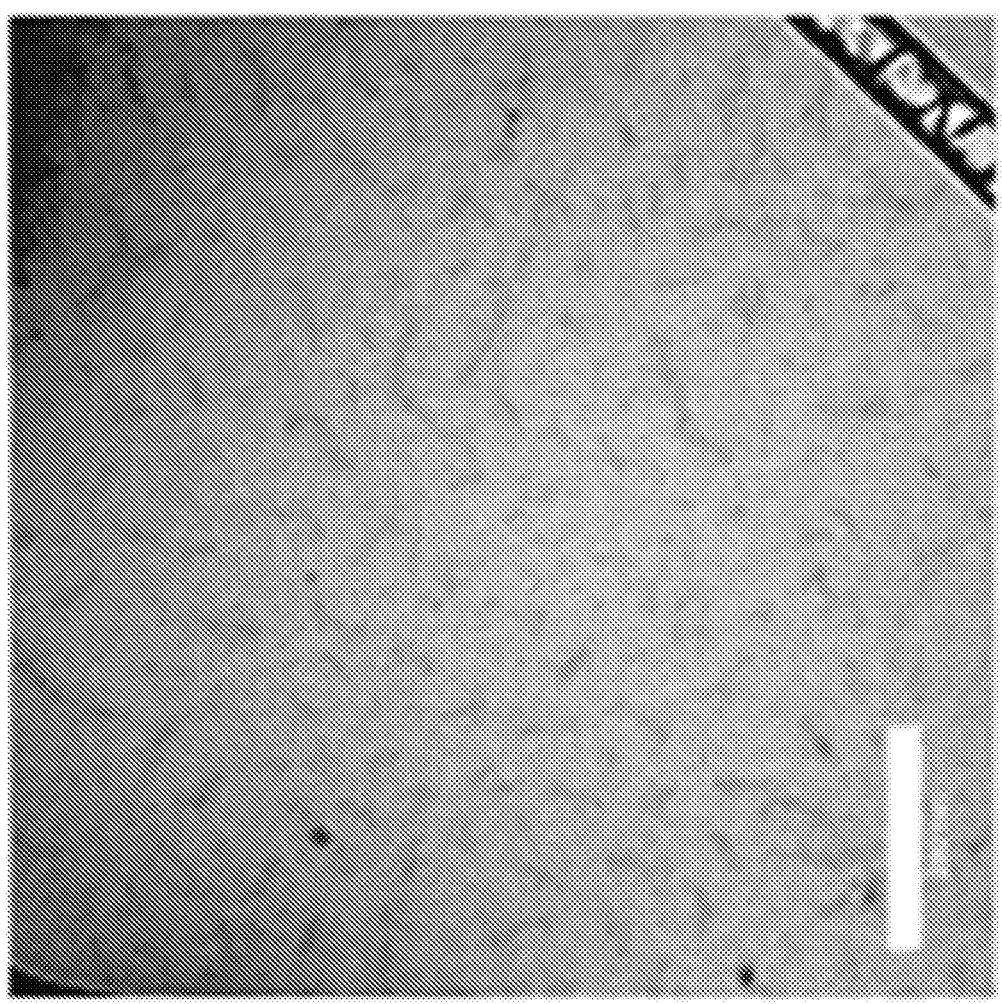
Figure 11D:
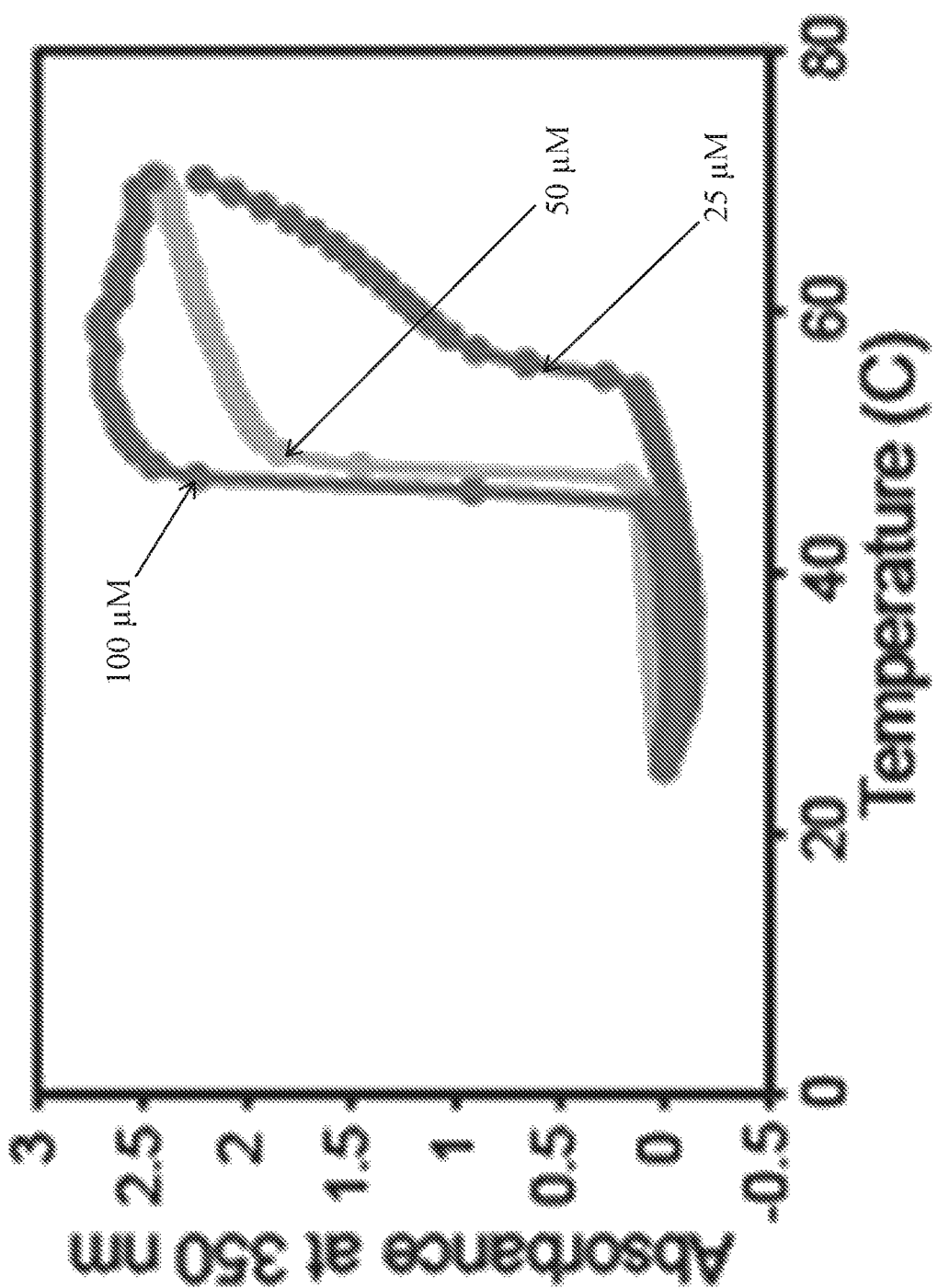
Figure 11E:
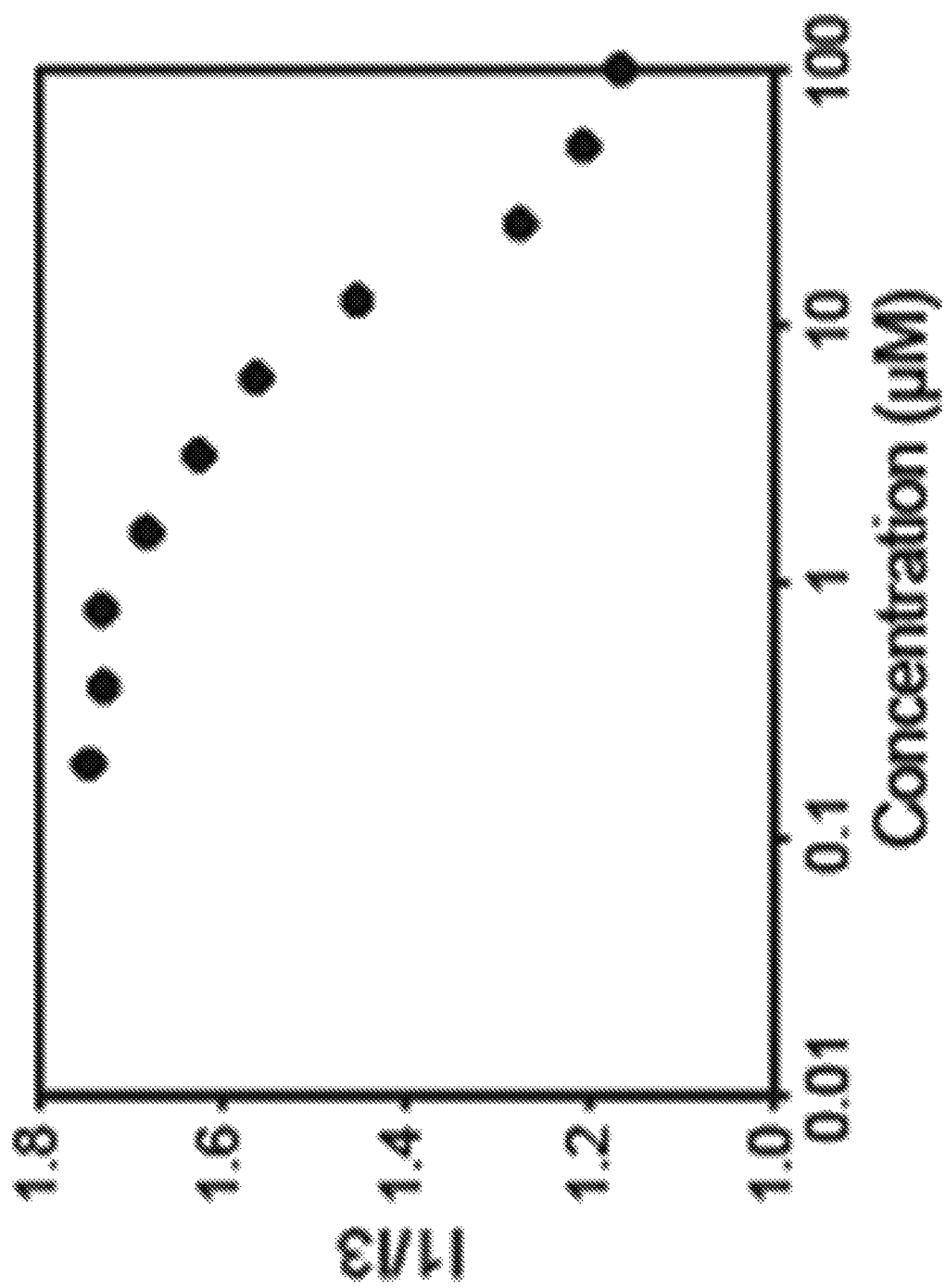
Figure 12A:
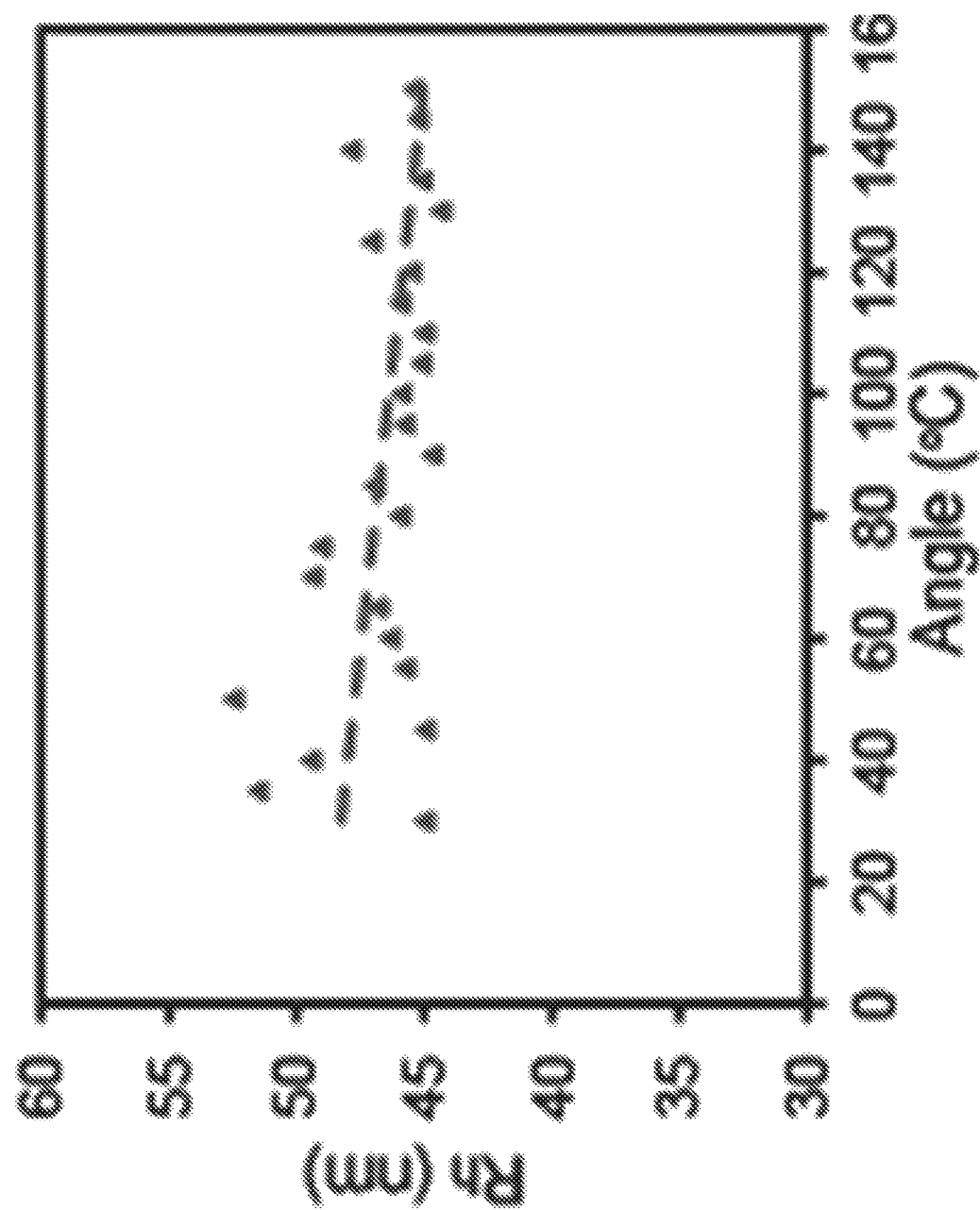
FIG. 12(A)-(E) show characterization of exemplary ATBP-N-Phenyl maleimide (SMM7) conjugates.
Figure 12B:
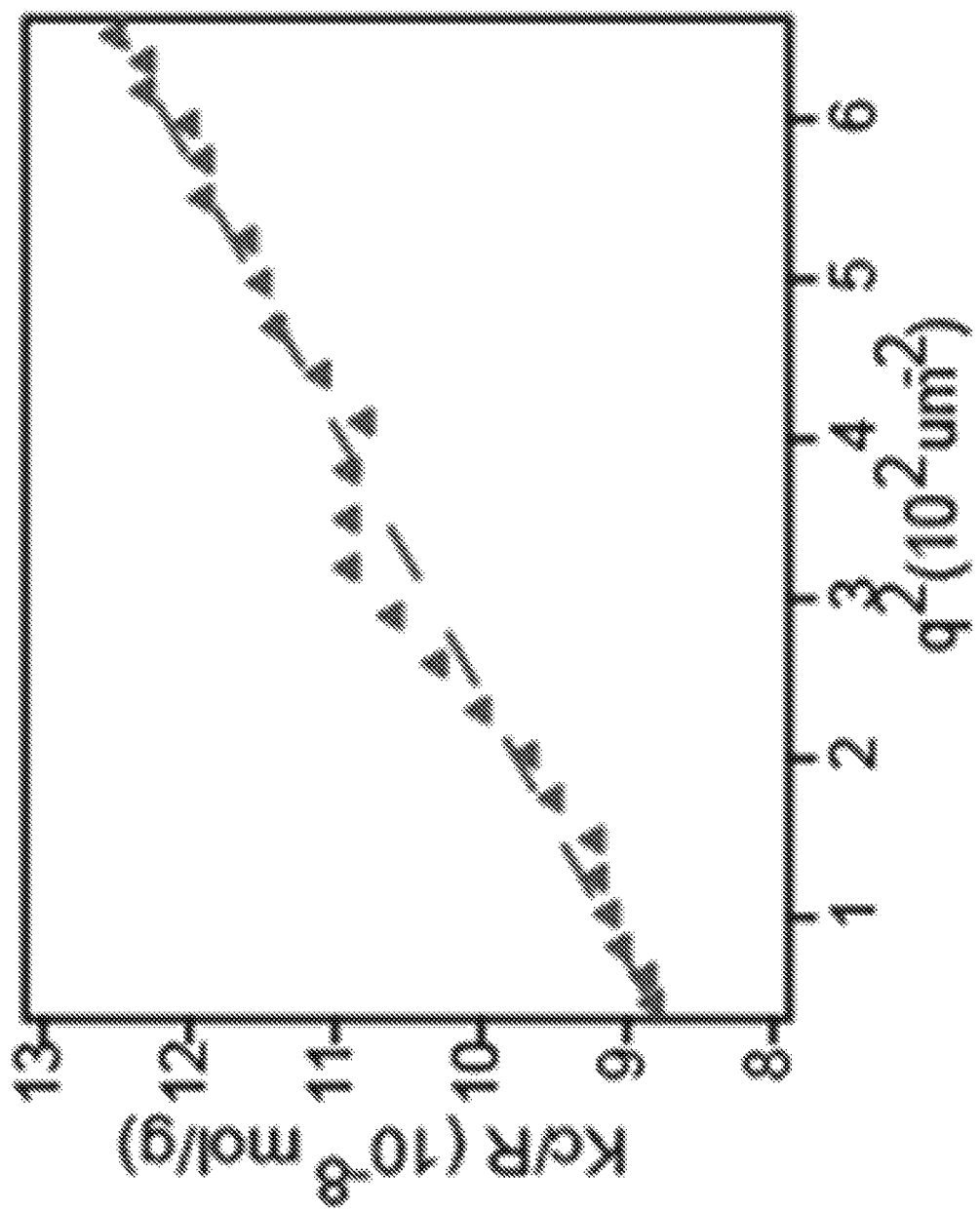
Figure 12C:
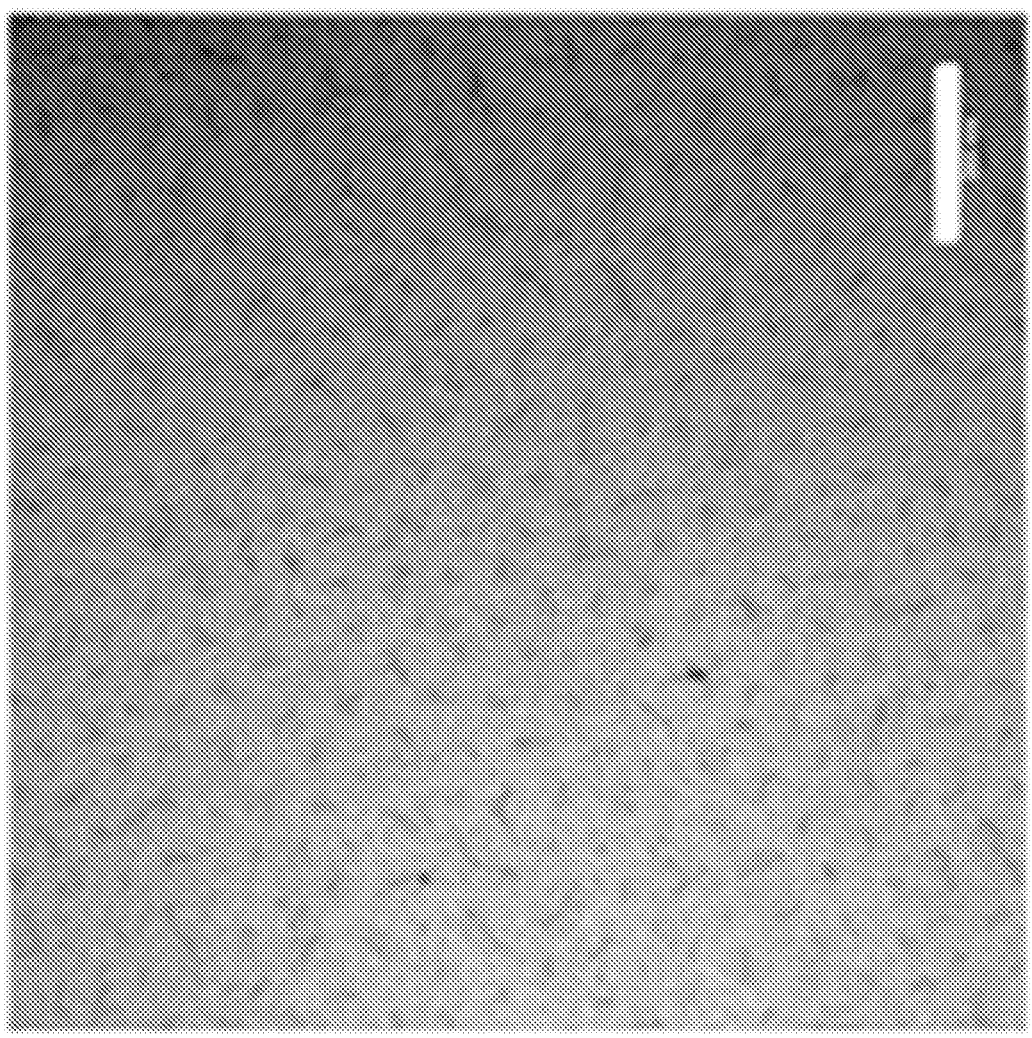
Figure 12D:
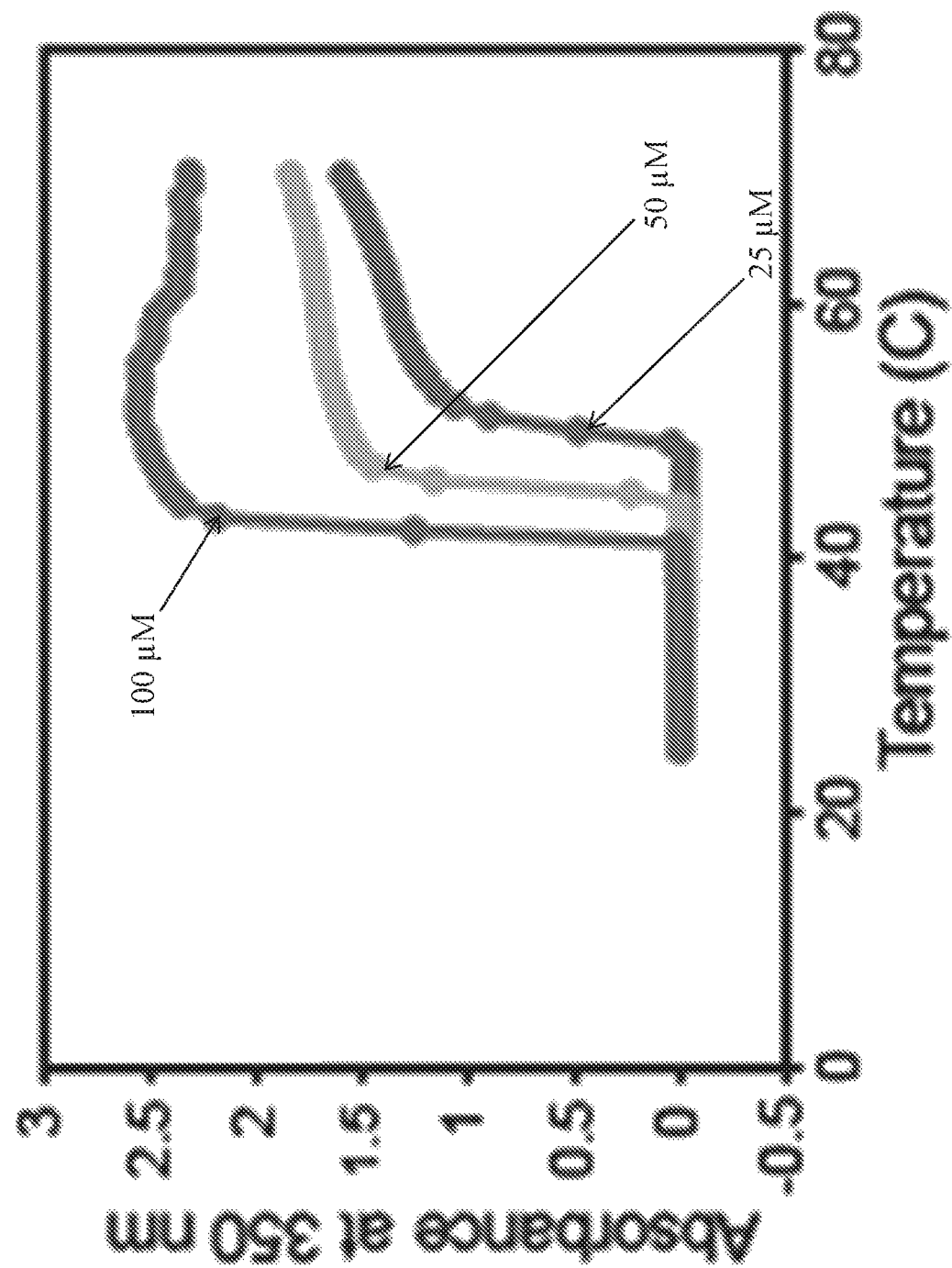
Figure 12E:
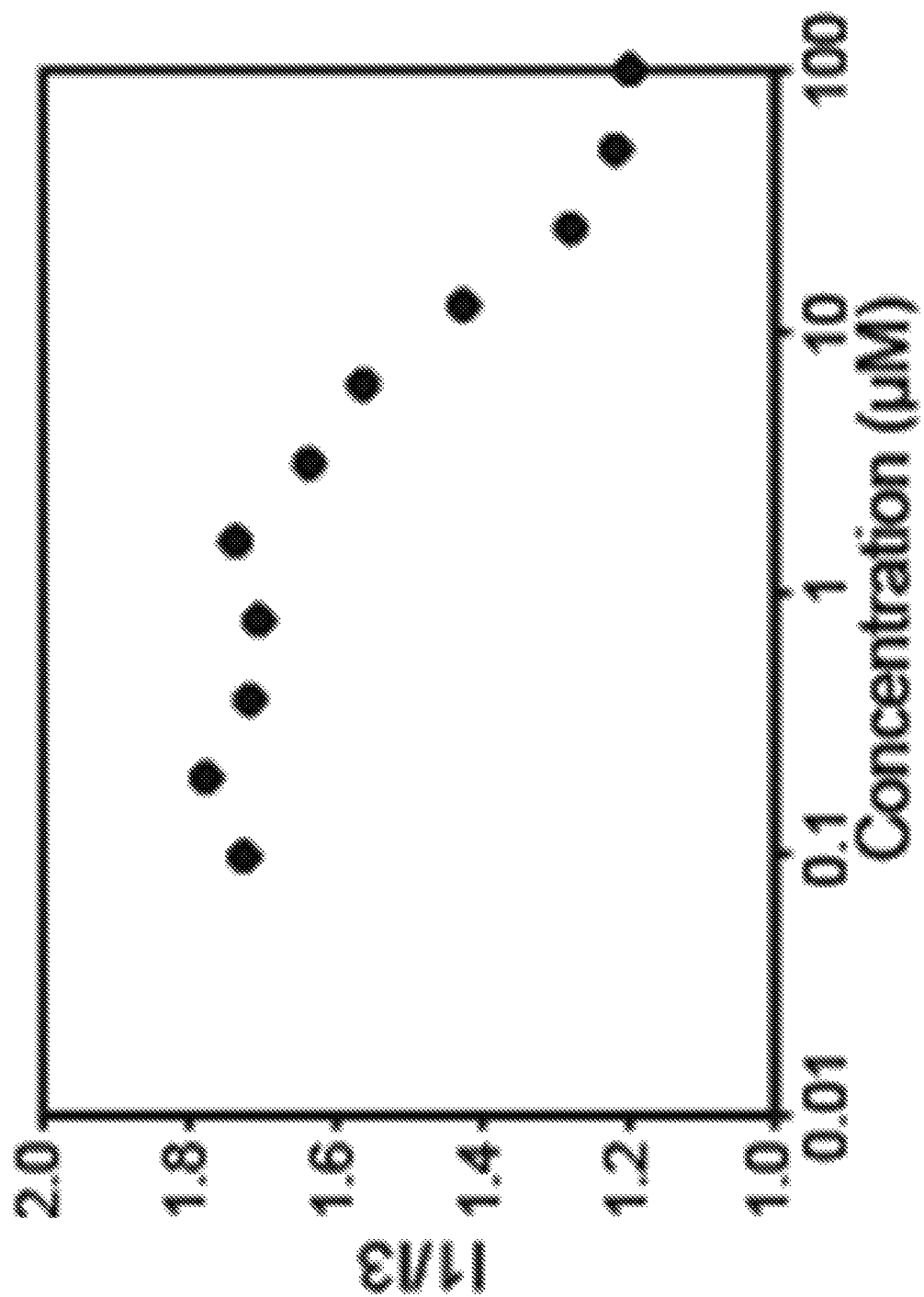
Figure 13A:
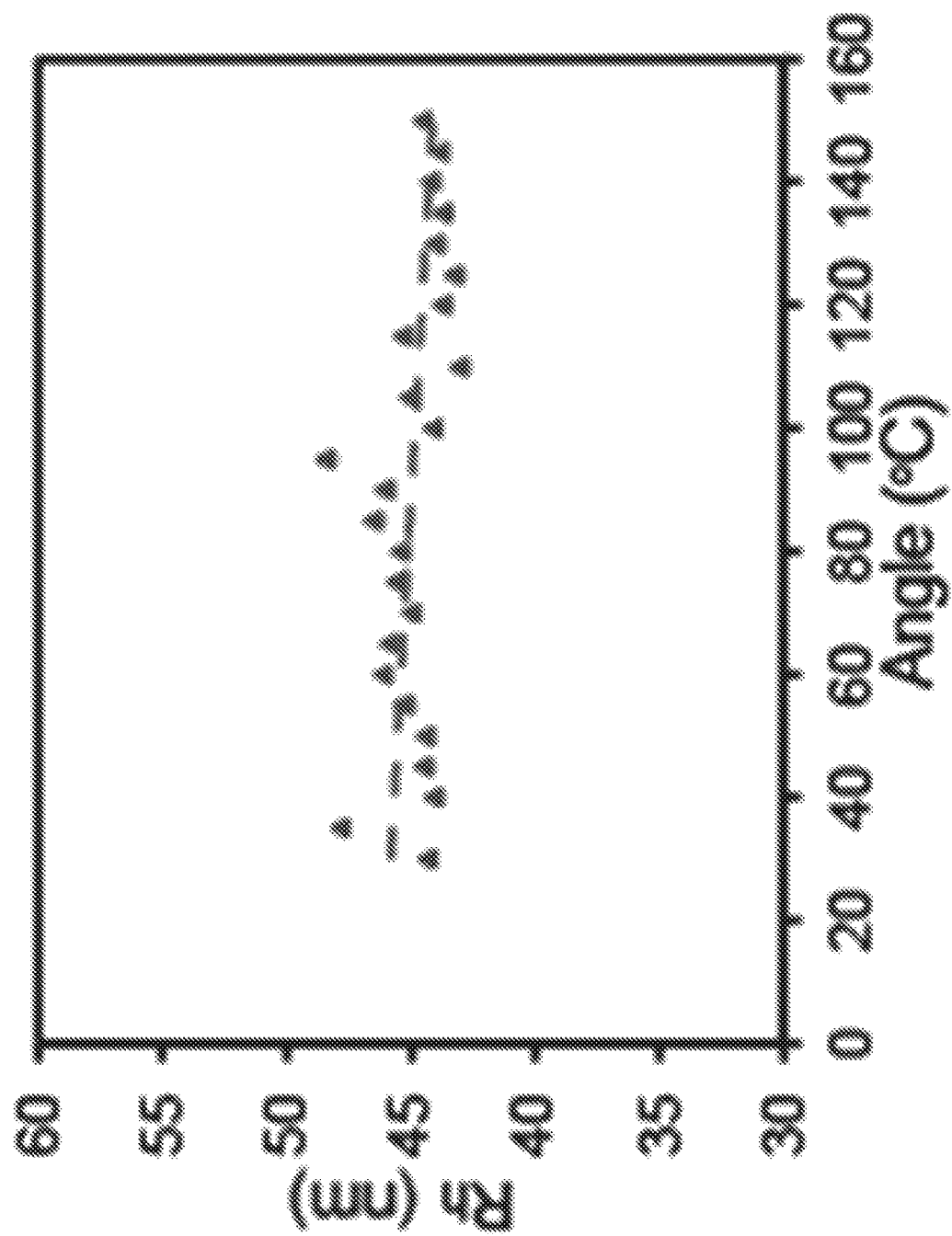
FIG. 13(A)-(E) show characterization of exemplary ATBP-N-$^t$butyl maleimide (SMM8) conjugates.
Figure 13B:
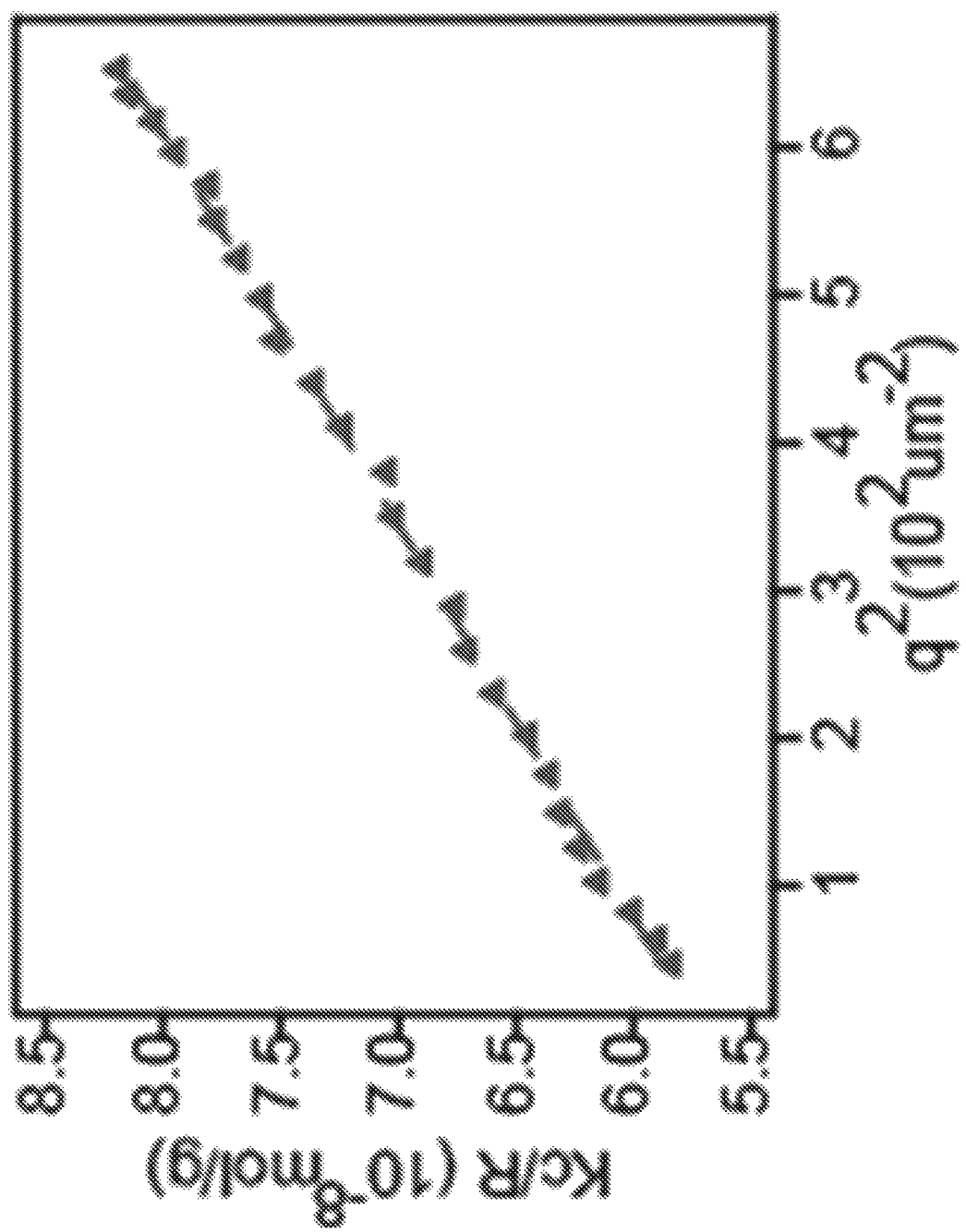
Figure 13C:
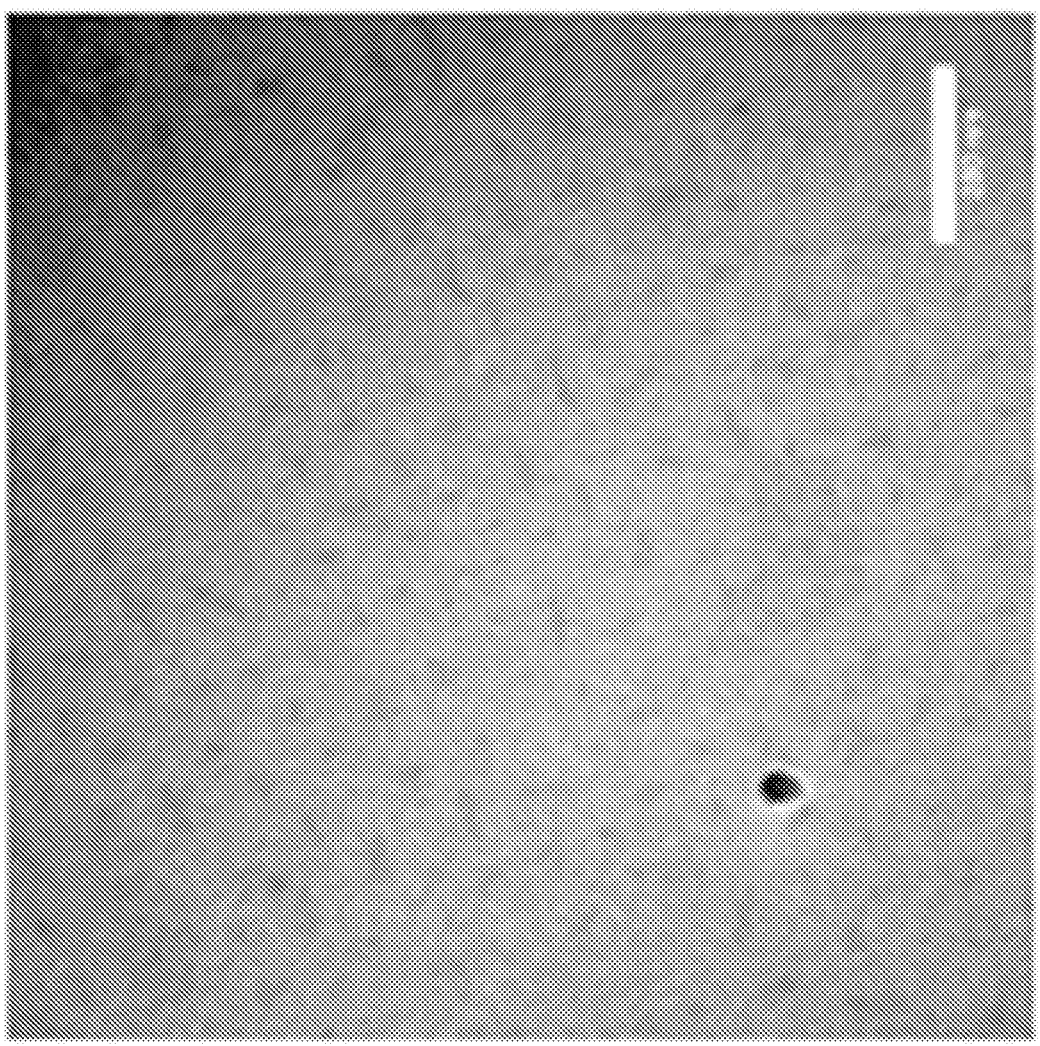
Figure 13D:
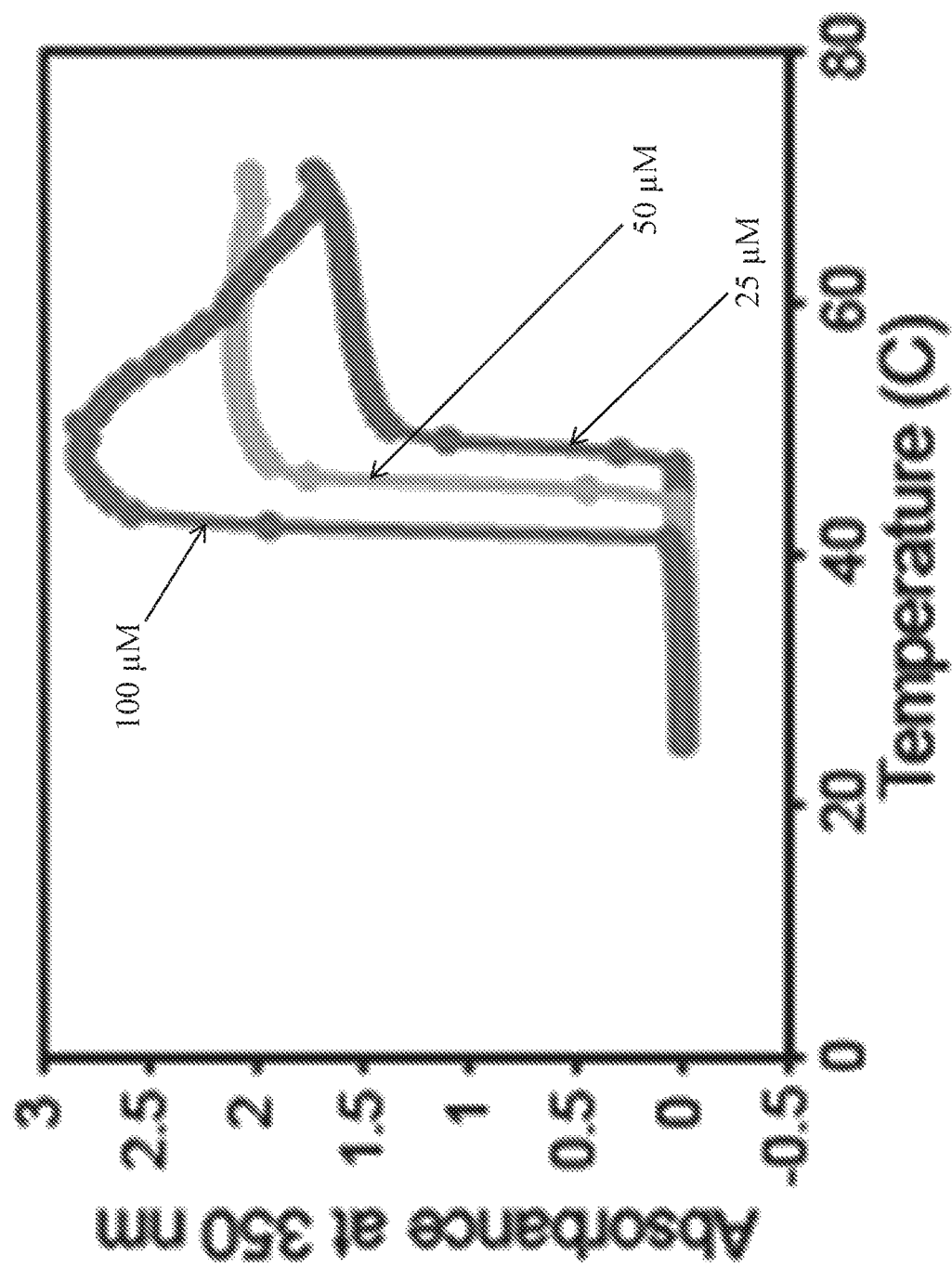
Figure 13E:
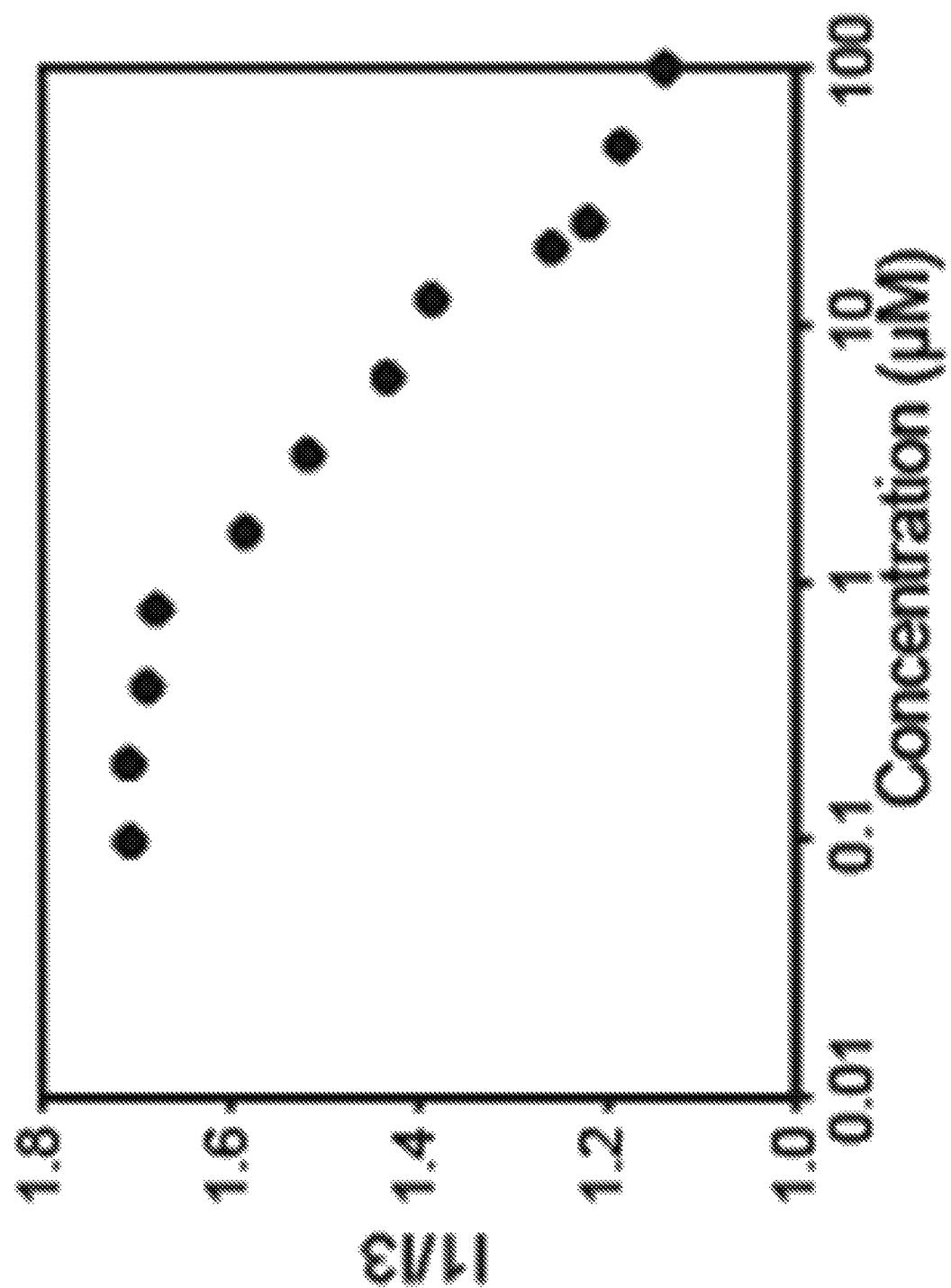

Synthesis of ATBP-Small Molecule Maleimide (SMM) Conjugate:

The ATBP was over-expressed at high yield in *E. coli* that was cultured in a shaker-flask and purified from the bacterial lysate by inverse transition cycling (ITC), a non-chromatographic protein purification technique. Several rounds of ITC yielded >100 mg $1^{-1}$ of pure ATBP. The molecular weight of the ATBP, as measured by matrix-assisted laser desorption/ionization time-of-flight mass spectrometry (MALDI-TOF-MS), is 64681 Da which is close to the theoretical mass of 64816 Da (FIG. 1(A), FIG. 5(A), and Table 1). SDS-PAGE confirmed that the ATBP purified by ITC was a pure and homogeneous product (FIG. 6).

Figure 1B:
Figure 1C:
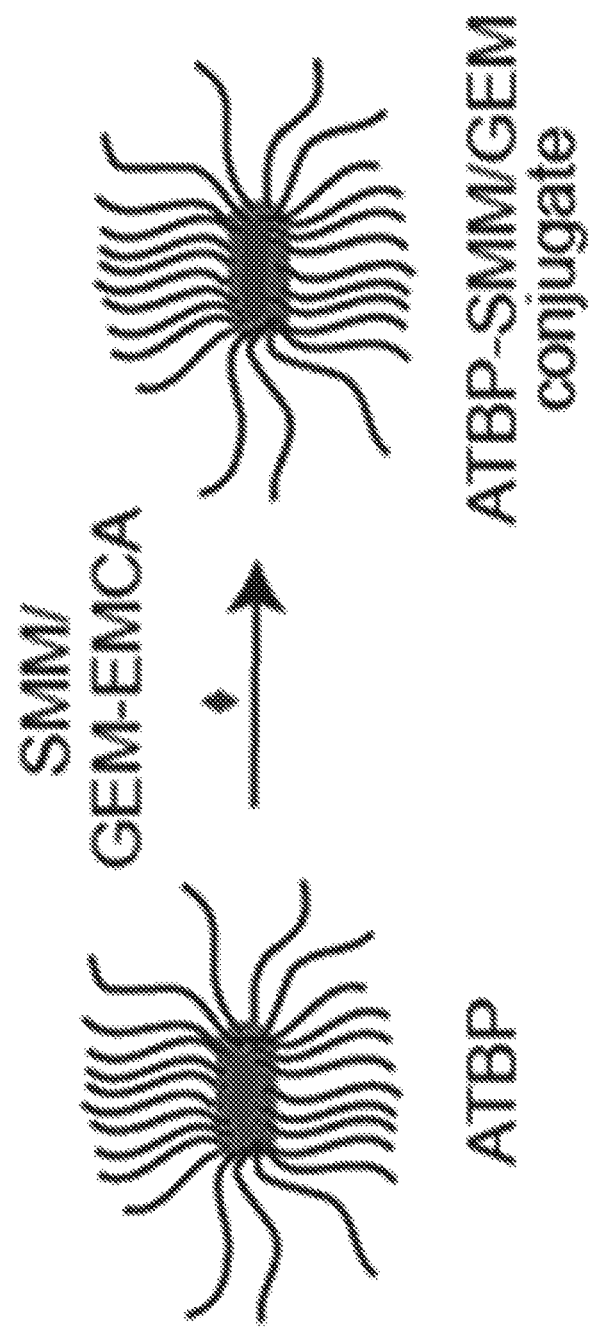
Figure 2A:
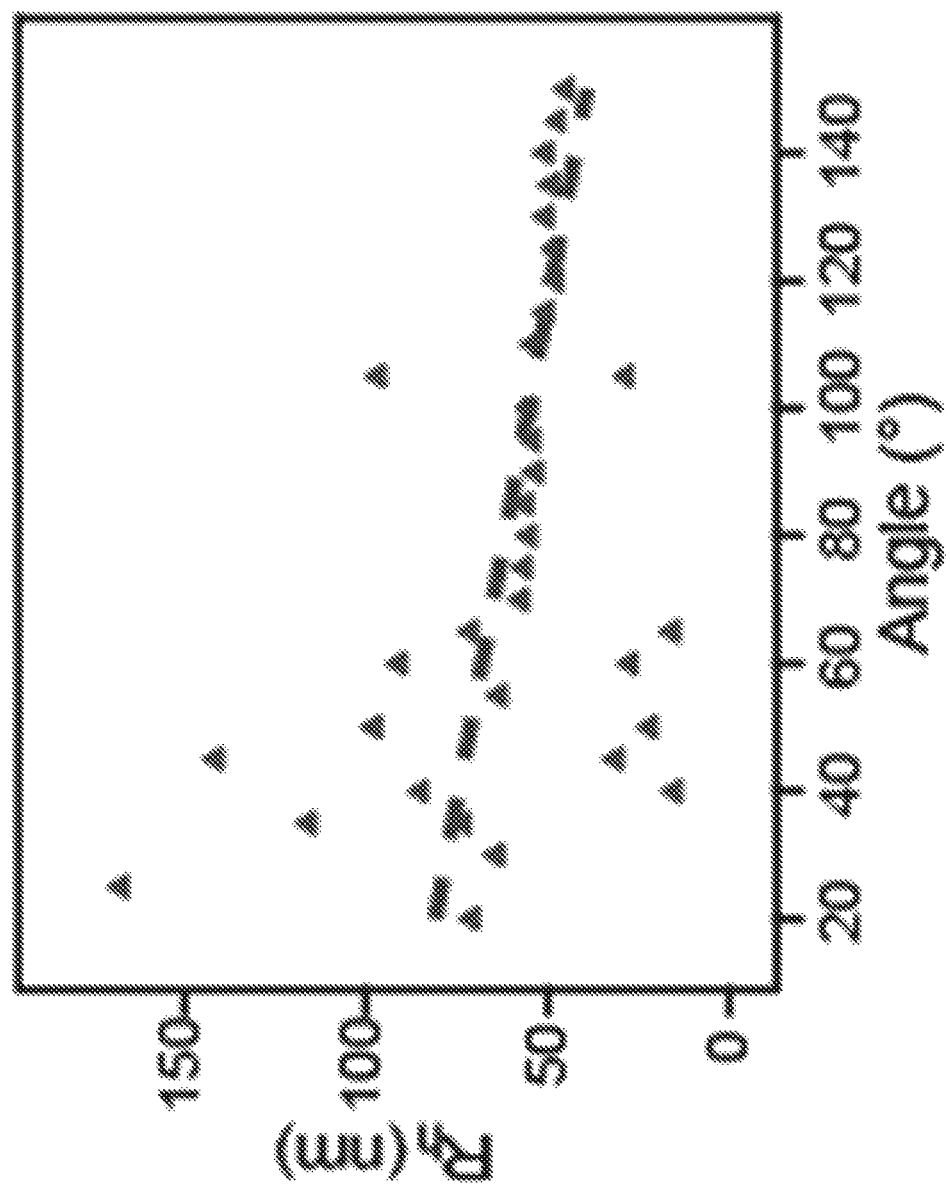
FIG. 2(A)-(E) show the characterization of exemplary ATBP-N-hydroxymaleimide (ATBP-SMM1) conjugates.
Figure 2B:
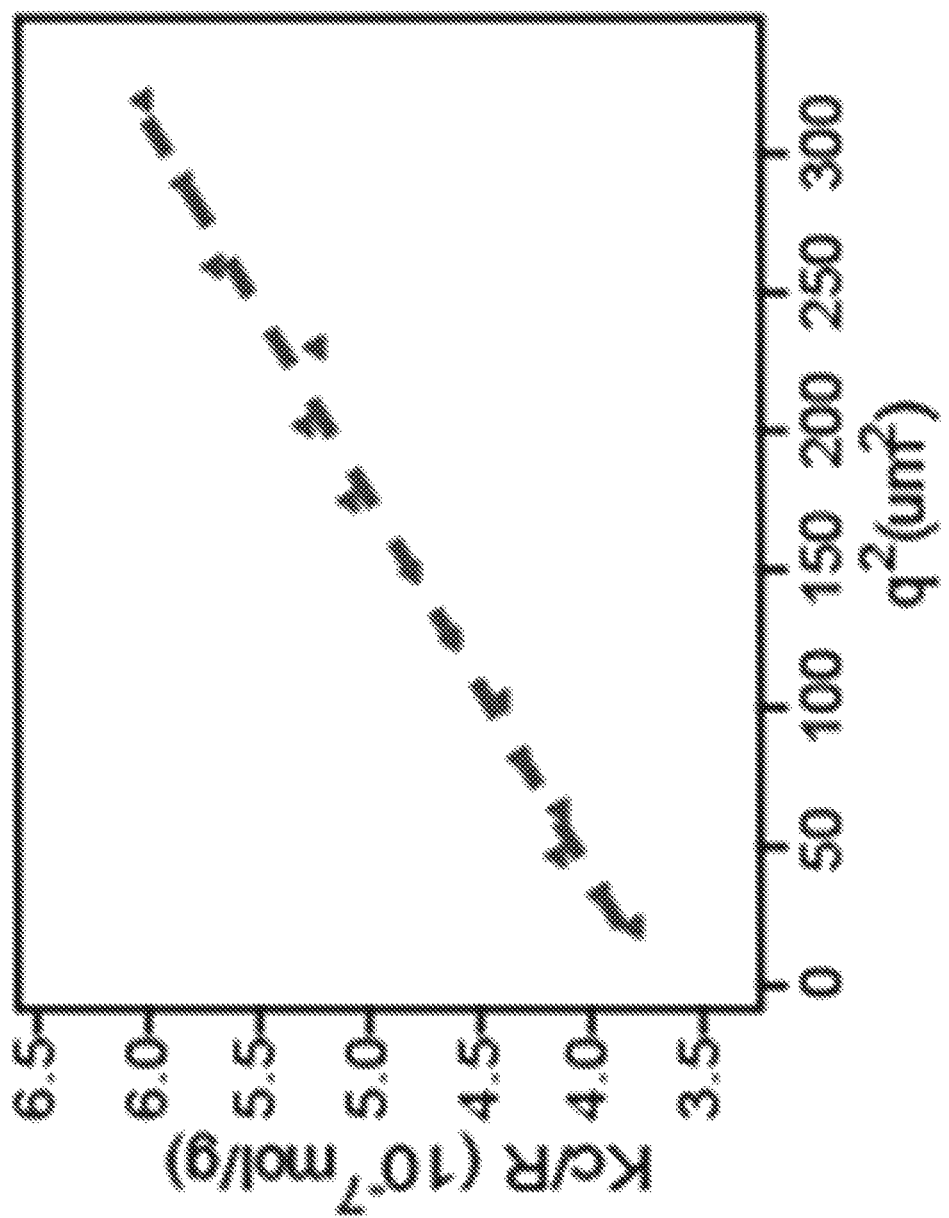
Figure 2C:
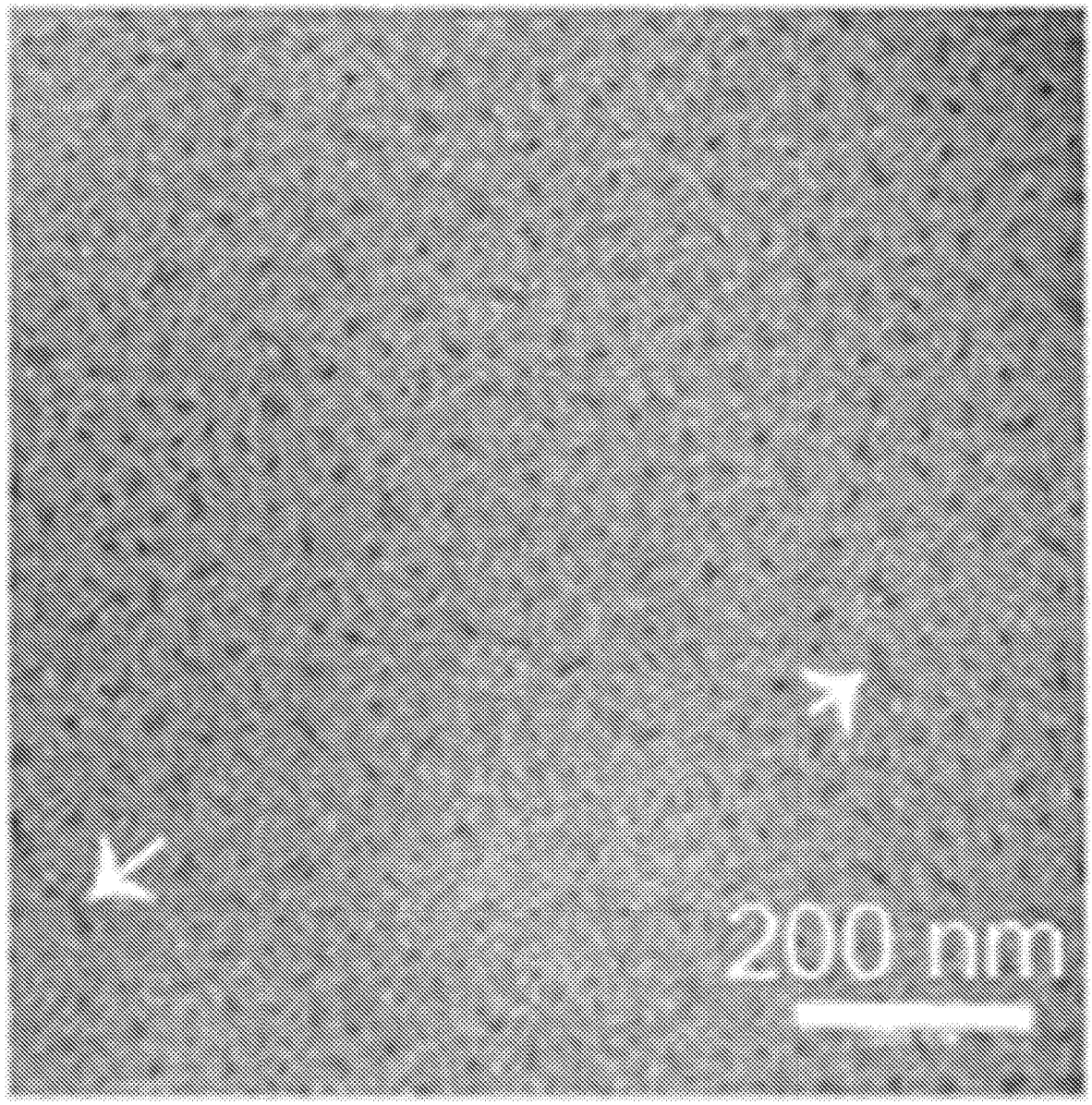
Figure 2D:
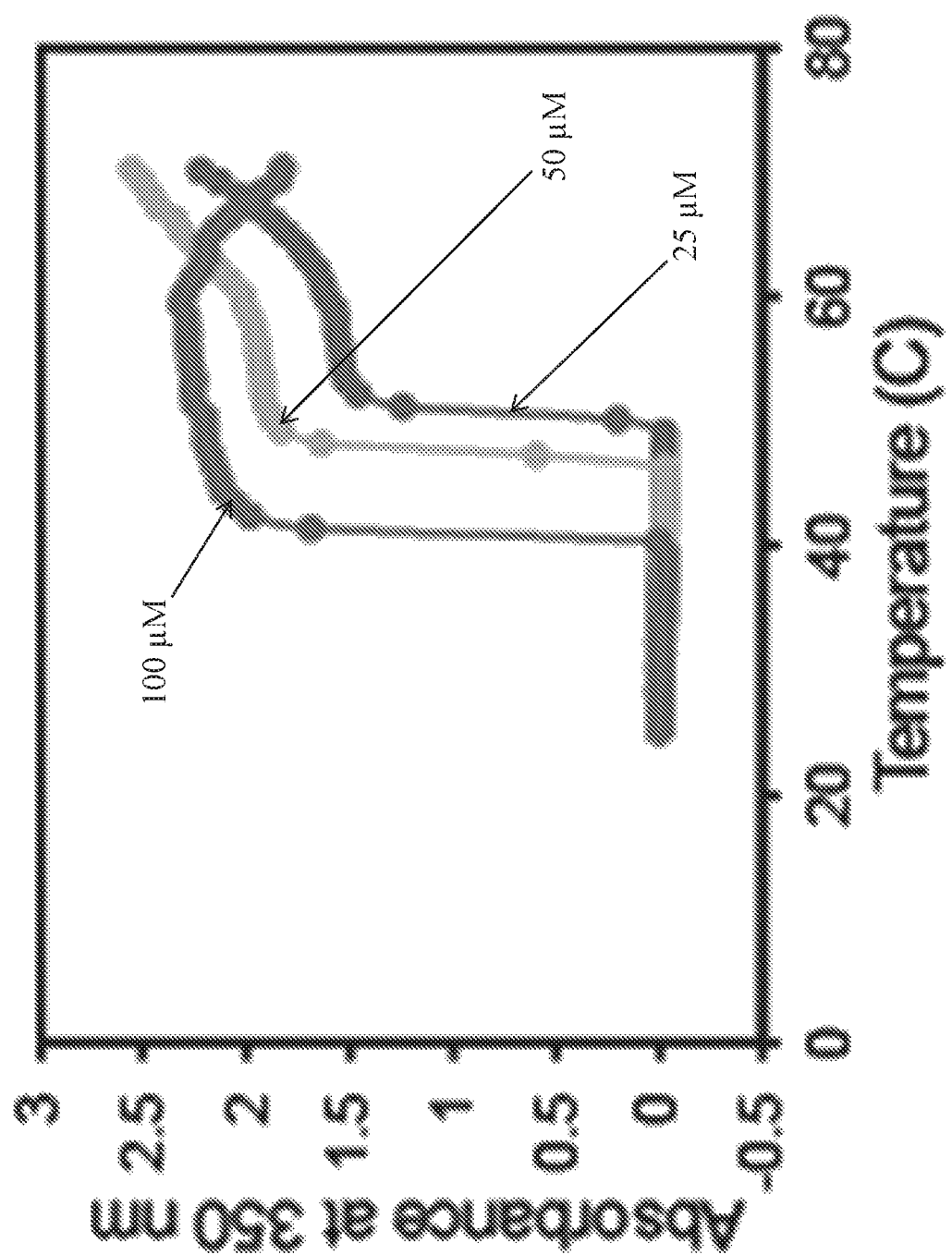
Figure 2E:
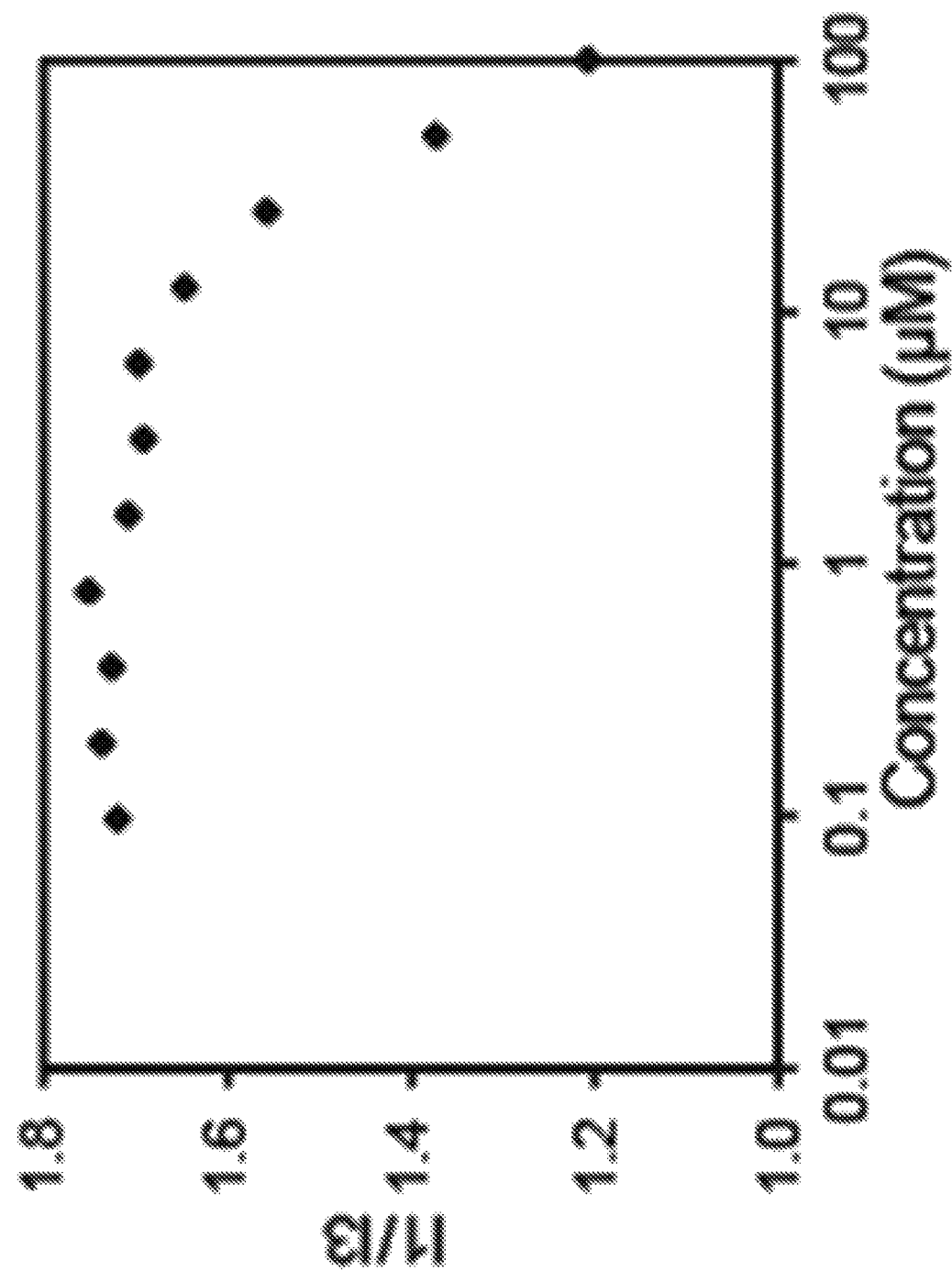

Next, the $(CGG)_8$ segment of the ATBP was modified by covalent conjugation of 8 different maleimide derivatives of hydrophilic small molecules to the ATBP. These model compounds were chosen with two considerations in mind: first, they span a range of hydrophilicity, as reflected by their Log D and second, they all contain a reactive maleimide moiety to enable their covalent coupling to the Cys residues of ATBP by a Michael addition reaction. FIG. 1(B) displays the structure of the model small molecule maleimide (SMM) derivatives organized by their Log D value at pH 7.4, whereby larger values indicate greater hydrophobicity. The log D value was calculated with the ACD/Labs PhysChem Suite. The ATBP-SMM conjugates have ~6-7 small molecules attached per ATBP, as determined by the Ellmans' reagent assay (Table 1).

TABLE 1

| SMM | LogD | $T_t$ (C) Concentration (µM) | | | $R_h$ (nm) | $R_g$ (nm) | $N_{agg}$ | ρ | CAC (µM) | #SMM/ ATBP |
|---|---|---|---|---|---|---|---|---|---|---|
| | | 25 | 50 | 100 | | | | | | |
| — | — | 47 | 44 | 40 | 50.1 | 42.6 | 62 | 0.85 | 3.60 | — |
| 1 | −1.06 ± 0.64 | 49 | 46 | 41 | 87.3 | 77.0 | 41 | 0.81 | 8.2 | 7.4 |
| 2 | −0.76 ± 0.33 | 49 | 46 | 41 | 123.5 | 141.0 | 50 | 1.14 | 6.6 | 6.9 |
| 3 | −0.66 ± 0.39 | 45 | 42 | 38 | 109.1 | 115.6 | 219 | 1.06 | 3.2 | 6.9 |
| 4 | 0.04 ± 0.40 | 47 | 44 | 39 | 82.6 | 85.5 | 60 | 1.03 | 6.1 | 6.6 |
| 5 | 0.15 ± 0.31 | 45 | 44 | 42 | 46.8 | 45.7 | 62 | 0.978 | 4.9 | 6.8 |
| 6 | 0.68 ± 0.31 | 47 | 46 | 40 | 62.3 | 62.5 | 115 | 1.004 | 3.8 | 7.1 |
| 7 | 1.09 ± 0.41 | 48 | 44 | 41 | 49.1 | 44.4 | 112 | 0.905 | 1.6 | 7.0 |
| 8 | 1.38 ± 0.32 | 44 | 47 | 41 | 46.2 | 44.5 | 93 | 0.963 | 1.5 | 6.4 |

[1]$T_t$ was measured by temperature-programmed turbidimetry.
[2]$R_h$ was determined by DLS; mean ± SD (n = 3).
[3]$R_g$ was determined by SLS; mean ± SD (n = 3).
[4]Aggregation number ($N_{agg}$): Number of molecules of ATBP-SMM conjugate in a nanoparticle, as determined by SLS.
[5]CAC was determined by pyrene assay.
[6]Number of SMM conjugated per AMP was measured using Ellman's reagent.

Characterization of ATBP-SMM Conjugate:

Next, the structure of the unmodified ATBP and the ATBP-SMM conjugates were characterized by dynamic light scattering (DLS), static light scattering (SLS), and cryogenic transmission electron microscopy (cryo-TEM), their thermal behavior by temperature-programmed turbidimetry, and their thermodynamic stability by a pyrene fluorescence assay. The ATBP-SMM micelles display a moderate angular dependence in their $R_h$. Across the entire set, the Rb of the ATBP-SMM conjugates show a three-fold variation in size, ranging from 40 to 123 nm (Table 1 and FIG. 5-13). While the SMM4-SMM8 conjugates have an $R_h$ that is in the 40-60 nm range, close to the $R_h$ of 50 nm observed for the parent ATBP, the more hydrophilic conjugates, namely SMM1-SMM4 have an Rb in the range of 80-120 nm. Clearly, conjugation of a SMM does not abrogate self-assembly of the ATBP, but the specific SMM and its hydrophilicity appears to have some effect on the overall size of the nanoparticles that are formed. No correlation was observed, however, between the $R_h$ of the nanoparticles and the number of SMM's conjugated per ATBP molecule.

Each ATBP-SMM conjugate was next analyzed by SLS to determine their radius of gyration ($R_g$). The ATBP-SMM conjugates have $R_g$ values ranging from 40 to 140 nm (Table 1 and FIG. 5-13) that parallel their $R_h$. The aggregation number ($N_{agg}$, number of ATBP molecules per nanoparticle) was also calculated by analysis of the partial Zimm plot, and the shape factor ($\rho=R_g/R_h$) was computed from the DLS and SLS data. The shape factors range from 0.89 to 1 (Table 1, FIG. 2, and FIG. 7-13); this range indicates that there are probably no significant differences in the morphology of these nanoparticles. Although it is not possible to precisely determine the morphology of nanoparticles by light scattering, shape factors of 0.89 to 1 are consistent with polydisperse rods with relatively low aspect ratios. The aggregation number ($N_{agg}$) also varies significantly between 60 and 220 for the different conjugates, but there is no correlation between $N_{agg}$ of the nanoparticles and the log D of the SMMs (Table 1).

To directly visualize the morphology of the nanoparticles, all SMM-ATBP conjugates were imaged by cryo-TEM. ATBP-SMM micelles are difficult to visualize by cryo-TEM due to their small size and low contrast, as polypeptides are highly hydrated and only slightly more electron-dense than water. Hence, only the tyrosine-rich core of ATBP-SMM nanoparticles can be imaged by cryo-TEM. Additionally, the hydrophobic core is also hydrated, albeit to a lesser extent than the corona, further reducing the overall contrast. Given these constraints, a 80 keV voltage was chosen to maximize the contrast in order to image the nanoscale structures. Despite these limitations, cryo-TEM shows that all ATBP-SMM conjugates self-assemble into nanoparticles that are evenly distributed throughout the ice layer (FIG. 2(C), Table 1 and FIG. 5-13). In agreement with the light-scattering data, the conjugates primarily consist of cylindrical nanoparticles, which is consistent with the shape factor measured by light scattering. For all eight model compounds, the combined evidence from all of these techniques indicate that the attachment of 6-7 copies of hydrophilic compounds with a log D less than 1.5 (FIG. 1(B)) does not disrupt the self-assembly of the ATBP into rod-like micelles, in which the conjugated molecules presumably sit near the hydrophobic core (FIG. 1(C)).

Next, the ATBP-SMM conjugates were characterized by temperature-programmed turbidimetry. The phase transition behavior of the ATBP is not significantly altered following conjugation of the SMM's (FIG. 2(D), Table 1, and FIG. 5-13). Similar to the unmodified ATBP, ATBP-SMM's also exhibit a characteristic transition temperature (T), below which they form a single, stably suspended nanoparticle phase in aqueous solvent, and above which they phase separate into two phases consisting of an insoluble ATB-rich phase and a solvent-rich phase. In contrast to the phase transition transition of ELP unimers, the phase transition of the ATBP-SMM conjugates occurs from a soluble nanoparticle phase to micron size aggregates, and their T's show a very weak dependence on ATBP concentration. The fact that all self-assembled ATBP-SMM conjugate nanoparticles display a similiar weak relationship between their $T_t$ and the solution concentration of the ATBP may suggest that their phase behavior is controlled by the high and invariant local ATBP concentration within the nanoparticles and not by the total concentration of the ATBP in solution.

The critical aggregation concentration (CAC) of the parent ATBP and ATBP-SMM conjugates were next determined by fluorescence spectroscopy using pyrene as a probe. As the concentration of the ATBP decreases, the fluorescence intensity ratio of the 370-373 nm peak to the 381-384 nm peak ($I_1/I_3$) increases sigmoidally with the increase in ATBP concentration, reflecting nanoparticle disassembly and release of pyrene from the lipophilic core of the nanoparticles into the aqueous environment. The CAC of TBAP-SMM conjugates are between 1.5-8.5 µM whereas that of the unmodified ATBP is about 3.6 µM (FIG. 2(E) and FIG. 5-13). With the exception of a few outliers, the conjugation of more hydrophilic SMMs—those with a negative log D—results in micelles with a larger CAC in comparison to the parent ATBP, while ATBP-SMM conjugate with a positive log D values have a lower CAC than that of unmodified ATBP, consistent with the notion that the thermodynamic stability of the self-assembled nanoparticle can scale with the hydrophobicity of the SMM that is sequestered in the core of the nanoparticle.

Figure 3A:
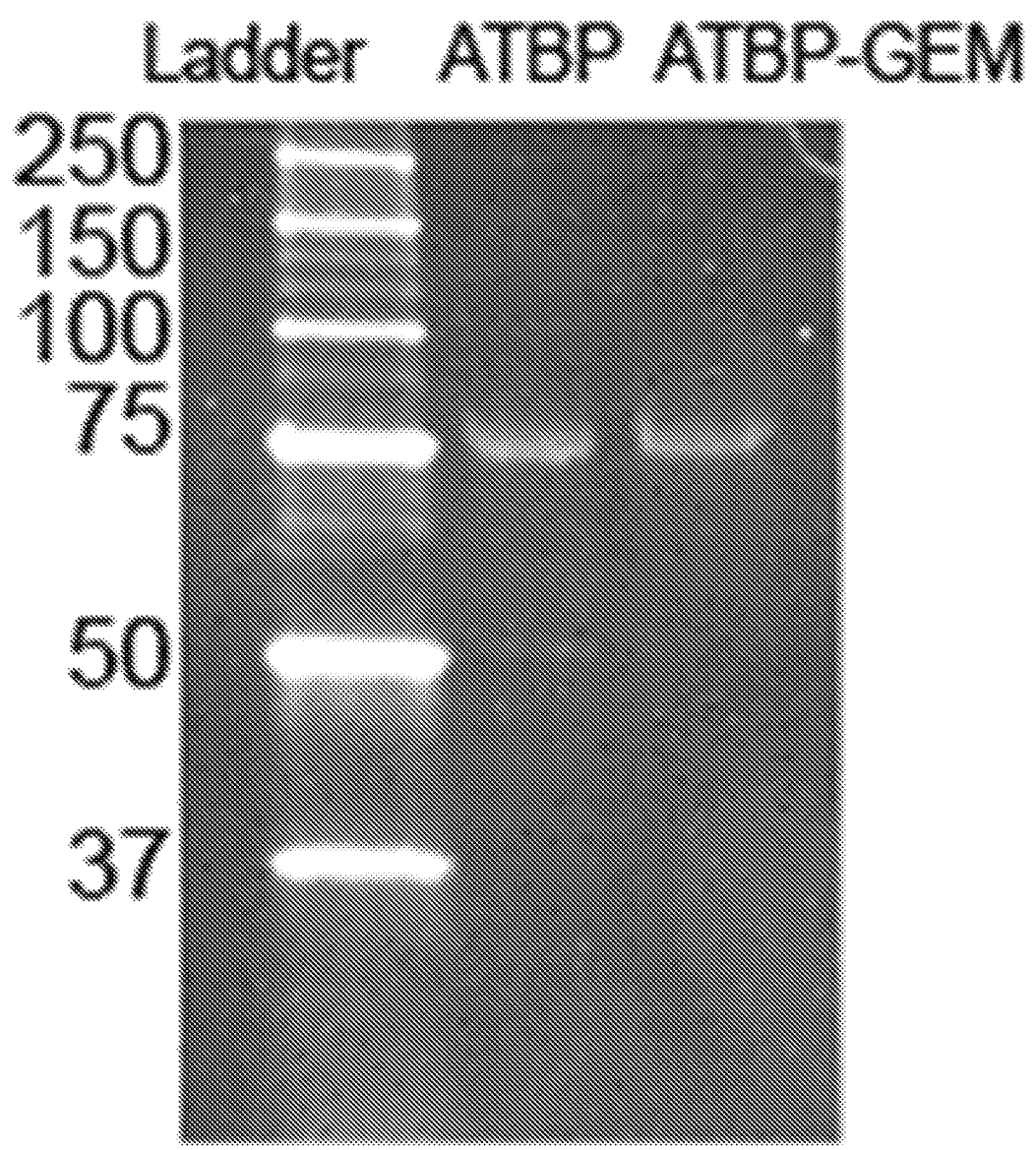
FIG. 3(A)-(H) show characterization of exemplary ATBP-GEM conjugates.
Figure 3B:
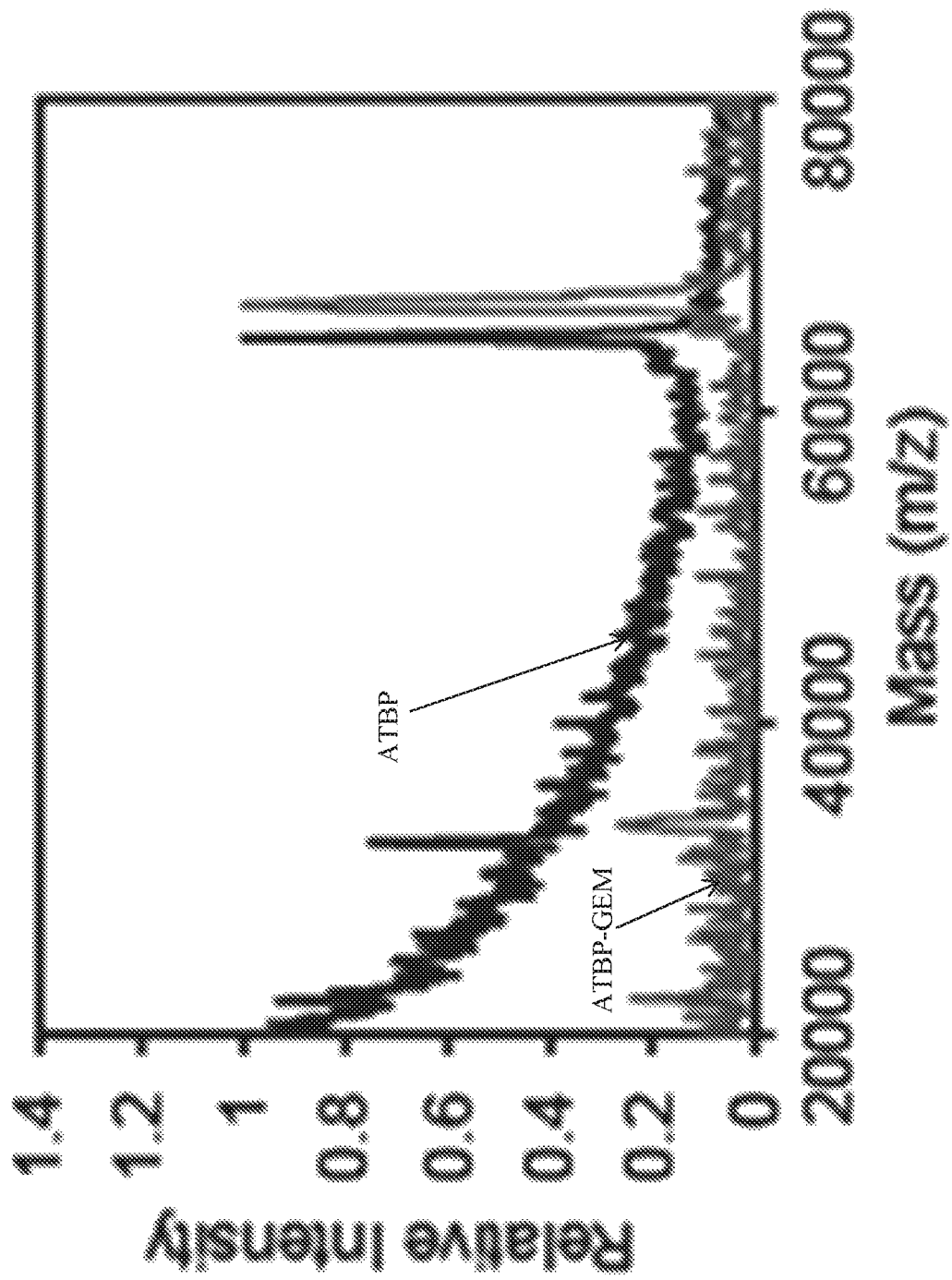

Synthesis of ATBP-GEM Conjugate:

To further investigate the utility of the ATBP to deliver a chemotherapeutic, a hydrophilic small-molecule drug was chosen for conjugation to the ATBP through a heterobifunctional linker, wherein one end of the linker is attached to the ATBP and the other end to a reactive moiety on the drug. Gemcitabine (GEM) was chosen as the drug because it is highly water soluble with a LogD value of −2.2 at pH 7.4—and that of the maleimide derivative is 0.43±0.82- and is used as a chemotherapeutic to treat a range of solid tumors including pancreatic, bladder, NSCLC, breast and ovarian cancers. Briefly, GEM is first activated with n-ε-maleimidocaproic acid (EMCA) to introduce a terminal maleimide (Scheme 1), and the activated GEM is covalently conjugated to the Cys of the ATBP (FIGS. 1(A) and (C)). The purified ATBP-GEM conjugate (FIG. 3(A)) contains ~4 GEM molecules per ATBP, as calculated by MALDI-TOF MS (FIG. 3(B) and Table 3), from the MW change between the conjugate and the parent ATBP (Table 2).

Scheme 1

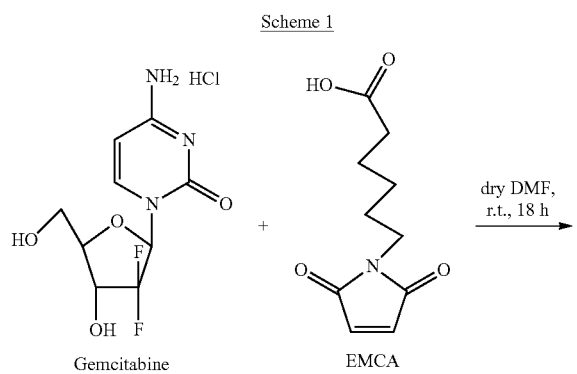

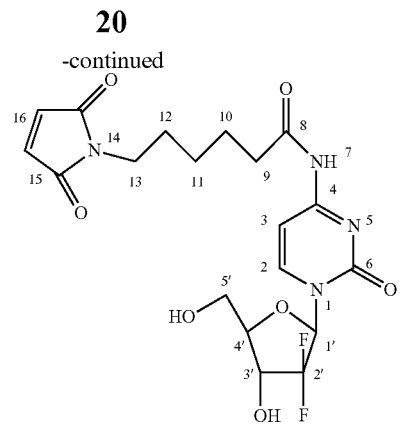

Gem-EMCA conjugate (I)

I + ATBP $\xrightarrow{\text{NaPO4 buffer, pH 7.4}}_{\text{DMF, r.t., 16 h, TCEP}}$

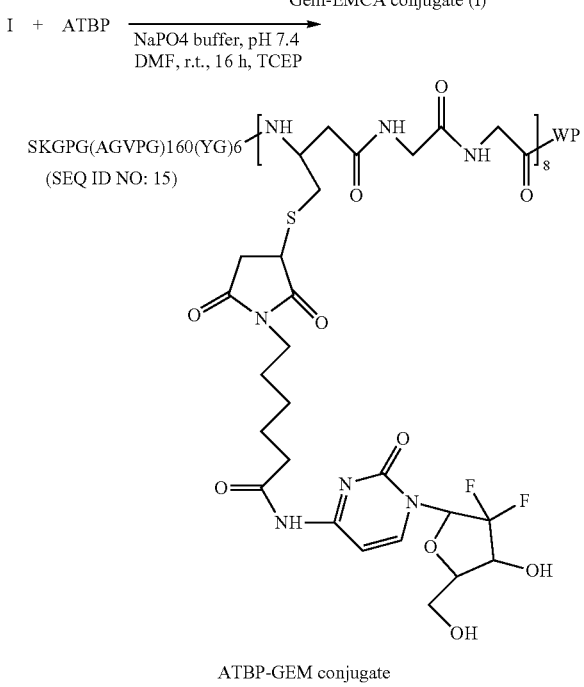

ATBP-GEM conjugate

Figure 3C:
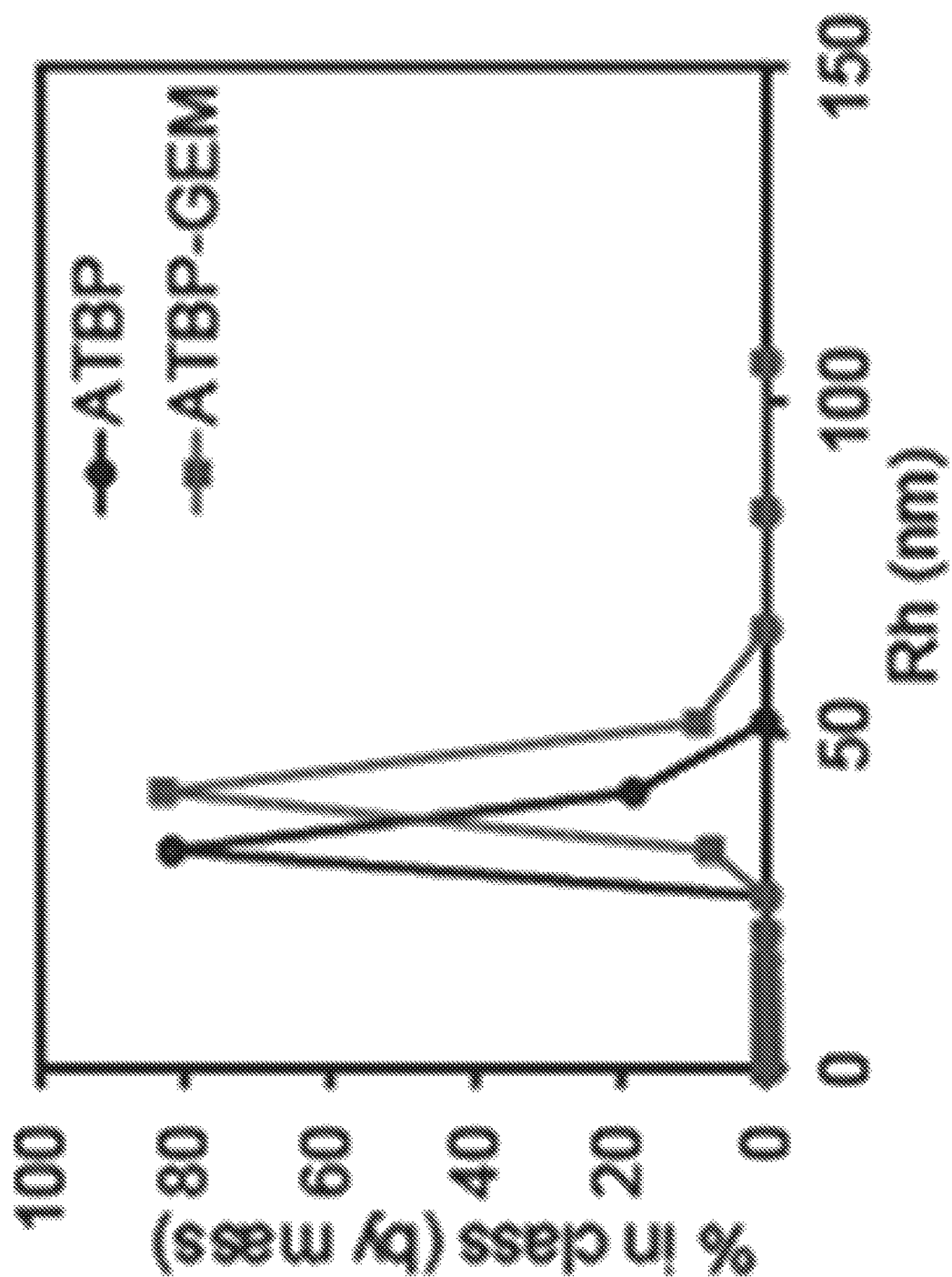
Figure 3D:
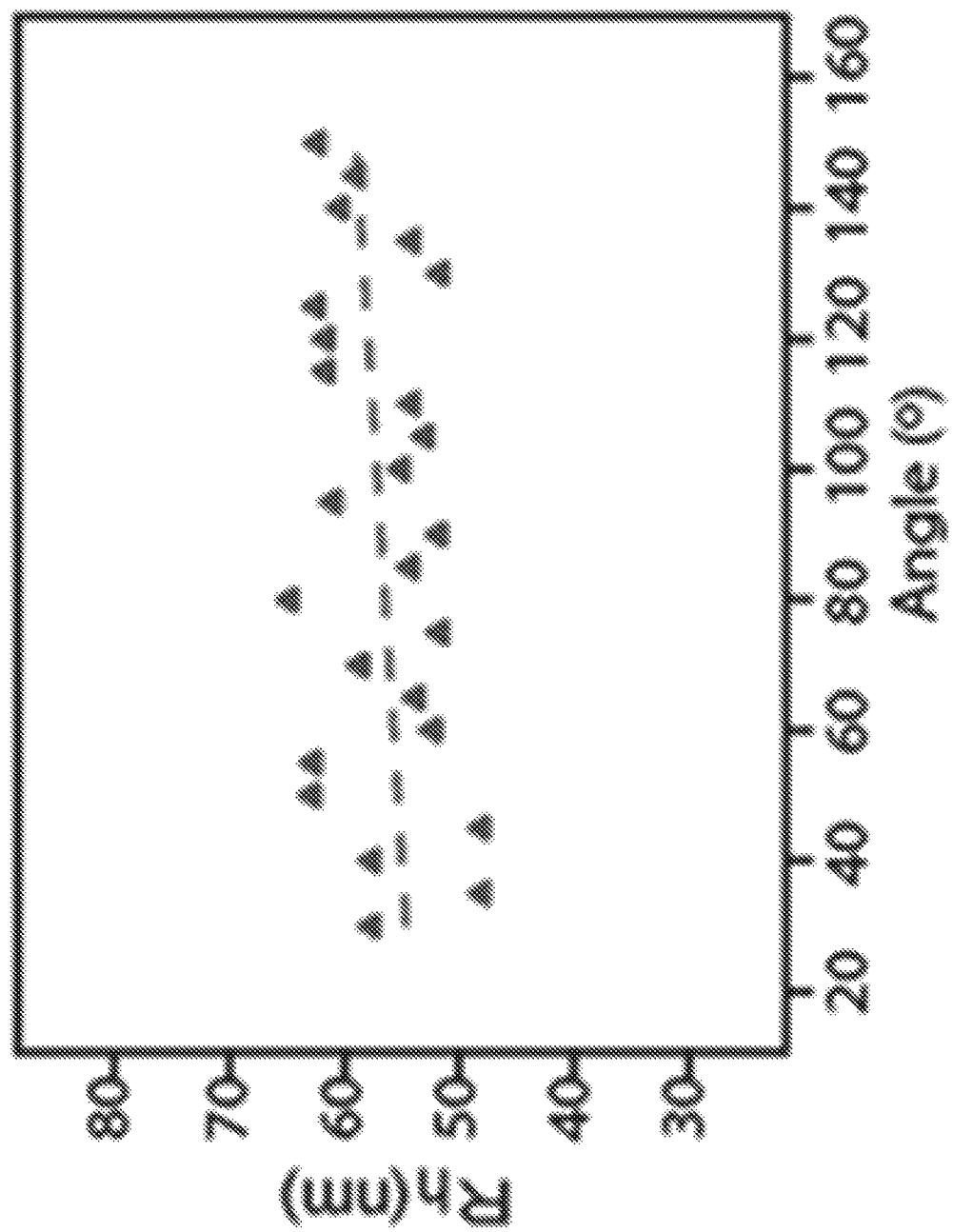
Figure 3E:
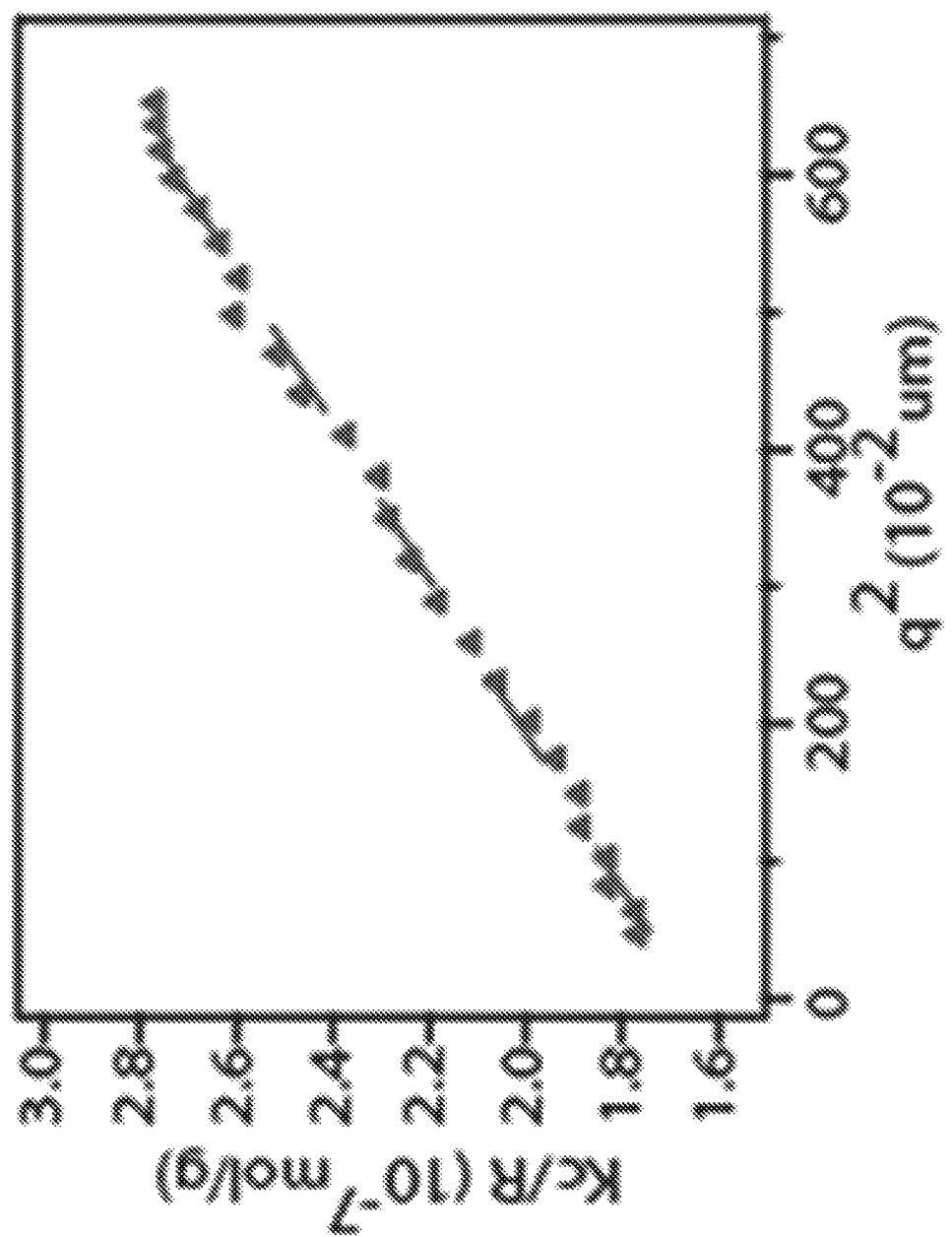
Figure 3F:
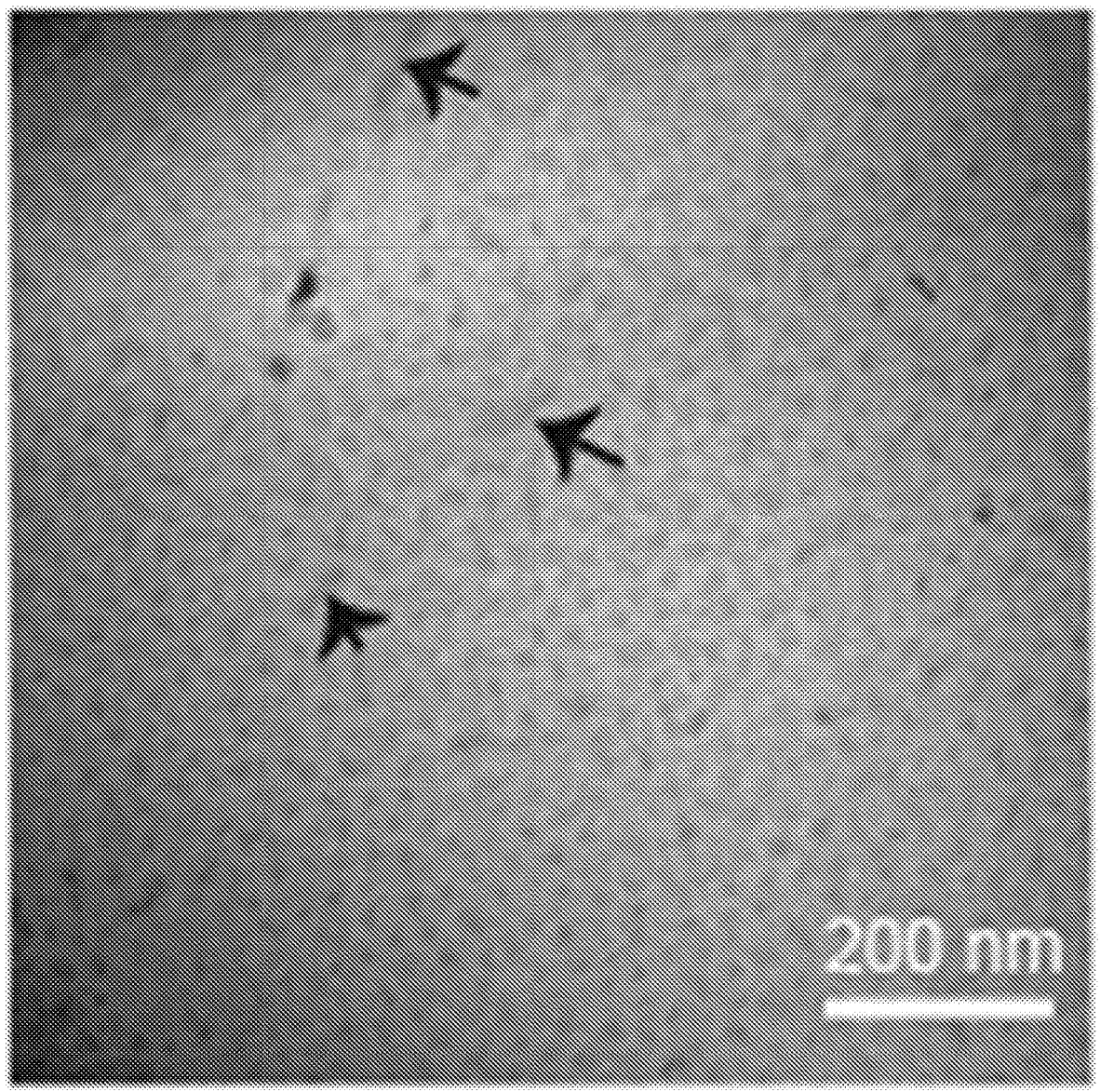
Figure 3G:
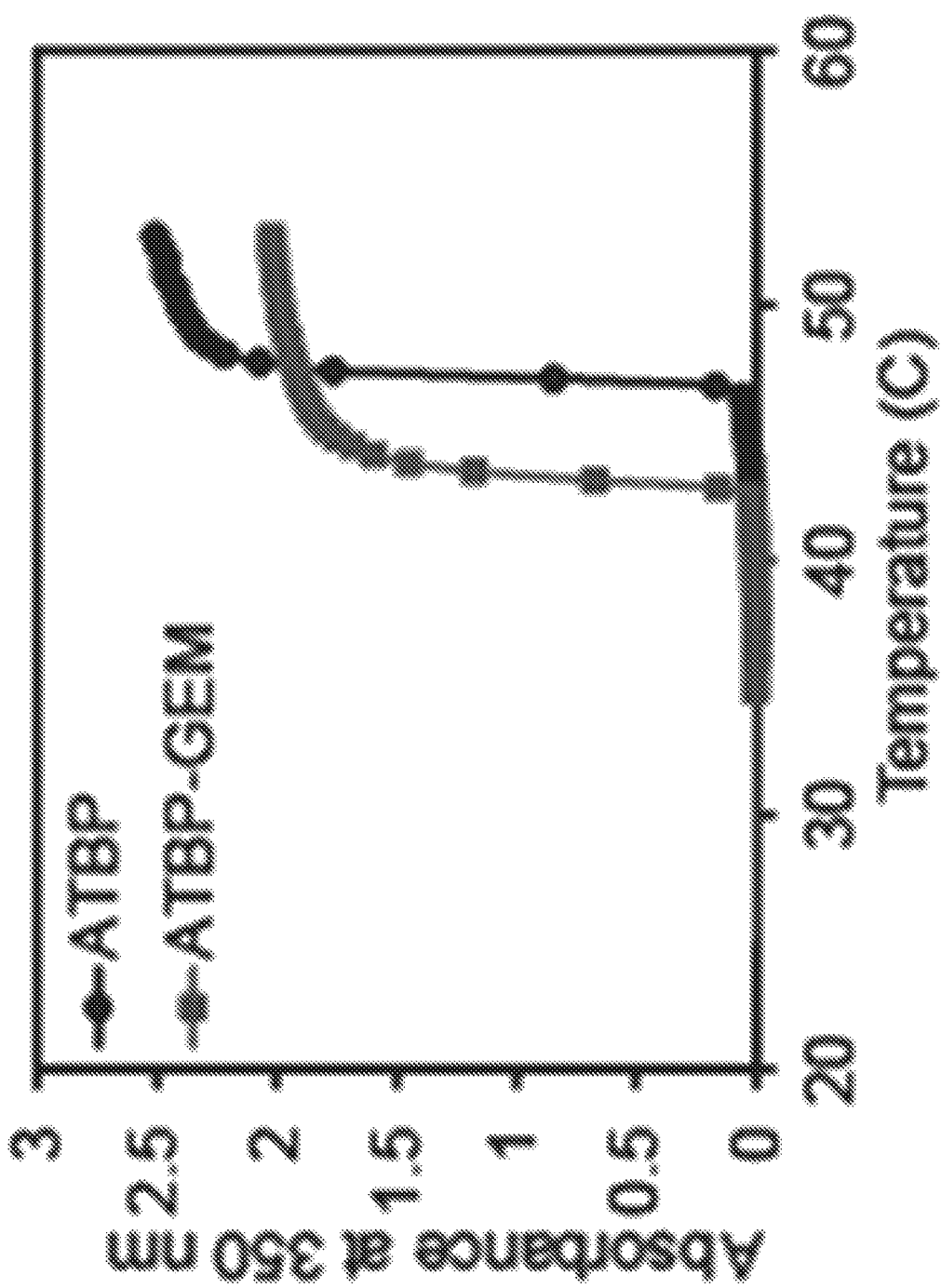
Figure 3H:
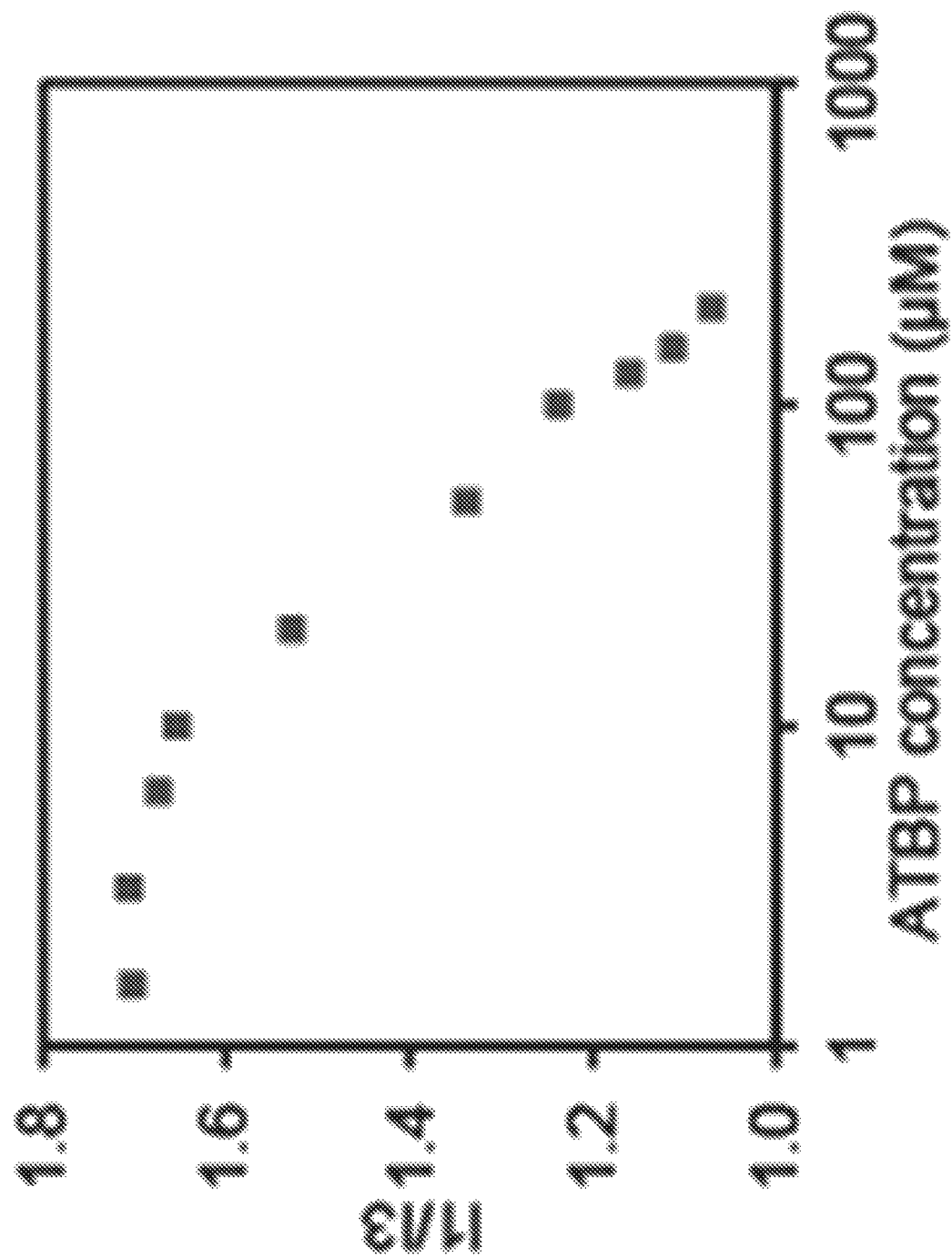
Figure 14:
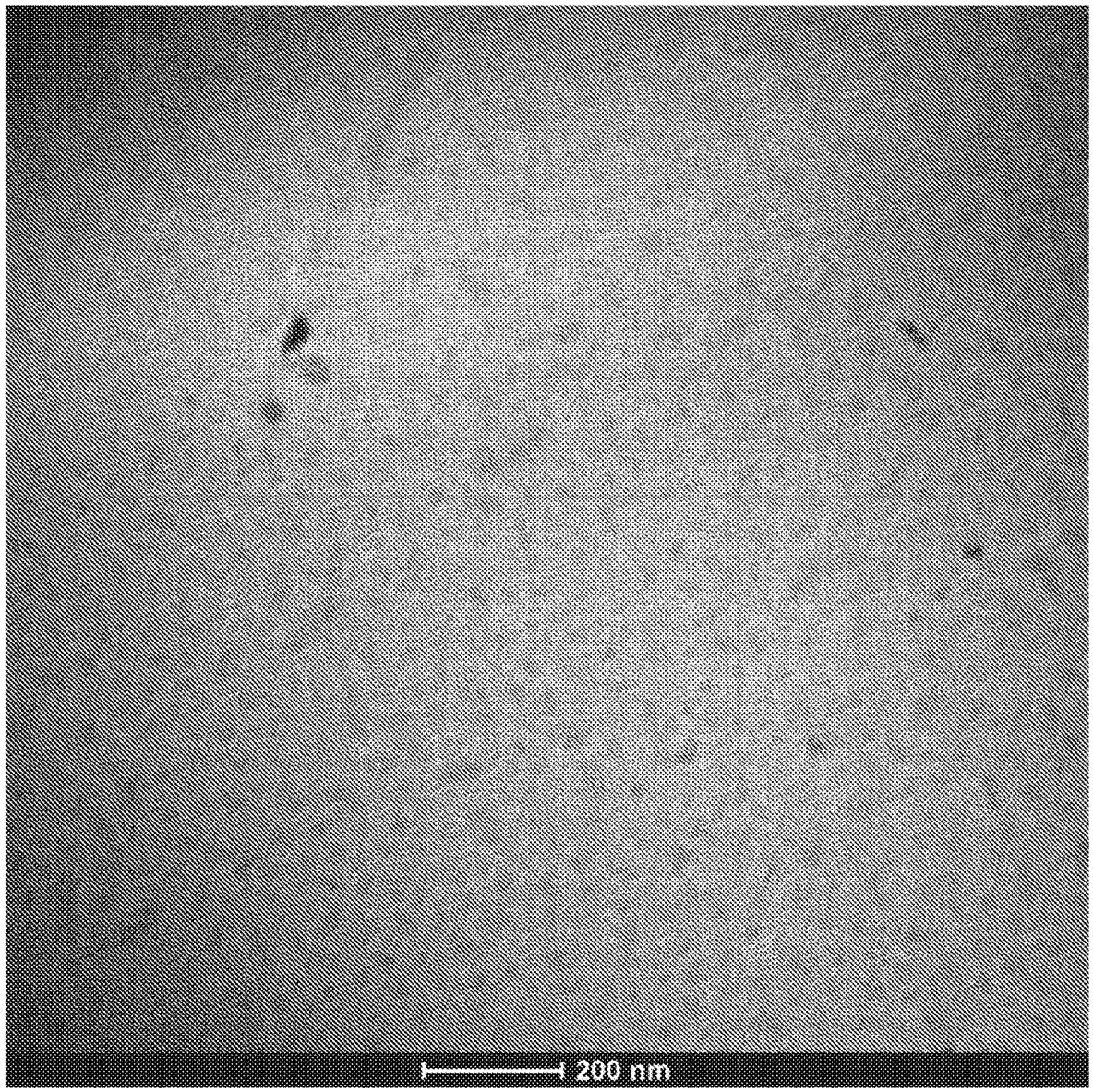
FIG. 14 is a cryo-TEM micrograph of exemplary ATBP-GEM conjugates.
Figure 15A:
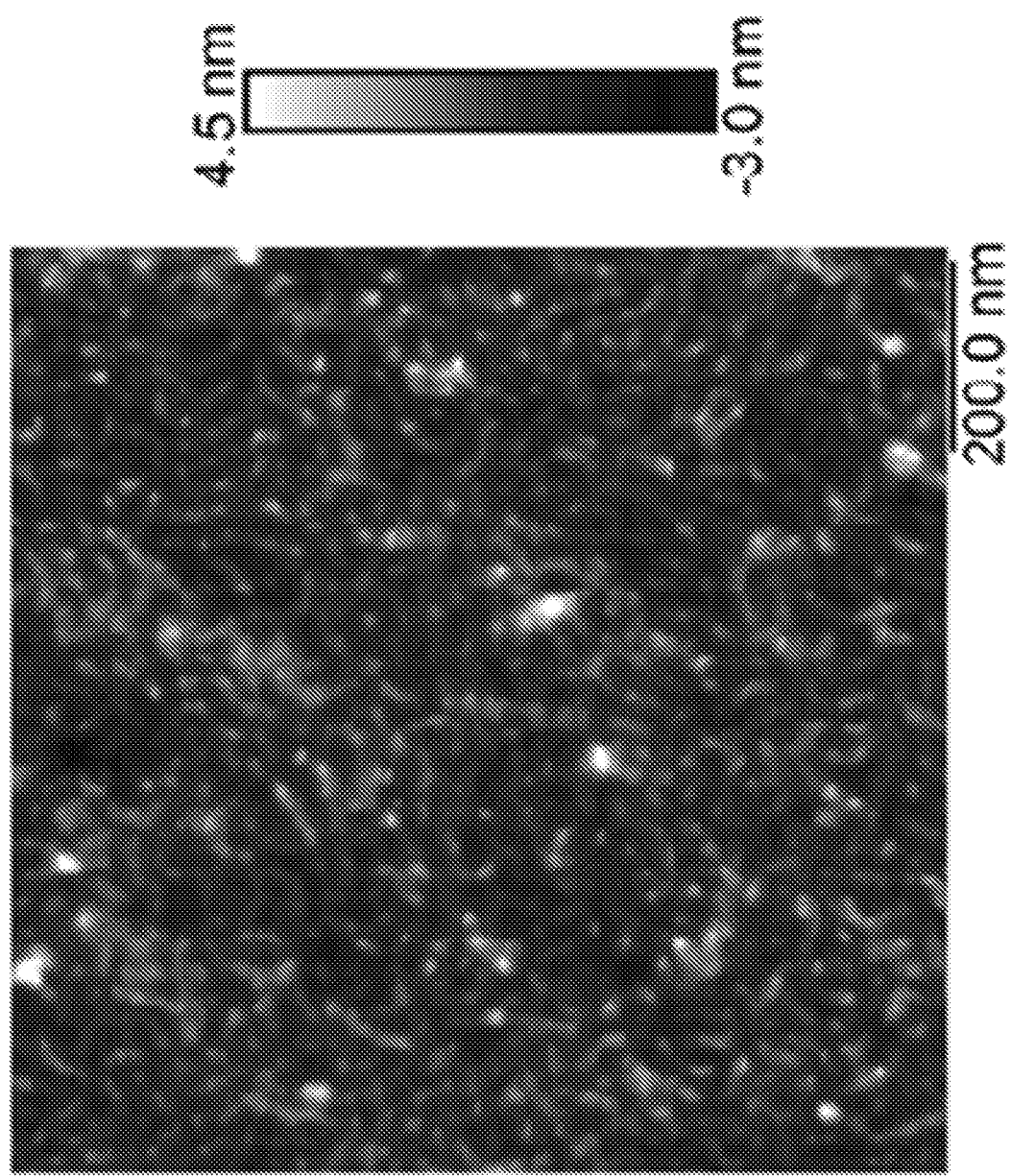
FIG. 15(A)-(B) are AFM images showing
Figure 15B:
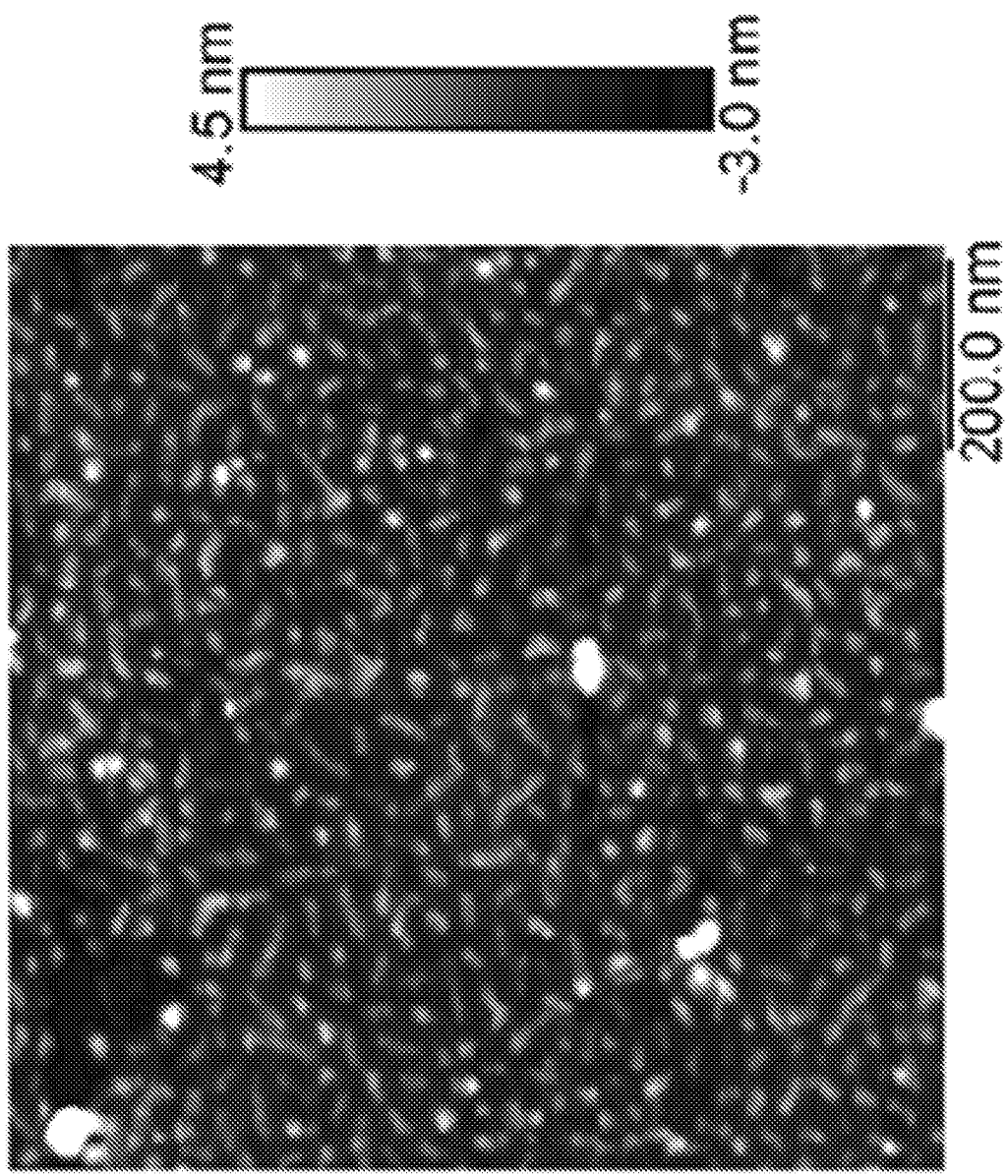
Figure 16A:
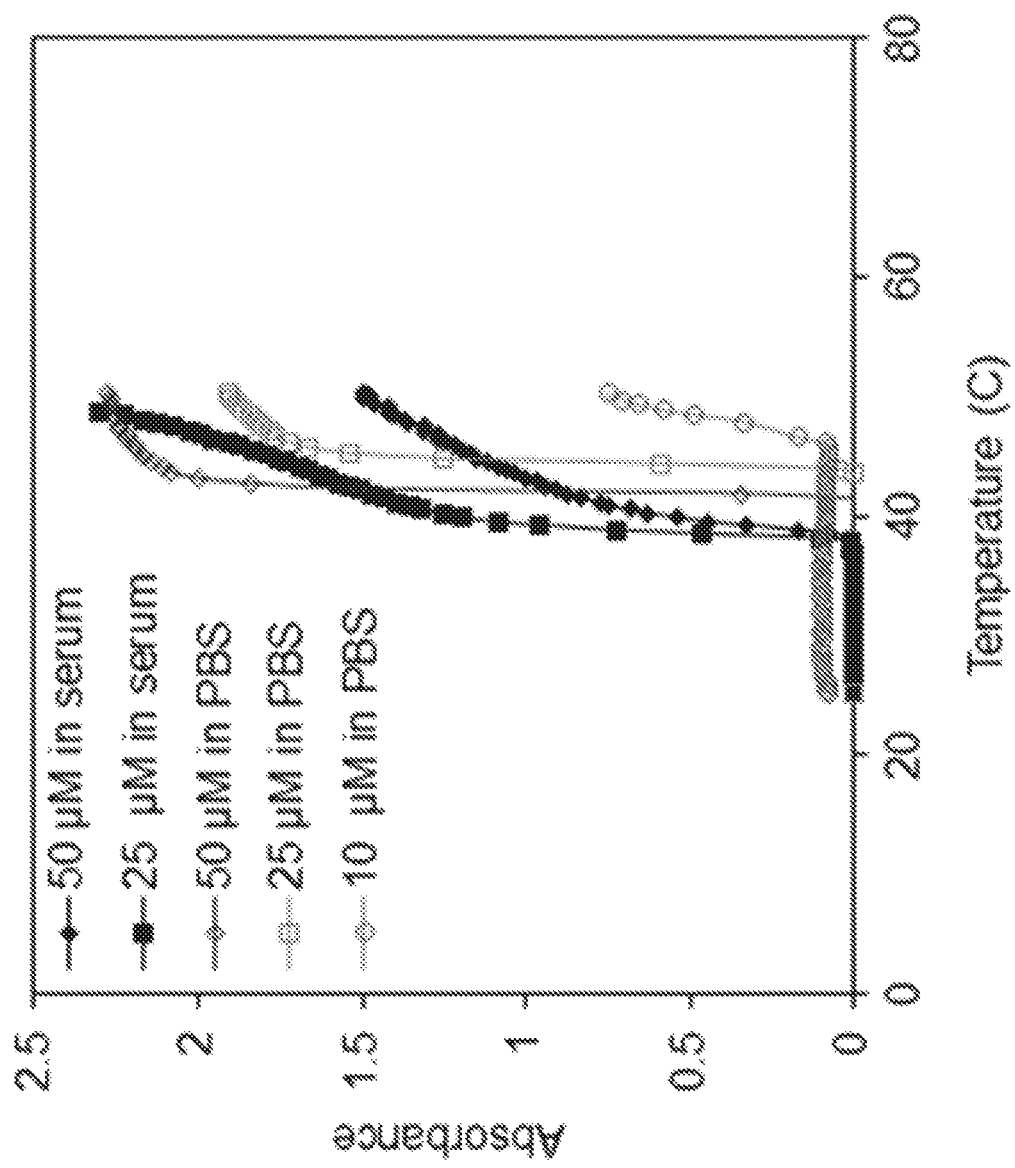
FIG. 16(A)-(B) are plots showing the determination of $T_t$ of exemplary ATBP-GEM conjugates. The $T_t$ was determined at 350 nm in 90% mouse serum and in PBS at FIG. 16(A): 10, 25 and 50 μM ATBP concentration and at FIG. 16(B): 1-10 μM using thermal turbidimetry.
Figure 16B:
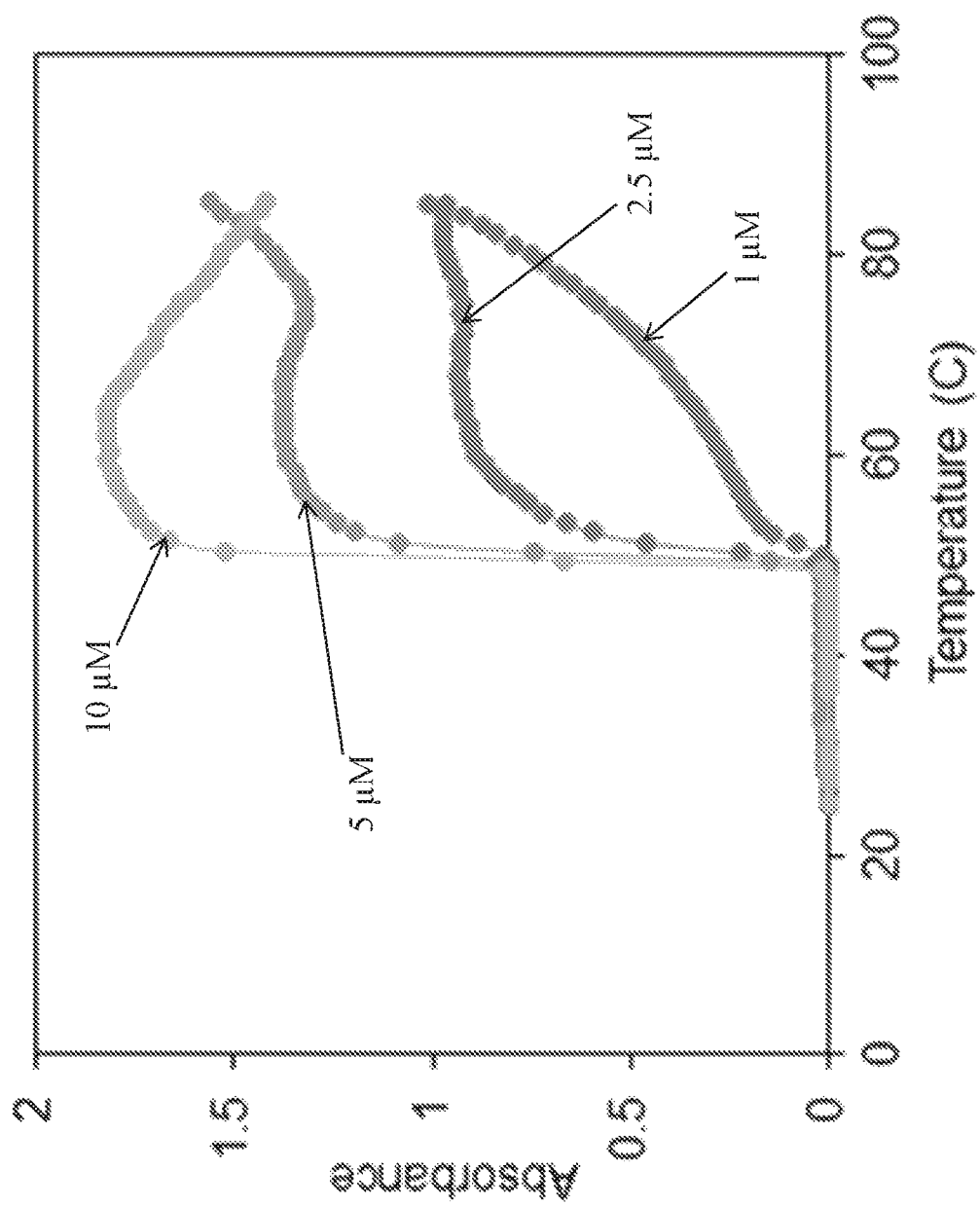
Figure 17:
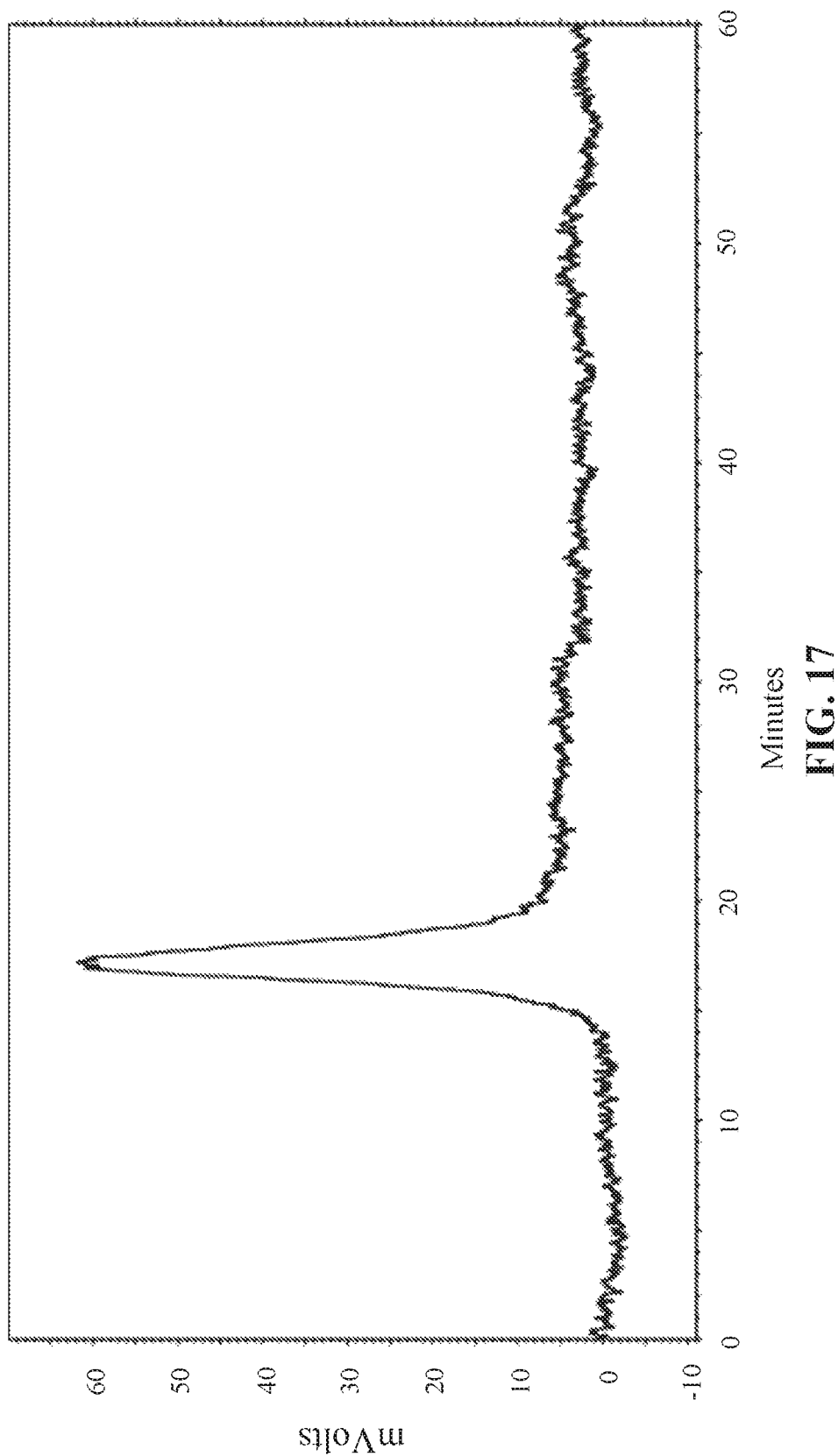
FIG. 17 is a plot showing the high-performance liquid chromatography (HPLC) trace of cy5-labelled exemplary ATBP-GEM conjugates. HPLC was run in a Shodex OHPak SB-804 column with an isocratic flow of 0.5 mL min$^{-1}$ of PBS: acetonitrile [70:30].

Characterization of ATBP-GEM Conjugate:

To demonstrate that the conjugation of GEM does not disrupt the self-assembly of the ATBP into nanoparticles, the ATBP-GEM conjugate was characterized by DLS, SLS, temperature-programmed turbidimetry, and fluorescence spectroscopy. DLS showed that the ATBP-GEM conjugate is similar in size to the nanoparticles of the other ATBP-SMM conjugates (FIG. 3(C) and Table 2). DLS of ATBP-GEM conjugate in PBS at 37° C. shows nanoparticles with a $R_h$ of about 56 nm (FIG. 3(D) and Table 2). The partial Zimm plot derived from SLS shows that the $R_g$ of ATBP-GEM conjugate is about 57 nm, and the aggregation number of the nanoparticles is about 109 (FIG. 3(E) and Table 2). The experimentally determined form factor (ρ)-calculated as $R_g/R_h$—is approximately 1.02, which is close to the theoretical value of 1 for cylindrical micelles. The shape and rod-like structure of the ATBP-GEM nanoparticles were confirmed by cryo-TEM (FIG. 3(F) and FIG. 14). The average length of the cylindrical nanoparticle determined by cryo-TEM ($L_{TEM}$) is 87±14 nm (n=20), and the average width ($D_{TEM}$) is 18.5±4.5 nm. The worm-like micellar morphologies were further verified by atomic force microscopy (AFM) under ambient condition (FIG. 15). The AFM images show distinct particles with a rod or worm-like morphology. The observed width of the worm-like micelle is much larger than their heights, which may be attributed to the spreading of the micelles on the mica surface during sample preparation and also because of the tip-induced broadening effect inherent to AFM. Next the $T_t$ of ATBP-GEM conjugate was measured and compared with that of the unmodified ATBP. The $T_t$ of the ATBP-GEM conjugate is 42° C. whereas the $T_t$ of the unmodified ATBP was 47° C. (FIG. 3(G)). Next, the $T_t$ of the ATBP-GEM conjugate was measured as a function of the ATBP concentration in mouse serum to investigate whether ATBP-GEM conjugate remains self-assembled as nanoparticles in a physiological milieu upon i.v. injection (FIG. 16(A)). In serum, the $T_t$ of the ATBP-GEM conjugate was independent of the ATBP concentration (FIG. 16(A)). This result demonstrates that the ATBP-GEM conjugate is a nanoparticle in serum because ELP-based nanoparticles—including those formed by the ATBP-GEM conjugate—have a $T_t$ that is nearly independent of concentration, whereas ELP unimers exhibit a steep, inverse log dependence upon ELP concentration. The CAC of ATBP-GEM nanoparticles, measured by a pyrene fluorescence assay, is 6.4 μM (FIG. 3(H)). The $T_t$ of the ATBP-GEM conjugate was also measured as a function of the ATBP concentration in the concentration range of 1-10 μM to investigate whether ATBP-GEM conjugate remains self-assembled as nanoparticles upon dilution (FIG. 16(B)). In the concentration range of 1-10 μM, the $T_t$ of the ATBP-GEM conjugate was found to be similarly as that of a solution of 25 and 50 μM concentration and that $T_t$ is independent of the ATBP concentration (FIG. 16(B)). This result indicates that the ATBP-GEM conjugate is also stable in the concentration range of at least 1-10 μM.

TABLE 2

Physicochemical properties of ATBP-GEM conjugate.

| ATBP sequence | SKGPG-(AGVPG)$_{160}$(YG)$_6$(CGG)$_8$WP |
|---|---|
| Molecular weight of ATBP (KDa) | 64.6 |
| [1]#GEM molecules per ATBP | 4 |
| [2]$R_h$ (nm) | 56 |
| [3]$R_g$ (nm) | 57 |
| [3]$N_{agg}$ (chains per nanoparticle) | 109 |
| [3]ρ ($R_g/R_h$) | 1.02 |
| [3]dn/dc (mL/g) | 1.69143E−04 |
| [4]CAC (μM) | 6.4 |

[1]# drug molecules per ATBP calculated from MALDI-MS.
[2]$R_h$ determined by DLS at 37° C. in PBS. Mean ± SD (n = 3).
[3]$R_g$, $N_{agg}$, ρ, dn/dc: determined by SLS.
[4]CAC was measured by pyrene fluorescence assay.

Example 2

In Vitro Characterization of ATBP-Conjugates

Methods

In Vitro Cytotoxicity:

HCT116 and Colo205 human colon cancer cells were procured from Duke Cell Culture Facility and were cultured in complete media containing Minimum Essential Medium Eagle (MEME) supplemented with 10% Fetal Bovine Serum (FBS). Cells were maintained at 37° C. and 5% $CO_2$ and passaged every 2-3 days. In vitro cellular toxicity was measured by a colorimetric assay, as follows: 1-5×10$^3$ HCT116 or Colo205 cells per 100 μL media were seeded on BD Falcon™ 96-well cell culture plates (BD; Franklin Lakes, N.J.) and allowed to adhere for 16-18 h. The media was then discarded and replenished with 100 μL of complete medium containing GEM, or ATBP-GEM conjugates and incubated at 37° C. for 72 h. 20 μL of CellTiter 96 AQueous™ (Promega; Madison, Wis.) 3-(4,5,-dimethyl2-yl)-5-(3-carboxymethoxyphenyl)-2-(4-sulfophenyl)-2H-tetrazolium (MTS) solution was added to each well and incubated at 37° C. After 2 h of incubation, the absorbance of the solution was measured at 490 nm with a Victor3 microplate reader (Perkin Elmer; Waltham, Mass.). To determine the $IC_{50}$, the data was fit to the equation: viability=1/(1+(ATBP-GEM/$IC_{50}$)$^p$), where ATBP-GEM is the equivalent GEM concentration in the well, the $IC_{50}$ is the amount of drug needed to kill 50% of the cells, and p represents the slope of the sigmoidal curve.

Fluorescent Labeling of ATBP-GEM Conjugate:

The ATBP-GEM conjugate (45 mg, 0.678 μmole) was resuspended in ~0.5 mL of reaction buffer (0.1 M NaPO$_4$, 1 mM EDTA, pH 7.4). Cyanine5-NHS ester (Lumiprobe, USA) (3.3 mg. 5.4 μmole) was resuspended in ~100 μL of DMF, then slowly transferred to the stirring ATBP-GEM solution and stirred for 4 h at 20° C. in the dark. After reaction, the unreacted Cyanine5-NHS ester was separated by gel filtration on a PD-10 column (GE Healthcare, Sweden). The eluate from the PD-10 column was diluted in PBS containing 20% acetonitrile and the mixture was spun in an Amicon Ultra-15 Centrifugal Filter Units (MWCO: 10 KDa, Millipore) at 2,500 rpm at 10° C. The Cy5-ATBP-GEM conjugate was washed twice with $NH_4HCO_3$ buffer (pH 7.4) and then freeze dried. High performance liquid chromatography (HPLC) was used to determine the purity of the Cy5 labeled ATBP-GEM conjugate (FIG. 15), using a Shodex OHPak SB-804 column (New York, N.Y.) and isocratic flow of 0.5 mL min$^{-1}$ of PBS:acetonitrile [70:30] in a LC10 HPLC (Shimadzu Scientific Instruments, Columbia, Md.).

Preparation of Cy-5 Labeled ATBP-GEM Micelles:

To prepare mixed micelles, 1% (w/w) cy5-labelled ATBP-GEM conjugate was mixed with ATBP-GEM conjugate in 30% acetonitrile and 70% PBS. The solution was vortexed and the buffer was replaced with PBS by repeated rounds of ultrafiltration (Amicon Ultra-15 Centrifugal Filter Unites).

Immunofluorescence Microscopy:

1×10$^4$ cells per well were seeded overnight on an 8-well chambered cover glass (Electron Microscopy Sciences; Hatfield, Pa.). Cells were treated with Cy5 labeled ATBP-GEM conjugate for 4 h, washed with PBS, and then fixed with 4% paraformaldehyde in PBS at room temperature for 15 min. Fixed cells were stained with 2 t M Hoechst 33342 (Invitrogen; Grand Island, N.Y.) and CellMask™ Green plasma membrane stain (1×) in Hank's balanced salt solution (HBSS) for 10 min. Cells were washed 3 times with PBS and then imaged immediately on a Nikon TE2000-U inverted fluorescent microscope using a 60×1.25NA oil immersion objective.

Results

Figure 4A:
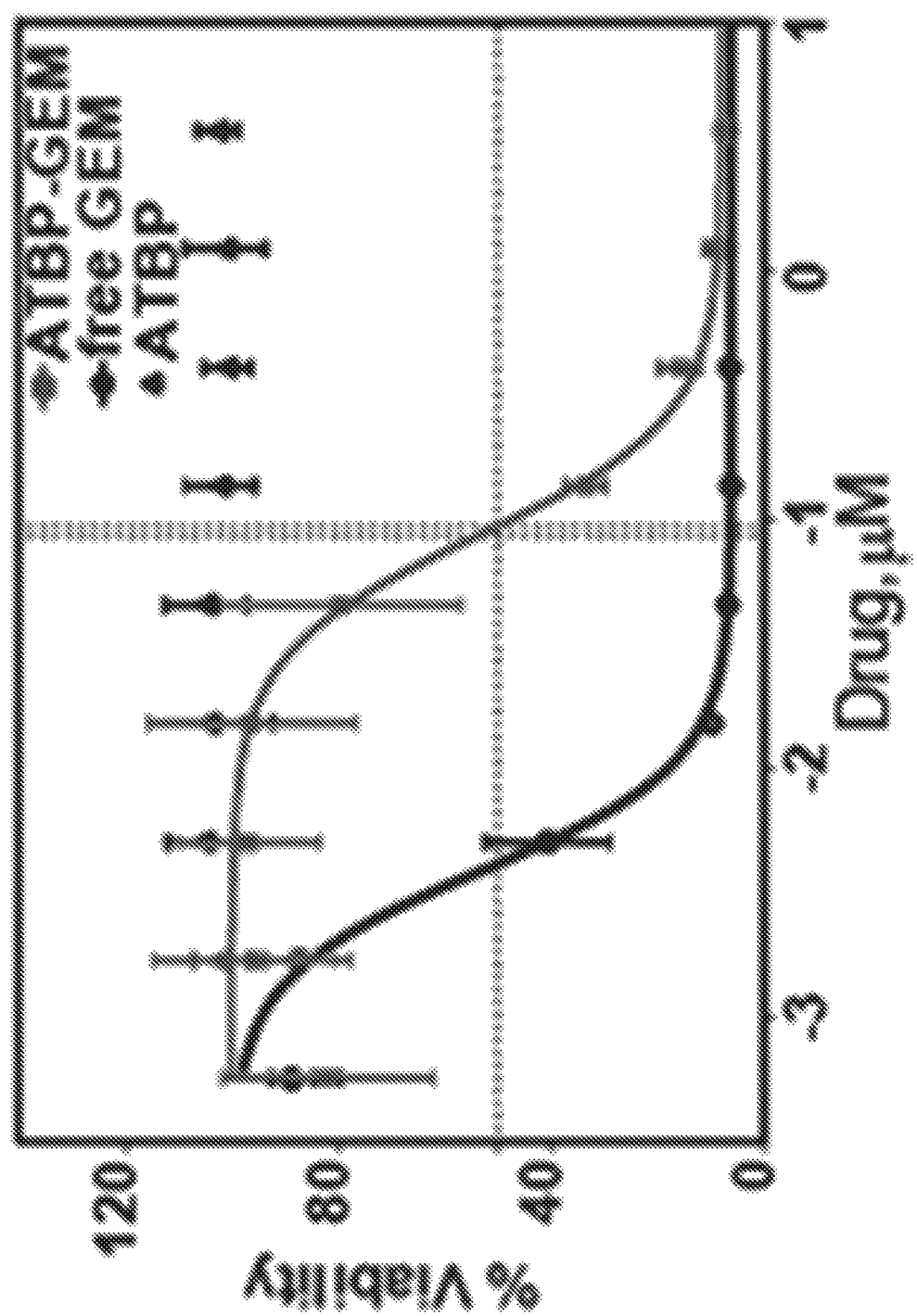
FIG. 4(A)-(F) show in vitro and in viw activity of exemplary ATBP-GEM nanoparticles.
Figure 4B:
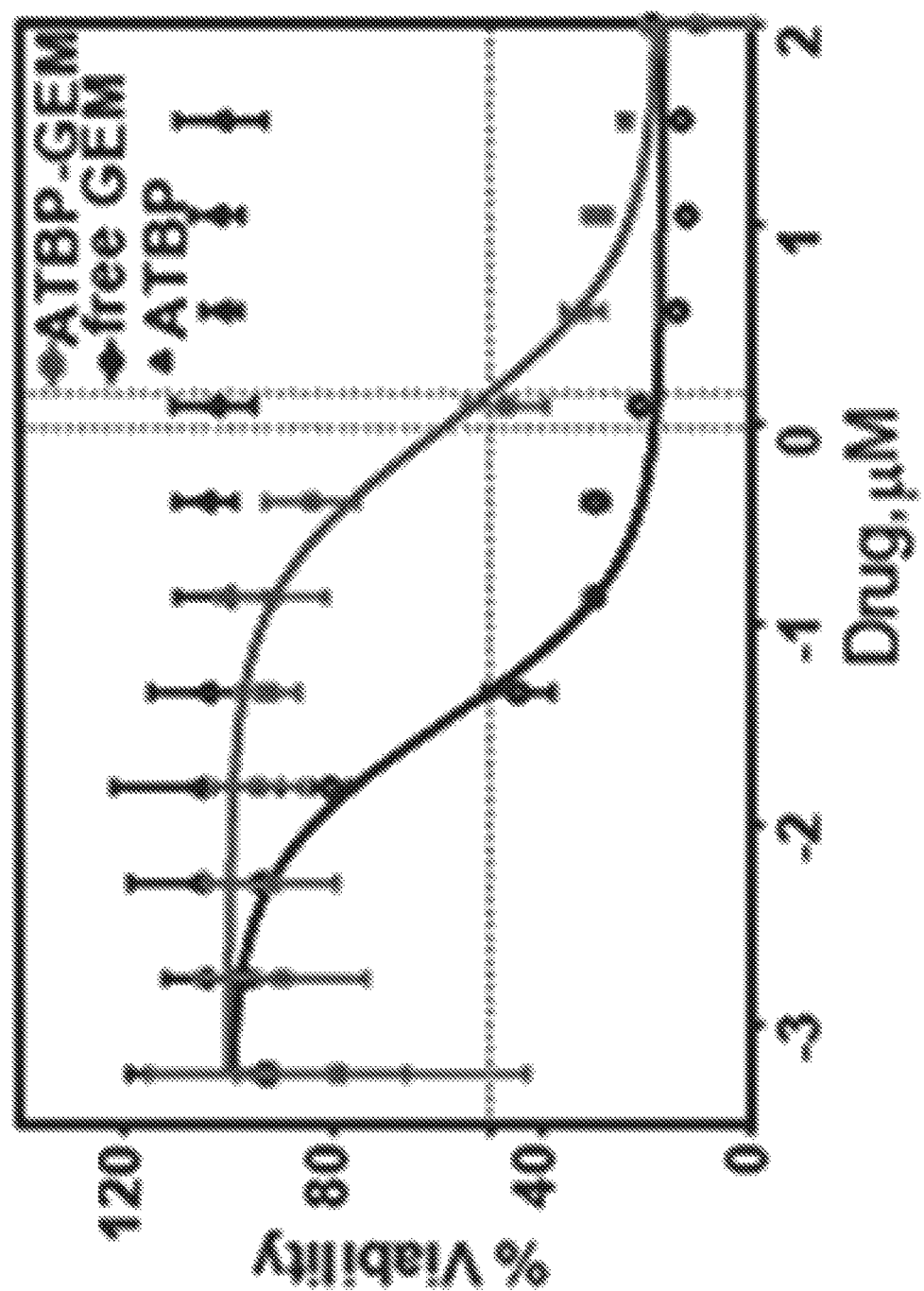

In Vitro Anti-Cancer Activity:

Two human colon carcinoma cell lines—HCT116 and Colo 205—were chosen to evaluate the in vitro toxicity of the ATBP-GEM conjugate, as GEM is used for the treatment of human colon carcinoma. After 72 h treatment of ATBP-GEM conjugate, the growth of HCT116 and Colo 205 cells is significantly inhibited (FIGS. 4(A) & (B)). The $IC_{50}$, described as the dose of GEM or GEM equivalent (for the ATBP-GEM nanoparticles) required to kill 500% of cells, is about 94 nM and about 1.44 μM for ATBP-GEM, and about 4.1 nM and about 46.4 nM for GEM for HCT-116 and Colo 205 cells respectively (Table 3). These results demonstrate that the ATBP-GEM nanoparticles prevent the in vitro growth of both HCT116 and Colo 205 cells.

TABLE 3

IC$_{50}$ of ATBP-GEM conjugate and free GEM in HCT-116 and Colo 205 cell line.

| IC$_{50}$ (nM) | HCT-116 cells | Colo 205 cells |
|---|---|---|
| Free GEM | 4.1 | 46.4 |
| ATBP-GEM | 94 | 1440 |

Figure 18A:
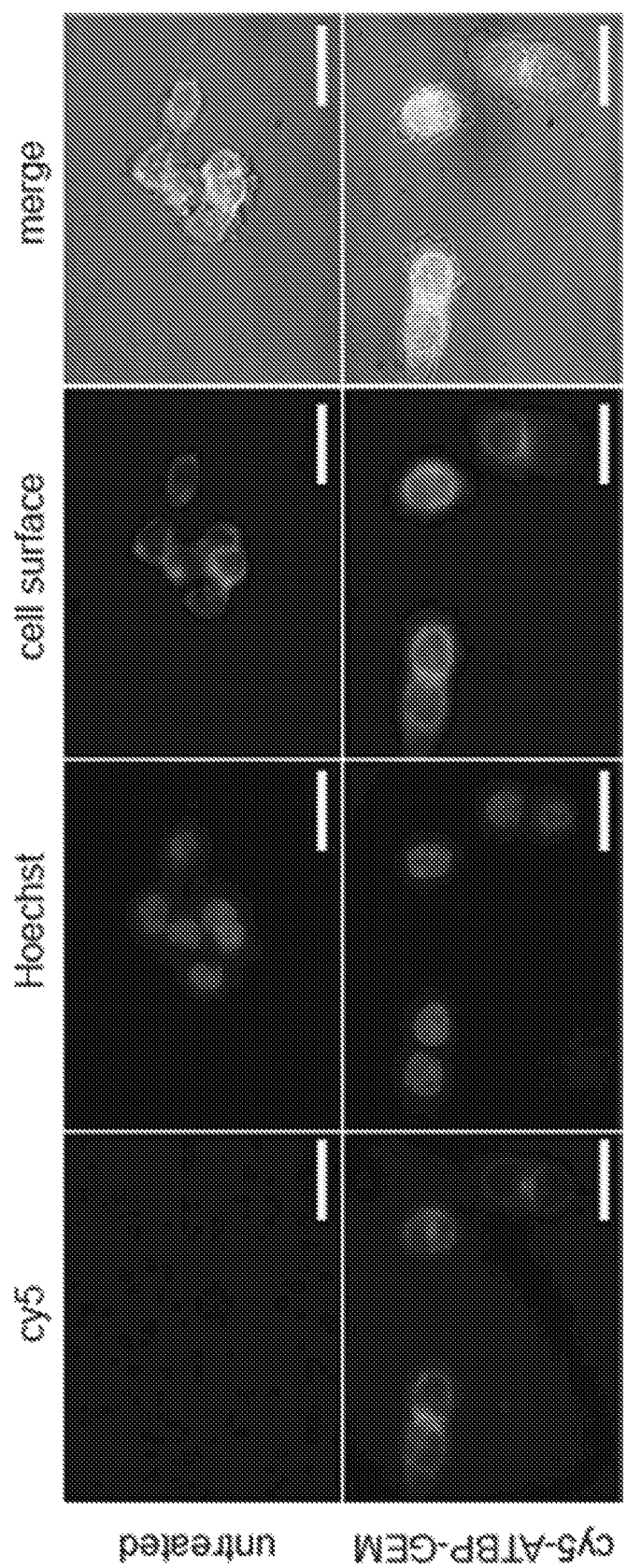
FIG. 18(A)-(B) are a series of images showing the cellular uptake of cy5 labelled exemplary ATBP-GEM conjugates.
Figure 18B:
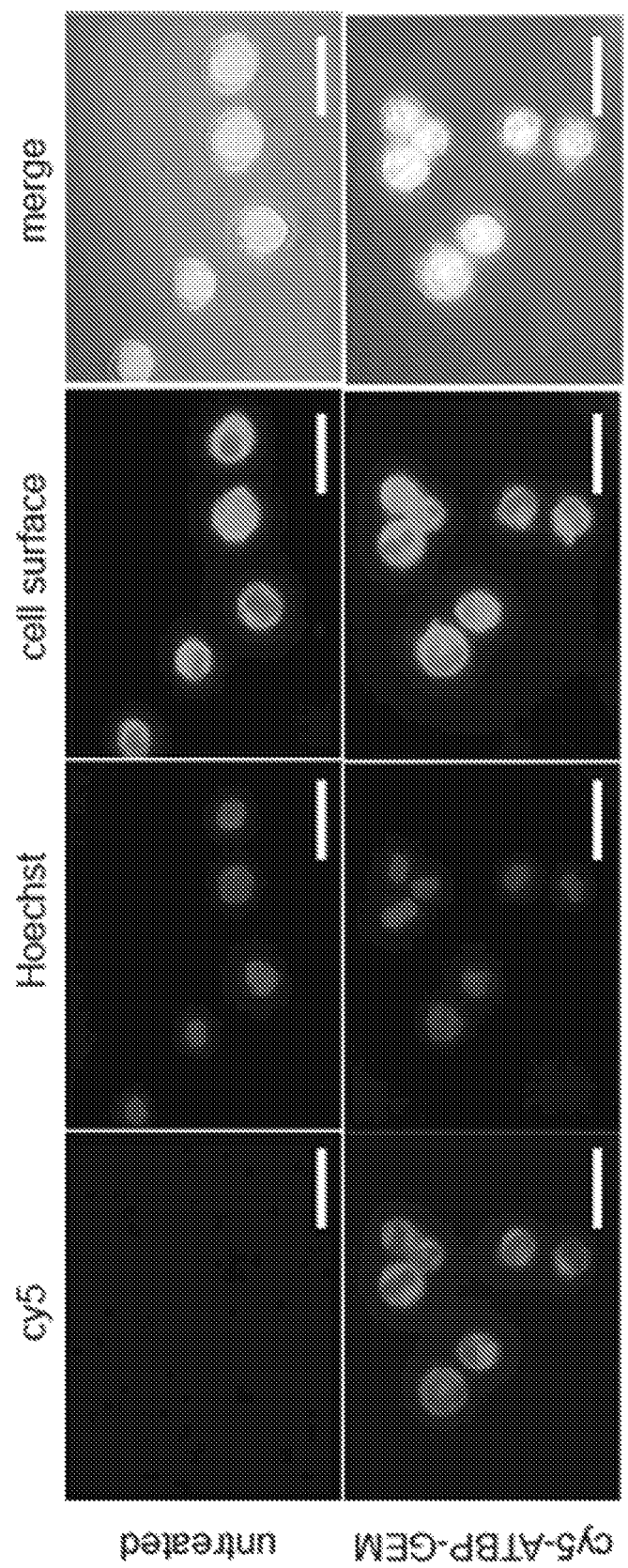

In Vitro Cellular Uptake Study:

Next the uptake of the ATBP-GEM nanoparticles by HCT-116 and Colo205 cell lines was evaluated. Cells were treated with cyanine 5 (cy5) labeled ATBP-GEM nanoparticles. After 4 h of treatment, cells were fixed with 4% formaldehyde, and stained with Hoechst 33342 and CellMask™ Green plasma membrane dyes. Inverted fluorescent microscopy images showed the accumulation of cy5-labeled ATBP-GEM nanoparticles in both cell lines, whereas no red fluorescence was observed in untreated cells (FIG. 18). The results revealed that significant cellular uptake of ATBP-GEM nanoparticle was observed in both cell lines.

Example 3

In Vivo Characterization of ATBP-Conjugates

Methods

Pharmacokinetics and In Vive Tumor Uptake:

To measure pharmacokinetics (PK), Cy5 labeled ATBP-GEM conjugate was intravenously infused into male nude mice (119.6 µg cy5 equiv·kg$^{-1}$ BW) via the tail vein. 10 µL blood was drawn from the tail vein at 40 s, 30 min, 1, 2, 4, 8, 24 and 48 h after infusion and diluted into 90 µL PBS containing heparin at a final concentration of 1,000 U mL$^{-1}$. All fluorescence measurements were performed on a Molecular Dynamics Typhoon 9410 Molecular Imager (GE Healthcare, USA). To determine estimates and confidence intervals of pharmacokinetic parameters, the dataset was fit to a non-compartment pharmacokinetic model using WinNonlin software. The plasma cy5 concentration (n=5) was fit to determine the initial volume of distribution (V$_Z$), and elimination half-life (t$_{1/2}$), and volume of distribution at steady-state (V$_{ss}$) (Table 4). From these data and the injected dose, D, other pharmacokinetic parameters were calculated including the plasma clearance. Units, estimates, and confidence intervals for the above fit are all presented in Table 4.

To quantify the accumulation of GEM and ATBP-GEM conjugate in tumors, cy5-GEM or cy5 labeled ATBPP-GEM conjugate was intravenously infused into male nude mice (119.6 µg cy5 equiv·kg$^{-1}$ BW) via the tail vein. At 1, 6 or 24 h after injection, tumors were obtained. Tissues were weighed, suspended in 0.1-0.5 mL of acidified isopropanol, and homogenized using 2 mm diameter zirconia beads and a MiniBeadbeater-1™ (Biospec; Bartlesville, Okla.) for 60 sat 5,000 beats per minute and centrifuged (13,000 RPM, 10 min, 4° C.). The supernatant was removed and assayed for fluorescence as described for pharmacokinetic analysis. Tumor drug concentrations were compared using ANOVA followed by post-hoc tests (Tukey HSD) determined using GraphPad Prism 6 software.

Dose Escalation and Tumor Regression:

Male nude mice (6-8 weeks old) bearing subcutaneous HCT116 tumors were treated when the mice had a tumor volume of 75-100 mm$^3$. All treatments were administered by tail vein infusion (50 µL/min) in a total volume of 500 µL of PBS. Dose escalation was performed with ATBP-GEM conjugate with a dose of 5, 10, 15, 20, and 25 mg·kg$^{-1}$ BW (BW: body weight) of free drug equivalent.

For the regression study, mice with subcutaneously implanted HCT116 tumors were treated with PBS, 25 mg·kg$^{-1}$ BW free GEM or, 25 mg·kg$^{-1}$ BW of ATBP-GEM (drug equivalent) three times on days 0, 2 and 4. The PBS control or drugs were administered by tail vein infusion (50 µL/min) of 500 µL. Tumor dimensions and BW were determined 3-4 times a week, and the tumor volume was calculated using the equation: volume [mm$^3$]=length×width×width×1/2.

BW of mice were monitored and the mice were euthanized upon exceeding 15% loss in BW or if their tumors volume was greater than 1000 mm$^3$. Duke University's IACUC defines 15% body weight loss as severe morbidity; a humane death endpoint. The maximum tolerated dose (MTD) was determined in mice with tumors. Kaplan-Meier analysis was used to compare the cumulative survival and the Sidak test, Tukey Test, Wilcoxon test were carried out using GraphPad Prism 6 software.

Results

Figure 4C:
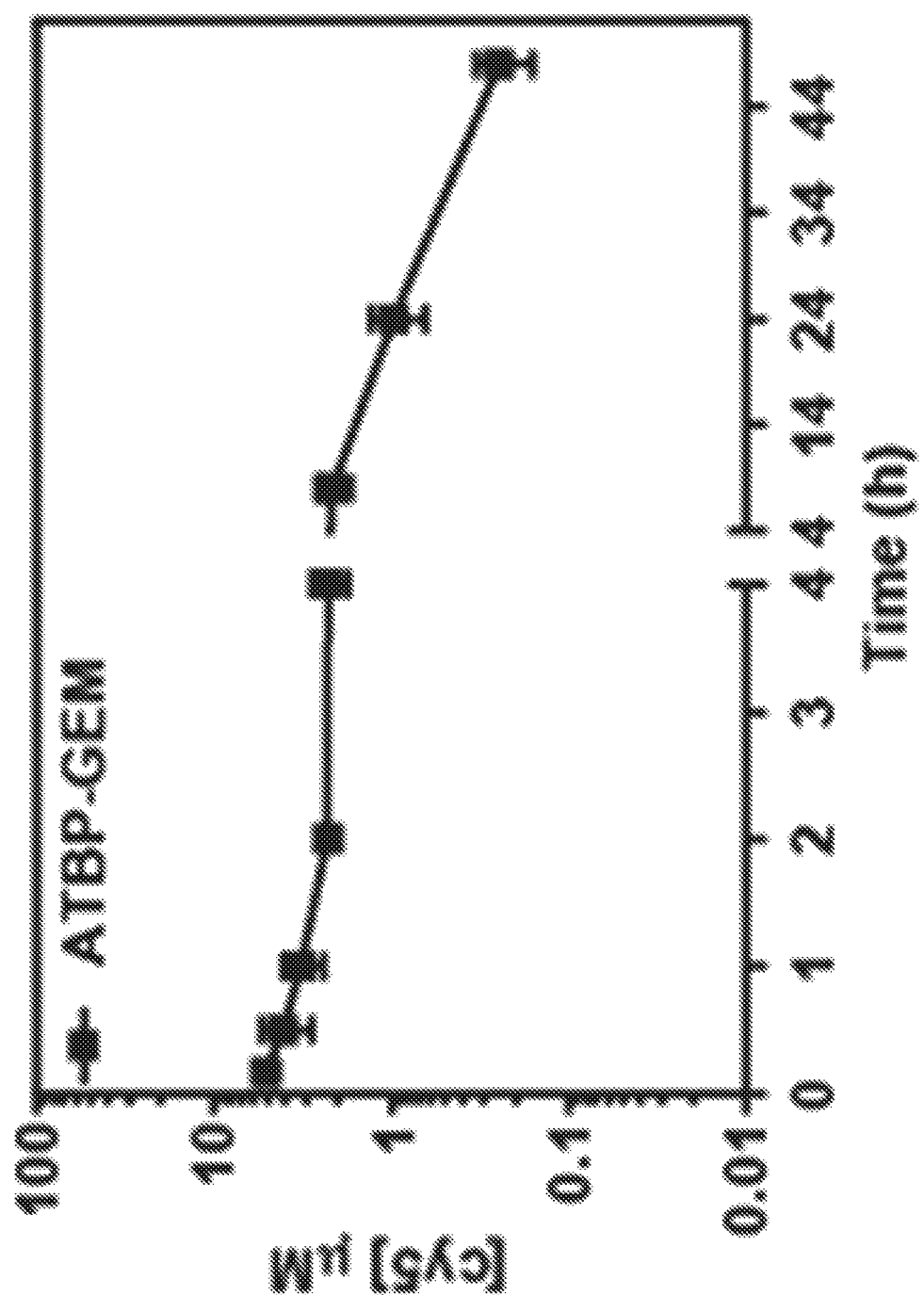

Determination of PK and Tumor Uptake of ATBP-GEM Conjugate:

To evaluate the plasma half-life of ATBP-GEM conjugate, cy5 labeled ATBP-GEM nanoparticles were intravenously infused and the concentration of drug in plasma was determined as a function of time post-administration (FIG. 4(C)). The pharmacokinetic parameters were determined using a non-compartment pharmacokinetic method using WinNonlin software, which yielded a terminal half-life for the ATBP-GEM nanoparticles of 12.8±2.2 h and a plasma AUC of 32.48±4.8 µgmL$^{-1}$ h (Table 4). In contrast the reported terminal half-life of free GEM is 204 min in nude mice. These data clearly demonstrate that the ATBP-GEM conjugates deliver at least a four-fold longer plasma terminal half-life than free drug, which is important for increased uptake in solid tumors via the enhanced permeability and retention (EPR) effect.

Figure 4D:
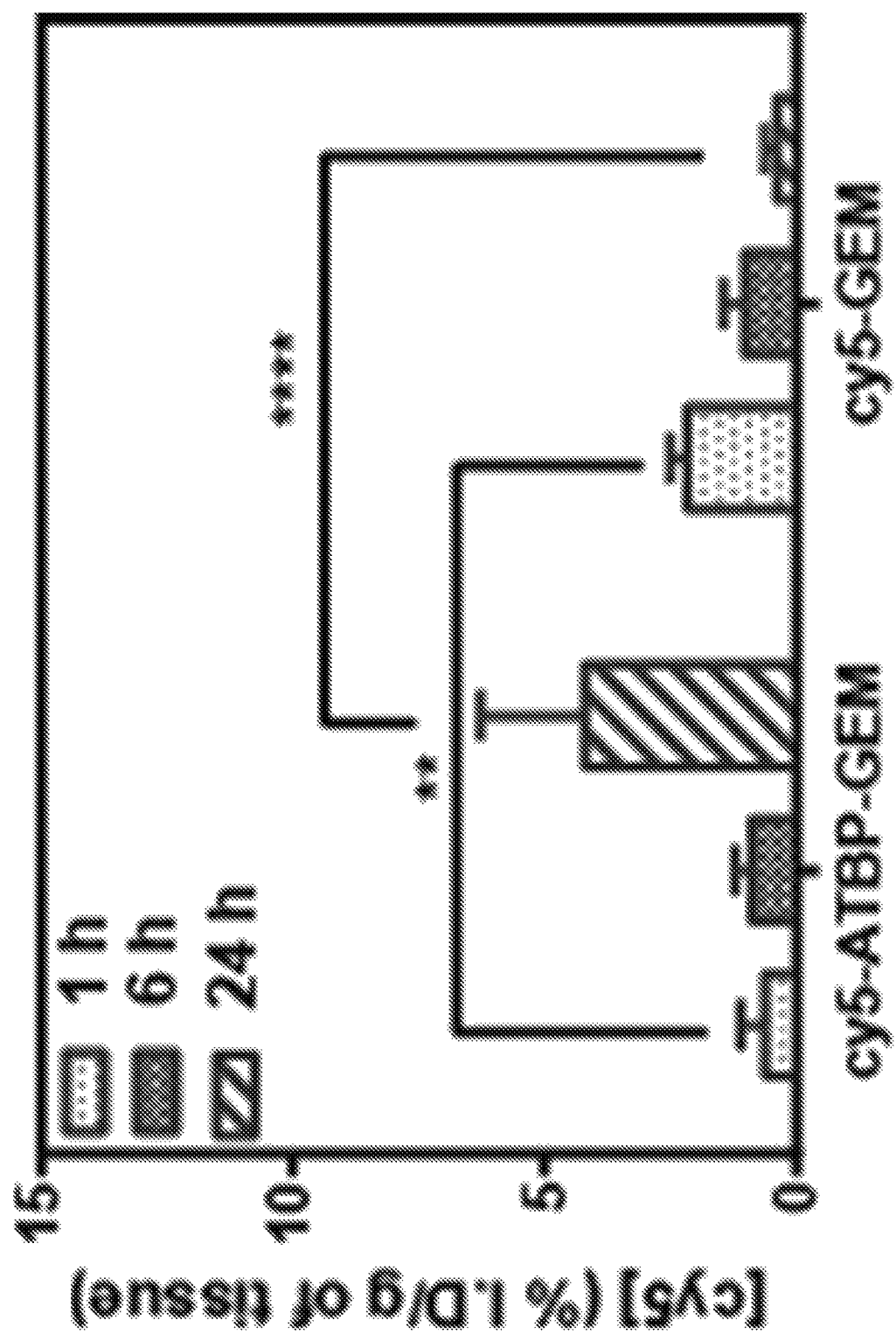
Figure 19:
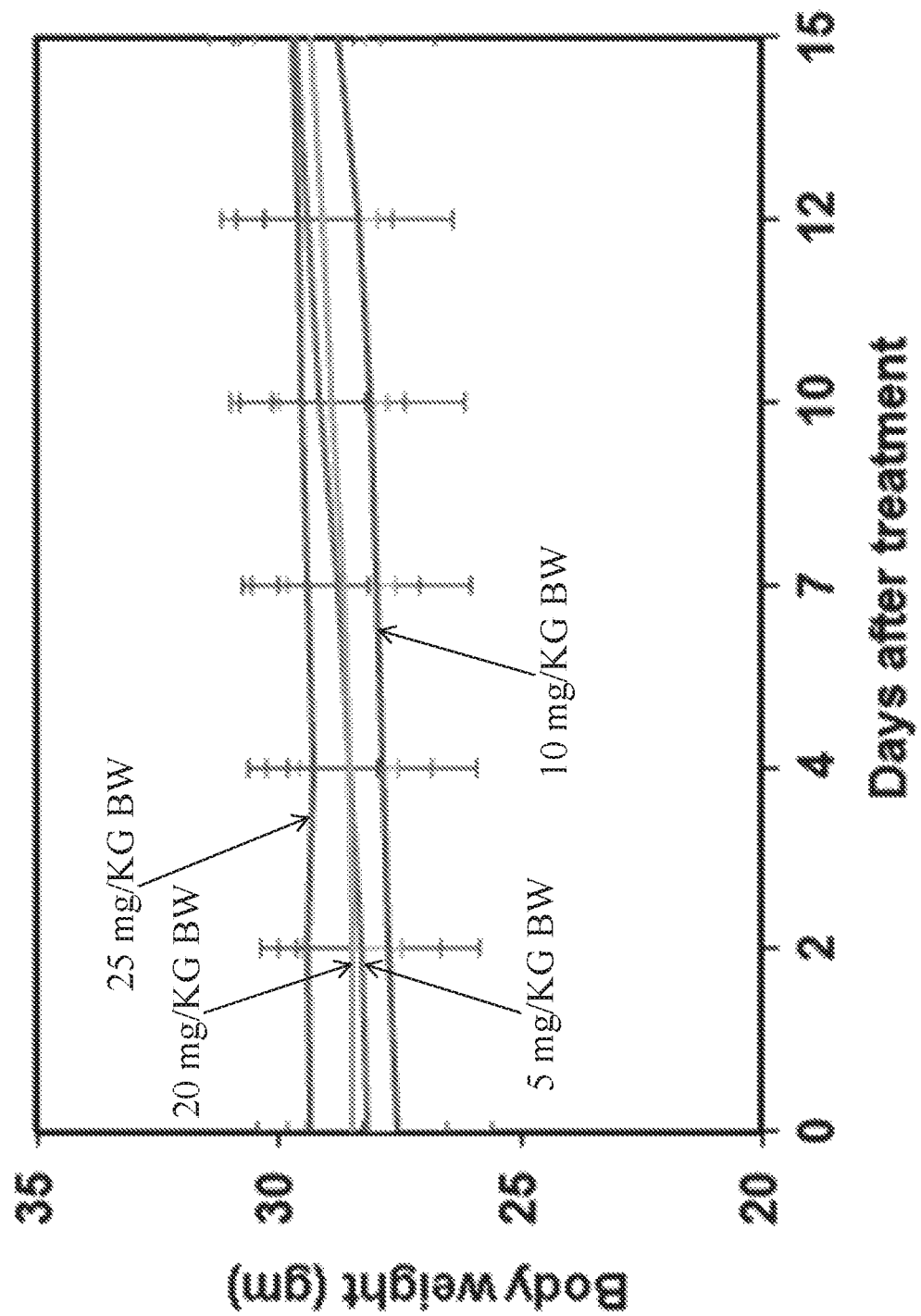
FIG. 19 is a plot showing the change in body weight of mice bearing a subcutaneous HCT-116 tumor. Treatments were intravenous (i.v.) administered on day 0. Treatments include single i.v. injection of exemplary ATBP-GEM at doses ranging from 5 to 25 mg GEM equiv/kg body weight (BW). Points represent the mean±SD (n=5).

The accumulation of GEM in tumors upon intravenous injection of ATBP-GEM nanoparticles and free GEM was also determined. Mice were administered cy5-GEM and cy5-ATBP-GEM nanoparticles, and tissue samples of treated mice were collected after 1 h, 6 h, and 24 h (FIG. 19). Notably, 24 h after administration, ATBP-GEM showed a 10-fold increase in drug concentration in the tumor, as compared with free drug at the same dose (FIG. 4(D); two way ANOVA and Sidak's test; p=0.0001).

TABLE 4

Pharmacokinetic parameters of ATBP-GEM nanoparticles.

| | ATBP-GEM |
|---|---|
| [1]C$_{max}$ (µgmL$^{-1}$) | 2.97 ± 0.3 |
| AUC $_{(last)}$ (µgmL$^{-1}$h) | 30.11 ± 4.64 |
| AUC $_{(total)}$ (µgmL$^{-1}$h) | 32.48 ± 4.8 |
| t$_{1/2}$ (h) | 12.8 ± 2.2 |
| [2]CL (mLh$^{-1}$) | 3.7 ± 0.04 |
| MRT$_{(last)}$ (h) | 13.5 ± 0.9 |
| MRT$_{(total)}$ (h) | 17.5 ± 2.5 |
| [2]Vss (L) | 0.06 ± 0.01 |

[1]Theoretical C$_{max}$: 119.6 µg/kg => 2.99 µg/mL plasma (close to experimentally obtained C$_{max}$ = 2.97 µg/mL).
[2]Dose-dependent parameters (CL and Vss) are "per kg body weight".

In Vivo Anti-Cancer Activity:

To evaluate and compare the tumor regression efficacy of ATBP-GEM nanoparticles with free GEM, ATBP-GEM was injected in a dose escalation experiment to evaluate its maximum tolerated dose (MTD). The MTD for ATBP-GEM was at least 25 mg GEM Equiv·kg$^{-1}$. BW (FIG. 19). The true MTD of ATBP-GEM nanoparticles is likely to be greater than 25 mg·kg$^{-1}$, as it was unable to administer a dose higher than 25 mg·kg$^{-1}$ because of the viscosity of the formulation and limits on the volume of solution that can be administered to a mouse.

Figure 4E:
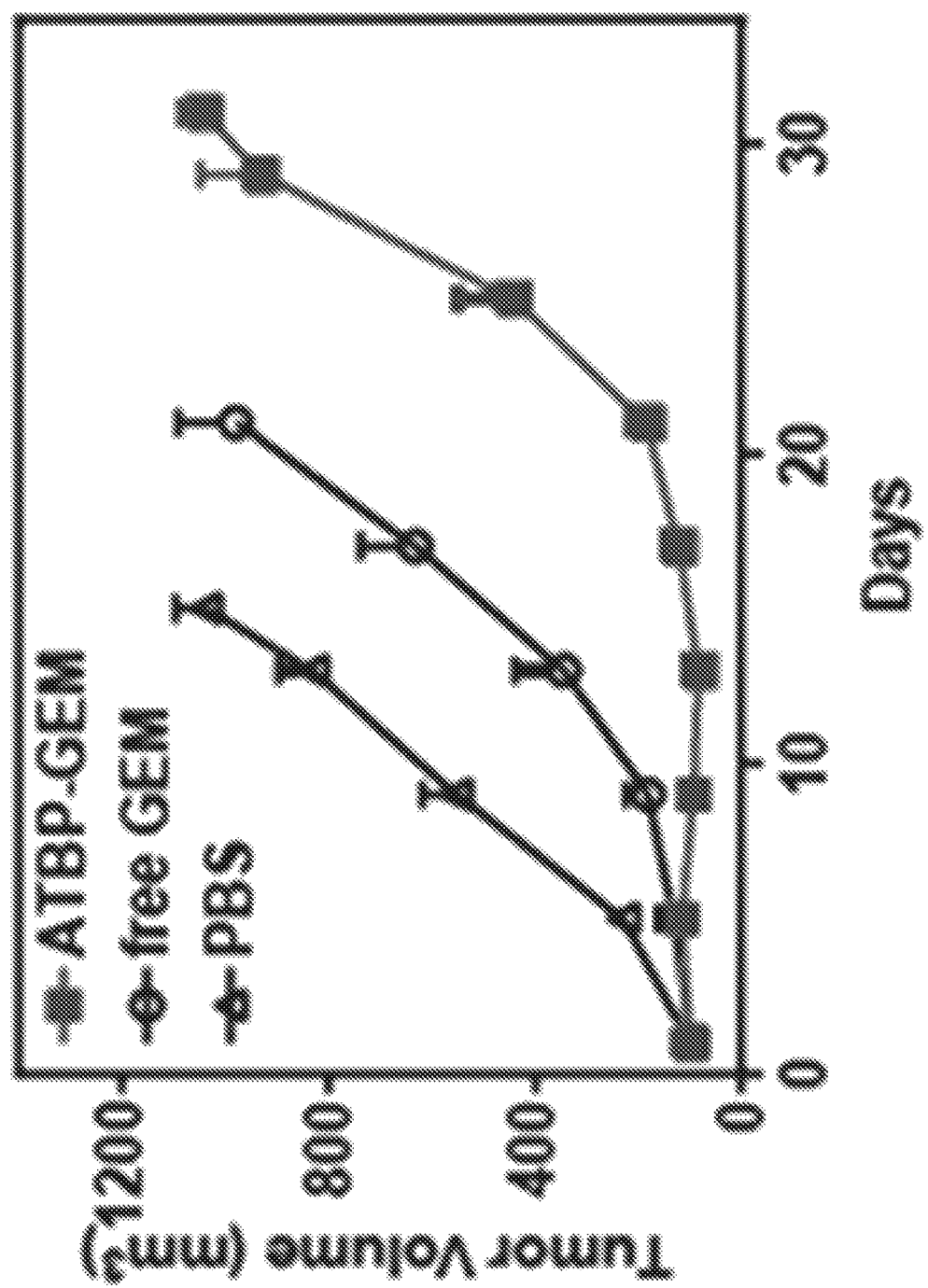
Figure 4F:
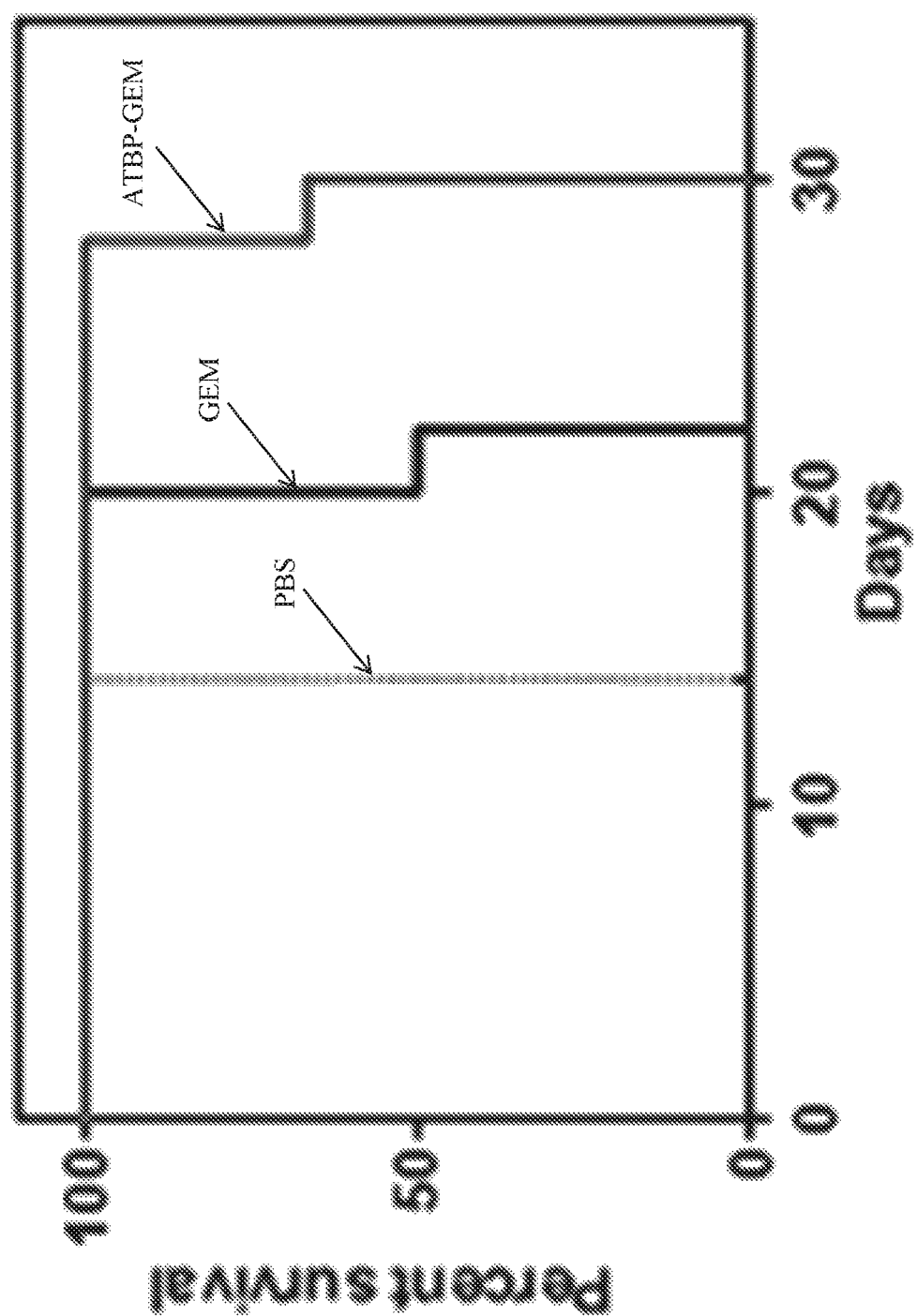

Next the tumor regression efficacy of ATBP-GEM in a subcutaneous HCT-116 xenograft model was determined. Mice with HCT-16 tumors were intravenously infused three times with PBS, GEM (25 mg·kg$^{-1}$), or ATBP-GEM nanoparticles (25 mg·kg$^{-1}$ of GEM equivalent) (FIG. 4(E)) on day 0, 2 and 4. 12 days after treatment, the mean tumor volume of ATBP-GEM treated was 82 mm$^3$ (n=6), free-drug treated mice was 343 mm$^3$ (n=6) for (Tukey; p=0.0001), and PBS treated mice were 832 mm$^3$ (n=6) for (Tukey; p=0.0001). The ATBP-GEM formulation outperformed free drug (p<0.0001) and PBS (p<0.0001) at the same drug dose in reducing tumor volume, which correlates with an increase in animal survival (FIG. 4(F)).

Figure 20:
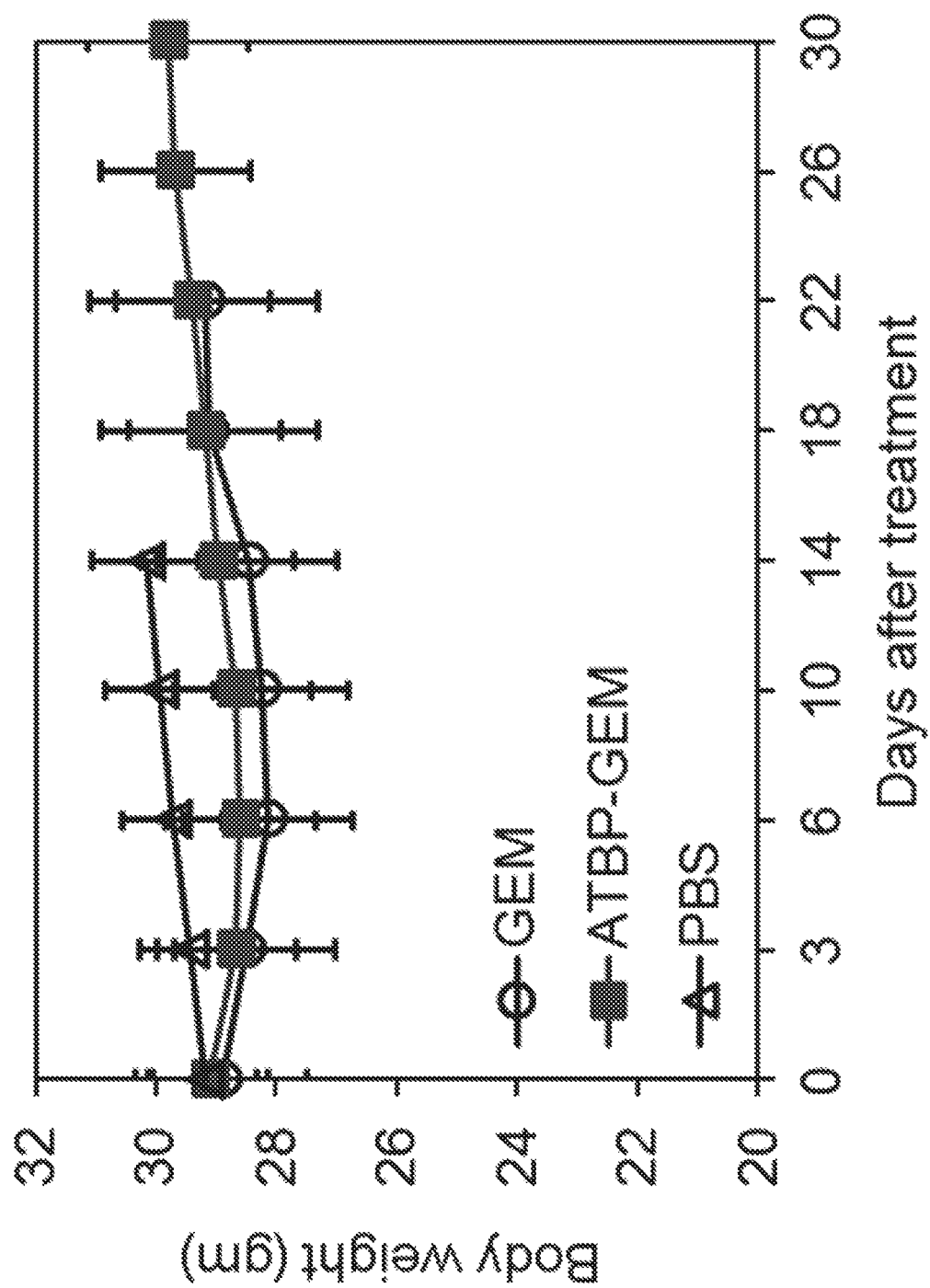
FIG. 20 is a plot showing body weight of mice (up to 30 days) bearing subcutaneous HCT-116 tumor and treated with exemplary ATBP-GEM, free GEM, and PBS.

The mice that received PBS (n=6) had a median survival time of 14 days, and treatment with free GEM (n=6) increased survival to 21 days (Kaplan-Meier, Log-rank test, p<0.0001). Treatment with ATBP-GEM further improved the survival to at least 30 days (Kaplan-Meier, Log-rank test, p<0.0001). Body-weight was also monitored throughout the treatment to identify the relative toxicity of free GEM and ATBP-GEM conjugate. All treatments were well tolerated for the period of the study, with body weight loss remaining well below the 15% cutoff that is a surrogate for significant systemic toxicity (FIG. 20).

The ATBP-GEM conjugate nanoparticles have a significantly longer plasma half-life and enhanced tumor accumulation compared to free drug. Furthermore, the ATBP-GEM conjugate nanoparticle shows significantly better anti-tumor efficacy in a murine model of the HCT-116 tumor compared to the same dose of free drug. The antitumor effect is also reflected in a significant improvement in the median survival of ATBP-GEM nanoparticle treated animals as compared to treatment with free drug. This study is the first demonstration of the design of highly soluble, thermally responsive self-assembled polypeptide nanoparticles which can be used to deliver numerous hydrophilic chemotherapeutics.

What is claimed is:

1. A composition comprising an aggregate of self-assembling polypeptides, wherein a self-assembling polypeptide comprises:
   (a) a first amino acid sequence $(X^1GVPG)_x$ (SEQ ID NO:1), wherein $X^1$ is an amino acid and x is 20 to 240;
   (b) a second amino acid sequence $(X^2G_m)_y$ (SEQ ID NO:2), wherein $X^2$ is Y, F or W, m is 0 to 3, and y is 1 to 50;
   (c) a third amino acid sequence $(CGG)_z$ (SEQ ID NO:3), wherein z is greater than 1; and
   (d) at least one molecule attached to the third amino acid sequence through a cysteine group, wherein the molecule has an octanol-water distribution coefficient (logD) of less than or equal to 1.5 at a pH of 7.4.

2. The composition of claim 1, wherein the molecule is a chemotherapeutic or an imaging agent.

3. The composition of claim 1, wherein the molecule is gemcitabine.

4. The composition of claim 1, wherein about 2 to about 15 molecules are attached to the third amino acid sequence.

5. The composition of claim 1, wherein the molecule is attached to the third amino acid sequence through a thiol group.

6. The composition of claim 1, wherein the first amino acid sequence is $(X^1GVPG)_m$ (SEQ ID NO:3), and wherein m is 120 to 200.

7. The composition of claim 1, wherein the second amino acid sequence is $(X^2G)_n$ (SEQ ID NO:4), and wherein n is 4 to 8.

8. The composition of claim 1, wherein the third amino acid sequence is $(CGG)_p$ (SEQ ID NO:5), and wherein p is 4 to 12.

9. The composition of claim 1, wherein $X^1$ is A.

10. The composition of claim 1, wherein $X^2$ is Y.

11. The composition of claim 1, wherein the first amino acid sequence is $(AGVPG)_{160}$ (SEQ ID NO:6).

12. The composition of any of claims 1 llclaim 1, wherein the second amino acid sequence is $(YG)_6$ (SEQ ID NO:7).

13. The composition of claim 1, wherein the third amino acid sequence is $(CGG)_8$ (SEQ ID NO:8).

14. The composition of claim 1, wherein each self-assembling polypeptide individually has a molecular weight of about 20 kDa to about 300 kDa.

15. The composition of claim 1, wherein the aggregate of self-assembling polypeptides is a nanoparticle.

16. The composition of claim 15, wherein the molecule is located in the core of the nanoparticle.

17. The composition of claim 15, wherein the nanoparticle has an average hydrodynamic radius of about 20 nm to about 200 nm.

18. The composition of claim 15, wherein the nanoparticle is rod-shaped or spherical.

19. The composition of any of claim 15, wherein the nanoparticle comprises about 50 to about 1000 self-assembling polypeptides per particle.

20. The composition of claim 1, further comprising a pharmaceutically acceptable carrier.

21. A method of killing multiple colon, panereatic, bladder, NSCLC, breast, and ovarian cancer cells comprising contacting multiple cancer cells with the composition of claim 1.

22. The method of claim 21, wherein the multiple cancer cells are in a human or a dog.

23. The method of claim 21, wherein the multiple cancer cells are in vitro.

24. A method of treating colon, pancreatic, bladder, NSCLC, breast, and ovarian cancers in a subject comprising administering to the subject the composition of any of claim 1.

25. The method of claim 24, wherein the subject is a human or a dog.

26. The method of claim 25, wherein the cancer comprises solid tumors.

* * * * *